US011952364B2

(12) United States Patent
Zhong et al.

(10) Patent No.: US 11,952,364 B2
(45) Date of Patent: Apr. 9, 2024

(54) TRK INHIBITORS USEFUL AS ANTICANCER DRUGS

(71) Applicant: TYLIGAND BIOSCIENCE (SHANGHAI) LIMITED, Shanghai (CN)

(72) Inventors: Boyu Zhong, Irving, TX (US); Tony Yantao Zhang, Fishers, IN (US); Yiju Cao, Shanghai (CN); Guangming Chen, Shanghai (CN)

(73) Assignee: TYLIGAND BIOSCIENCE (SHANGHAI) LIMITED, Shanghai (CN)

( * ) Notice: Subject to any disclaimer, the term of this patent is extended or adjusted under 35 U.S.C. 154(b) by 432 days.

(21) Appl. No.: 17/273,046

(22) PCT Filed: Sep. 3, 2019

(86) PCT No.: PCT/CN2019/104218
§ 371 (c)(1),
(2) Date: Mar. 3, 2021

(87) PCT Pub. No.: WO2020/048455
PCT Pub. Date: Mar. 12, 2020

(65) Prior Publication Data
US 2022/0388983 A1    Dec. 8, 2022

(30) Foreign Application Priority Data
Sep. 3, 2018   (CN) .......................... 201811019556.X

(51) Int. Cl.
| | | |
|---|---|---|
| C07D 401/14 | (2006.01) |
| A61K 31/4439 | (2006.01) |
| A61K 45/06 | (2006.01) |
| A61P 35/00 | (2006.01) |
| C07D 487/04 | (2006.01) |

(52) U.S. Cl.
CPC ........ *C07D 401/14* (2013.01); *A61K 31/4439* (2013.01); *A61K 45/06* (2013.01); *A61P 35/00* (2018.01); *C07D 487/04* (2013.01)

(58) Field of Classification Search
None
See application file for complete search history.

(56) References Cited

U.S. PATENT DOCUMENTS 8,513,263 B2   8/2013   Haas et al.

FOREIGN PATENT DOCUMENTS

| WO | 2006/087538 A1 | 8/2006 |
| WO | 2006/115452 A1 | 11/2006 |
| WO | 2008/052734 A1 | 5/2008 |
| WO | 2010/011538 A1 | 1/2010 |
| WO | 2010/033941 A1 | 3/2010 |
| WO | 2016/061228 A1 | 4/2016 |
| WO | 2016/089760 A1 | 6/2016 |
| WO | 2017/027544 A1 | 2/2017 |
| WO | 2017/075107 A1 | 5/2017 |
| WO | 2017/180462 A1 | 10/2017 |
| WO | 2018/022438 A1 | 2/2018 |
| WO | 2018/093669 A1 | 5/2018 |

OTHER PUBLICATIONS

Kallman et al., Organic Process Research & Development (2014), 18(4), pp. 501-510.*
Vaishnavi A et. al. TRKing Down an Old Oncogene in a New Era of Targeted Therapy, Cancer Discovery Jan. 2015, 5(1): 25-34.
Ross A. Okimoto et. al. TRKing Down Response and Resistance to TRK Inhibitors, Cancer Discovery Jan. 2016, 6(1): 14-16.
Yekaterina B. Khotskaya et al. Targeting TRK family proteins in cancer, Pharmacology & Therapeutics 173 (2017) 58-66.
Francesco Passiglia et al. The potential of neurotrophic tyrosine kinase (NTRK) inhibitors for treating lung cancer, Expert Opinion on Investigational Drugs, 2016 vol. 25, No. 4, 385-392.
Bruce W. Konicek et al. Merestinib (LY2801653) inhibits neurotrophic receptor kinase (NTRK) and suppresses growth of NTRK fusion bearing tumors, Oncotarget, 2018, vol. 9, No. 17, pp. 13796-13806.
Stransky N et al, The Landscape of kinase fusions in cancer, Nature Communications, Sep. 10 2014, 5:4846.
Drilon A et al., Efficacy of Larotrectinib in TRK Fusion-Positive Cancers in Adults and Children, N Engl J Med, Feb. 22, 2018;378(8):731-739.
Doebele, R. C. et al., An oncogenic NT RK fusion in a soft tissue sarcoma patient with response to the tropomyosin-related kinase (TRK) inhibitor LOXO-101, *Cancer Discov.* Oct. 2015, 5(10), 1049-1057.
C. Rolfo et al, Entrectinib: a potent new TRK, ROS1, and ALK inhibitor, *Expert Opin. Investig. Drugs* 2015, 24(11), 1493-1500.
Xiaobo Liu et al., Design, Synthesis and Biological Evaluation of 6,7-Disubstituted-4-phenoxyquinoline Derivatives Bearing Pyridazinone Moiety as c-Met Inhibitors, Molecules. Jul. 2018; 23(7): 1543.
Bo Mi Ku, et al., Acquired resistance to AZD9291 as an upfront treatment is dependent on ERK signaling in a preclinical model, *PLoS One*, 2018; 13(4): e0194730.
Nathaniel Robichaud et al., Translational control in the tumor microenvironment promotes lung metastasis: Phosphorylation of eIF4E in neutrophils, Proceesings of the National Academy of Sciences of the United States of America, Feb. 20, 2018, vol. 115(10): E2202-E2209.
S Betty Yan, et al., MET-targeting antibody (emibetuzumab) and kinase inhibitor (merestinib) as single agent or in combination in a cancer model bearing MET exon 14 skipping, Investigational New Drugs, Nov. 29, 2017, 36(4): 536-544.

(Continued)

*Primary Examiner* — Brian J Davis
(74) *Attorney, Agent, or Firm* — LADAS & PARRY LLP

(57) ABSTRACT

A group of tropomyosin receptor kinase inhibitors including an amido-phenoxy-indazole structure fragment. These compounds show potent inhibitory effects on various oncogenic kinases, especially TRK, and thus can be used to treat tumors or cancers.

24 Claims, 3 Drawing Sheets

(56) References Cited

OTHER PUBLICATIONS

Ewa M. Kosciuzuk et al., Merestinib blocks Mnk kinase activity in acute myeloid leukemia progenitors and exhibits antileukemic effects in vitro and in vivo, Blood, Jul. 21, 2016; 128(3): 410-414.

* cited by examiner

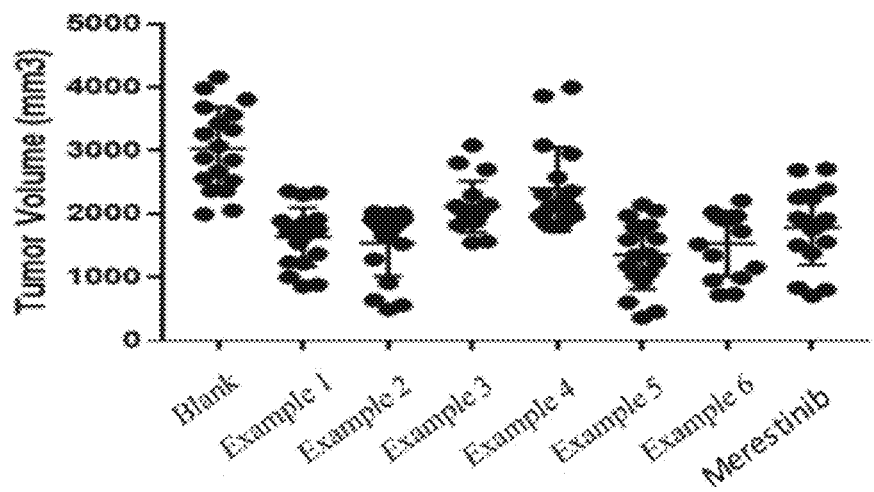
Fig. 1-A
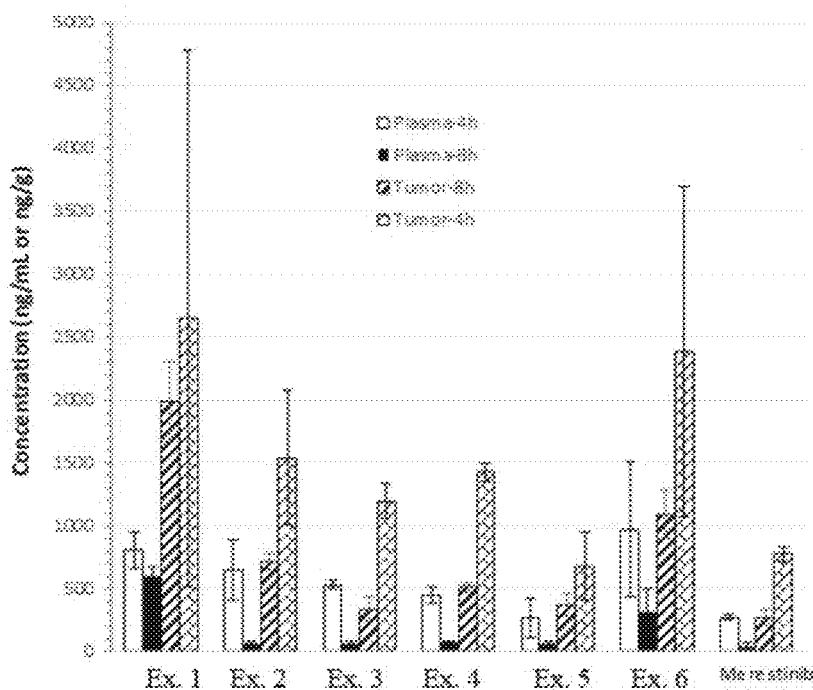
Fig. 1-B (12 days post-dosing)

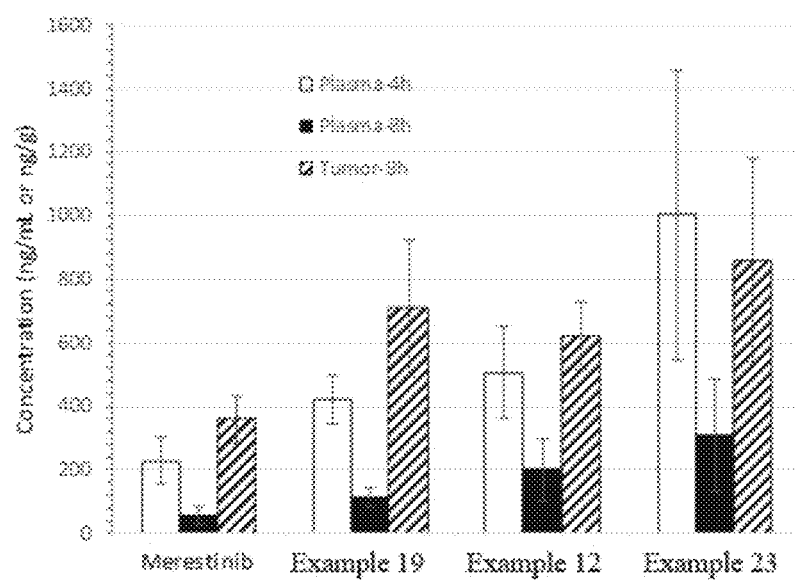
Fig. 1-C (18 days post-dosing)

TRK INHIBITORS USEFUL AS ANTICANCER DRUGS

RELATED APPLICATION

This application is an application under 35 U.S.C. 371 of International Application No. PCT/CN2019/104218 filed on 3 Sep. 2019, which claims the benefit of Chinese Application No. 201811019556.X filed on 3 Sep. 2018, the entire content of which is incorporated by reference.

TECHNICAL FIELD

The present disclosure relates to a group of compounds having new structures, pharmaceutical compositions comprising these compounds, methods for preparing these compounds, and use of these compounds in the treatment of cancers. Specifically, the present disclosure relates to a group of compounds having a structure of substituted "phenyl-pyridone-amido-phenoxy-(pyrazole-substituted) indazole", which exhibit Trk inhibitory activity and thus can be used to treat cancers.

BACKGROUND

Tropomyosin Receptor Kinase family, also known as Trk, includes three receptors, TrkA, TrkB and TrkC, encoded by neurotrophic tyrosine kinase receptor genes NTRK1, NYRK2 and NTRK3, respectively. Trk is a type of neurotrophic factor (NT) receptors, which can be found in a variety of tissues and can be activated by neurotrophic factors. Among these neurotrophic factors, there are nerve growth factor (NGF) that can activate TrkA, the brain-derived neurotrophic factor (BDNF) and NT-4/5 that can activate TrkB, and NT3 that can activate TrkC.

Neurotrophic factor binds to Trk protein to induce receptor dimerization and phosphorylation, and activate downstream signal amplification and conduction of PI3K, RAS/MAPK/ERK and PLC-gamma. Thus, Trk is closely related to cell proliferation, differentiation, metabolism, and apoptosis.

Specifically, they are involved in neuron development, including the growth and function of neuronal synapses, memory formation and maintenance, and neuron protection after ischemia and other types of injury. It has been reviewed in WO2010/033941, that, studies have shown that inhibitors of the Trk/neurotrophic factor pathway are effective in a variety of preclinical models of pain; the overexpression, activation, amplification and/or mutation of Trk are related to many cancers, accordingly, some small molecule Trk inhibitors have been shown to inhibit tumor growth and prevent tumor metastasis in preclinical and clinical models of cancer; inhibiting the Trk/neurotrophic factor pathway has also been shown to be effective in treating inflammatory diseases (such as inflammatory lung disease, interstitial cystitis, inflammatory bowel disease and inflammatory skin disease), neurodegenerative diseases (such as multiple sclerosis, Parkinson's disease, Alzheimer's disease), diseases related to the imbalance of bone remodeling (such as osteoporosis, rheumatoid arthritis and bone metastases).

Specifically, in terms of the relationship between Trk and cancer treatment, Trk protein can bind to neurotrophic factors to induce dimerization and phosphorylation of Trk receptors, and activate downstream signal amplification and conduction of PI3K, RAS/MAPK/ERK and PLC-gamma. Changes in the Trk pathway mainly include gene fusion, protein overexpression, and single nucleotide mutations. These changes are related to the pathogenesis of many cancers. Among them, NTRK gene fusion is by far the clearest carcinogenic event (Stransky N et al., The Landscape of kinase fusions in cancer. Nature Communication, September 2014, 10; 1-10). Studies have shown that when chromosomal mutations undergo NTRK gene fusion, it can lead to excessive activation of Trk downstream signals, which can lead to or promote the development of a variety of cancers (Vaishnavi et al., TRKing Down an Old Oncogene in a New Era of Targeted Therapy, Cancer Discovery 2015; 5:25-34). These cancers include, but are not limited to, neuroblastoma, ovarian cancer, breast cancer, prostate cancer, pancreatic cancer, salivary gland cancer, multiple myeloma, astrocytoma and medulloblastoma, neuroglioma, melanoma, thyroid cancer, lung adenocarcinoma, large cell neuroendocrine tumors, colorectal cancer, head and neck cancer, sarcoma (especially infant fibrosarcoma cancer), intrahepatic cholangiocarcinoma, glioblastoma, glioma, secretory breast carcinoma, mammary secretory carcinoma, acute myeloid leukemia, congenital mesoderm nephroma, congenital fibrosarcoma, acute lymphoblastic leukemia, colon adenocarcinoma, gastrointestinal stromal tumor, etc. Among them, NTRK1 gene fusion has been shown to be a driver mutation for lung adenocarcinoma, cholangiocarcinoma, colorectal cancer, papillary thyroid cancer, spitzoid tumor and glioblastoma; NTRK2 gene fusion has been shown to be a driver mutations of sarcoma, astrocytoma, lung adenocarcinoma and head and neck cancer; NTRK3 gene fusion has been shown to be a driver mutations in low-grade glioma, secretory breast cancer, papillary thyroid cancer, acute myeloid leukemia, congenital mesoderm nephroma, congenital fibrosarcoma, acute lymphoblastic leukemia, colon adenocarcinoma, thyroid cancer, skin melanoma, head and neck cancer, and pediatric glioma (Vaishnavi et al., 2015). Therefore, compounds that target Trk and inhibit the catalytic activity of Trk are expected to become effective treatment options for these cancers.

Several types of small molecule inhibitors of Trk for the treatment of cancers have been reported. International patent applications WO2006/115452 and WO2006/087538 describe several small molecule compounds called Trk inhibitors that can be used to treat pains and cancers. WO2008/052734 and WO2010/033941 respectively describe compounds with ma imidazo[1,2-B]pyridazine structure, which can be used to treat Trk-mediated diseases or as Trk inhibitors. WO2017/075017 reviews various structural types of Trk inhibitors, including but not limited to substituted pyrazolo[1,5-a]pyrimidine compounds, macrocyclic compounds, substituted imidazo[1,2-B]pyridazines compounds, compounds having —NH(C=X)NH— structure, and compounds having indazole amido structure.

WO2010/011538 describes a group of amidophenoxyindazole compounds that can be used as C-Met inhibitors. Recent research reports (Bruce W Konicek et al., Merestinib (LY2801653 inhibits neurotrophic receptor kinase (NTRK) and suppresses growth of NTRK fusion bearing tumors, Oncotarget, 2018, Vol. 9, (No 17), pp: 13796-13806), the oral multikinase inhibitor Meretinib (LY2801653), which targets several oncogenic kinases MET, AXL, RON and MKNK1/2, has been shown to inhibit neurotrophic receptor kinase (NTRK) and inhibit the growth of tumors carrying NTRK gene fusions.

Currently, several compounds targeting NTRK have been in clinical development, such as LOXO-101 (Larotrectinib), Entrectinib, Carbozantinib, Merestinib, DS-6051b, PLX7486, TSR-Oil, etc. The clinical research results of LOXO-101 (Larotrectinib) are very encouraging. The tumors of the tested patients are distributed in more than ten different types, including thyroid cancer, colorectal cancer, lung cancer, melanoma, infantile fibrosarcoma, salivary adenoma, bile duct cancer, GIST, etc. The overall patient response rate (ORR) reached 75%, of which 62% was partial response, and 13% was complete response. After 1 year of treatment, 71% of patients still responded to treatment, and 55% of patients had no disease progression (Drilon A et al., Efficacy of Larotrectinib in TRK Fusion-Positive Cancers in Adults and Children, N Engl J Med 2018 Feb. 22; 378(8): 731-739).

However, in view of the excellent anti-tumor effects of targeted Trk inhibitors, there is still a need for more potent compounds that target Trk. These compounds are expected to have improved physicochemical properties, druggable properties and/or fewer drug interactions.

The present disclosure provides novel, specifically substituted amidophenoxyindazole compounds with Trk inhibitory activity. These compounds, especially the preferred compounds of the present disclosure, have an improved substitution pattern as compared to those in the prior art, which not only retain considerable and even enhanced Trk inhibitory activity, but can also reduce the production of active intermediates in the body; physical and chemical properties such as solubility are significantly improved, thus providing good pharmaceutical properties, e.g. easier to disintegrate and absorb in the body; at the same time, the inhibitory effect on the cytochrome p450 enzyme system is weakened, thereby having reduced drug interactions. In addition, the compound of the present disclosure, especially the preferred compound of the present disclosure, also exhibits excellent anti-tumor activity as compared to the existing Trk inhibitors in the prior art, and can be enriched in tumor tissues and plasma at a higher concentration, at the same time, it also shows significantly improved metabolic stability with longer metabolic half-life and lower inherent clearance rate, which can provide long-lasting efficacy or reduce the required drug dosage. In particular, the tricyclic structure-containing compound of the present disclosure endues Trk inhibitory activity on the molecule, a different activity spectrum, and better druggability (such as lower inhibition of cytochrome p450 enzymes, better metabolic stability in vivo etc.).

SUMMARY OF THE DISCLOSE

The inventors discovered through research that certain specifically substituted indazole-phenoxy-aminoacyl-dihydropyridyl compounds are Trk inhibitors, can be used to treat or prevent diseases or disorders in which Trk activity plays a role or is involved, or can be treated by inhibiting Trk, especially can be used to treat or prevent tumors or cancers by inhibiting Trk, more especially tumors or cancers caused by NTRK gene fusion.

The first aspect of the present disclosure provides a compound of formula I, isomers thereof, or pharmaceutically acceptable salts or solvates thereof,

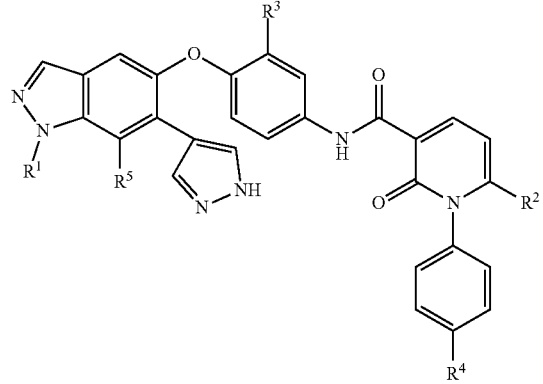

I wherein
- $R^1$ is $C_{1-6}$ alkyl or $C_{3-6}$ cycloalkyl, optionally substituted by one or more halogens, $-OR^a$, $C_{1-6}$ alkyl or amino;
- $R^5$ is H, halogen, $-OR^a$ or optionally substituted $C_{1-6}$ alkyl, and the substituent is selected from one or more halogen, $-OR^a$, $C_{1-6}$ alkyl or amino;
- or $R^1$ and $R^5$ together with the atoms to which they are attached form a cyclic structure with the following general formula:

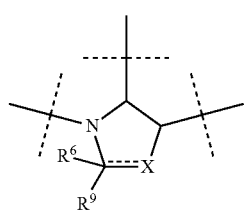

(a)

where X is $-CR^7R^8-$, $=CR^7-$, $-CR^7R^8-CR^7R^8-$ or $-CR^7=CR^8-$;
- $R^6$, $R^7$, $R^8$ and $R^9$ are each independently H, halogen, $-OR^a$, optionally substituted $C_{1-6}$ alkyl or $C_{3-6}$ cycloalkyl, wherein the substituent is selected from one or more halogen, $-OR^a$, $C_{1-6}$ alkyl or amino; or
- $R^6$ and $R^9$ or $R^7$ and $R^8$ attached to the same carbon atom can form $=O$ or $=S$ together, or form a $C_{3-6}$ cycloalkyl group together with the carbon atom to which they are attached;
- $R^2$ is $C_{1-6}$ alkyl optionally substituted by one or more halogens, $C_{1-6}$ alkyl, $C_{1-6}$ alkoxy or amino; $C_{3-6}$ cycloalkyl or $C_{3-6}$ heterocyclic group optionally substituted by one or more halogens, $-OR^a$, $C_{1-6}$ alkyl or amino; nitro, cyano, acyl, halogen, mercapto, $C_{1-6}$ alkylthio, $C_{1-6}$ alkylsulfonyl, $C_{1-6}$ alkyl sulfinyl or carboxy;
- $R^3$ and $R^4$ are each independently selected from H, halogen, nitro, cyano, acyl or carboxy;
- $R^a$ is H or $C_{1-6}$ alkyl;
- provided that $R^1$ and $R^2$ are not methyl at the same time.

In one embodiment of the compound of formula I, $R^1$ is $C_{1-6}$ alkyl, such as but not limited to methyl, ethyl, propyl, isopropyl, butyl, sec-butyl, isobutyl, tert-butyl, N-pentyl, isopentyl, neopentyl, n-hexyl, 2-methylpentyl, 3-methylpentyl, 2,3-dimethylbutyl, 2,2-dimethylbutyl, 2-ethylbutyl; preferably methyl, ethyl or isopropyl, optionally substituted by 1, 2 or 3 halogens (preferably fluorine), hydroxyl, $C_{1-6}$ alkoxy (preferably methoxy or ethoxy) or amino.

In one embodiment of the compound of formula I, $R^1$ is $C_{3-6}$ cycloalkyl, preferably cyclopropyl, cyclobutyl, cyclopentyl or cyclohexyl, optionally substituted by 1, 2 or 3 halogens (preferably fluorine), hydroxy, $C_{1-6}$ alkyl (preferably methyl, ethyl or isopropyl), $C_{1-6}$ alkoxy (preferably methoxy or ethoxy) or amino, such as but not limited to 2-fluoro cyclopropyl, 2- and/or 3-fluorocyclobutyl, 2- and/or 3-fluorocyclopentyl, 2-, 3- and/or 4-fluorocyclohexyl, or these groups substituted at the corresponding positions by hydroxy, methyl, ethyl, isopropyl, methoxy, ethoxy or amino.

In one embodiment of the compound of formula I, $R^5$ is H.

In one embodiment of the compound of formula I, $R^5$ is halogen, hydroxy, $C_{1-6}$ alkoxy or $C_{1-6}$ alkyl, such as but not limited to fluorine, chlorine, bromine, iodine, hydroxy, methoxy, ethoxy, propoxy, isopropoxy, methyl, ethyl, propyl, isopropyl, etc., optionally substituted by 1, 2 or 3 halogens (preferably F), $C_{1-6}$ alkoxy (preferably methoxy or ethoxy), $C_{1-6}$ alkyl (preferably methyl, ethyl) or amino.

In one embodiment of the compound of formula I, $R^1$ and $R^5$ together with the atoms to which they are attached form a structure of formula (a), wherein $R^6$ and $R^9$ are each independently H, halogen, hydroxy, $C_{1-6}$ alkyl, or $C_{3-6}$ cycloalkyl, and X is —$CR^7R^8$— or —$CR^7R^8$—$CR^7R^8$—, wherein $R^7$ and $R^8$ are each independently H, halogen, hydroxy, $C_{1-6}$ alkyl, or $C_{3-6}$ cycloalkyl. Preferably, $R^6$ and R are each independently H, halogen, or $C_{3-6}$ cycloalkyl, and X is —$CR^7R^8$— or —$CR^7R^8$—$CR^7R^8$, wherein $R^7$ and $R^8$ are each independently H, halogen, or $C_{3-6}$ cycloalkyl.

In this embodiment, it is also preferred that one of $R^6$ and $R^9$ and/or one of $R^7$ and $R^8$ is a $C_{3-6}$ cycloalkyl group, such as cyclopropyl, cyclobutyl, cyclopentyl or cyclohexyl.

In this embodiment, it is also preferred that one or both of $R^6$ and $R^9$ and/or one or both of $R^7$ and $R^8$ are halogen, preferably fluorine.

In this embodiment, it is most preferred that $R^6$ and $R^9$ are both H, and X is —$CR^7R^8$—, wherein $R^7$ and $R^1$ are both H; it is also most preferred that $R^6$ and $R^9$ are both H, and X is —CHF— or —$CF_2$—; it is also most preferred that $R^6$ and $R^9$ are both H, and X is —$CR^7R^8$—$CR^7R^8$—, wherein $R^7$ and $R^8$ are both H; it is also most preferred that $R^6$ and $R^9$ are both H, and X is —$CH_2$—$CF_2$— or —CHF—CHF—.

In one embodiment of the compound of formula I, $R^1$ and $R^5$ together with the atoms to which they are attached form a structure of formula (a), wherein $R^6$ and $R^9$ are each independently H, halogen, hydroxy, $C_{1-6}$ alkyl, or $C_{3-6}$ cycloalkyl, and X is =$CR^7$— or —$CR^7$=$CR^8$—, wherein $R^7$ and $R^8$ are each independently H, halogen, $C_{1-6}$ alkyl, or $C_{3-6}$ cycloalkyl. More preferably, $R^6$ and $R^9$ are each independently H, halogen (preferably fluorine) or $C_{3-6}$ cycloalkyl, and X is =$CR^7$— or —$CR^7$=$CR^8$—, wherein $R^7$ and $R^8$ are each independently H, halogen (Preferably fluorine) or $C_{3-6}$ cycloalkyl.

In this embodiment, it is also preferred that one of $R^6$ and $R^9$ and/or one of $R^7$ and $R^8$ is a $C_{3-6}$ cycloalkyl group, such as cyclopropyl, cyclobutyl, cyclopentyl or cyclohexyl.

In one embodiment of the compound of formula I, $R^1$ and $R^5$ together with the atoms to which they are attached form the structure of formula (a), wherein X is —$CR^7R^8$— or —$CR^7R^8$—$CR^7R$—, wherein $R^6$ and $R^9$ or $R^7$ and $R^8$ attached to the same carbon atom together form =O or =S, or form cyclopropyl, cyclobutyl, cyclopentyl or cyclohexyl together with the carbon atom to which they are attached; preferably $R^7$ and $R^8$ attached to the same carbon atom form cyclopropyl, cyclobutyl, cyclopentyl or cyclohexyl.

In one embodiment of the compound of formula I, $R^2$ is $C_{1-6}$ alkyl, such as but not limited to methyl, ethyl, propyl, isopropyl, butyl, sec-butyl, isobutyl, tert-butyl, n-pentyl, isopentyl, neopentyl, n-hexyl, 2-methylpentyl, 3-methylpentyl, 2,3-dimethylbutyl, 2,2-dimethylbutyl, 2-ethylbutyl; preferably methyl, ethyl, isopropyl, optionally substituted by 1, 2 or 3 halogens (preferably fluorine), $C_{1-6}$ alkyl (preferably methyl, ethyl or isopropyl)), $C_{1-6}$ alkoxy (preferably methoxy or ethoxy) or amino; most preferably methyl, ethyl, isopropyl or trifluoromethyl.

In one embodiment of the compound of formula I, $R^2$ is $C_{3-6}$ cycloalkyl or $C_{3-6}$ heterocyclyl, such as but not limited to cyclopropyl, cyclobutyl, cyclopentyl or cyclohexyl, or tetrahydrofuran, tetrahydrothiophene, azetidine, acridine, tetrahydropyrrole, thiazolidine, oxazolidine, piperidine, piperazine, morpholine, thiomorpholine, thiazine; preferably cyclopropyl; they are optionally substituted by 1, 2 or 3 halogens (preferably fluorine), hydroxyl, $C_{1-6}$ alkyl (preferably methyl, ethyl or isopropyl), $C_{1-6}$ alkoxy (preferably methoxy or ethoxy) or amino.

In one embodiment of the compound of formula I, $R^3$ and $R^4$ are each independently selected from H or halogen, preferably F, Cl, Br, or I; more preferably F.

The compound of formula I of the present disclosure encompasses the above embodiments independently, in combination, or any combinations or sub-combinations, and also encompasses embodiments resulting from any combination of any preferred, more preferred or most preferred embodiments as defined above.

One embodiment of the compound of formula I in the first aspect of the present disclosure is a compound of formula I-a, isomers thereof, or pharmaceutically acceptable salts or solvates thereof, I-a

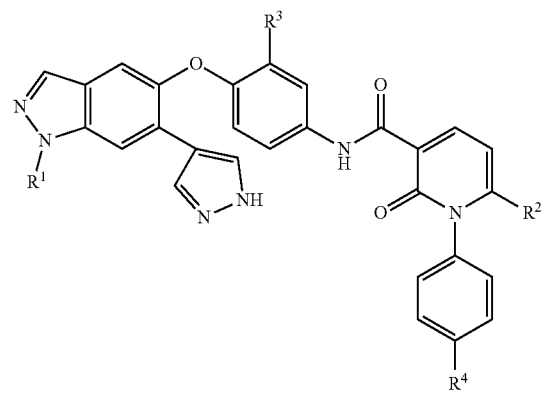

wherein $R^1$ is $C_{1-6}$ alkyl;

$R^2$ is $C_{1-6}$ alkyl or $C_{3-6}$ cycloalkyl optionally substituted with one or more halogens;

$R^3$ and $R^4$ are each independently selected from H or halogen; and provided that $R^1$ and $R^2$ are not methyl at the same time.

The first aspect of the present disclosure also preferably provides a compound of formula I-b, isomers thereof, or pharmaceutically acceptable salts or solvates thereof, I-b

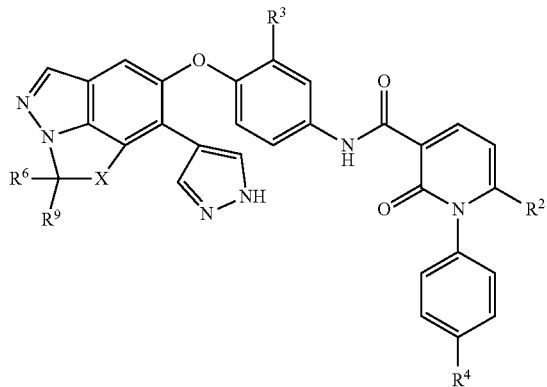

wherein
$R^2$ is $C_{1-6}$ alkyl or $C_{3-6}$ cycloalkyl optionally substituted with one or more halogens;
$R^3$ and $R^4$ are each independently selected from H or halogen;
$R^6$ and R are each independently H, halogen, hydroxy, $C_{1-6}$ alkyl or $C_{3-6}$ cycloalkyl, and
X is —CR$^7$R$^8$— or —CR$^7$R$^8$—CR$^7$R$^8$—, wherein R$^7$ and R$^8$ are each independently H, halogen, hydroxy, $C_{1-6}$ alkyl or $C_{3-6}$ cycloalkyl, or R$^7$ and R$^8$ attached to the same carbon atom together to form a $C_{3-6}$ cycloalkyl group.

The first aspect of the present disclosure also provides a compound of formula II, isomers thereof, or pharmaceutically acceptable salts or solvates thereof,

II

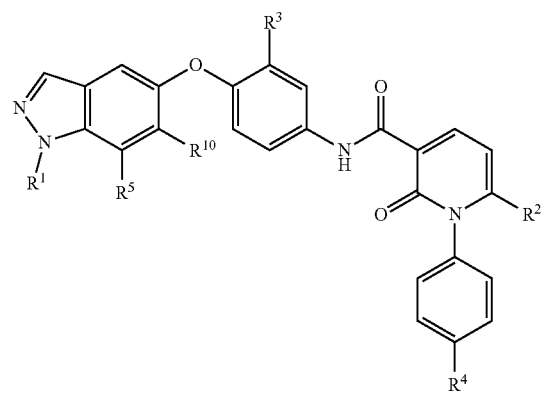

wherein
$R^1$ is $C_{1-6}$ alkyl or $C_{3-6}$ cycloalkyl, which is optionally substituted by one or more halogens, —OR$^a$, —SR$^a$, $C_{1-6}$ alkyl or amino;
$R^5$ is H, halogen, —OR$^a$, —SR$^a$, or optionally substituted $C_{1-6}$ alkyl, and the substituent is selected from one or more halogens, —OR$^a$, —SR$^a$, $C_{1-6}$ alkyl or amino; or
$R^1$ and $R^5$ together with the atoms to which they are attached form a cyclic structure with the following general formula:

(a)

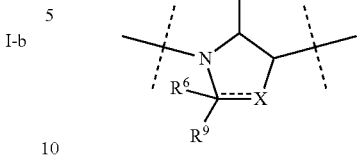

where X is —CR$^7$R$^8$—, =CR$^7$—, —CR$^7$R$^8$—CR$^7$R$^8$— or —CR$^7$=CR$^8$—;
$R^6$, $R^7$, $R^8$ and $R^9$ are each independently H, halogen, —OR$^a$, —SR$^a$, optionally substituted $C_{1-6}$ alkyl or $C_{3-6}$ cycloalkyl, wherein the substituent is selected from one or more halogens, —OR$^a$, —SR$^a$, $C_{1-6}$-alkyl or amino; or
$R^6$ and $R^9$ or $R^7$ and $R^8$ attached to the same carbon atom can form =O or =S together, or form a $C_{3-6}$ cycloalkyl group together with the carbon atom to which they are attached;
$R^2$ is $C_{1-6}$ alkyl optionally substituted by one or more halogen, $C_{1-6}$ alkyl, $C_{1-6}$ alkoxy, $C_{1-6}$alkylthio or amino; $C_{1-6}$ cycloalkyl or $C_{1-6}$ heterocyclyl optionally substituted by one or more halogen, —OR$^a$, —SR$^a$, $C_{1-6}$ alkyl or amino substituted; nitro, cyano, acyl, halogen, —SR$^b$, —SO$_2$R$^b$, —SOR$^b$, C(O)R$^b$ or CO$_2$R$^b$; or $R^2$ is —NR$^a$R$^b$ or —OR$^b$;
$R^3$ and $R^4$ are each independently selected from H, halogen, nitro, cyano, acyl or carboxy;
$R^{10}$ is hydrogen, halogen, cyano, nitro, —NR$^a$R$^b$, —OR$^b$, —SR$^b$, C(O)R$^b$, CO$_2$R$^b$; $C_{1-6}$ alkyl, $C_{2-6}$ alkenyl, $C_{2-6}$ alkynyl, $C_{3-6}$ cycloalkyl, $C_{3-6}$ heterocycloalkyl, 6-10 membered aryl, 5-10 membered heteroaryl; $C_{1-6}$ alkyl or $C_{2-6}$ alkenyl or $C_{2-6}$ alkynyl, substituted by one or more halogens, $C_{1-6}$ alkyl, $C_{1-6}$ alkoxy, $C_{1-6}$ alkylthio or amino; $C_{3-6}$ cycloalkyl or $C_{3-6}$ heterocycloalkyl, substituted by one or more hydroxy, halogen, $C_{1-6}$ alkyl, $C_{1-6}$ alkoxy, $C_{1-6}$ alkylthio or amino; 6-10 membered aryl or 5-10 membered heteroaryl, substituted by one or more hydroxy, halogen, $C_{1-6}$ alkyl, $C_{1-6}$ alkoxy, $C_{1-6}$ alkylthio or amino;
$R^a$ and $R^b$ are each independently H, $C_{1-6}$ alkyl optionally substituted by one or more halogens, CN or nitro, or $C_{3-6}$ cycloalkane optionally substituted by one or more halogens, CN or nitro, or $R^a$ and $R^b$ together with the N to which they connected form a 3-6 membered ring optionally substituted with one or more halogens, CN or nitro;
provided that $R^1$ and $R^2$ are not methyl at the same time.

In one embodiment of the compound of formula II, $R^1$ is $C_{1-6}$ alkyl, such as but not limited to methyl, ethyl, propyl, isopropyl, butyl, sec-butyl, isobutyl, tert-butyl, n-pentyl, isopentyl, neopentyl, n-hexyl, 2-methylpentyl, 3-methylpentyl, 2,3-dimethylbutyl, 2,2-dimethylbutyl, 2-ethylbutyl; preferably methyl, ethyl or isopropyl, they are optionally substituted by 1, 2 or 3 halogens (preferably fluorine), hydroxyl, $C_{1-6}$ alkoxy (preferably methoxy or ethoxy), mercapto, $C_{1-6}$ alkylthio (preferably methylthio or ethylthio), or amino, most preferably methyl.

In one embodiment of the compound of formula II, $R^1$ is $C_{3-6}$ cycloalkyl, preferably cyclopropyl, cyclobutyl, cyclopentyl or cyclohexyl, which are optionally substituted by 1, 2 or 3 halogens (preferably fluoro), hydroxy, $C_{1-6}$ alkyl (preferably methyl, ethyl, or isopropyl), $C_{1-6}$ alkoxy (preferably methoxy or ethoxy), mercapto, $C_{1-6}$ alkylthio (preferably methylthio or ethylthio) or amino, such as but not limited to 2-fluorocyclopropyl, 2- and/or 3-fluorocyclobutyl, 2- and/or 3-fluorocyclopentyl, 2-, 3- and/or 4-fluorocyclohexyl, or these groups substituted by hydroxyl, mercapto, methyl, ethyl, isopropyl, methoxy, ethoxy, methylthio, ethylthio, or amino at the corresponding positions.

In one embodiment of the compound of formula II, $R^5$ is H, halogen, hydroxy, $C_{1-6}$ alkoxy, mercapto, $C_{1-6}$ alkylthio, or $C_{1-6}$ alkyl, such as but not limited to H, fluorine, chlorine, bromine, iodine, hydroxyl, methoxy, ethoxy, propoxy, isopropoxy, methyl, ethyl, propyl, isopropyl, mercapto, methylthio, ethylthio, propylthio, isopropylthio, etc., optionally substituted by 1, 2 or 3 halogens (preferably F), $C_{1-6}$ alkoxy (preferably methoxy or ethoxy), $C_{1-6}$ alkylthio (preferably methylthio or ethylthio), $C_{1-6}$ alkyl (preferably methyl, ethyl) or amino; most preferably $R^5$ is H.

In one embodiment of the compound of formula II, $R^1$ and $R^5$ together with the atoms to which they are attached form a structure of formula (a), wherein $R^6$ and $R^9$ are each independently H, halogen, hydroxyl, mercapto, $C_{1-6}$ alkyl, $C_{1-6}$ alkoxy, $C_{1-6}$ alkylthio, or $C_{3-6}$ cycloalkyl, and X is —$CR^7R^8$— or —$CR^7R^8$—$CR^7R^8$—, wherein $R^7$ and $R^8$ are each independently H, halogen, hydroxyl, mercapto, $C_{1-6}$ alkyl, $C_{1-6}$ alkoxy, $C_{1-6}$ alkylthio, or $C_{3-6}$ cycloalkyl. Preferably, $R^6$ and $R^9$ are each independently H, halogen, $C_{1-6}$ alkyl, or $C_{3-6}$ cycloalkyl, and X is —$CR^7R^8$— or —$CR^7R^8$—$CR^7R^8$—, wherein $R^7$ and $R^8$ are each independently H, halogen, $C_{1-6}$ alkyl or $C_{3-6}$ cycloalkyl.

In this embodiment, it is also preferred that one of $R^6$ and $R^9$ and/or one of $R^7$ and $R^8$ is a $C_{3-6}$ cycloalkyl group, such as cyclopropyl, cyclobutyl, cyclopentyl, or cyclohexyl.

In this embodiment, it is also preferred that one or both of $R^6$ and $R^9$ and/or one or both of $R^7$ and $R^8$ are halogen, preferably fluorine.

In this embodiment, it is most preferred that $R^6$ and $R^9$ are both H, and X is —$CR^7R^8$—, wherein $R^7$ and $R^8$ are both H; it is also most preferred that $R^6$ and $R^9$ are both H, and X is —CHF— or —$CF_2$—; it is also most preferred that $R^6$ and $R^9$ are both H, and X is —$CR^7R^8$—$CR^7R^8$—, wherein $R^7$ and $R^8$ are both H; it is also most preferred that $R^6$ and $R^9$ are both H, and X is —$CH_2$—$CF_2$—, —$CH_2$—CHF—, —CHF—CHF— or —$CF_2$—$CF_2$—.

In one embodiment of the compound of formula II, $R^1$ and $R^5$ together with the atoms to which they are attached form a structure of formula (a), wherein $R^6$ and $R^9$ are each independently H, halogen, hydroxyl, mercapto, $C_{1-6}$ alkyl, $C_{1-6}$ alkoxy, $C_{1-6}$ alkylthio, or $C_{3-6}$ cycloalkyl, and X is =$CR^7$— or —$CR^7$=$CR^8$—, wherein $R^7$ and $R^8$ are each independently H, halogen, $C_{1-6}$ alkyl, or $C_{3-6}$ cycloalkyl. More preferably, $R^6$ and $R^9$ are each independently H, halogen (preferably fluorine), $C_{1-6}$ alkyl or $C_{3-6}$ cycloalkyl, and X is =$CR^7$— or —$CR^7$=$CR^8$—, wherein $R^7$ and $R^8$ are each Independently H, halogen (preferably fluorine), $C_{1-6}$ alkyl, or $C_{3-6}$ cycloalkyl.

In this embodiment, it is also preferred that one of $R^6$ and $R^9$ and/or one of $R^7$ and $R^8$ is a $C_{3-6}$ cycloalkyl group, such as cyclopropyl, cyclobutyl, cyclopentyl, or cyclohexyl.

In one embodiment of the compound of formula II, $R^1$ and $R^5$ together with the atoms to which they are attached form a structure of formula (a), wherein X is —$CR^7R^8$— or —$CR^7R^8$—$CR^7R$—, wherein $R^6$ and $R^9$ or $R^7$ and $R^8$ attached to the same carbon atom together form =O or =S, or together with the carbon atom to which they are attached form cyclopropyl, cyclobutyl, cyclopentyl or cyclohexyl; preferably $R^7$ and $R^8$ attached to the same carbon atom together form cyclopropyl, cyclobutyl, cyclopentyl, or cyclohexyl.

In one embodiment of the compound of formula II, $R^2$ is —$NR^aR^b$, wherein $R^a$ and $R^b$ are each independently selected from H, $C_{1-6}$ alkyl optionally substituted with one or more halogens (preferably fluorine), or $C_{3-6}$ cycloalkyl optionally substituted one or more halogens (preferably fluorine), or $R^a$ and $R^b$ together with the N to which they are attached form a 3-6 membered ring optionally substituted by one or more halogens, preferably fluorine, $R^a$ and $R^b$ are preferably each independently selected from H or $C_{1-6}$ alkyl, specific $R^2$ includes but is not limited to —$NH_2$, —NH-Me, —NH-Et, —NH-nPr, —NH-iPr, —NH-cPr, —NH-nBu, —NH-sec-Bu, —NH-iBu, —NH-tBu, —NH-cBu, —NH—pentyl, —NH-isopentyl, —NH-neopentyl, —NH-cyclopentyl, —NH-hexyl, —NH-(2- or 3-ethyl)butyl, —NH-(2,3-dimethyl)butyl, —NH-(2-propyl)propyl Groups, —$N(Me)_2$, —N(Me)(Et), —$N(Et)_2$, —$N(Pr)_2$ and these corresponding groups wherein the alkyl or cycloalkyl groups on these substituted amino groups are substituted with one or more halogen such as fluorine, etc.; it is more preferable that $R^a$ and $R^b$ are H at the same time.

In one embodiment of the compound of formula II, $R^2$ is —$SR^b$, wherein $R^b$ is selected from H, $C_{1-6}$ alkyl optionally substituted by one or more halogens (preferably fluorine), or $C_{3-6}$ cycloalkyl optionally substituted by one or more halogens (preferably fluorine), preferably $C_{1-6}$ alkyl optionally substituted by halogens (preferably fluorine) or $C_{3-6}$ cycloalkyl optionally substituted by halogens (preferably fluorine), specific $R^2$ includes but is not limited to —SH, —S-Me, —S-Et, —S-nPr, —S-iPr, —S-cPr, —S-nBu, —S-sec-Bu, —S-iBu, —S-tBu, —S-cBu, —S-pentyl, —S-isopentyl, —S-neopentyl, —S-cyclopentyl, —S-hexyl, —S-(2- or 3-Ethyl)butyl, —S-(2,3-dimethyl)butyl, —S-(2-propyl)propyl, —$SCF_3$, —$SCF_2H$, —$SCH_2CF_3$, —$SCH_2CH_2F$, —$SCH_2CHF_2$, —S-cPrF, etc., preferably $R^2$ is —SMe.

In one embodiment of the compound of formula II, $R^2$ is —$OR^b$, wherein $R^b$ is selected from H, $C_{1-6}$ alkyl optionally substituted by halogens (preferably fluorine) or $C_{3-6}$ cycloalkyl optionally substituted by halogens (preferably fluorine), preferably $C_{1-6}$ alkyl optionally substituted by halogens (preferably fluorine) or $C_{3-6}$ cycloalkyl optionally substituted by halogens (preferably fluorine), specific $R^2$ includes but is not limited to —OH, —OMe, —OEt, —O-nPr, —O-iPr, —O-cPr, —O-nBu, —O-sec-Bu, —O-iBu, —O-tBu, —O-cBu, —O-pentyl, —O-isopentyl, —O-neopentyl, —O-hexyl, —O-(2- or 3-ethyl)butyl, —O-(2,3-dimethyl)butyl, —O-(2-propyl)propyl, —$OCF_3$, —$OCF_2H$, —$OCH_2CF_3$, —O-cPrF, etc., preferably $R^2$ is —OH, —OMe, —OEt, —O-nPr, —O-iPr, —O-cPr, —$OCF_3$, —$OCF_2H$, —$OCH_2CF_3$, and most preferably $R^2$ is —OMe.

In one embodiment of the compound of formula II, $R^2$ is —$SO_2R^b$ or —$SOR^b$, wherein $R^b$ is selected from H, $C_{1-6}$ alkyl optionally substituted by halogens (preferably fluorine), or $C_{3-6}$ cycloalkyl optionally substituted by halogens (preferably fluorine), preferably $C_{1-6}$ alkyl optionally substituted by halogens (preferably fluorine), such as but not limited to —$SO_2H$, —SOMe, —$SO_2Me$, —SOEt, —$SO_2Et$, —SO-nPr, —$SO_2$-nPr, —SO-iPr, —$SO_2$-iPr, —SO-cPr, —$SO_2$-cPr, —SO-nBu, —$SO_2$-nBu, —SO-sec-Bu, —$SO_2$-sec-Bu, —SO-iBu, —$SO_2$-iBu, —SO-tBu, —$SO_2$-tBu, —SO-cBu, —$SO_2$-cBu, —SO-pentyl, —$SO_2$-pentyl, —SO— isopentyl, —$SO_2$-isopentyl, —SO-neopentyl, —$SO_2$-neopentyl, —SO-hexyl, —$SO_2$-hexyl, —$SOCF_3$, —$SO_2CF_3$, —$SOCF_2H$, —$SO_2CF_2H$, —$SOCH_2CF_3$, —$SO_2CH_2CF_3$, —SO-cPrF, —$SO_2$-cPrF, etc., preferably $R^2$ is —SOMe, —SO-Et, —$SO_2$-Me, —$SO_2$-Et, —$SOCF_3$, —$SO_2CF_3$.

In one embodiment of the compound of formula II, $R^2$ is —C(O)$R^b$ or —CO$_2R^b$, wherein $R^b$ is as defined above for $R^b$ in —SO$_2R^b$ or —SO$R^b$.

In one embodiment of the compound of formula II, $R^2$ is $C_{1-6}$ alkyl, such as but not limited to methyl, ethyl, propyl, isopropyl, butyl, sec-butyl, isobutyl, tert-butyl, n-pentyl, isopentyl, neopentyl, n-hexyl, 2-methylpentyl, 3-methylpentyl, 2,3-dimethylbutyl, 2,2-dimethylbutyl, 2-ethylbutyl; preferably methyl, ethyl, isopropyl, optionally substituted by 1, 2 or 3 halogens (preferably fluorine), $C_{1-6}$ alkyl (preferably methyl, ethyl or isopropyl)), $C_{1-6}$ alkoxy (preferably methoxy or ethoxy), $C_{1-6}$ alkylthio (preferably methylthio or ethylthio) or amino; most preferably methyl, ethyl, isopropyl, trifluoromethyl or cyclopropyl.

In one embodiment of the compound of formula II, $R^2$ is $C_{3-6}$ cycloalkyl or $C_{3-6}$ heterocyclyl, such as but not limited to cyclopropyl, cyclobutyl, cyclopentyl or cyclohexyl, or tetrahydrofuran, tetrahydrothiophene, azetidine, acridine, tetrahydropyrrole, thiazolidine, oxazolidine, piperidine, piperazine, morpholine, thiomorpholine, thiazine, imidazolidine, etc.; preferably cyclopropyl; any of them is optionally substituted by 1, 2 or 3 halogens (preferably fluorine), hydroxyl, mercapto, $C_{1-6}$alkyl (preferably methyl, ethyl or isopropyl), $C_{1-6}$ alkoxy (preferably methoxy or ethoxy), $C_{1-6}$alkylthio (preferably methylthio or ethylthio) or amino.

In one embodiment of the compound of formula II, $R^3$ and $R^4$ are each independently selected from H or halogen, preferably F, Cl, Br, or I; more preferably F.

In one embodiment of the compound of formula II, $R^{10}$ is hydrogen, halogen, cyano, nitro; —NR$^aR^b$, —OR$^b$, —SR$^b$, C(O)$R^b$, CO$_2R^b$, $C_{1-6}$ alkyl, $C_{3-6}$ cycloalkyl, $C_{3-6}$ heterocyclyl, as defined above for $R^2$; $C_{2-6}$ alkenyl, $C_{2-6}$ alkynyl, 6-10 membered aryl, 5-10 membered heteroaryl; $C_{2-6}$ alkenyl or $C_{2-6}$ alkynyl substituted by one or more hydroxy, halogen, $C_{1-6}$ alkyl, $C_{1-6}$ alkoxy, $C_{1-6}$ alkylthio, or amino; 6-10 membered aryl or 5-10 membered heteroaryl substituted by one or more hydroxy, halogen, $C_{1-6}$ alkyl, Cia alkoxy, $C_{1-6}$ alkylthio, or amino.

In this embodiment, $R^{10}$ is preferably a 5-6 membered heteroaryl group, including but not limited to pyrazole, pyridine, pyrimidine, pyridazine, pyrazine, pyrrole, imidazole, oxazole, isoxazole, triazolyl, tetrazole, oxadiazole, thiazole, isothiazole, thiadiazole, furan, thiophene, and saturated and partially unsaturated forms of these heteroaryl groups, such as piperidine, piperazine, pyrrolidine, imidazolidine, oxazolidine, thiazolidine, tetrahydrofran, etc.; morpholine, -amino; $C_{1-6}$ alkyl or $C_{3-6}$ cycloalkyl, including but not limited to methyl, ethyl, n-propyl, isopropyl, cyclopropyl, n-butyl, isobutyl, sec-butyl, tert-butyl, cyclobutyl, n-pentyl, isopentyl, neopentyl, cyclopentyl, n-hexyl, (2- or 3-ethyl)butyl, (2,3-dimethyl)butyl, (2-propyl)propyl, cyclohexyl; $C_{2-6}$ alkenyl or $C_{2-6}$ alkynyl, including but not limited to vinyl, 2-propenyl, 1, 2 or 3-butenyl, ethynyl, 2-propynyl, 1, 2 or 3-butynyl; more preferably pyrazole, pyridine, —NH$_2$, morpholine; $R^{10}$ is most preferably 1H-pyrazol-4-yl.

One embodiment of the compound of formula II in the first aspect of the present disclosure is a compound of formula II-a, isomers thereof, or pharmaceutically acceptable salts or solvates thereof,

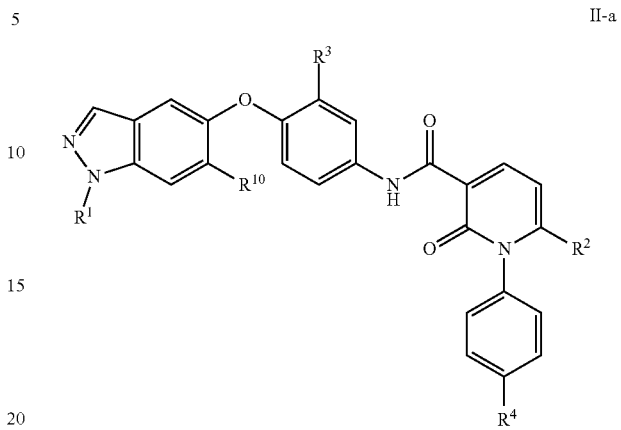

II-a wherein
$R^1$ is $C_{1-6}$ alkyl;
$R^2$ is halogen, cyano, $C_{1-6}$ alkyl optionally substituted by one or more halogens or $C_{3-6}$ cycloalkyl optionally substituted by one or more halogens; or $R^2$ is —NR$^aR^b$, —SR$^b$ or —OR$^b$;
$R^3$ and R are each independently selected from H or halogen;
$R^{10}$ is —NR$^aR^b$, a $C_{3-6}$ heterocyclic group optionally substituted by one or more halogens, or a 5-10 membered heteroaryl optionally substituted by one or more halogens;
$R^a$ and $R^b$ are each independently H, $C_{1-6}$ alkyl optionally substituted by one or more halogens or $C_{3-6}$ cycloalkyl optionally substituted by one or more halogens, or $R^a$ and $R^b$ together with N they are attached to form a 3-6 membered ring optionally substituted with one or more halogens; provided that $R^1$ and $R^2$ are not methyl at the same time.

In a preferred embodiment of the compound of formula II-a, $R^1$ is $C_{1-6}$ alkyl, preferably methyl; $R^2$ is $C_{1-6}$ alkyl optionally substituted by one or more halogens, preferably fluorine, or $C_{3-6}$ cycloalkyl optionally substituted by one or more halogens, preferably fluorine, or —OR$^b$; $R^3$ and R are each independently selected from halogen; $R^{10}$ is a 5-6 membered heteroaryl group, preferably pyridyl or pyrazolyl; $R^b$ is selected from $C_{1-6}$ alkyl optionally substituted by one or more halogens, preferably F or $C_{3-6}$ cycloalkyl optionally substituted by one or more halogens, preferably F.

In another preferred embodiment of the compound of formula II-a, $R^1$ is $C_{1-6}$ alkyl, preferably methyl; $R^2$ is —OR$^b$, wherein $R^b$ is selected from $C_{1-6}$ alkyl optionally substituted by one or more halogens, preferably F, or $C_{3-6}$ cycloalkyl optionally substituted by one or more halogens, preferably fluorine, $R^2$ is preferably methoxy, ethoxy, propoxy, cyclopropoxy, isopropoxy, trifluoroethoxy, trifluoromethoxy, difluoromethoxy; $R^3$ and $R^4$ are each independently selected from halogen, preferably fluorine; $R^{10}$ is a 5-6 membered heteroaryl group, preferably pyridyl or pyrazolyl.

In another preferred embodiment of the compound of formula II-a, $R^1$ is $C_{1-6}$ alkyl, preferably methyl; $R^2$ is —OR$^b$, wherein $R^b$ is selected from $C_{1-6}$ alkyl optionally substituted by one or more halogens, preferably F, or $C_{3-6}$ cycloalkyl optionally substituted by one or more halogens, preferably fluorine, $R^2$ is preferably methoxy, ethoxy, propoxy, cyclopropoxy, isopropoxy, trifluoroethoxy, trifluoromethoxy, difluoromethoxy; $R^3$ and $R^4$ are each independently selected from halogen, preferably fluorine; $R^{10}$ is —$NR^aR^b$ or $C_{3-6}$ heterocyclyl, wherein $R^a$ or $R^b$ are each independently selected from H, $C_{1-6}$ alkyl optionally substituted by one or more halogens, preferably fluorine, or $R^a$ and $R^b$ together with the N to which they are attached form a 3-6 membered ring, $R^{10}$ is preferably —$NH_2$ or morpholinyl.

One embodiment of the compound of formula II in the first aspect of the present disclosure is a compound of formula II-b, isomers thereof, or pharmaceutically acceptable salts or solvates thereof, II-b

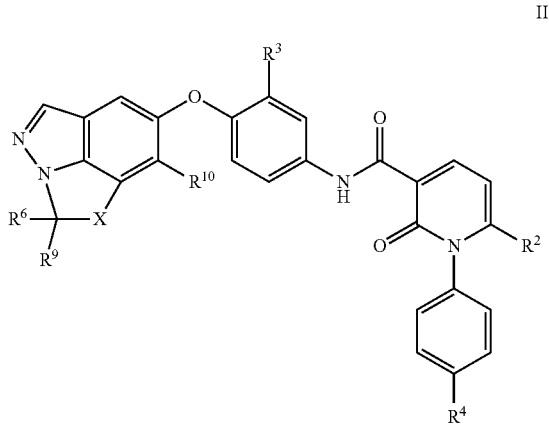

where
- X is —$CR^7R^8$—, =$CR^7$—, —$CR^7R^8$—$CR^7R^8$— or —$CR^7$=$CR^8$—;
- $R^6$ and $R^9$ are each independently H, halogen, —OH, $C_{1-6}$ alkyl or $C_{3-6}$ cycloalkyl;
- $R^7$ and $R^8$ are each independently H, halogen, —OH, $C_{1-6}$ alkyl optionally substituted with one or more halogens or $C_{3-6}$ cycloalkyl optionally substituted with one or more halogens, or $R^7$ and $R^8$ together with the C to which they are attached form a $C_{3-6}$ cycloalkyl group;
- $R^2$ is halogen, cyano, $C_{1-6}$ alkyl optionally substituted by one or more halogens, or $C_{3-6}$ cycloalkyl optionally substituted by one or more halogens; or $R^2$ is —$NR^aR^b$, —$SR^b$ or —$OR^b$;
- $R^3$ and $R^4$ are each independently selected from H or halogen;
- $R^{10}$ is —$NR^aR^b$, a $C_{3-6}$ heterocyclic group optionally substituted by one or more halogens, or a 5-10 membered heteroaryl optionally substituted by one or more halogens;
- $R^a$ and $R^b$ are each independently H, $C_{1-6}$ alkyl optionally substituted by one or more halogens, or $C_{3-6}$ cycloalkyl optionally substituted by one or more halogens, or $R^a$ and $R^b$ together with the N to which they are attached form a 3-6 membered ring optionally substituted with one or more halogens.

In a preferred embodiment of the compound of formula II-b, X is —$CR^7R^8$— or —$CR^7R^8$—$CR^7R^8$—;
$R^2$ is $C_{1-6}$ alkyl optionally substituted by one or more halogens, preferably fluorine, or $C_{3-6}$ cycloalkyl optionally substituted by one or more halogens, preferably fluorine, or —$OR^b$; $R^3$ and $R^4$ are each independently selected from halogen; $R^{10}$ is a 5-6 membered heteroaryl group, preferably pyridyl or pyrazolyl; $R^b$ is selected from $C_{1-6}$ alkyl optionally substituted by one or more halogens, preferably F, or $C_{3-6}$ cycloalkyl optionally substituted by one or more halogens, preferably F.

In another preferred embodiment of the compound of formula II-b, X is —$CR^7R^8$— or —$CR^7R^8$—$CR^7R^8$—; $R^2$ is —$OR^b$, wherein $R^b$ is selected from $C_{1-6}$ alkyl optionally substituted by one or more halogens, preferably fluorine or $C_{3-6}$ cycloalkyl optionally substituted by one or more halogens, preferably fluorine, $R^2$ is preferably methoxy, ethoxy, propoxy, cyclopropoxy, isopropoxy, trifluoroethoxy, trifluoromethoxy, difluoromethoxy; $R^3$ and $R^4$ are each independently selected from halogen, preferably fluorine; $R^{10}$ is a 5-6 membered heteroaryl group, preferably pyridyl or pyrazolyl.

In another preferred embodiment of the compound of formula II-b, X is —$CR^7R^8$— or —$CR^7R^8$—$CR^7R^8$—; $R^2$ is —$OR^b$, wherein $R^b$ is selected from $C_{1-6}$ alkyl optionally substituted by one or more halogens, preferably F, or $C_{3-6}$ cycloalkyl optionally substituted by one or more halogens, preferably fluorine, $R^2$ is preferably methoxy, ethoxy, propoxy, cyclopropoxy, isopropoxy, trifluoroethoxy, trifluoromethoxy, difluoromethoxy; $R^3$ and $R^4$ are each independently selected from halogen, preferably fluorine; $R^{10}$ is —$NR^aR^b$ or $C_{3-6}$ heterocyclyl, wherein $R^a$ and $R^b$ are each independently selected from H, $C_{1-6}$ alkyl optionally substituted by one or more halogens, preferably fluorine, or $R^a$ and $R^b$ together with the N to which they are attached form a 3-6 membered ring optionally substituted by one or more halogens, preferably fluorine, $R^{10}$ is preferably —$NH_2$ or morpholinyl.

In a preferred embodiment of a compound of formula II-b, X is =$CR^7$— or —$CR^7$=$CR^8$—; $R^2$ is a $C_{1-6}$ alkyl group optionally substituted by one or more halogens, preferably fluorine, or $C_{3-6}$ cycloalkyl optionally substituted by one or more halogens, preferably with fluorine, or —$OR^b$; $R^3$ and $R^4$ are each independently selected from halogen; $R^{10}$ is a 5-6 membered heteroaryl group, preferably pyridyl or pyrazolyl; $R^b$ is selected from $C_{1-6}$ alkyl optionally substituted by one or more halogens, preferably F, or $C_{3-6}$ cycloalkyl optionally substituted by one or more halogens, preferably fluorine.

In another preferred embodiment of the compound of formula II-b, X is =$CR^7$— or —$CR^7$=$CR^8$—; $R^2$ is —$OR^b$, wherein $R^b$ is selected from $C_{1-6}$ alkyl optionally substituted by one or more halogens, preferably F, or $C_{3-6}$ cycloalkyl optionally substituted by one or more halogens, preferably fluorine, $R^2$ is preferably methoxy, ethoxy, propoxy, cyclopropoxy, isopropoxy, trifluoroethoxy, trifluoromethoxy, difluoromethoxy; $R^3$ and $R^4$ are each independently selected from halogen, preferably fluorine; $R^{10}$ is a 5-6 membered heteroaryl group, preferably pyridyl or pyrazolyl.

In another preferred embodiment of the compound of formula II-b, X is X is =$CR^7$— or —$CR^7$=$CR^8$—; $R^2$ is —$OR^b$, wherein $R^b$ is selected from $C_{1-6}$ alkyl optionally substituted by one or more halogens, preferably F, or $C_{3-6}$ cycloalkyl optionally substituted by one or more halogens, preferably fluorine, $R^2$ is preferably methoxy, ethoxy, propoxy, cyclopropoxy, isopropoxy, trifluoroethoxy, trifluoromethoxy, difluoromethoxy; $R^3$ and $R^4$ are each independently selected from halogen; $R^{10}$ is —$NR^aR^b$ or $C_{3-6}$ heterocyclyl, wherein $R^a$ and $R^b$ are each independently selected from H, $C_{1-6}$ alkyl optionally substituted by one or more halogens, preferably fluorine, or $R^a$ and $R^b$ together with the N to which they are attached form a 3-6 membered ring optionally substituted by one or more halogens, preferably fluorine, $R^{10}$ is preferably —$NH_2$ or morpholino.

In each preferred embodiment of the compound of formula II-b as above, $R^6$ and $R^9$ are each independently H, halogen, $C_{1-6}$ alkyl optionally substituted by one or more halogens, preferably fluorine, or $C_{3-6}$ cycloalkyl optionally substituted by one or more halogens, preferably fluorine, and $R^7$ and $R^8$ are each independently H, halogen, $C_{1-6}$ alkyl optionally substituted by one or more halogens, preferably fluorine, or $C_{3-6}$ cycloalkyl optionally substituted by one or more halogens, preferably fluorine, or $R^7$ and $R^8$ together with the C atom to which they are attached form a $C_{3-6}$ cycloalkyl.

The compound of formula II of the present disclosure encompasses the above embodiments independently, in combination, or any combinations or sub-combinations, as well as embodiments resulting from any combination of any preferred, more preferred, or most preferred definitions as above.

The first aspect of the present disclosure also provides a compound of formula III, isomers thereof, or pharmaceutically acceptable salts or solvates thereof,

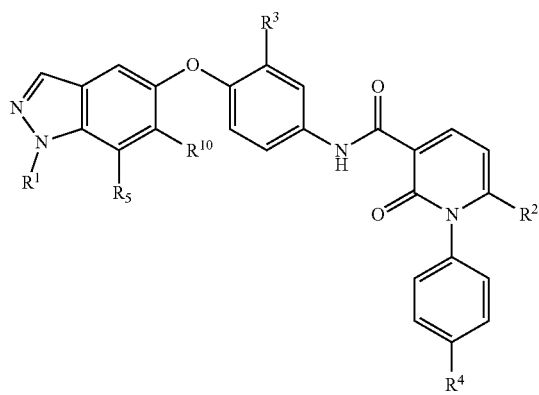

III wherein
$R^1$ is $C_{1-6}$ alkyl or $C_{3-6}$ cycloalkyl, optionally substituted by one or more halogens, —$OR^a$, —$SR^a$, $C_{1-6}$ alkyl or amino;

$R^5$ is H, halogen, —$OR^a$, —$SR^a$, or $C_{1-6}$ alkyl optionally substituted by one or more halogens, —$OR^a$, —$SR^a$, $C_{1-6}$ alkyl or amino; or $R^1$ and $R^5$ together with the atoms to which they are attached form a cyclic structure with the following general formula:

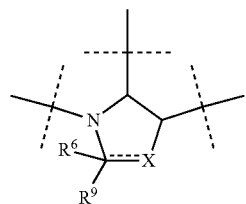

(a)

where X is —$CR^7R^8$—, =$CR^7$—, —$CR^7R^8$—$CR^7R^8$— or —$CR^7$=$CR^8$—;

$R^6$, $R^7$, $R^8$ and $R^9$ are each independently H, halogen, —$OR^a$, —$SR^a$, optionally substituted $C_{1-6}$ alkyl or optionally substituted $C_{3-6}$ cycloalkyl, wherein the substituent is selected from one or more halogens, —$OR^a$, —$SR^a$, $C^{1-6}$ alkyl or amino; or $R^6$ and $R^9$ or $R^7$ and $R^8$ attached to the same carbon atom together form =O or =S, or together with the carbon atom to which they are attached form a $C_{3-6}$ cycloalkyl group;

$R^2$ is —$NR^aR^b$ or —$OR^b$;

$R^3$ and $R^4$ are each independently selected from H, halogen, nitro, cyano, acyl or carboxy;

$R^{10}$ is hydrogen, halogen, cyano, nitro, —$NR^aR^b$, —$OR^b$, —$SR^b$, $C(O)R^b$, $CO_2R^b$; $C_{1-6}$ alkyl, $C_{2-6}$ alkenyl, $C_{2-6}$ alkynyl, $C_{3-6}$ Cycloalkyl, $C_{3-6}$ heterocycloalkyl, 6-10 membered aryl, 5-10 membered heteroaryl; $C_{1-6}$ alkyl or $C_{2-6}$ alkenyl or $C_{2-6}$ alkynyl, substituted by one or more halogens, $C_{1-6}$ alkyl, $C_{1-6}$ alkoxy, $C_{1-6}$ alkylthio or amino; $C_{3-6}$ cycloalkyl or $C_{3-6}$ heterocycloalkyl, substituted by one or more hydroxy, halogen, $C_{1-6}$ alkyl, $C_{1-6}$ alkoxy, $C_{1-6}$ alkylthio or amino; 6-10 membered aryl or 5-10 membered heteroaryl, substituted by one or more hydroxy, halogen, $C_{1-6}$ alkyl, $C_{1-6}$ alkoxy, $C_{1-6}$ alkylthio or amino;

$R^a$ and $R^b$ are each independently H, $C_{1-6}$ alkyl optionally substituted by one or more halogens, CN, or nitro, or $C_{3-6}$ cycloalkyl optionally substituted by one or more halogens, CN, or nitro, or $R^a$ and $R^b$ together with the N to which they are attached form a 3-6 membered ring optionally substituted with one or more halogens, CN, or nitro.

In one embodiment of the compound of formula III, $R^1$ is $C_{1-6}$ alkyl, such as but not limited to methyl, ethyl, propyl, isopropyl, butyl, sec-butyl, isobutyl, tert-butyl, n-pentyl, isopentyl, neopentyl, n-hexyl, 2-methylpentyl, 3-methylpentyl, 2,3-dimethylbutyl, 2,2-dimethylbutyl, 2-ethylbutyl; preferably methyl, ethyl or isopropyl, optionally substituted by 1, 2 or 3 halogens (preferably fluorine), hydroxyl, $C_{1-6}$ alkoxy (preferably methoxy or ethoxy), mercapto, $C_{1-6}$ alkylthio (preferably methylthio or ethylthio) or amino, most preferably methyl.

In one embodiment of the compound of formula III, $R^1$ is $C_{3-6}$ cycloalkyl, preferably cyclopropyl, cyclobutyl, cyclopentyl or cyclohexyl, optionally substituted by 1, 2 or 3 halogens (preferably fluoro), hydroxy, $C_{1-6}$ alkyl (preferably methyl, ethyl or isopropyl), $C_{1-6}$ alkoxy (preferably methoxy or ethoxy), mercapto, $C_{1-6}$ alkylthio (preferably methylthio or ethylthio) or amino, such as but not limited to 2-fluorocyclopropyl, 2- and/or 3-fluorocyclobutyl, 2- and/or 3-fluorocyclopentyl, 2-, 3- and/or 4-fluorocyclohexyl, or these groups substituted by hydroxyl, mercapto, methyl, ethyl, isopropyl, methoxy, ethoxy, methylthio, ethylthio or amino at the corresponding positions.

In one embodiment of the compound of formula III, $R^5$ is H, halogen, hydroxyl, $C_{1-6}$ alkoxy, mercapto, $C_{1-6}$ alkylthio, or $C_{1-6}$ alkyl, such as but not limited to H, fluorine, chlorine, bromine, iodine, hydroxyl, methoxy, ethoxy, propoxy, isopropoxy, methyl, ethyl, propyl, isopropyl, mercapto, methylthio, ethylthio, propylthio, isopropylthio, etc., optionally substituted by 1, 2 or 3 halogens (preferably F), $C_{1-6}$ alkoxy (preferably methoxy or ethoxy), $C_{1-6}$ alkylthio (preferably methylthio or ethylthio), $C_{1-6}$ alkyl (preferably methyl, ethyl) or amino; most preferably $R^5$ is H.

In one embodiment of the compound of formula III, $R^1$ and $R^5$ together with the atoms to which they are attached form a structure of formula (a), wherein $R^6$ and $R^9$ are each independently H, halogen, hydroxyl, mercapto, $C_{1-6}$ alkyl, $C_{1-6}$ alkoxy, $C_{1-6}$ alkylthio or $C_{3-6}$ cycloalkyl, and X is —$CR^7R^8$— or —$CR^7R^8$—$CR^7R^8$—, wherein $R^7$ and $R^8$ are each independently H, halogen, hydroxyl, mercapto, $C_{1-6}$ alkyl, $C_{1-6}$ alkoxy, $C_{1-6}$ alkylthio or $C_{3-6}$ cycloalkyl. Preferably, $R^6$ and $R^9$ are each independently H, halogen, $C_{1-6}$alkyl, or $C_{3-6}$ cycloalkyl, and X is —$CR^7R^8$— or —$CR^7R^8$—$CR^7R^8$—, wherein $R^7$ and $R^8$ are each independently H, halogen, $C_{1-6}$ alkyl or $C_{3-6}$ cycloalkyl.

In this embodiment, it is also preferred that one of $R^6$ and $R^9$ and/or one of $R^7$ and $R^8$ is a $C_{3-6}$ cycloalkyl, such as cyclopropyl, cyclobutyl, cyclopentyl, or cyclohexyl.

In this embodiment, it is also preferred that one or both of $R^6$ and $R^1$ and/or one or both of $R^7$ and $R^8$ are halogen, preferably fluorine.

In this embodiment, it is most preferred that $R^6$ and $R^9$ are both H, and X is —$CR^7R^8$—, wherein $R^7$ and $R^8$ are both H; it is also most preferred that $R^6$ and $R^9$ are both H, and X is —CHF— or —$CF_2$—; it is also most preferred that $R^6$ and $R^9$ are both H, and X is —$CR^7R^8$—$CR^7R^8$—, wherein $R^7$ and $R^1$ are both H; it is also most preferred that $R^6$ and $R^9$ are both H, and X is —$CH_2$—$CF_2$—, —$CH_2$—CHF—, —CHF—CHF— or —$CF_2$—$CF_2$—.

In one embodiment of the compound of formula III, $R^1$ and $R^5$ together with the atoms to which they are attached form a structure of formula (a), wherein $R^6$ and $R^9$ are each independently H, halogen, hydroxyl, mercapto, $C_{1-6}$ alkyl, $C_{1-6}$ alkoxy, $C_{1-6}$ alkylthio or $C_{3-6}$ cycloalkyl, and X is =$CR^7$— or —$CR^7$=$CR^8$—, wherein $R^7$ and $R^8$ are each independently H, halogen, $C_{1-6}$ alkyl or $C_{3-6}$ cycloalkyl. More preferably, $R^6$ and $R^9$ are each independently H, halogen (preferably fluorine), $C_{1-6}$ alkyl or $C_{3-6}$ cycloalkyl, and X is =$CR^7$— or —$CR^7$=$CR^8$—, wherein $R^7$ and $R^8$ are each independently H, halogen (preferably fluorine), $C_{1-6}$ alkyl or $C_{3-6}$cycloalkyl.

In this embodiment, it is also preferred that one of $R^6$ and $R^9$ and/or one of $R^7$ and $R^8$ is a $C_{3-6}$ cycloalkyl, such as cyclopropyl, cyclobutyl, cyclopentyl, or cyclohexyl.

In one embodiment of the compound of formula III, $R^1$ and $R^5$ together with the atoms to which they are attached form a structure of formula (a), wherein X is —$CR^7R^8$— or —$CR^7R^8$—$CR^7R^8$—, wherein $R^6$ and $R^9$ or $R^7$ and $R^8$ attached to the same carbon atom together form =O or =S, or together with the carbon atom to which they are attached form cyclopropyl, cyclobutyl, cyclopentyl, or cyclohexyl; preferably $R^7$ and $R^8$ attached to the same carbon atom together form cyclopropyl, cyclobutyl, cyclopentyl, or cyclohexyl.

In one embodiment of the compound of formula III, $R^2$ is —$NR^aR^b$, wherein $R^a$ and $R^b$ are each independently selected from H, $C_{1-6}$ alkyl optionally substituted with one or more halogens (preferably fluorine) or $C_{3-6}$ cycloalkyl optionally substituted by one or more halogens (preferably fluorine), or $R^a$ and $R^b$ together with the N to which they are attached form a 3-6 membered ring optionally substituted by one or more halogens, preferably fluorine, $R^a$ and $R^b$ each independently are selected from H or $C_{1-6}$ alkyl, specific $R^2$ includes but is not limited to —$NH_2$, —NH-Me, —NH-Et, —NH-nPr, —NH-iPr, —NH-cPr, —NH-nBu, —NH-sec-Bu, —NH-iBu, —NH-tBu, —NH-cBu, —NH-pentyl, —NH— isopentyl, —NH-neopentyl, —NH-cyclopentyl, —NH-hexyl, —NH-(2- or 3-ethyl)butyl, —NH-(2,3-dimethyl)butyl, —NH-(2-propyl)propyl, —N(Me)$_2$, —N(Me)(Et), —N(Et)$_2$, —N(Pr)$_2$, and the corresponding groups wherein the alkyl or cycloalkyl groups substituted on the amino group are substituted by one or more halogens such as fluorine, etc., it is more preferable that $R^a$ and $R^b$ are H at the same time.

In one embodiment of the compound of formula III, $R^2$ is —$OR^b$, wherein $R^b$ is selected from H, $C_{1-6}$ alkyl optionally substituted by one or more halogens (preferably fluorine), or $C_{3-6}$ cycloalkyl optionally substituted by one or more halogens (preferably fluorine), preferably $C_{1-6}$ alkyl optionally substituted by halogen (preferably fluorine) or $C_{3-6}$ cycloalkyl optionally substituted by halogen (preferably fluorine), specific $R^2$ includes but is not limited to —OH, —OMe, —OEt, —O-nPr, —O-iPr, —O-cPr, —O-nBu, —O-sec-Bu, —O-iBu, —O-tBu, —O-cBu, —O-pentyl, —O-isopentyl, —O-neopentyl, —O-hexyl, —O-(2- or 3-ethyl)butyl, —O-(2,3-dimethyl)butyl, —O-(2-propyl)propyl, —$OCF_3$, —$OCF_2H$, —$OCH_2CF_3$, —O-cPrF, etc, the preferred $R^2$ is —OH, —OMe, —OEt, —O-nPr, —O-iPr, —O-cPr, —$OCF_3$, —$OCF_2H$, —$OCH_2CF_3$, most preferably $R^2$ is —OMe.

In one embodiment of the compound of formula III, $R^3$ and $R^4$ are each independently selected from H or halogen, preferably F, Cl, Br or I; more preferably F.

In an embodiment of the compound of formula III, $R^{10}$ is hydrogen, halogen, cyano, nitro; —$NR^aR^b$, —$OR^b$, —$SR^b$, C(O)$R^b$, $CO_2R^b$, $C_{1-6}$ alkyl, $C_{3-6}$ cycloalkyl, $C_{3-6}$ heterocyclyl, as specifically defined above in the definition of $R^2$ for the compound of formula II; $C_{2-6}$ alkenyl, $C_{2-6}$ alkynyl, 6-10 membered aryl, 5-10 membered heteroaryl; $C_{2-6}$ alkenyl or $C_{2-6}$ alkynyl, substituted by one or more hydroxy, halogen, $C_{1-6}$ alkyl, $C_{1-6}$ alkoxy, $C_{1-6}$ alkylthio or amino; 6-10 membered aryl or 5-10 membered heteroaryl, substituted by one or more hydroxy, halogen, $C_{1-6}$ alkyl, $C_{1-6}$alkoxy, $C_{1-6}$ alkylthio or amino.

In this embodiment, $R^{10}$ is preferably a 5-6 membered heteroaryl, including but not limited to pyrazole, pyridine, pyrimidine, pyridazine, pyrazine, pyrrole, imidazole, oxazole, isoxazole, triazolyl, tetrazole, oxadiazole, thiazole, isothiazole, thiadiazole, furan, thiophene, and the saturated and partially unsaturated forms of these heteroaryl groups, such as piperidine, piperazine, pyrrolidine, imidazolidine, oxazolidine, thiazolidine, tetrahydrofuran, etc.; morpholine, -amino; $C_{1-6}$ alkyl or $C_{3-6}$ cycloalkyl, including but not limited to methyl, ethyl, n-propyl, isopropyl, cyclopropyl, n-butyl, iso-butyl, sec-butyl, tert-butyl, cyclobutyl, n-pentyl, isopentyl, neopentyl, cyclopentyl, n-hexyl, (2- or 3-ethyl) butyl, (2,3-dimethyl)butyl, (2-propyl)propyl, cyclohexyl; $C_{2-6}$ alkenyl or $C_{2-6}$ alkynyl, including but not limited to vinyl, 2-propenyl, 1, 2 or 3-butenyl, ethynyl, 2-propynyl, 1, 2 or 3-butynyl; more preferably pyrazole, pyridine, —$NH_2$, morpholine; $R^{10}$ is most preferably 1H-pyrazol-4-yl.

One embodiment of the compound of formula III in the first aspect of the present disclosure is a compound of formula III-a, isomers thereof, or pharmaceutically acceptable salts or solvates thereof, III-a

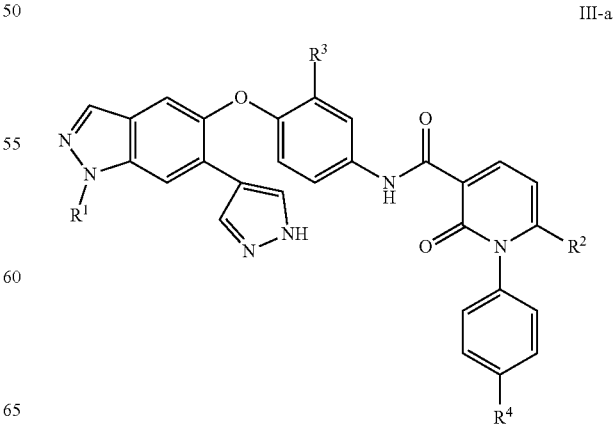

wherein

R$^1$ is C$_{1-6}$ alkyl;

R$^2$ is —NR$^a$R$^b$ or —OR$^b$;

R$^3$ and R$^4$ are each independently selected from H or halogen;

R$^a$ and R$^b$ are each independently selected from H, C$_{1-6}$ alkyl optionally substituted by one or more halogens, or C$_{3-6}$ cycloalkyl optionally substituted by one or more halogens, or R$^a$ and R$^b$ together with the N to which they are attached form a 3-6 membered ring optionally substituted with one or more halogens.

In a preferred embodiment of the compound of formula III-a, R$^1$ is C$_{1-6}$ alkyl, preferably methyl; R$^2$ is —OR$^b$, wherein R$^b$ is selected from C$_{1-6}$ alkyl optionally substituted by one or more halogens, preferably F, or C$_{3-6}$ cycloalkyl optionally substituted by one or more halogens, preferably F, R$^2$ is preferably methoxy, ethoxy, propoxy, cyclopropoxy, isopropoxy, trifluoro-ethoxy, trifluoromethoxy, difluoromethoxy; R$^3$ and R$^4$ are each independently selected from halogen, preferably fluorine.

In another preferred embodiment of the compound of formula III-a, R$^1$ is C$_{1-6}$ alkyl, preferably methyl; R$^2$ is —NR$^a$R$^b$, wherein R$^a$ and R$^b$ are each independently selected from H, C$_{1-6}$ alkyl optionally substituted by one or more halogens, preferably fluorine, or C$_{3-6}$ cycloalkyl optionally substituted by one or more halogen, preferably fluorine, or R$^a$ and R$^b$ together with the N to which they are attached form a 3-6 membered ring optionally substituted by one or more halogens, preferably fluorine; R$^3$ and R$^4$ are each independently selected from halogen, preferably fluorine.

One embodiment of the compound of formula III in the first aspect of the present disclosure is a compound of formula III-b, isomers thereof, or pharmaceutically acceptable salts or solvates thereof,

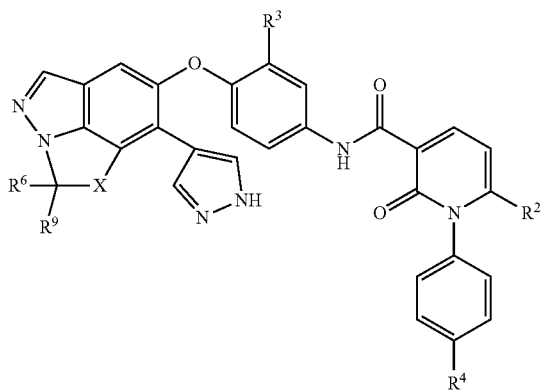

III-b wherein

R$^2$ is —NR$^a$R$^b$ or —OR$^b$;

X is —CR$^7$R$^8$—, =CR$^7$—, —CR$^7$R$^8$—CR$^7$R$^8$—, or —CR$^7$=CR$^8$—;

R$^6$ and R$^9$ are each independently H, halogen, —OH, C$_{1-6}$ alkyl or C$_{3-6}$ cycloalkyl;

R$^7$ and R$^8$ are each independently H, halogen, —OH, C$_{1-6}$ alkyl optionally substituted with one or more halogens, or C$_{3-6}$ cycloalkyl optionally substituted with one or more halogens, or R$^7$ and R$^8$ attached to the same carbon atom together form a C$_{3-6}$ cycloalkyl;

R$^3$ and R$^4$ are each independently selected from H or halogen;

R$^a$ and R$^b$ are each independently H, C$_{1-6}$ alkyl optionally substituted by one or more halogens, or C$_{3-6}$ cycloalkyl optionally substituted by one or more halogens, or R$^a$ and R$^b$ together with the N to which they are attached form a 3-6 membered ring optionally substituted with one or more halogens.

In a preferred embodiment of a compound of formula III-b, X is —CR$^7$R$^8$— or —CR$^7$R$^8$—CR$^7$R—; R$^2$ is —OR$^b$, wherein R$^b$ is selected from C$_{1-6}$ alkyl optionally substituted by one or more halogens, preferably F, or C$_{3-6}$ cycloalkyl optionally substituted by one or more halogens, preferably F, R$^2$ is preferably methoxy, ethoxy, propoxy, cyclopropoxy, isopropoxy, trifluoro-ethoxy, trifluoromethoxy, difluoromethoxy; R$^3$ and R$^4$ are each independently selected from halogen, preferably fluorine.

In another preferred embodiment of the compound of formula III-b, X is —CR$^7$R$^8$— or —CR$^7$R$^8$—CR$^7$R$^8$—; R$^2$ is —NR$^a$R$^b$, wherein R$^a$ and R$^b$ are each independently H, C$_{1-6}$ alkyl optionally substituted by one or more halogens, preferably fluorine, or C$_{3-6}$ cycloalkyl optionally one or more halogens, preferably fluorine, or R$^a$ and R$^b$ together with the N to which they are attached form a 3-6 membered ring optionally substituted by one or more halogens, preferably fluorine; R$^3$ and R$^4$ are each independently selected from halogen, preferably fluorine.

In a preferred embodiment of a compound of formula III-b, X is =CR$^7$— or —CR$^7$=CR$^8$—; R$^2$ is —OR$^b$, wherein R$^b$ is selected from C$_{1-6}$ alkyl optionally substituted by one or more halogens, preferably F, or C$_{3-6}$ cycloalkyl optionally substituted by one or more halogens, preferably F, R$^2$ is preferably methoxy, ethoxy, propoxy, cyclopropoxy, isopropoxy, trifluoro-ethoxy, trifluoromethoxy, difluoromethoxy; R$^3$ and R$^4$ are each independently selected from halogen, preferably fluorine.

In another preferred embodiment of the compound of formula III-b, X is =CR$^7$— or —CR$^7$=CR$^8$—; R$^2$ is —NR$^a$R$^b$, wherein R$^a$ and R$^b$ are each independently H, C$_{1-6}$ alkyl optionally substituted by one or more halogens, preferably fluorine, or C$_{3-6}$ cycloalkyl optionally substituted by one or more halogens, preferably fluorine, or R$^a$ and R$^b$ together with the N to which they are attached form a 3-6 membered ring optionally substituted by one or more halogens, preferably fluorine; R$^3$ and R$^4$ are each independently selected from halogen, preferably fluorine.

In each preferred embodiment of the compound of formula III-b above, R$^6$ and R$^9$ are each independently H, halogen, C$_{1-6}$ alkyl optionally substituted by one or more halogens, preferably fluorine, or C$_{3-6}$ cycloalkyl optionally substituted by one or more halogens, preferably fluorine; and R$^7$ and R$^8$ are each independently H, halogen, C$_{1-6}$ alkyl optionally substituted by one or more halogens, preferably fluorine, or C$_{3-6}$ cycloalkyl optionally substituted by one or more halogens, preferably fluorine, or R$^7$ and R$^8$ attached to the same carbon atom together form a C$_{3-6}$ cycloalkyl group.

The compound of formula III of the present disclosure encompasses the above embodiments individually, in combination, or any combinations, or sub-combinations, and also encompasses these embodiments resulting from any combination of any preferred, more preferred or most preferred definitions as above.

Preferred compounds of formula I are selected from the following list of structures
compound 1
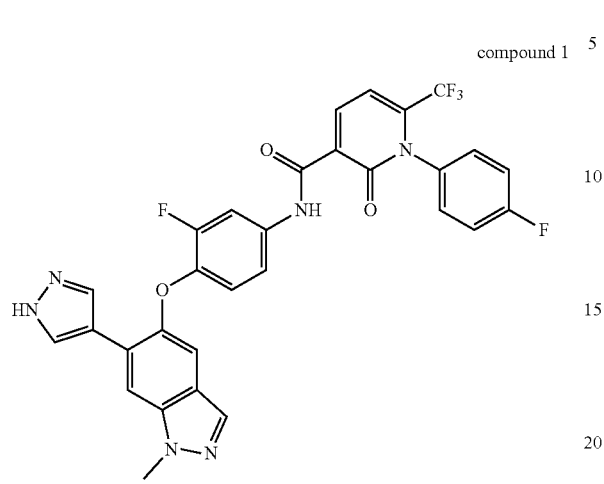
compound 2
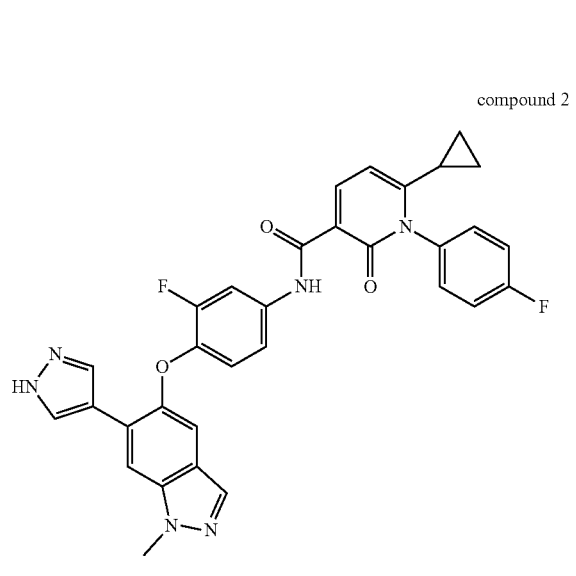
compound 3
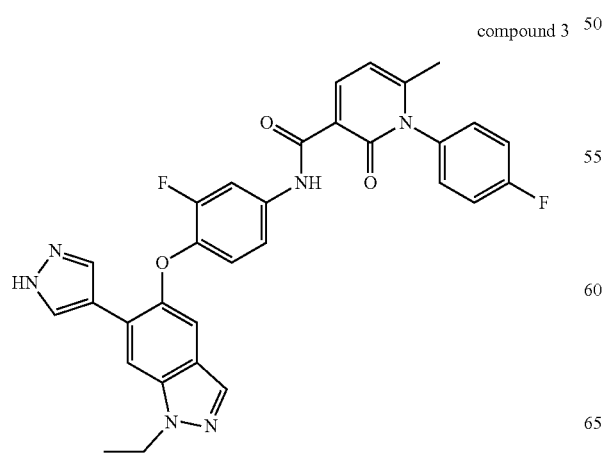
-continued
compound 4
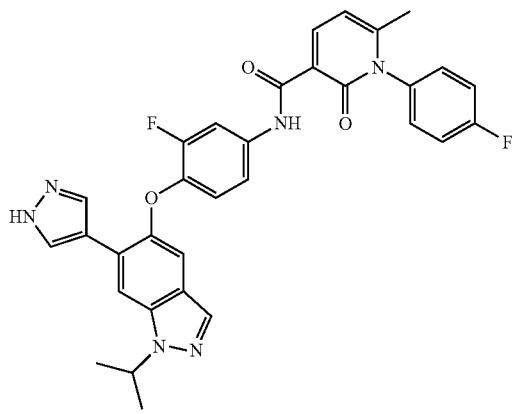
compound 5
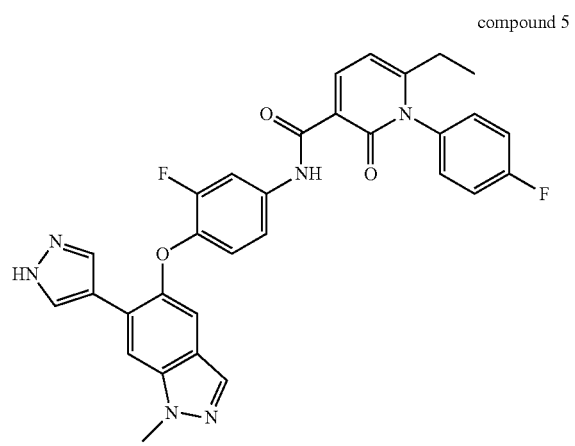
compound 6
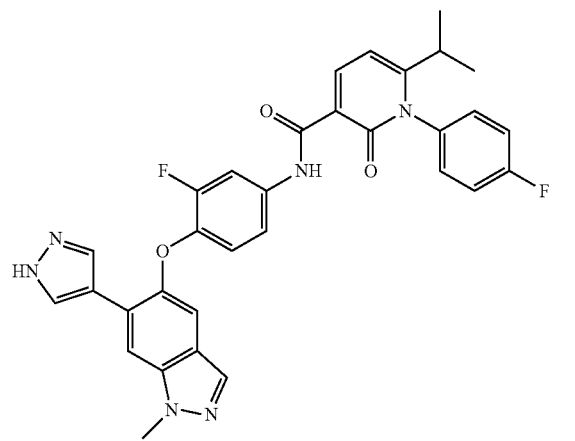

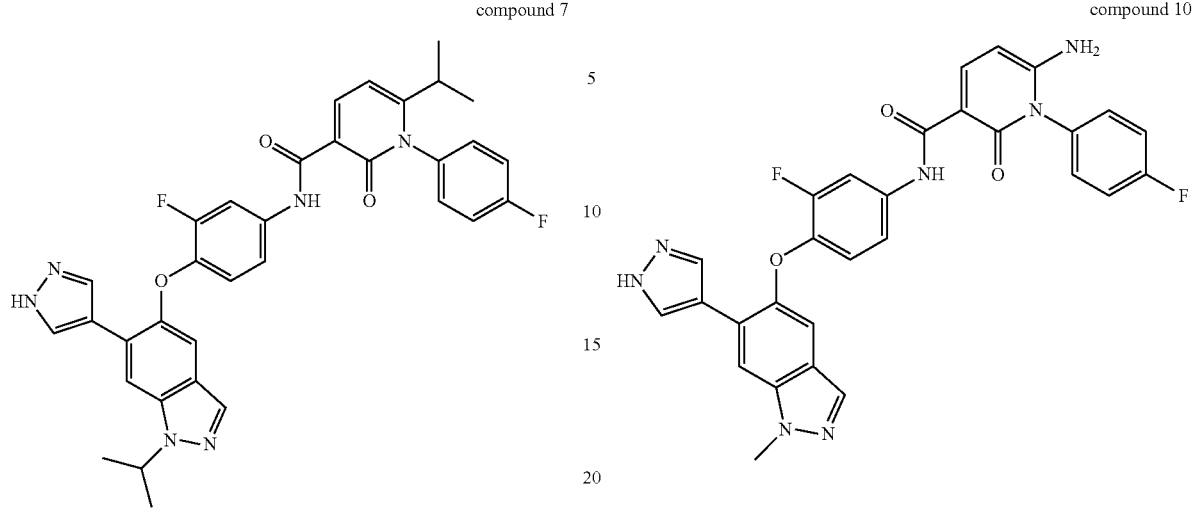
compound 7
compound 10
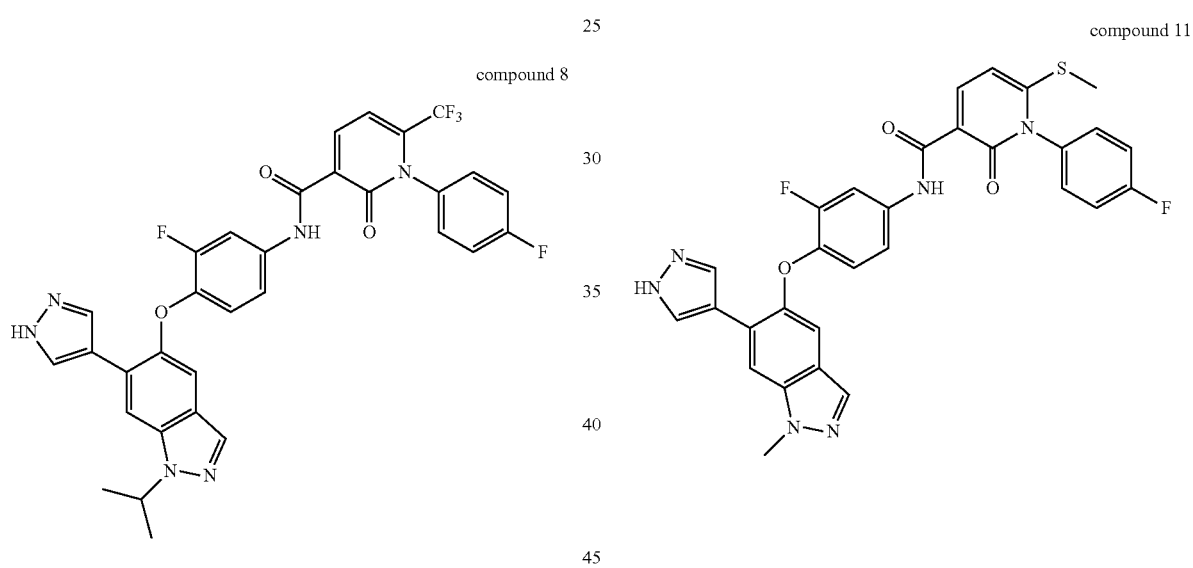
compound 8
compound 11
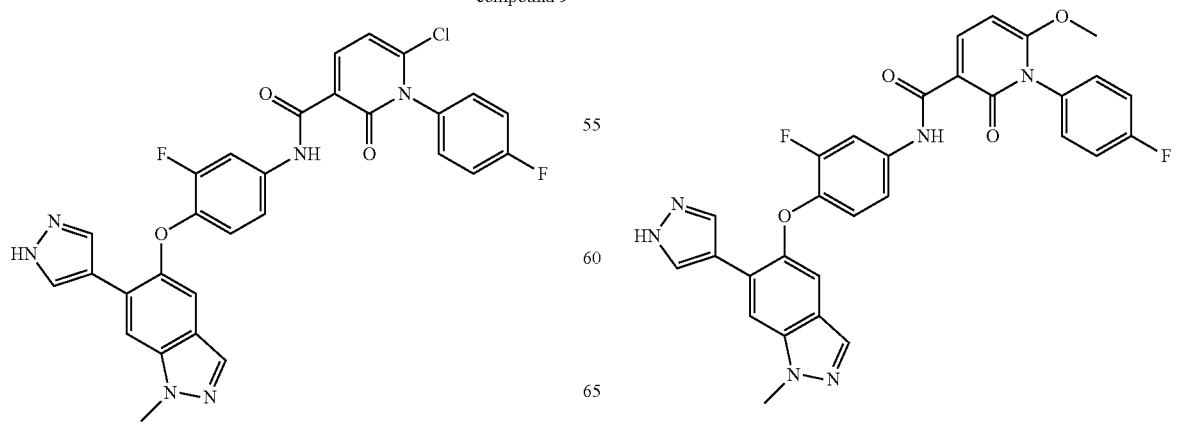
compound 9
compound 12 compound 13
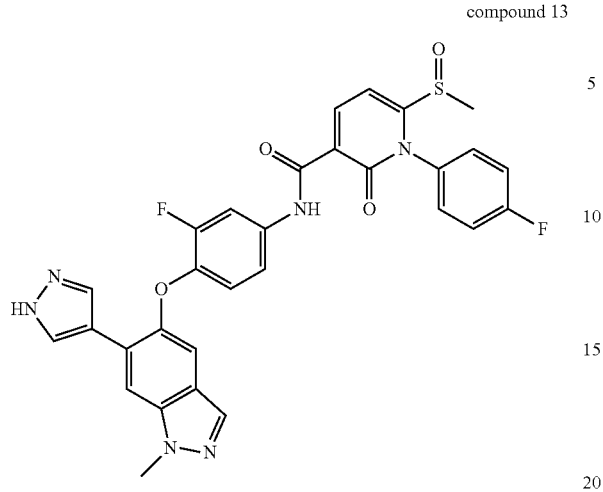
compound 14
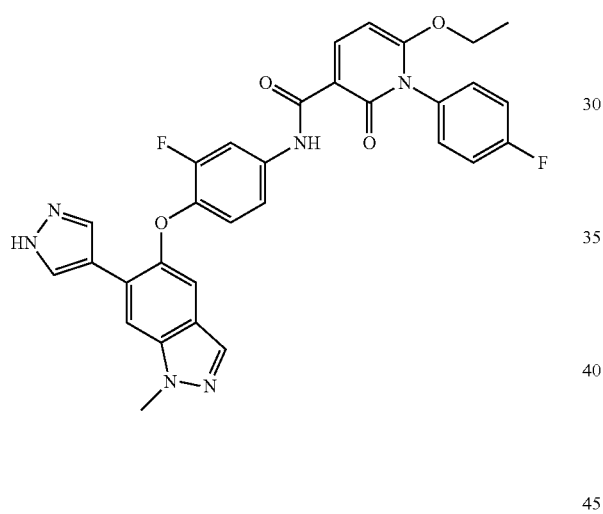
compound 15
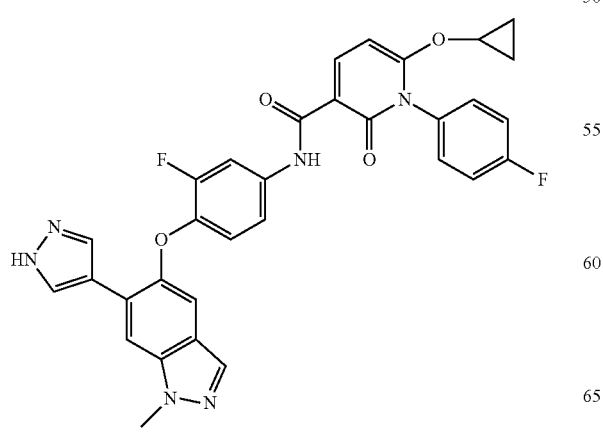
compound 16
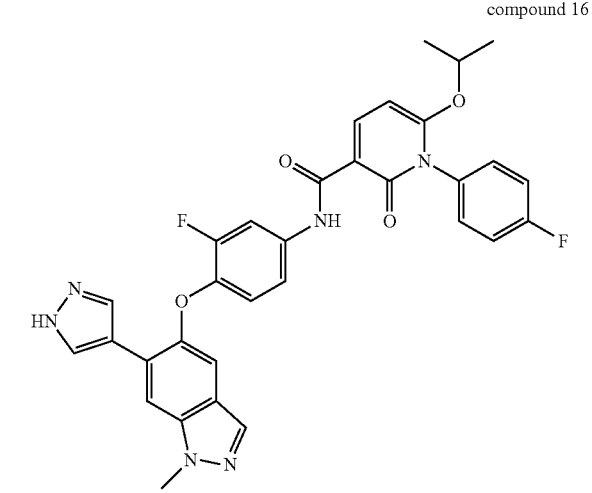
compound 17
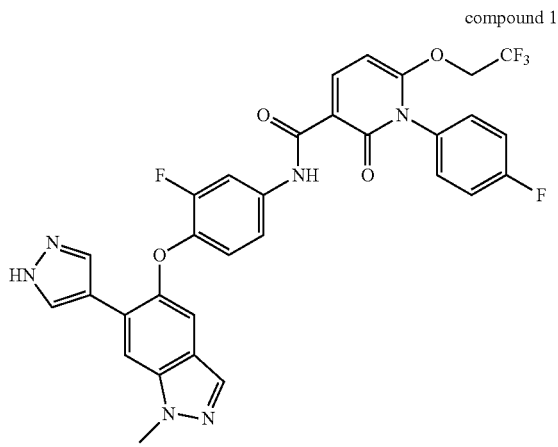
compound 18
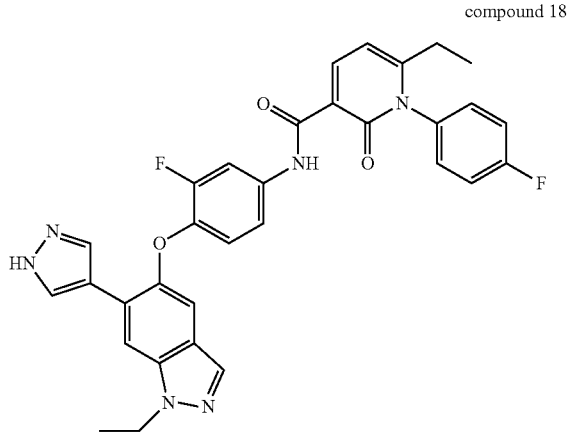

compound 19
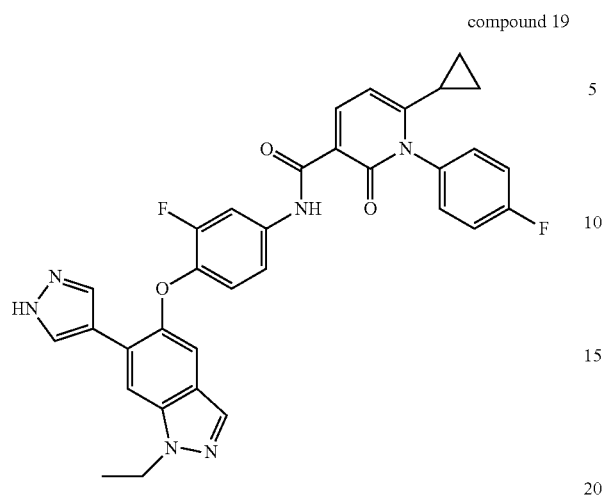
compound 22
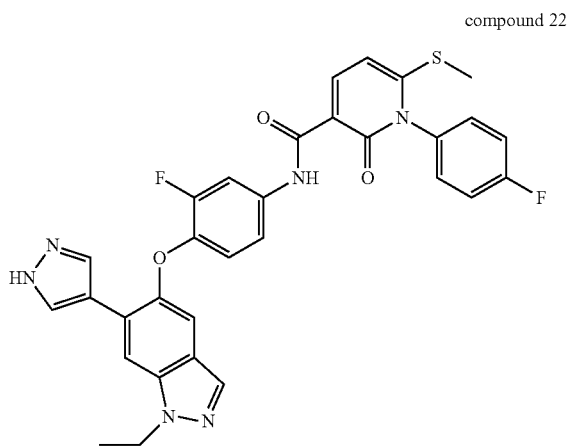
compound 20
compound 23
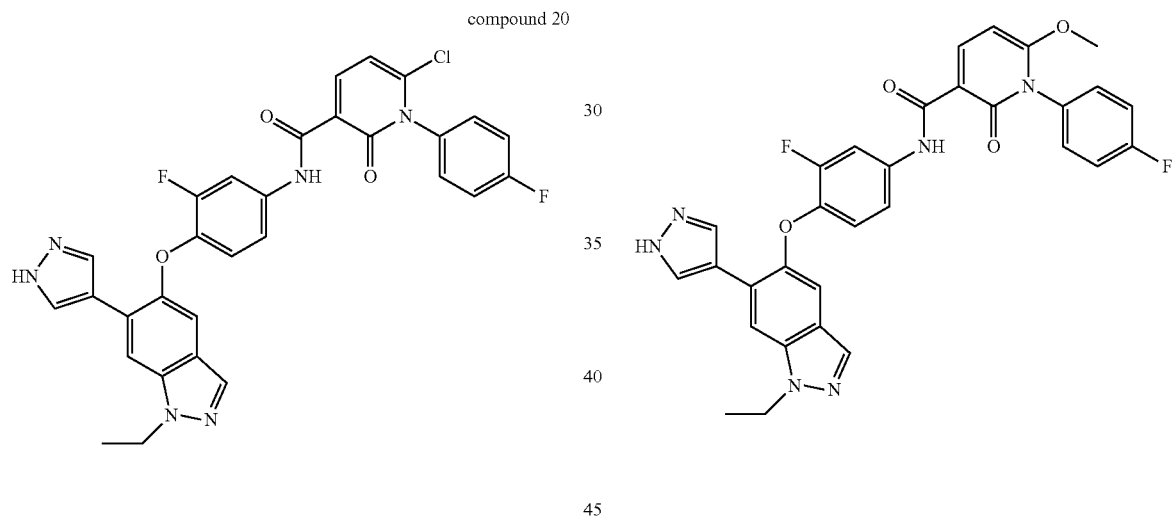
compound 21
compound 24
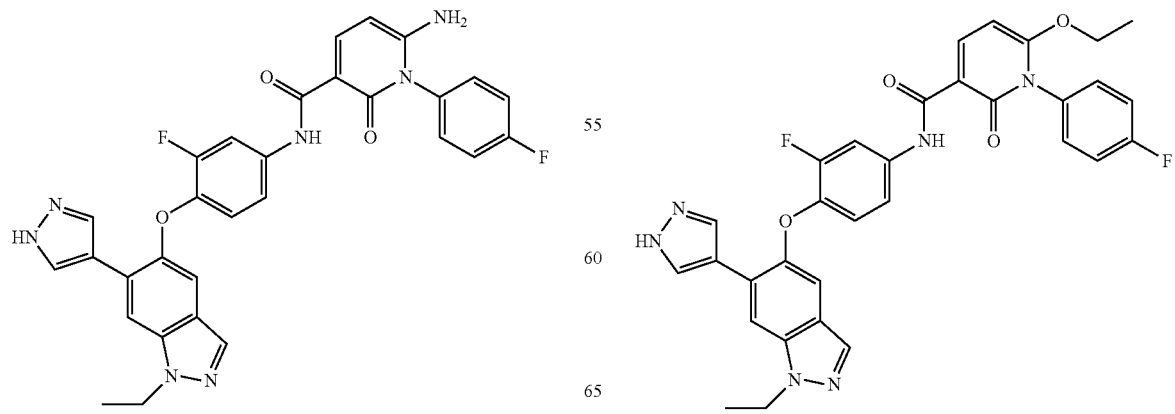

compound 25
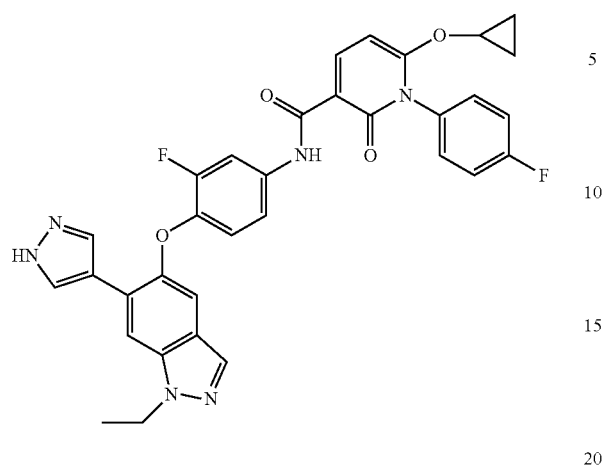
compound 28
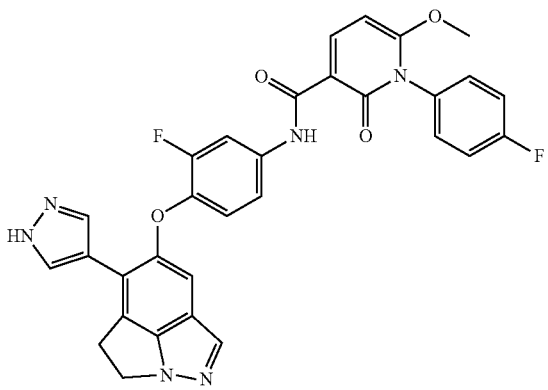
compoud 26
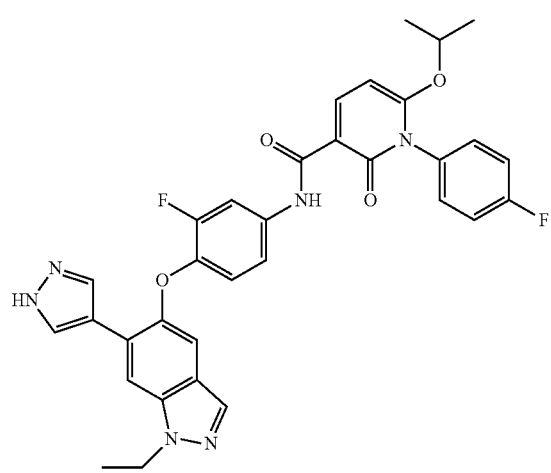
compound 29
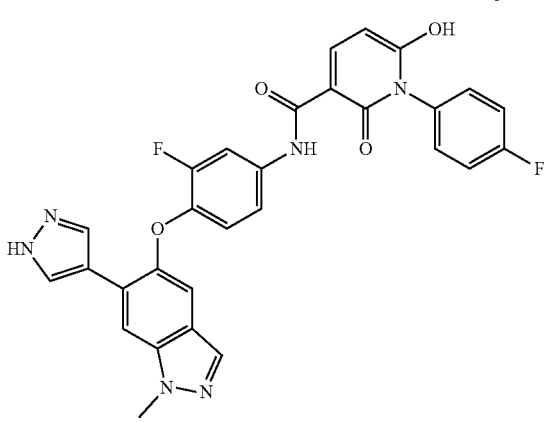
compound 27
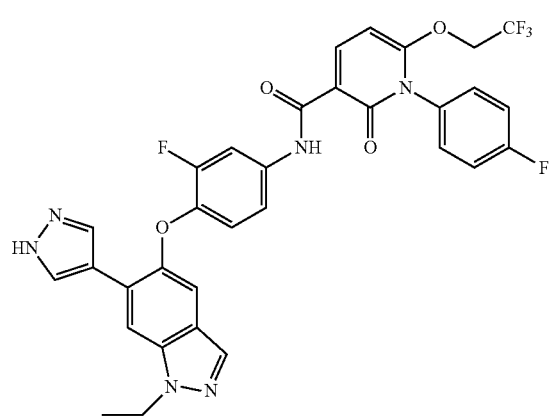
compound 30
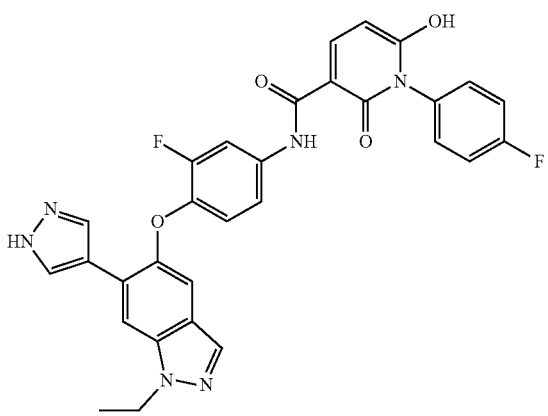

compound 31
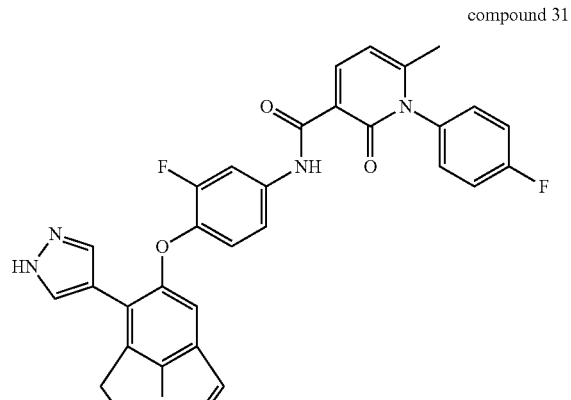
compound 34
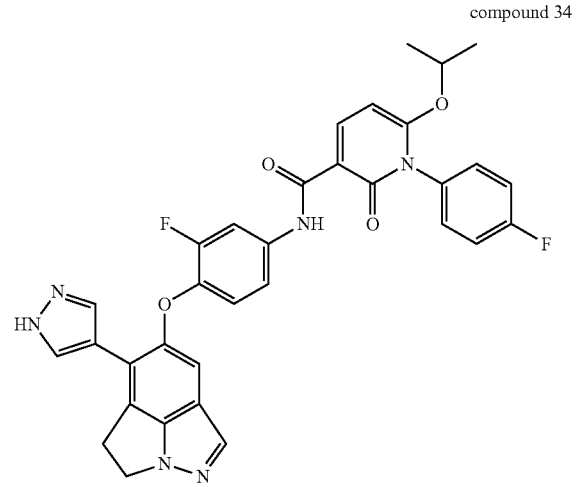
compound 32
compound 35
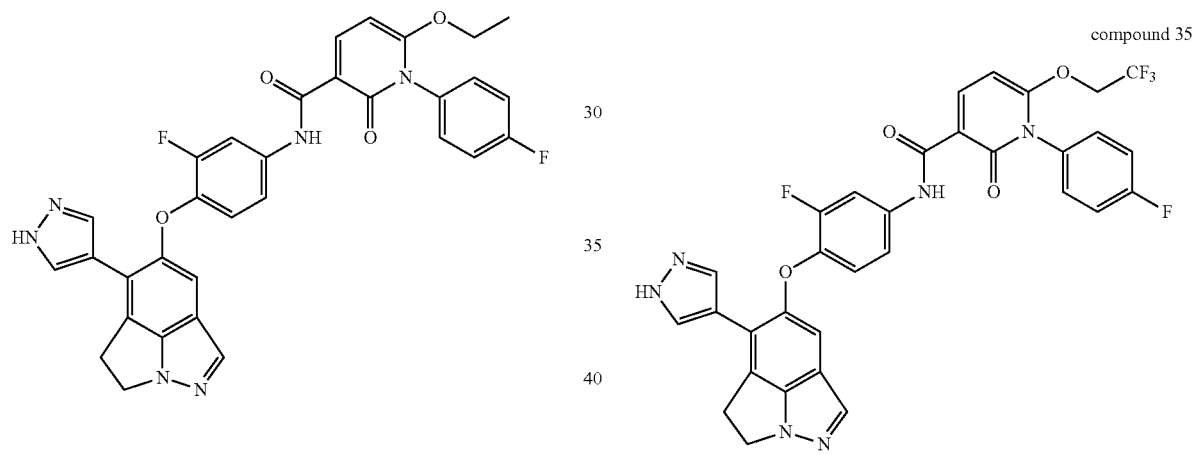
compound 33
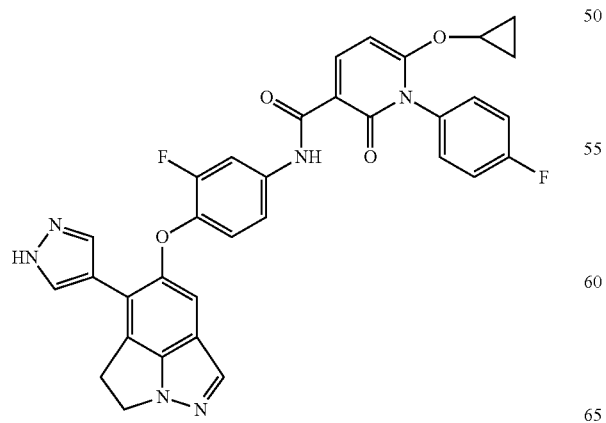
compound 36
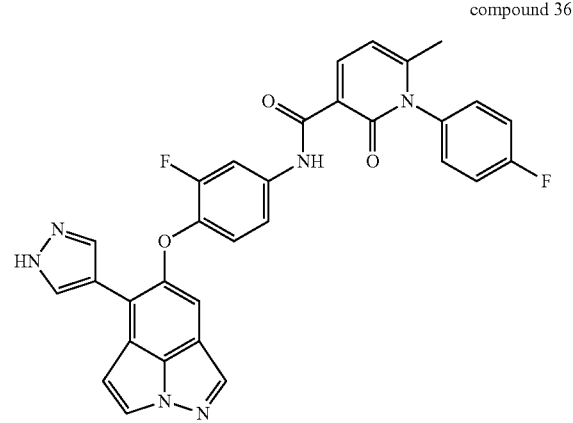

compound 37
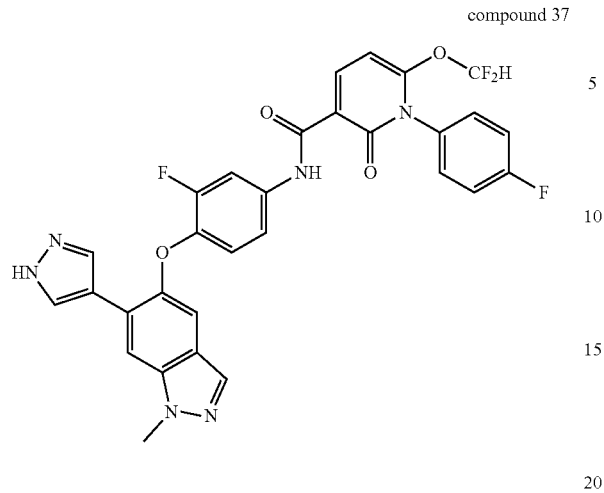
compound 40
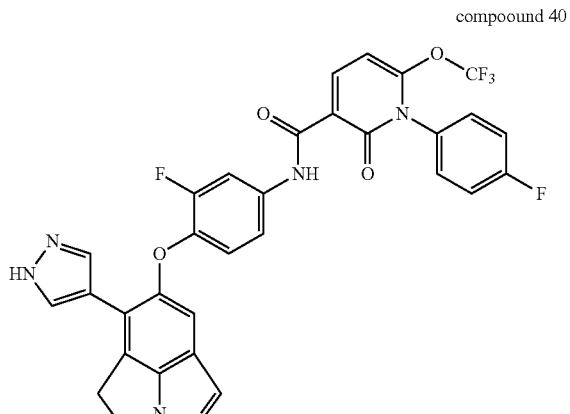
compound 38
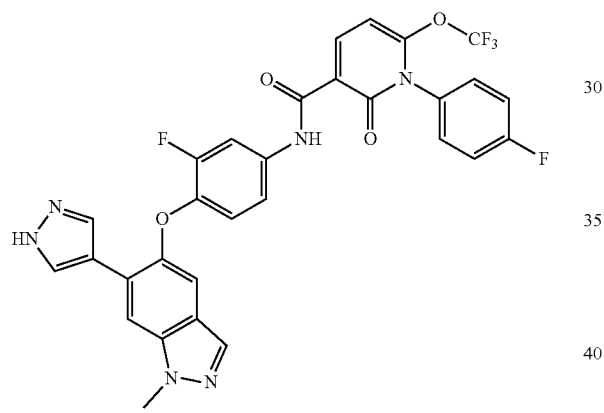
compound 41
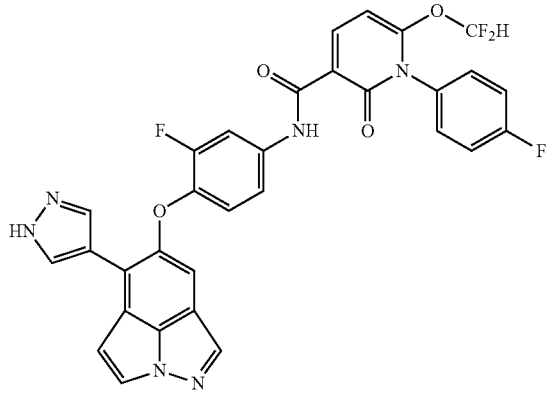
compound 39
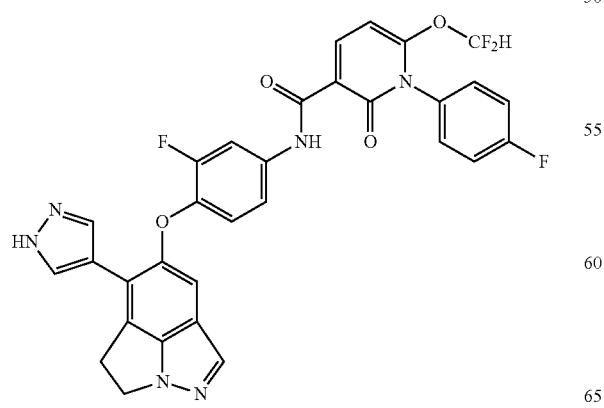
compound 42
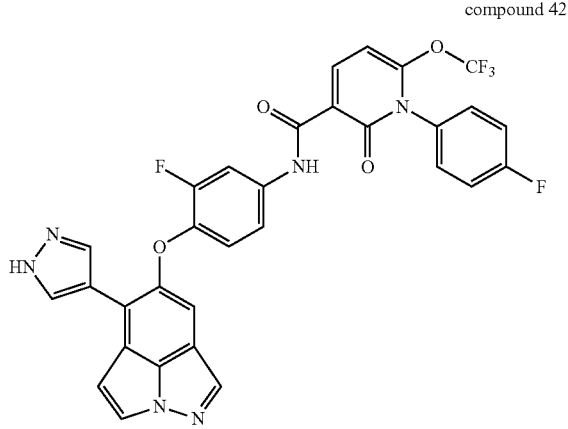

compound 43
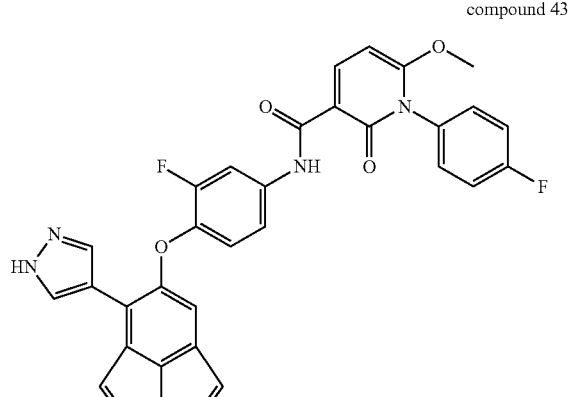
compound 44
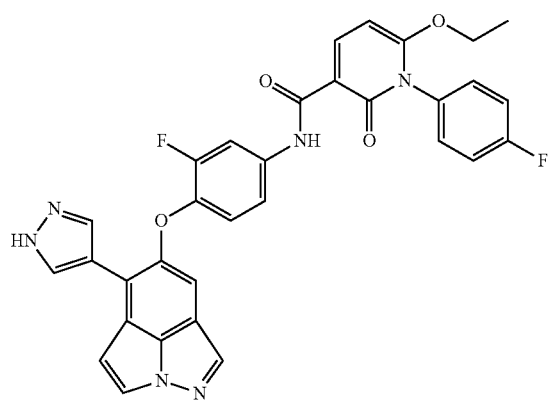
compound 45
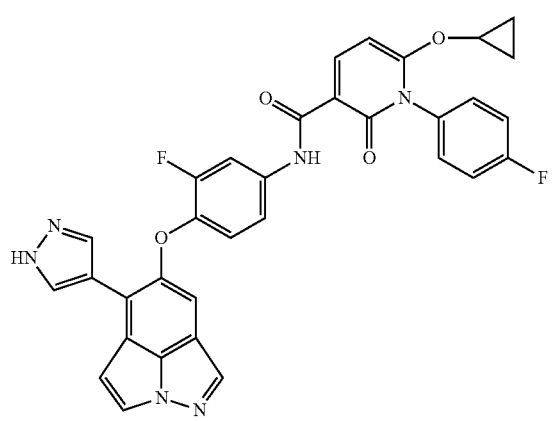
compound 46
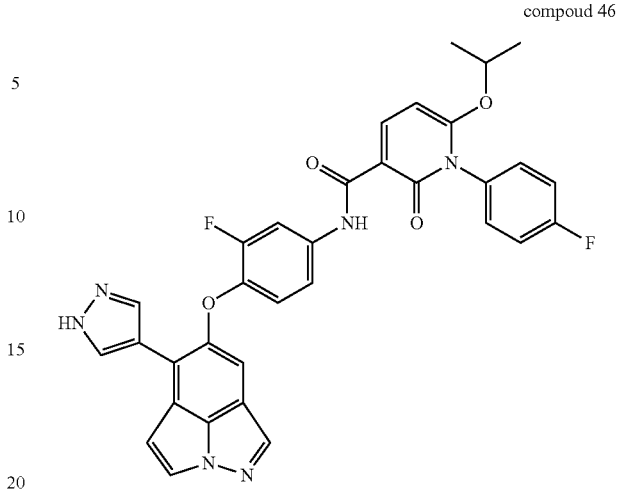
ompound 47
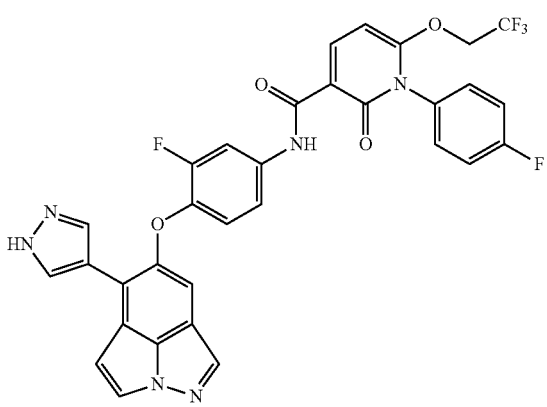
compound 48
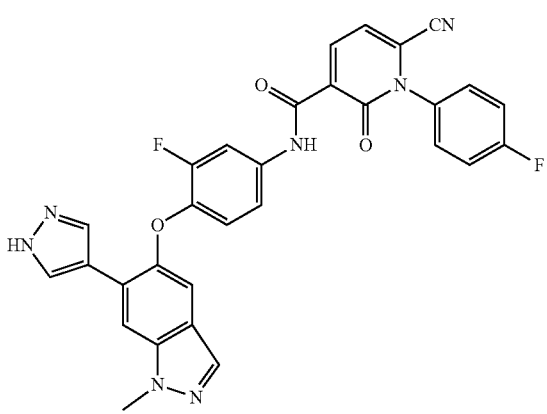

compound 49
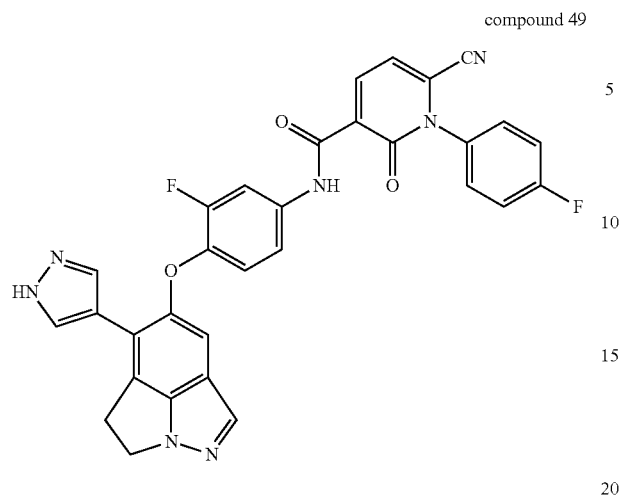
compound 50
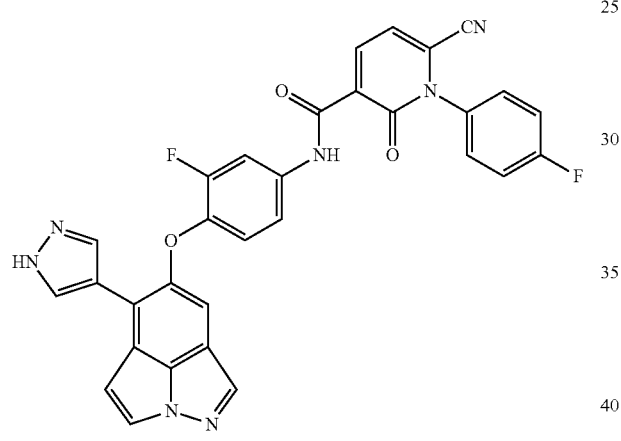
or isomers thereof, or pharmaceutically acceptable salts or solvates thereof.
The most preferred compounds of the present disclosure are selected from the following compounds:
compound 1
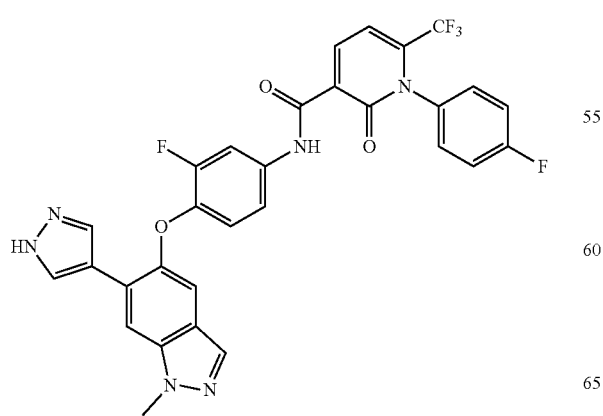
compound 2
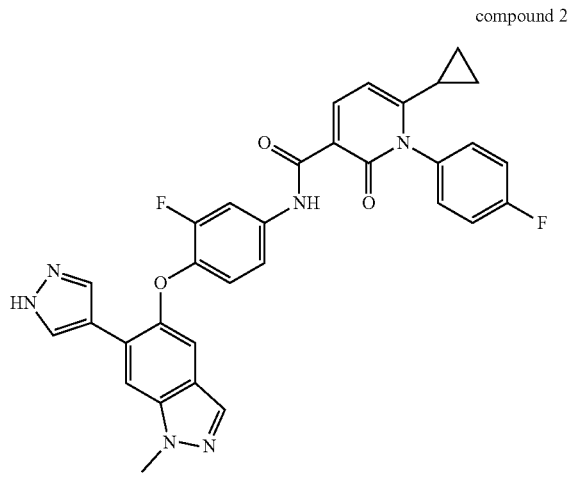
compound 3
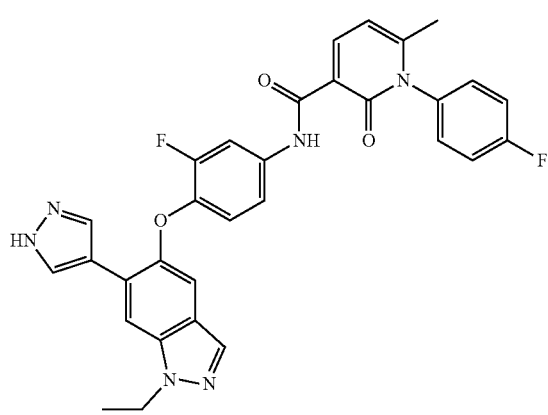
compound 4
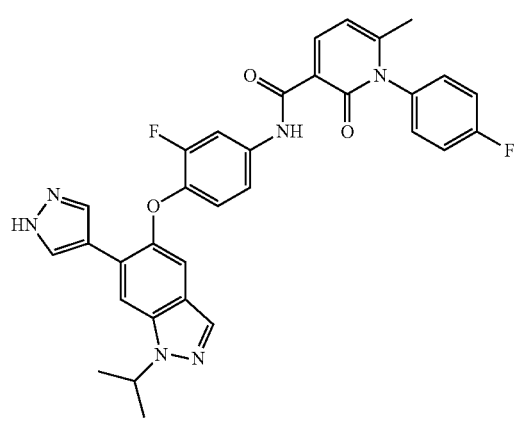

-continued
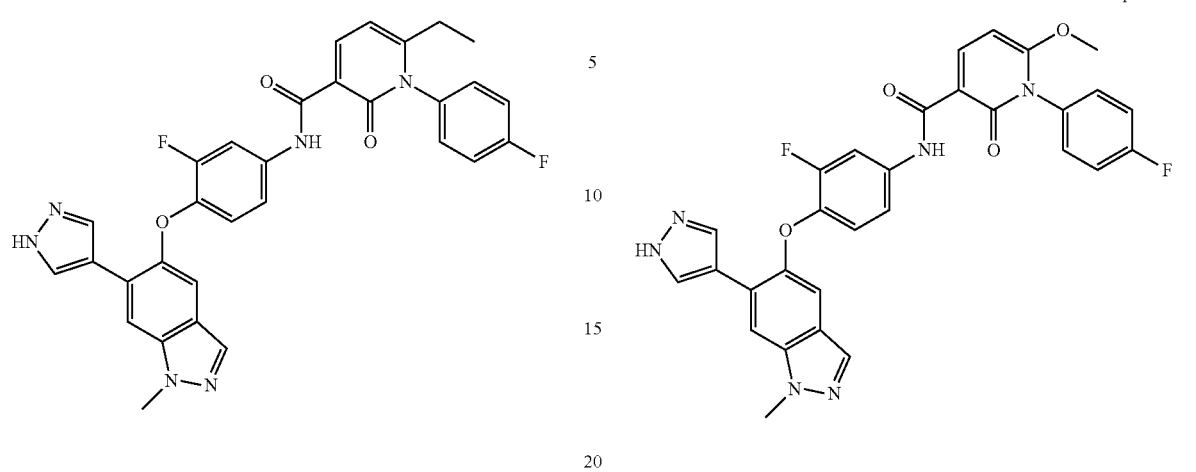
compound 5
compound 12
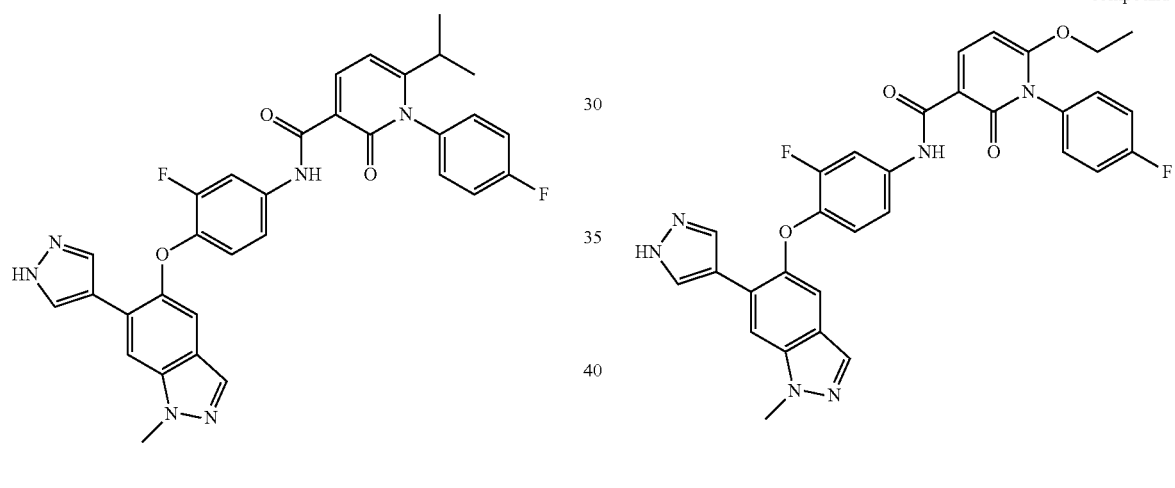
compound 6
compound 14
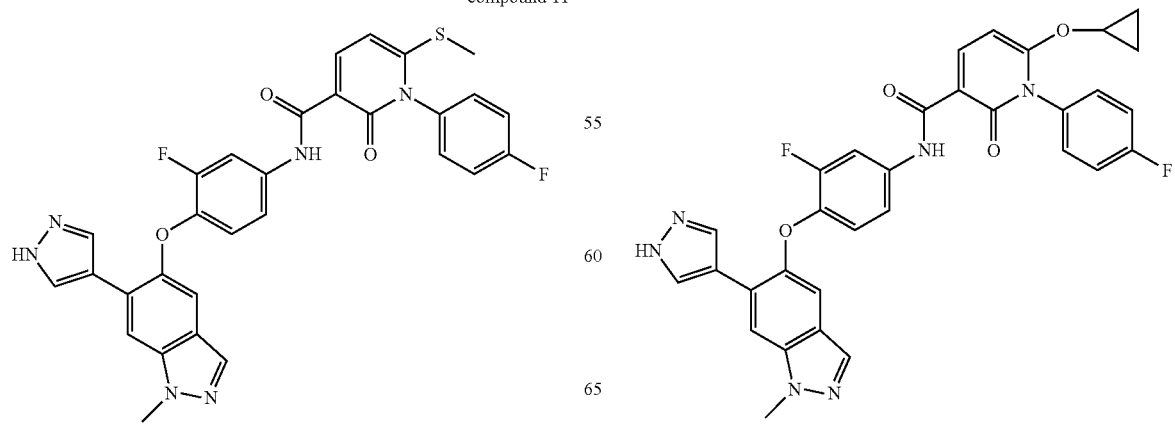
compound 11
compound 15 compound 16 compound 17 compound 19 compound 23 compound 25

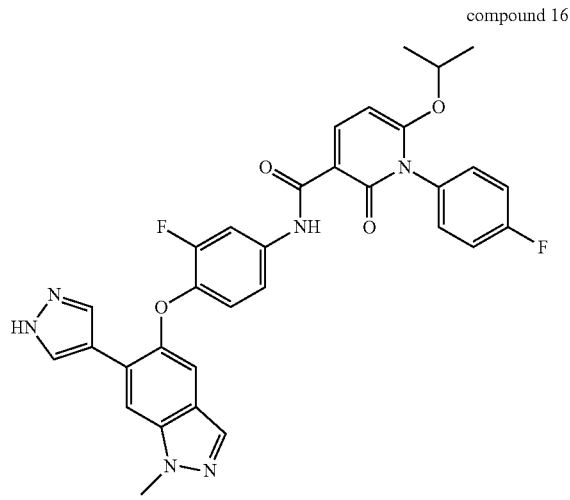
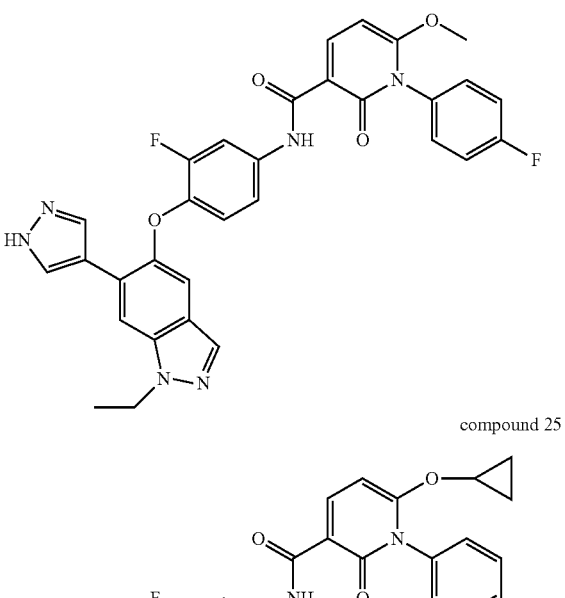

The present disclosure encompasses pharmaceutically acceptable salts of the compounds of formula I, II, III and preferred embodiments thereof, that is, a salt of compounds of the present disclosure that is non-toxic, biologically tolerable, or otherwise biologically suitable for administering to a subject. The above-mentioned compounds of formula I, II and III of the present disclosure are amine compounds, and therefore may react with various inorganic or organic acids to form pharmaceutically acceptable salts, such as but not limited to salts formed with hydrochloric acid, sulfuric acid, phosphoric acid, hydrobromic acid, nitric acid, formic acid, acetic acid, propionic acid, maleic acid, malonic acid, succinic acid, fumaric acid, tartaric acid, citric acid, glycolic acid, pyruvic acid, oxalic acid, benzoic acid, benzenesulfonic acid, p-toluenesulfonic acid, cinnamic acid, mandelic acid, methanesulfonic acid, ethanesulfonic acid, salicylic acid, etc. Such pharmaceutically acceptable acid addition salts and their common preparation methods are well-known in the art, generally refer to for example S. M. Berge et. al., "*Pharmaceutical Salts*", J. Pharm. Sci., 1977, 66:1-19, and "*Handbook of Pharmaceutical Salts, Properties, Selection, and Use*", edited by Stahl and Wermuth, Wiley-VCH and VHCA, Zurich, 2002.

Preferred pharmaceutically acceptable salts of the compounds of formula I, II and III of the present disclosure are salts formed with p-toluenesulfonic acid, benzenesulfonic acid, and methanesulfonic acid.

It should be understood that the compounds described herein, unless otherwise specified, encompass and include all isomers and stable isotopic variants of the compounds of the present disclosure, such as deuterated compounds. All isotopic variants of the compounds provided herein, whether radioactive or not, should be included within the scope of the present disclosure.

It should also be understood that the compounds of formula I, II, and III or their pharmaceutically acceptable salts can be isolated in the form of solvates, so any such solvates are included in the scope of the present disclosure. Where appropriate or feasible, the compounds of formula I, II, and III may also exist in the form of their prodrugs. The pharmaceutically acceptable prodrugs of the compounds of formula I, II, and III have chemically or metabolically cleavable groups; and through solvolysis or in the body under physiological conditions, it becomes a compound of formula I, II, and III with pharmacological activity, which can be formed in a conventional manner and by means of the functional group of the compound.

The term "$C_{1-6}$ alkyl" as used herein refers to a saturated straight chain or branched monovalent chain group having 1, 2, 3, 4, 5 or 6 carbon atoms, preferably 1 to 4 carbon atoms, more preferably 1 to 3 carbon atoms. Examples include but are not limited to, methyl, ethyl, n-propyl, isopropyl, n-butyl, iso-butyl, sec-butyl, tert-butyl, n-pentyl, isopentyl, neopentyl, n-hexyl, 2-methylpentyl, 3-methylpentyl, 2,3-dimethylbutyl, 2,2-dimethylbutyl, 2-ethylbutyl.

The term "$C_{1-6}$ alkoxy" as used herein refers to an —O—$C_{1-6}$ alkyl group, where $C_{1-6}$ alkyl is as defined above.

The term "$C_{1-6}$ alkylthio" as used herein refers to a —S—$C_{1-6}$ alkyl group, where $C_{1-6}$ alkyl is as defined above.

The term "halogen" as used herein refers to fluorine, chlorine, bromine, and iodine, preferably fluorine or chlorine.

The term "amino" as used herein refers to —$NH_2$, —NH—$C_{1-6}$ alkyl or —N-$(_{C1-6}$ alkyl$)_2$, where $C_{1-6}$alkyl is as defined above.

The term "$C_{3-6}$ cycloalkyl" as used herein refers to a saturated cyclic alkyl group containing 3, 4, 5 or 6 ring carbon atoms. Examples include but are not limited to, cyclopropyl, cyclobutyl, cyclopentyl, cyclohexyl. The cycloalkyl group is optionally substituted with a substituent selected from the group consisting of hydroxy or amino, $C_{1-6}$ alkyl, $C_{1-6}$ alkoxy or halogen as defined above.

The term "$C_{3-6}$ heterocyclyl" as used herein refers to a saturated cyclic alkyl group containing 3, 4, 5 or 6 ring carbon atoms, which, in addition to at least three carbon atoms, also contains at least one, such as 1-3 or for example 1 or 2 heteroatoms selected from O, S and N. The point of attachment of the $C_{3-6}$ heterocyclic group may be on a heteroatom or on a carbon atom. Examples of heterocyclic groups include but are not limited to, tetrahydrofuran, tetrahydrothiophene, azetidine, acridine, tetrahydropyrrole, thiazolidine, oxazolidine, piperidine, piperazine, morpholine, thiomorpholine, thiazine etc. The $C_{3-6}$ heterocyclic group is optionally substituted by a hydroxyl group or a substituent selected from the group consisting of amino, $C_{1-6}$ alkyl, $C_{1-6}$alkoxy or halogen as defined above.

The term "aryl" as used herein refers to a monovalent aromatic carbocyclic monocyclic or bicyclic ring system containing 6 to 10 carbon ring atoms. Examples of aryl moieties include phenyl and naphthyl. Phenyl is the preferred aryl group. The aryl group is optionally substituted by a hydroxyl group or a substituent selected from the group consisting of amino, $C_{1-6}$ alkyl, $C_{1-6}$ alkoxy, $C_{1-6}$ alkylthio or halogen as defined above.

The term "5-10 membered heteroaryl" as used herein means a monovalent aromatic monocyclic or bicyclic ring system with 5 to 10 ring atoms, which contains 1, 2, 3 or 4 hetero atoms selected from N, O, and S, the other ring atoms are carbon. The point of attachment of the heteroaryl group can be on a heteroatom or on a carbon atom. Examples of heteroaryl moieties include but are not limited to, pyrrolyl, furyl, thienyl, imidazolyl, oxazolyl, thiazolyl, triazolyl, oxadiazolyl, thiadiazolyl, tetrazolyl, pyridyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzisoxazolyl, benzothiazolyl, benzisothiazolyl, benzoxadiazolyl, benzothiadiazolyl, benzotriazolyl, purinyl, quinolinyl, isoquinolinyl, quinazolinyl or quinoxalinyl; preferably a monovalent aromatic monocyclic ring of 5 to 6 ring atoms system comprising 1-3 heteroatoms selected from N, O, and S, and the remaining ring atoms are carbon. Examples of preferred 5-6 membered heteroaryl moieties include but are not limited to, pyrrolyl, furyl, thienyl, imidazolyl, oxazolyl, thiazolyl, pyridyl, pyrazinyl, pyrazolyl, pyridazinyl, pyrimidine or isoxazolyl. The aforementioned heteroaryl group is optionally substituted by a hydroxyl group or a substituent selected from the group consisting of amino, $C_{1-6}$ alkyl, $C_{1-6}$ alkoxy, $C_{1-6}$ alkylthio or halogen as defined above.

The term "nitro" as used herein refers to the —$NO_2$ group.

The term "cyano" as used herein refers to the —CN group.

The term "acyl" as used herein refers to —C(O)R, where R refers to $C_{1-6}$ alkyl as defined above.

The term "mercapto" as used herein refers to the —SH group.

The term "$C_{1-6}$ alkylsulfonyl" as used herein refers to —$S(O)_2$—$C_1$-$C_6$ alkyl.

The term "$C_{1-6}$ alkylsulfinyl" as used herein refers to —S(O)—$C_1$-$C_6$ alkyl.

The term "carboxy" as used herein refers to the —C(O)—OH group.

The term "solvate" as used herein refers to a solvent addition form containing stoichiometric or non-stoichiometric solvents, including any solvated form of the compounds of the present disclosure, including for example, solvates with water, such as hydrates, or solvates with organic solvents, such as methanol, ethanol, or acetonitrile, namely as methanolate, ethanolate, or acetonitrile compound respectively; or in the form of any polymorph. It should be understood that such solvates of the compounds of the present disclosure also include solvates of pharmaceutically acceptable salts of the compounds of the present disclosure.

The term "isomer" as used herein encompasses any "stereoisomer", "racemate", "geometric isomer" and/or "tautomers" possibly existing for the compounds of formulae I, II, III of the present disclosure, and the methods for determining the stereochemistry of the isomers and methods for separating the same are well known to those skilled in the art, so the present disclosure encompasses all possible isomeric forms of the compounds of formula I as defined above, and pharmaceutically acceptable salts or solvates thereof.

The disclosure also encompasses "isotopic variants" of the compounds defined herein. The term "isotopic variant" as used herein refers to a compound that contains unnatural proportions of isotopes on one or more of the atoms constituting the compound. For example, an "isotopic variant" of a compound may contain one or more non-radioactive isotopes, such as deuterium ($^2H$ or D), carbon-13 ($^{13}C$), nitrogen-15 ($^{15}N$), etc. It should be understood that in compounds containing such isotopic substituents, the following atoms can be changed if they exist. For example, any hydrogen can be $^2$H/D, any carbon can be $^{13}$C, or any nitrogen can be $^{13}$N. The presence of such atoms and their arrangement are determined by those skilled in the art. Likewise, the present disclosure includes the preparation of isotopic variants of the compound of the present disclosure containing a radioisotope, in which case, for example, the obtained compound can be used as a drug and/or for substrate tissue distribution study. The radioisotopes tritium (i.e. $^3$H) and carbon-14 (i.e. $^{14}$C) can be particularly used for this purpose because they are easy to combine and have established detection methods. In addition, compounds substituted with positron emitting isotopes (such as $^{11}$C, $^{18}$F, $^{15}$O, and $^{13}$N) can be prepared, which can be used in positron emission tomography (PET) studies for substrate receptor occupancy detection.

The compounds of formula I, II, and III defined in the present disclosure are Trk inhibitors. As shown in the activity example section below, the compounds of formula I, II, and III of the present disclosure, especially the compounds of the examples of the present disclosure, showed inhibitory effects on multiple NTRK gene fusions in the cell assays shown, with IC50 of 0.1 nM~10 µM range, preferably 0.1 nM-0.5 µM range. Therefore, the compounds of the present disclosure can be used to treat or prevent diseases or disorders that can be treated by inhibiting Trk or diseases or disorders in which Trk activity plays a role or are involved, especially used to treat or prevent tumors or cancers by inhibiting Trk, especially used for targeted treatment of tumor or cancer patients bearing NTRK gene fusion.

In addition to exhibiting Trk inhibitory activity, the compounds of formula I, II, and III of the present disclosure and their pharmaceutically acceptable salts, especially the compounds of the examples, due to their structural modifications, also show, as compared with the prior Trk inhibitors, improved active target distribution and anti-cancer indications and effects; improved dissolution and dispersion properties, which are advantageous in preparing simpler and economical formulations; improved P450 (such as 2C8 and 2C9, etc.) inhibitory activities, thereby having less potential drug interactions; improved metabolic stability; reducing the formation of metabolically active intermediates (M1 and/or M2, Oncotarget, 2018, 9(17), 13796-13806), thereby reducing toxic side effects, and providing a more friendly medicine performance.

In addition, the present inventors also investigated the inhibitory activity of the compounds of the present disclosure on various other kinases, and the results showed that the compounds of the present disclosure as defined herein, in addition to inhibiting the activities of TRKA, TRKB, and TRKC kinases, also inhibit other confirmed, under-research, and emerging kinase targets of anticancer drugs (ROS1, RAF1, PDGFRB, CSF1R, LCK, IKKa, IKKb, PLK, AXL, TIE, LOK, TIE1, DDR) and the anti-cancer drug targets in application and their drug resistant mutant targets (FLT3, FLT3 (N841I), FLT3 (K663Q), FLT3 (D835V), FLT3 (ITD), KIT, KIT (L576P), KIT (V559D), KIT (V559D, T670I), MET, MET (Y1235D), MET (Y1250T), RET, RET (M918T), etc., showing >90% inhibitory activity against many kinases including the above in the kinase activity assays. For details, reference can be made to Table 10 in the Activity Example section below. Therefore, the compounds of the present disclosure are expected to exhibit a broad-spectrum anti-cancer effect in clinical applications.

Therefore, the second aspect of the present disclosure provides the above-defined compounds of formula I, II, III, isomers thereof, or pharmaceutically acceptable salts or solvates thereof for use as Trk inhibitors.

The second aspect of the present disclosure also provides the above-defined compounds of formula I, II, III, isomers thereof, or their pharmaceutically acceptable salts or solvates for use as drugs, especially as inhibitors of the kinases listed in Table 10.

In a specific embodiment, the present disclosure provides the above-defined compounds of formula I, II, III, isomers thereof, or pharmaceutically acceptable salts or solvates thereof that are used as anticancer drugs by inhibiting Trk.

The third aspect of the present disclosure provides a method for treating or preventing mammalian tumors or cancers, comprising administering an effective amount of the above-defined compound(s) of formula I, II, III, isomers thereof, or their pharmaceutically acceptable salts or solvates, or a pharmaceutical composition comprising an effective amount of the above-defined compound(s) of formula I, II, III, isomers thereof, or pharmaceutically acceptable salts or solvates thereof, to a mammal in need thereof.

The fourth aspect of the present disclosure provides a pharmaceutical composition for the treatment or prevention of tumors or cancers, comprising the above-defined formula I, II, III compound(s), isomers thereof, or their pharmaceutically acceptable salts or solvates, and pharmaceutical carriers, diluents or excipients.

The fifth aspect of the present disclosure provides the use of the compounds of formula I, II, and III defined above, isomers thereof, or their pharmaceutically acceptable salts or solvates in the manufacture of a medicament for treating or preventing diseases or conditions in which the Trk activity plays a role or is involved. Preferably, the present disclosure provides the use of the compounds of formula I, II, and III defined above, isomers thereof, or their pharmaceutically acceptable salts or solvates in the manufacture of a medicament for treating or preventing tumors or cancers, especially those tumors or cancers as defined below by inhibiting Trk; specifically, the cancer bears NTRK gene fusion.

The fifth aspect of the present disclosure also provides the use of the compounds of formula I, II, and III defined above, isomers thereof, or their pharmaceutically acceptable salts or solvates in the manufacture of a medicament for treating or preventing diseases or conditions in which the kinases listed in Table 10 herein plays a role or are involved. Preferably, the present disclosure provides the use of the compounds of formula I, II, and III defined above, isomers thereof, or their pharmaceutically acceptable salts or solvates in the manufacture of a medicament for treating or preventing tumors or cancers, especially those tumors or cancers as defined below, by mediating the kinases as listed in Table 10 herein.

The sixth aspect of the present disclosure provides a pharmaceutical combination comprising the compounds of formula I, II, III, isomers thereof, or their pharmaceutically acceptable salts or solvates of the present disclosure, administered concurrently or sequentially with one or more other drugs functioning via the same or different mechanisms. Examples of the other drugs include but are not limited to, other Trk inhibitors, kinase inhibitors, anti-inflammatory drugs, analgesics, opioids, anticancer chemotherapeutics, and antibody drugs.

In a preferred embodiment, the "Trk" with regard to the compounds, compositions, methods and uses of the present disclosure is any one of TrkA, TrkB or TrkC; in a more preferred embodiment, the "Trk" with regard to the compounds, compositions, methods and uses of the present disclosure is TrkA, TrkB, or TrkC, or at least two of them.

For the above-mentioned compounds of the present disclosure for use as a medicine, the methods of the present disclosure, the pharmaceutical composition, the pharmaceutical combination or the use, the compound of formula I is preferably

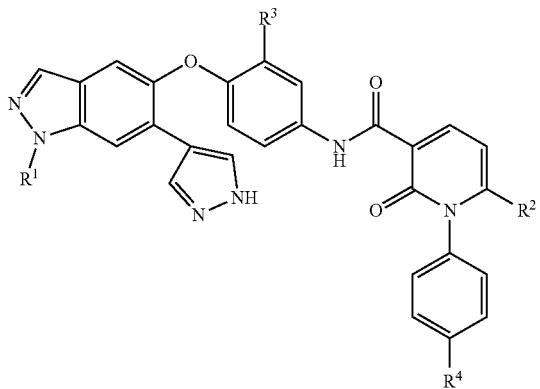

I-a wherein
$R^1$ is $C_{1-6}$ alkyl;
$R^2$ is $C_{1-6}$ alkyl or $C_{3-6}$ cycloalkyl, optionally substituted with one or more halogens;
$R^3$ and $R^4$ are each independently selected from H or halogen; and
provided that $R^1$ and $R^2$ are not methyl at the same time; or isomers thereof or pharmaceutically acceptable salts or solvates hereof;
or

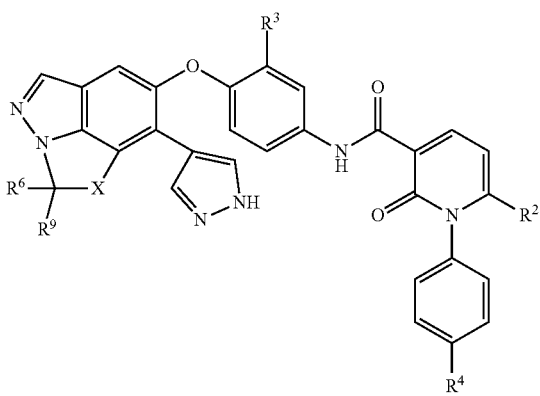

I-b wherein
$R^2$ is $C_{1-6}$ alkyl or $C_{3-6}$ cycloalkyl, optionally substituted with one or more halogens;
$R^3$ and $R^4$ are each independently selected from H or halogen;
$R^6$ and $R^9$ are each independently H, halogen, hydroxy, $C_{1-6}$ alkyl or $C_{3-6}$ cycloalkyl, and
X is —$CR^7R^8$— or —$CR^7R^8$—$CR^7R^8$—, wherein $R^7$ and $R^8$ are each independently H, halogen, hydroxy, $C_{1-6}$ alkyl or $C_{3-6}$ cycloalkyl, or $R^7$ and $R^8$ attached to the same carbon atom together form a $C_{3-6}$ cycloalkyl group; or isomers thereof or pharmaceutically acceptable salts or solvates thereof.

For the compounds of the present disclosure for use as a medicine, the method of the present disclosure, the pharmaceutical composition, the pharmaceutical combination or the use, also preferred are directed to the compounds of formula II-a, II-b, III-a, III-b and their preferred embodiments; more preferred are the specific compounds listed above, namely Compound 1-Compound 50; most preferred are the "most preferred compounds of the present disclosure" listed above, isomers thereof or pharmaceutically acceptable salts or solvates thereof.

The term "cancer" or "tumor" as used above refers to neoplastic cell growth and proliferation, either malignant or benign, and all precancerous cells and carcinous cells and tissues. For the compounds, methods, pharmaceutical compositions and uses of the present disclosure, the cancer or tumor includes but not limited to sarcoma (especially infant fibrosarcoma carcinoma), skin cancer, neuroblastoma, ovarian cancer, breast cancer, prostate cancer, pancreatic cancer, salivary gland cancer, multiple myeloma, astrocytoma and medulloblastoma, neuroglioma, melanoma, thyroid cancer, lung adenocarcinoma, large cell neuroendocrine tumor, head and neck cancer, and colorectal cancer, cholangiocarcinoma, glioblastoma, glioma, secretory breast cancer, mammary secretory carcinoma, acute myeloid leukemia, congenital mesodermal nephroma, congenital fibrosarcoma, acute lymphoblastic leukemia, colon adenocarcinoma, gastrointestinal stromal tumors. For the compounds, methods, pharmaceutical compositions and uses of the present disclosure, the cancer or tumor is preferably lung adenocarcinoma, intrahepatic cholangiocarcinoma, colorectal cancer, papillary thyroid cancer, spitzoid tumor, glioblastoma, sarcoma, astrocytoma, head and neck cancer, low-grade glioma, secretory breast cancer, acute myeloid leukemia, congenital mesoderm nephroma, congenital fibrosarcoma, acute lymphoblastic leukemia, colon adenocarcinoma, thyroid cancer, skin melanoma, and pediatric glioma.

For the compounds, methods, pharmaceutical compositions and uses of the present disclosure, preferably, the cancer or tumor is a cancer or tumor in which Trk activity plays a role or is involved, or a cancer or tumor that can be treated with a Trk inhibitor, or a cancer or tumor caused by NTRK gene fusion, including but not limited to the above-mentioned tumor types and their preferred ranges.

The term "treatment" or "treating" as used herein refers to the administration of one or more of the compounds of formula I, II, and III described herein, or isomers thereof, or pharmaceutically acceptable salts or solvates thereof, to a mammal such as a human suffering from the disease or having symptoms of the disease, for use to cure, alleviate, relieve, or affect the disease or the symptoms of the disease. In an embodiment of the disclosure, the disease is a tumor or cancer as defined above.

The term "prevention" or "preventing" as used herein is well known in the art and refers to the administration of one or more of the compounds of formula I, II, III described herein, or isomers thereof, or pharmaceutically acceptable salts or solvates thereof, to a mammal such as a human suspected of suffering from or susceptible to the cancers or tumors as defined above, to reduce the risk of suffering from the defined diseases. The term "prevention" or "preventing" encompasses the use of the compounds of the present disclosure prior to the diagnosis or determination of any clinical and/or pathological symptoms.

The term "effective amount" as used herein refers to an amount or dose that is generally sufficient to produce a beneficial therapeutic effect on a tumor patient in need of the treatment. Those skilled in the art can determine the effective amount or dosage of the active ingredient in the present disclosure by conventional methods in combination with conventional influencing factors.

The term "mammal" as used herein includes but is not limited to guinea pigs, dogs, cats, rats, mice, hamsters, and primates including humans.

The above-mentioned pharmaceutical composition of the present disclosure can be formulated by techniques known to those skilled in the art, such as the techniques disclosed in the 20th Edition of "*Remington's Pharmaceutical Sciences*". The pharmaceutical composition of the present disclosure can be used by any convenient route and in any convenient administration form. For example, it can be administered via gastrointestinal tract, via nose, via lung, via muscle or vasculature, or via skin. The administration form can be tablets, powders, capsules, solutions, dispersions, suspensions, syrups, sprays, suppositories, gels, emulsions, patches, etc. These pharmaceutical compositions may contain conventional ingredients in pharmaceutical preparations, such as diluents, carriers, pH adjusters, sweeteners, disintegrants and the like.

The compound of the present disclosure can be administered as the sole active ingredient, or can be administered in combination with another drug or therapy, which can have or produce the same or different pharmacological effects. For example, the additional drugs include but are not limited to other Trk inhibitors, kinase inhibitors, antibody drugs, immunotherapeutic, other anti-cancer agents, anti-inflammatory drugs, analgesics, cardiovascular drugs, lipid-lowering drugs, antibacterial agents, antiviral agents, antidiabetic, antiproliferative agents, antiangiogenic or antiallergic agents, etc. These drugs and therapies are known to those skilled in the art.

When the compounds of formula I, II, and III are administered in combination with other drugs, the dosage of other drugs co-administered will of course vary depending on the type of the drug co-used, the specific drug used, the condition to be treated, the general health of the patient, the judgement of physician or veterinarian.

The compounds of the present disclosure can also be combined with anti-tumor therapies, including but not limited to surgery, radiation therapy, transplantation (for example, stem cell transplantation, bone marrow transplantation), tumor immunotherapy and chemotherapy and the like.

The drug(s) used in combination with the compound(s) of the present disclosure, that is, the co-used drugs, can be administered simultaneously, separately, or sequentially with the compound(s) of the present disclosure through the same or different administration routes. They can be contained in the same pharmaceutical composition, or in separate form, such as a combination product, preferably in the form of a kit. They can be manufactured and/or formulated by the same or different manufacturers. Moreover, the compound(s) of the present disclosure and the additional drug(s) can be added to the combination therapy together (i) before dispensing the combined product to physicians (for example, in the case of a kit containing the compound(s) of the present disclosure and the additional drug(s)); (ii) by the physician himself (or under the guidance of the physician) immediately before administration; (iii) by the patient himself, for example during the sequential administration of the compound(s) of the present disclosure and additional drug(s).

The seventh aspect of the present disclosure provides a preparation method of the compound of formula I of the present disclosure, which comprises:
(a) reacting the compound of formula A

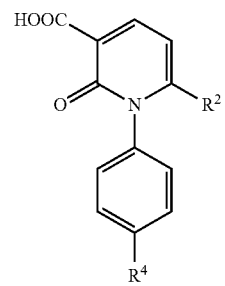

A with the compound of formula B in the presence of a condensing reagent,

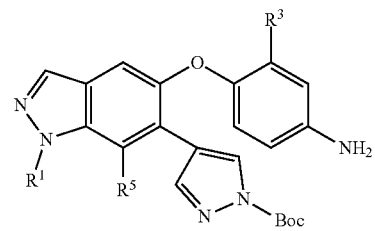

B to form an amide, obtaining the compound of formula C,

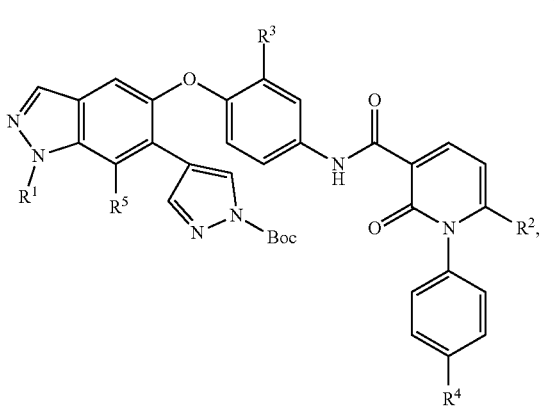

C or (a') reacting the compound of formula A

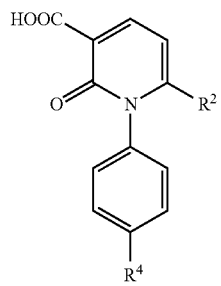

A

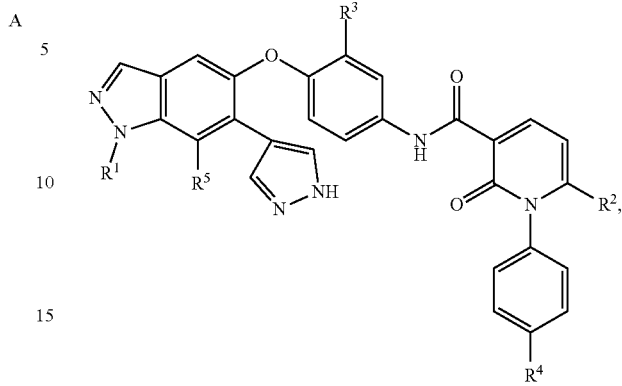

I where $R^1$ to $R^5$ are as defined above.

In steps (a) and (a'), the amide formation reaction can be carried out under condensation reaction conditions known in the art, for example, can be carried out under peptide coupling reaction conditions known in the art.

Preferably, in steps (a) and (a'), the amide formation reaction can be carried out in the presence of EDCI, HCl, HOBT and DIPEA in a suitable solvent (e.g. DMF).

The compound of formula A can be prepared as follows:

(1) reacting the compound of formula 1 with the compound of formula D in the presence of a condensing reagent,

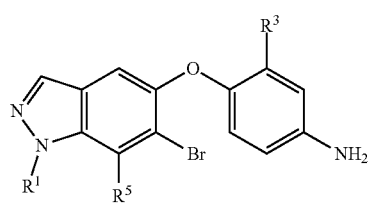

D

1

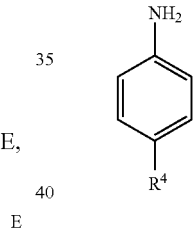

to form an amide, obtaining the compound of formula E,

E

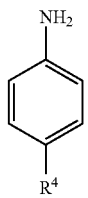

with the compound of formula 2,

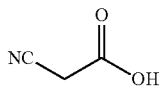

2 to obtain the compound of formula 3,

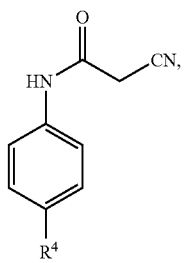

3 then subjecting the compound of formula E to a Suzuki coupling reaction, to obtain the compound of formula C;

and (b) deprotecting the compound of formula C to obtain the compound of formula I, (2) reacting the compound of formula 3 with the compound of formula 4,

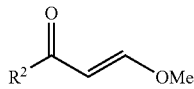

to obtain the compound of formula 5,

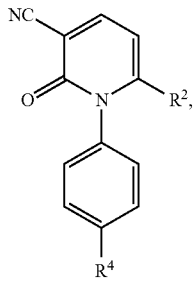

(3) adding concentrated $H_2SO_4/H_2O$ to the compound of formula 5, and reacting to obtain the compound of formula A,

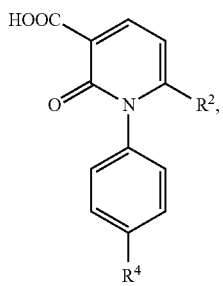

A where $R^2$ and $R^4$ are as defined above.

The compound of formula A can also be prepared in the form of formula A-2 as follows:

(1) reacting the compound of formula A-2-1

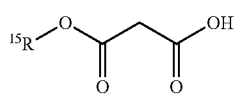

A-2-1 with the compound of formula A-1-1

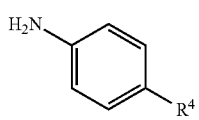

A-1-1 to obtain the compound of formula A-2-2,

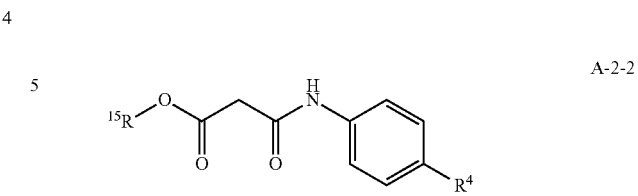

A-2-2

(2) reacting the compound of formula A-2-2 with the compound of formula A-2-3,

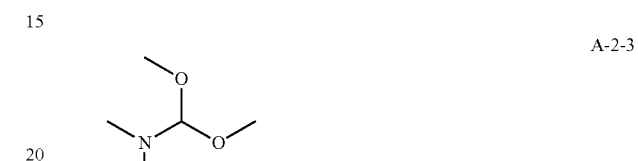

A-2-3 to obtain the compound A-2-4,

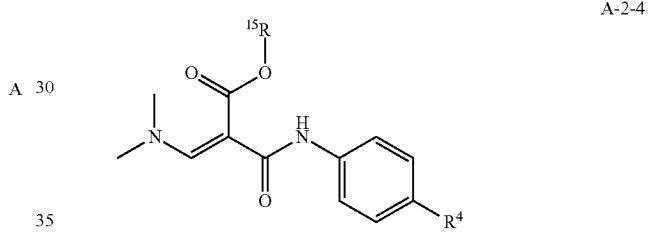

A-2-4

(3) reacting the compound A-2-4 with the compound A-2-5,

A-2-5 to obtain the compound A-2-6,

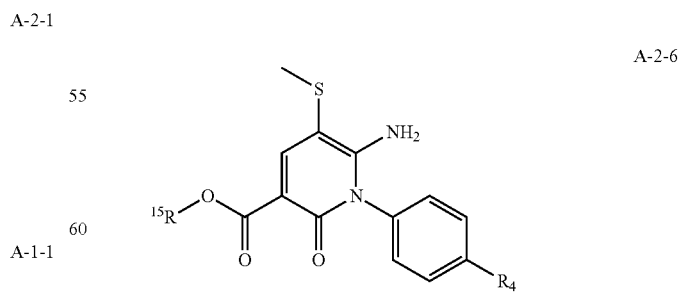

A-2-6

(4) reducing the compound A-2-6, such as hydrogenation reduction, to remove the methylthio group, to obtain the compound A-2-7

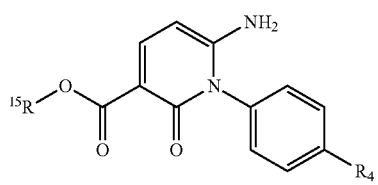

(5) hydrolyzing the compound A-2-7 to obtain the compound A-2-8,

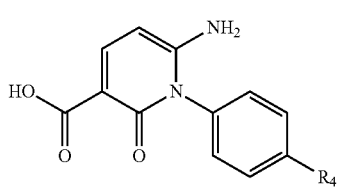

(6) converting the amino group of the compound A-2-8 to halogen, to obtain the compound A-2-9,

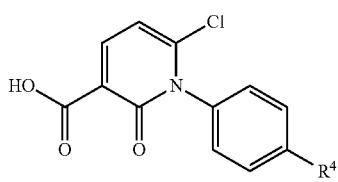

(7) subjecting the halogen of the compound A-2-9 to nucleophilic substitution, for example with nucleophilic reagent $R^{11}X$—Na (X can be O, S, C, N, etc.) to obtain the compound A-2,

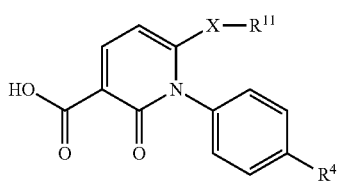

wherein $R^4$ is as defined above, and $R^{15}$ is selected from $C_{1-6}$ alkyl, benzyl, α-methylbenzyl ester, or p-methoxybenzyl ester, and the like etc. $R^{11}$ is selected from H, $C_{1-6}$ alkyl substituted with one or more halogens, or $C_{3-6}$ cycloalkyl substituted with one or more halogens.

The compound of formula A can also be prepared as follows:

(1) reacting the compound of formula A-3-1

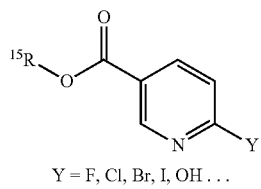

Y = F, Cl, Br, I, OH ...

with the compound of formula Z—$R^2$, such as $R^2I$, $R^2Br$, $R^2Cl$, $R^2B(OH)_2$, $R^2NH$, $R^2OH$, $R^2SH$, Togni reagent, difluorocarbene reagent, such as but not limited to substitution, condensation, coupling reaction, to obtain the compound A-3-2,

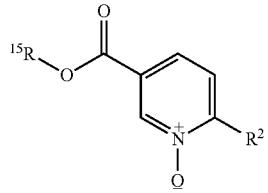

(2) oxidizing the compound A-3-2, for example with a peroxide, to obtain the compound A-3-3, (3) subjecting the compound A-3-3 to rearrangement, to obtain the compound A-3-4, (4) reacting the compound A-3-4 with the compound A-3-5, such as Chen-Lam reaction, Ullmann reaction,

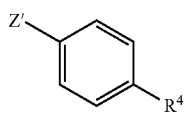

Z' is B(OH)₂, I or Br, to obtain the compound A-3-6,

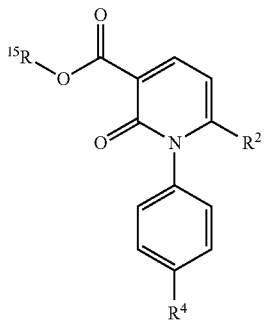

A-3-6

(5) hydrolyzing the compound A-3-6 to obtain the compound A-3,

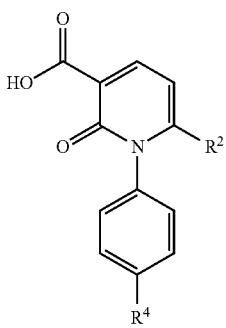

A-3 wherein R² and R⁴ are as defined above, R¹⁵ is selected from $C_{1-6}$ alkyl, benzyl, or substituted benzyl, etc.; Togni reagent is 1-(trifluoromethyl)-3,3-dimethyl-1,2-benziodoxole (CAS number: 887144-97-0), and the difluorocarbene reagent is selected from such reagents well known to those skilled in the art, including but not limited to organosilicon reagents such as $TMSCF_2X$ (X is selected from halogen such as fluorine, chlorine, bromine, and iodine) and 2,2-difluoro-2-fluorosulfonyl acetic acid.

When R⁵ in the compound of formula B is H, the compound of formula B is a compound of formula B-1:

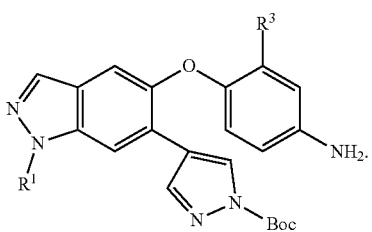

B-1

The compound of formula B-1 can be prepared as follows, including:

(1) subjecting the compound of formula 6 to bromination reaction,

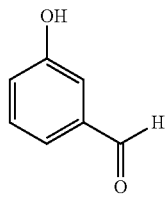

6 to obtain the compound of formula 7

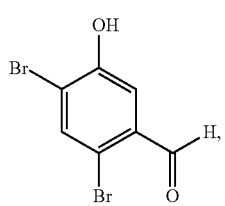

7

(2) reacting the compound of formula 7 with the compound of formula 8,

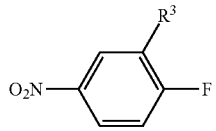

8 to obtain the compound of formula 9

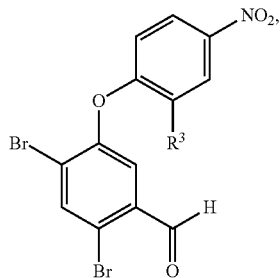

9

(3) reacting the compound of formula 9 with R¹—NHNH₂ to obtain the compound of formula 10

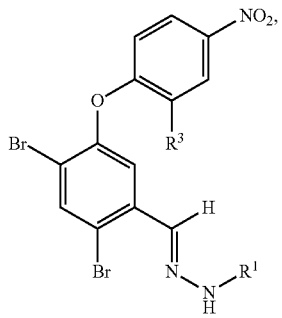

10

(4) subjecting the compound of formula 10 to a cyclization reaction to obtain the compound of formula 11,

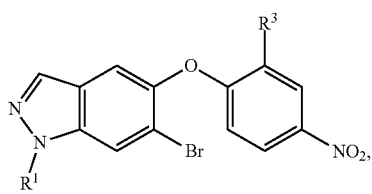

11

(5) subjecting the compound of formula 11 to Suzuki coupling reaction to obtain the compound of formula 12,

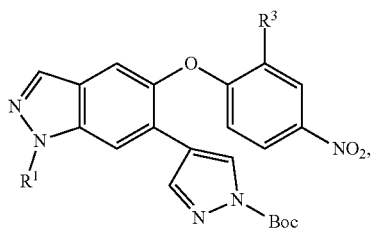

12

(6) hydrogenating the compound of formula 12, for example in the presence of palladium on carbon, to obtain the compound of formula B-1,

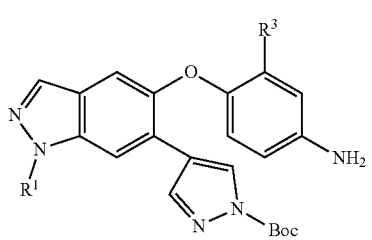

B-1 wherein R¹ and R³ are as defined above.

When $R^5$ in the compound of formula D is H, the compound of formula D is a compound of formula D-1:

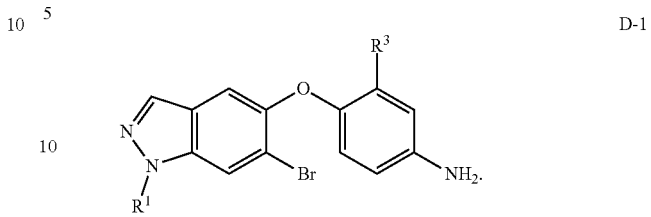

D-1

The compound of formula D-1 can be prepared by hydrogenating the compound of formula 11, for example by reacting in the presence of palladium on carbon.

When $R^5$ in the compound of formula B is not H, the compound of formula B may be a compound of formula B-2:

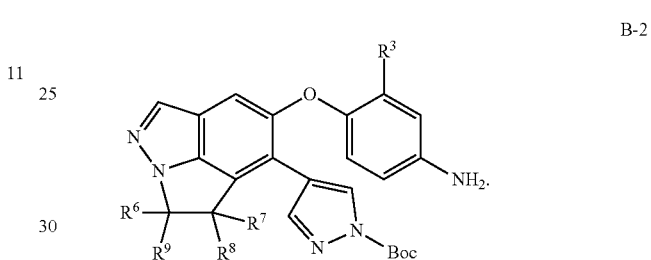

B-2

The compound of formula B-2 can be prepared as follows, including:

(1) converting the compound of formula 16

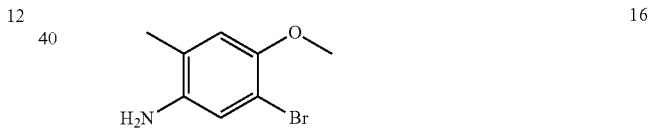

16 to the indolequinone of formula 17, for example, reacting the compound of formula 16 with trichloroacetaldehyde and hydroxylamine under the catalysis of hydrochloric acid, and then under the action of concentrated sulfuric acid or Lewis acid (such as boron trifluoride, etc.), to obtain the compound of formula 17,

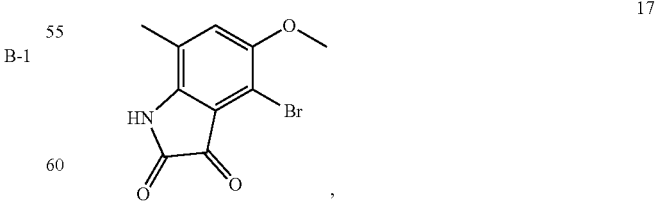

17

(2) subjecting the compound of formula 17 to a selective reduction reaction, such as with hydrazine hydrate or with titanium tetrachloride and metallic zinc, to obtain the compound of formula 18,

18

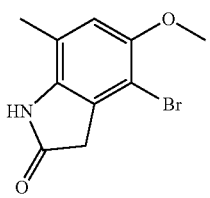

(3) reacting the compound of formula 18 with R⁷X and R⁸X successively, wherein X is halogen (preferably bromine or iodine), to obtain the compound of formula 19 (wherein $R^7$ and $R^8$ are as defined above, and each independently is an optionally substituted $C_{1-6}$ alkyl or $C_{3-6}$ cycloalkyl); or reacting with DAST (diethylaminosulfur trifluoride) to obtain the compound of formula 19 (wherein $R^7$ and $R^8$ are fluorine),

19

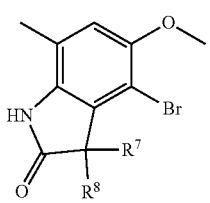

(4) reducing the compound of formula 19, for example, in the presence of lithium aluminum hydride or borane, to obtain the compound of formula 20,

20

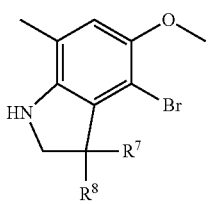

then, subjecting the compound of formula 20 to a diazotization reaction before cyclization, to obtain the compound of formula 21, for example, reacting the compound of formula 20 with a diazotization reagent (such as sodium nitrite) in the presence of a strong acid (such as tetrafluoroboric acid), and then carrying out the cyclization reaction in the presence of potassium acetate, 18-crown-6 and a suitable solvent (such as chloroform), to obtain the compound of formula 21 (wherein $R^6$ and R are both H);

21

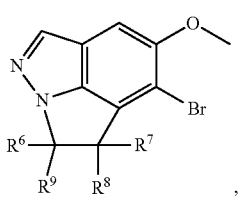

or (4') ① reacting the compound of formula 19 with Lawesson's reagent to convert the carbonyl compound into a thiocarbonyl compound, or reacting the compound of formula 19 with an organometallic compound containing $R^6$ and $R^9$ moieties (such as using Grignard reagent) to introduce the $R^6$ and $R^9$ structural fragments, or directly proceeding to step ②;

② subjecting the product obtained in step ① or directly subjecting the compound of formula 19 to diazotization reaction, and then to cyclization, to obtain the compound of formula 21, for example, reacting the product obtained in step ① or the compound of formula 19 with a diazotization reagent (such as sodium nitrite) in the presence of a strong acid (such as tetrafluoroboric acid), and then carrying out the cyclization reaction in the presence of potassium acetate, 18-crown-6 and a suitable solvent (such as chloroform), to obtain the compound of formula 21 (wherein $R^6$ and $R^9$ attached to the same carbon atom together form =S; or $R^6$ and $R^9$ are as defined above, and each independently is an optionally substituted $C_{1-6}$ alkyl or $C_{3-6}$ cycloalkyl; or $R^6$ and $R^9$ attached to the same carbon atom together form =O), (5) subjecting the compound of formula 21 to a demethylation reaction, for example, in the presence of boron tribromide, to obtain the compound of formula 22,

22

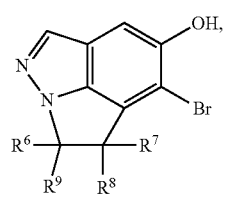

(6) reacting the compound of formula 22 with the compound of formula 8, for example, in the presence of potassium carbonate in a suitable solvent,

8

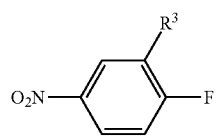

to obtain the compound of formula 23

23

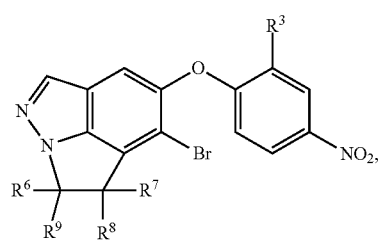

(7) subjecting the compound of formula 23 to Suzuki coupling reaction to obtain the compound of formula 24,

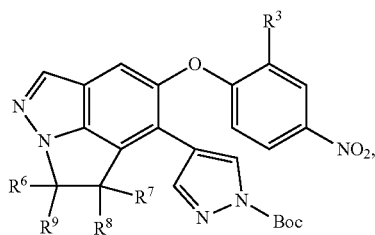

24

(8) hydrogenating the compound of formula 24, for example, in the presence of palladium on carbon, to obtain the compound of formula B-2,

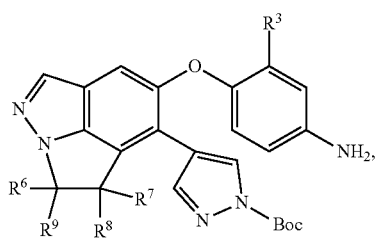

B-2 wherein $R^3$, $R^6$, $R^7$, $R^8$ and $R^9$ are as defined above, unless the context has specifically indicated or is chemically unrealizable.

The compound of formula B-2 can also be prepared as the compound of formula B-2-18 and B-2-19 as follows:

(1) reacting the compound of formula B-2-1

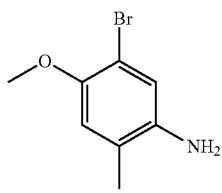

B-2-1 with trichloroacetaldehyde and hydroxylamine under acid catalysis, to obtain the compound B-2-2,

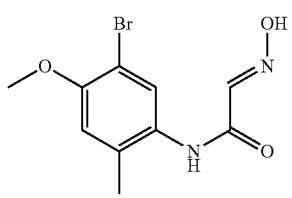

B-2-2

(2) subjecting the compound B-2-2 to ring closure under acidic conditions, such as under the action of sulfuric acid, to obtain the compound B-2-3,

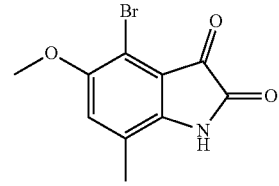

B-2-3

(3) hydrolyze and decarboxylating the compound B-2-3 to obtain the compound B-2-4,

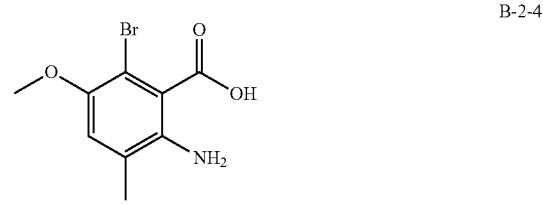

B-2-4

(4) esterifying the compound B-2-4 to obtain the compound B-2-5,

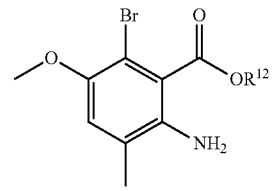

B-2-5

(5) treating the compound B-2-5 with a nitrite or an ester, to obtain the indazole compound B-2-6,

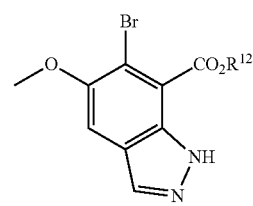

B-2-6

(6) protecting the indazole of the compound B-2-6, for example with THP, to obtain the compound B-2-7,

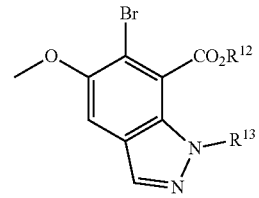

B-2-7

(7) reducing the compound B-2-7 to obtain the compound B-2-8,

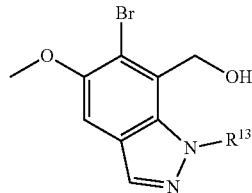

B-2-8

(8) activating the hydroxyl group in the compound B-2-8 to obtain the compound B-2-9,

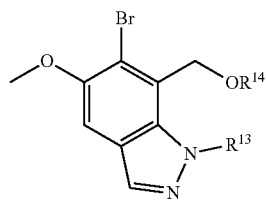

B-2-9

(9) reacting the compound B-2-9 with TMS-CN to obtain the compound B-2-10,

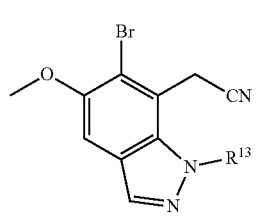

B-2-10

(10) selectively reducing the compound B-2-10 to obtain the aldehyde B-2-11,

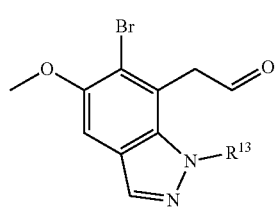

B-2-11

(11) continuing to reduce the compound B-2-11 to the alcohol B-2-12,

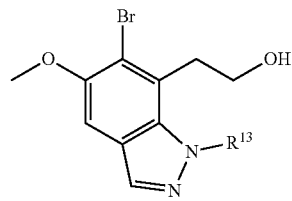

B-2-12

(12) activating the hydroxyl group in the compound B-2-12 while removing the protective group $R^{13}$, to obtain the compound B-2-13,

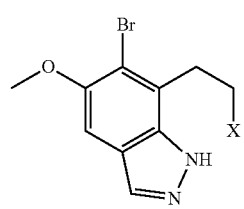

B-2-13

(13) subjecting the compound B-2-13 to ring closure under the action of a base, to obtain the compound B-2-14,

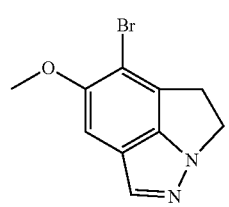

B-2-14

(14) demethylating the compound B-2-14 under the action of an acid, to obtain the phenol B-2-15,

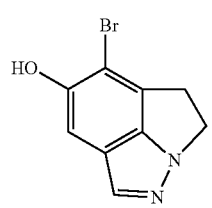

B-2-15

(15) reacting the compound B-2-15 with the compound 8 under a basic condition,

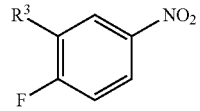

8 to obtain the compound B-2-16,

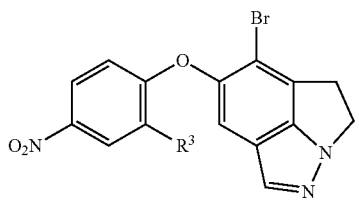
B-2-16

(16) coupling the compound B-2-16, such as coupling with an organoboron reagent under palladium catalysis, to obtain the compound B-2-17,

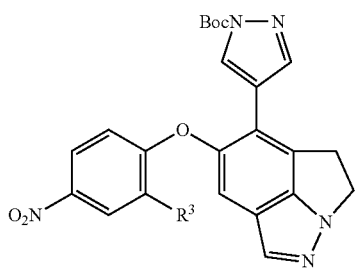
B-2-17

(17) reducing the nitro group in the compound B-2-17 to obtain the compound B-2-18,

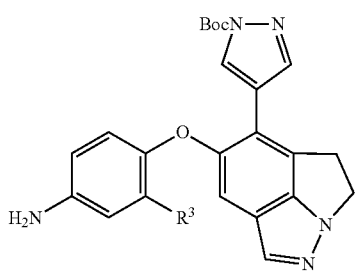
B-2-18

(18) subjecting any product from the above steps 13-17 to oxidative aromatization, and the compound B-2-19 can be obtained according to the same synthetic route described above,

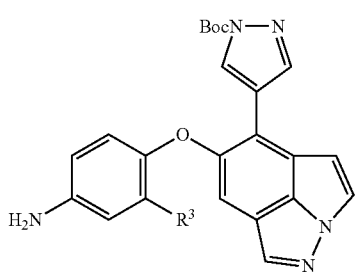
B-2-19 wherein $R^3$ is as defined above; wherein $R^{12}$ is selected from $C_{1-6}$ alkyl, such as methyl; $R^{13}$ is a N protecting group, such as but not limited to THP; $R^{14}$ is an OH activation group, such as but not limited to Ms; X is a leaving group group, such as OMs, OTs, chlorine, bromine, preferably chlorine.

When $R^5$ in the compound of formula D is not H, the compound of formula D may be a compound of formula D-2:

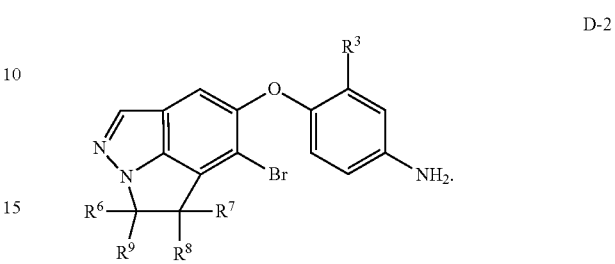
D-2

The compound of formula D-2 can be prepared by hydrogenating the compound of formula 23, for example, by reacting in the presence of palladium on carbon.

The compounds of formula II and the compounds of formula III of the present disclosure can be similarly prepared by those skilled in the art with reference to the above synthetic routes. Unless specifically stated, the raw materials or intermediates used in the above synthetic routes can be commercially obtained by those skilled in the art or conventionally obtained by methods known in the art.

The Suzuki coupling reaction described herein is to react a halogenated aromatic hydrocarbon (such as brominated aromatic hydrocarbons) with an organic boron reagent (such as aryl borate or aryl boronic acid) in the presence of a palladium catalyst (preferably PdCl$_2$(dppf) or PdCl$_2$Di-t-BPF) under the known Suzuki coupling reaction conditions. The aryl borate is preferably

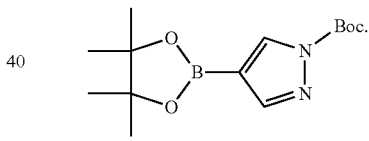

The organoboron reagents used herein are prepared by methods known in the art.

The term "condensing agent" as used herein includes but is not limited to carbodiimide condensing agents, such as 1-ethyl-(3-dimethylaminopropyl)carbodiimide (EDCI), dicyclohexyl carbodiimide (DCC), diisopropylcarbodiimide (DIC), phosgene derivatives such as N,N'-carbonyldiimidazole (CDI) or isobutyl chloroformate, phosphorus compounds such as n-propane phosphonic anhydride (PPA), diethyl cyanophosphonate, diphenylphosphoryl azide (DPPA), bis(2-oxo-3-oxazolidinyl) phosphoryl chloride, benzotriazol-1-yloxy tri(dimethylamino)phosphonium hexafluorophosphate or benzotriazole-1-yloxy tris(pyrrolidinyl) phosphonium hexafluorophosphate (PyBOP), uronium compounds such as O-(7-azabenzotriazol-1-yl)-N,N,N'N'-tetramethyluronium hexafluorophosphate (HATU), O-(benzotriazol-1-yl)-N,N,N',N'-tetramethyluronium hexafluorophosphate (HBTU), O-(1H-6-chlorobenzotriazol-1-yl)-1,1,3,3-tetramethyluronium tetrafluoroborate (TCTU), 2-(2-oxo-1-(2H)-pyridyl)-1,1,3,3-tetramethyluronium tetrafluoroborate (TPTU), any of the reagents is optionally used in combination with other adjuvants, such as 1-hydroxybenzotriazole (HOBt) or N-hydroxysuccinimide (HOSu), and a base such as alkali metal carbonates such as sodium carbonate or potassium carbonate, or tertiary amine bases such as triethylamine, N,N-diisopropylethylamine, N-methylmorpholine (NMM), N-methylpiperidine (NMP), pyridine or 4-N,N-dimethylaminopyridine (DMAP). The preparation of the compounds of formula I is further detailed in the following general synthetic methods and examples.

General Synthetic Methods

The compounds of formula I, II, and III of the present disclosure or their solvates or pharmaceutically acceptable salts can be prepared by a variety of methods, including the methods given below, the methods given in the examples, or similar methods. The following illustrates general synthetic schemes for the synthesis of the compounds of the present disclosure. Suitable reaction conditions for each reaction step are known to those skilled in the art or can be routinely determined. The raw materials and reagents used in the preparation of these compounds are generally commercially available, or can be prepared by the methods described below, methods similar to those given below, or methods known in the art. If necessary, the raw materials and intermediates in the synthesis reaction process can be separated and purified by conventional techniques, including but not limited to filtration, distillation, crystallization, chromatography etc. The materials can be characterized by conventional methods including physical constants and spectral data.

Those skilled in the art can recognize whether there are stereocenters in the compounds of formula I, II, and III. At all stages of the reaction, the resulting mixture of isomers can be separated into individual isomers, such as diastereomers or enantiomers, or into any desired mixture of isomers, such as for mixtures of racemates or diastereomers, see for example "*Stereochemistry of Organic Compounds*" by E. L. Eliel, S. H. Wilen, and L. N. Mander (Wiley-Interscience, 1994).

The process steps used to synthesize the compounds of the present disclosure can be under reaction conditions known per se (including those specifically mentioned), in the absence or usually in the presence of a solvent or diluent (including, for example, those solvents or diluents that are inert to the reagents used and can dissolve the reagents used), in the absence or presence of catalysts, condensing agents or neutralizing agents (for example, ion exchangers, such as cation exchangers, such as H+ form), depending on the properties of the reaction and/or the reactants at a reduced, normal or elevated temperature (e.g., about $-100°$ C. to about $190°$ C., including, for example, about $-78°$ C. to about $150°$ C., for example, about $0°$ C. to about $125°$ C., room temperature, $-20$ to $40°$ C. or reflux temperature), under atmospheric pressure or in a closed container, under pressure when appropriate, and/or under an inert atmosphere such as argon or nitrogen.

Unless otherwise stated in the description of the method, solvents suitable for any particular reaction include: those specifically mentioned, or, for example, water; esters, such as lower alkanoic acid lower alkyl esters, such as ethyl acetate; ethers, such as aliphatic ethers, such as diethyl ether, or cyclic ethers, such as tetrahydrofuran or dioxane; liquid aromatic hydrocarbons, such as benzene or toluene; alcohols, such as methanol, ethanol, or 1- or 2-propanol; nitriles, such as acetonitrile; halogenated hydrocarbons, such as dichloromethane or chloroform; amides, such as dimethylformamide or dimethylacetamide; bases, such as heterocyclic nitrogen bases, such as pyridine or N-methyl pyrrolidin-2-one; carboxylic acid anhydrides, such as lower alkanoic acid anhydrides, such as acetic anhydride; cyclic, linear or branched hydrocarbons, such as cyclohexane, hexane or isopentane; or mixtures of these solvents, such as aqueous solutions. Such solvent mixtures can also be used for workup, for example by chromatography or partitioning.

The present disclosure also relates to a preparation method in which a compound that can be obtained in the form of an intermediate in each of the preparation methods described above and any step in the following processes is used as a starting material and the remaining process steps are carried out, or in which the starting materials are formed in situ under the reaction conditions or are used in the form of derivatives, for example in protected form or salt form, or the compounds obtainable according to the method of the disclosure are produced under the conditions of the method and are further processed in situ.

Scheme 1 below illustrates a general synthetic route that can be used to prepare the compounds of formula I. Each variable of the general formula in the following process has the same meaning as above, unless otherwise stated. Wherein, when $R^4$ in the compound of formula A is F, the compound of formula A is a compound of formula A-1.

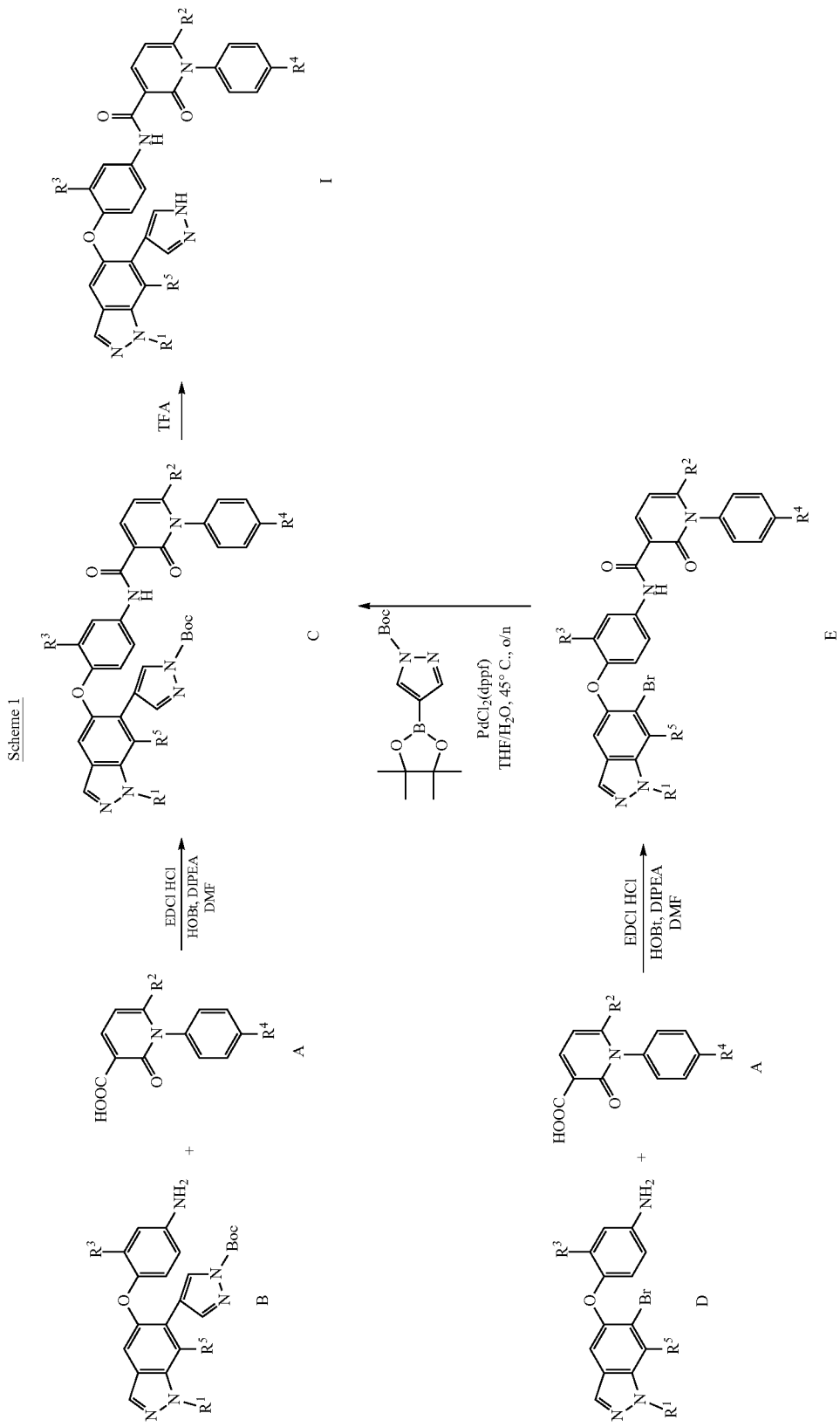
Scheme 1

The following schemes 2 to 5 illustrate the synthetic route of the compound of formula A during the synthesis of the compound of formula I, and the synthesis of the intermediates further used therein.
Scheme 2
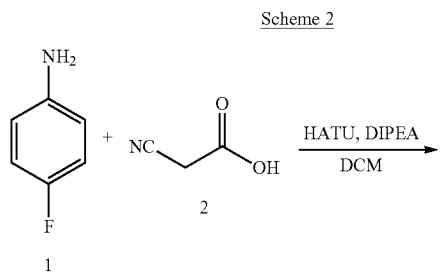
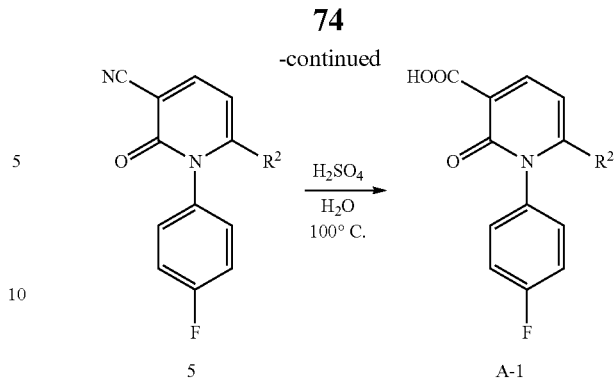
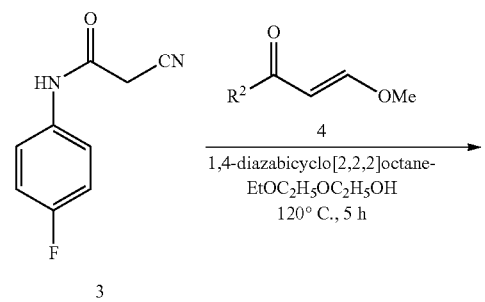
Scheme 3
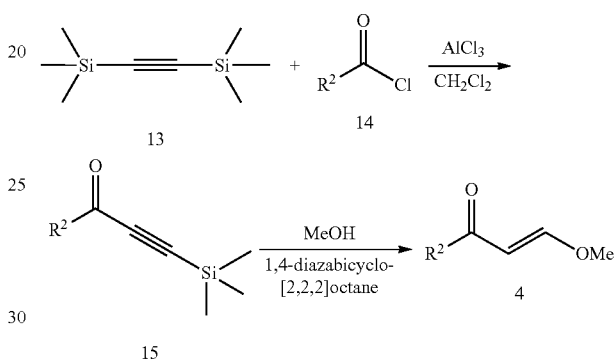
Scheme 4
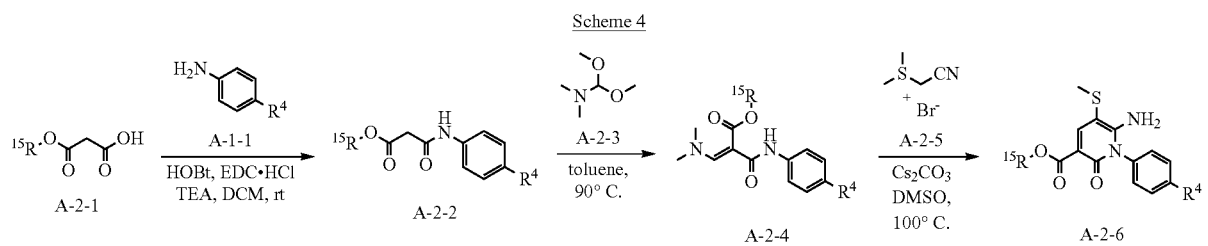
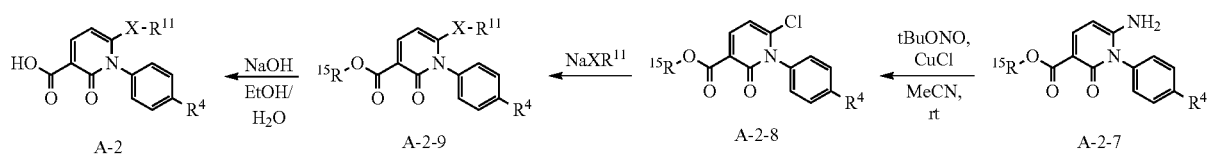

Scheme 5
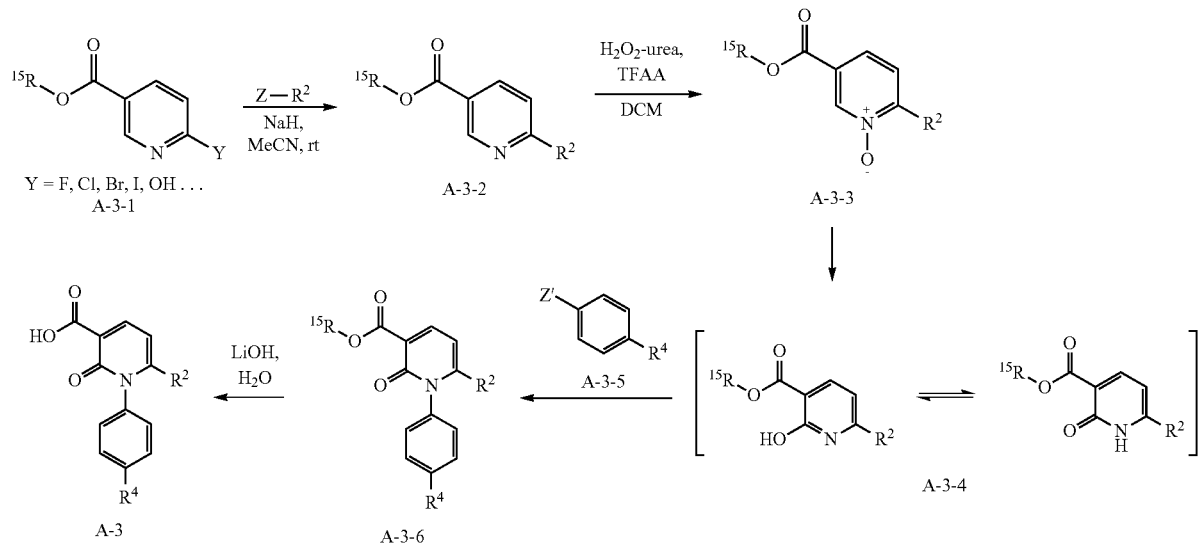
The following schemes 6 to 8 illustrate the synthetic routes of the compounds of formula B-1, formula D-1 and formula B-2 and their specific embodiments B-2-18 and B-2-19 in the synthesis process of the compound of formula I, and the synthesis of intermediates further used therein.
Scheme 6
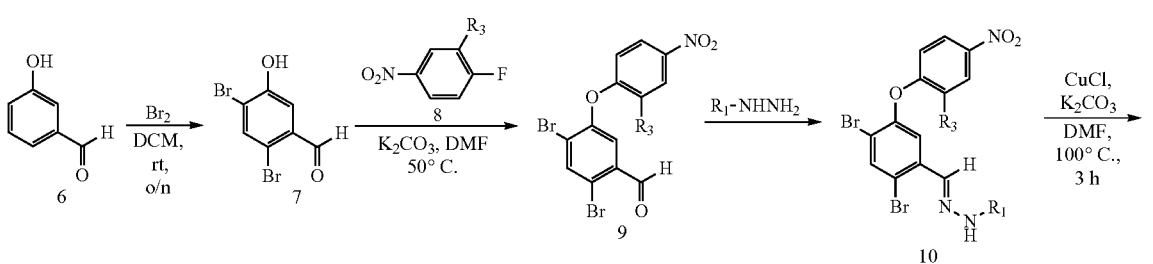
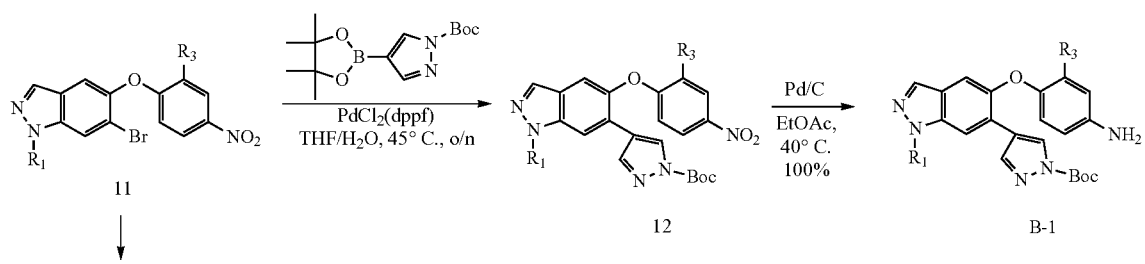
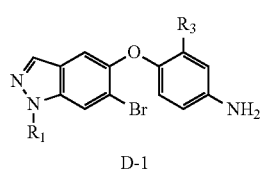

Scheme 7
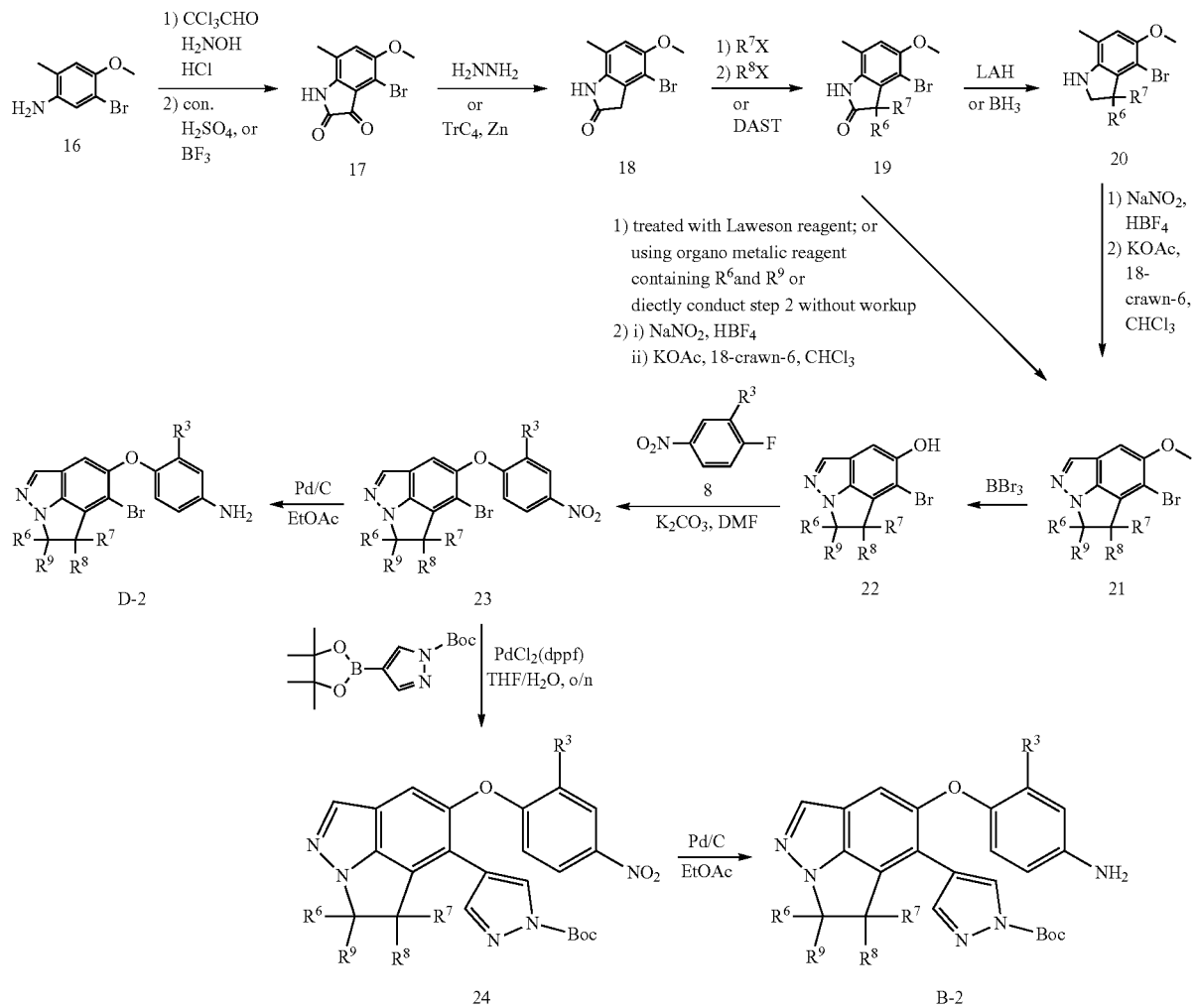
Scheme 8
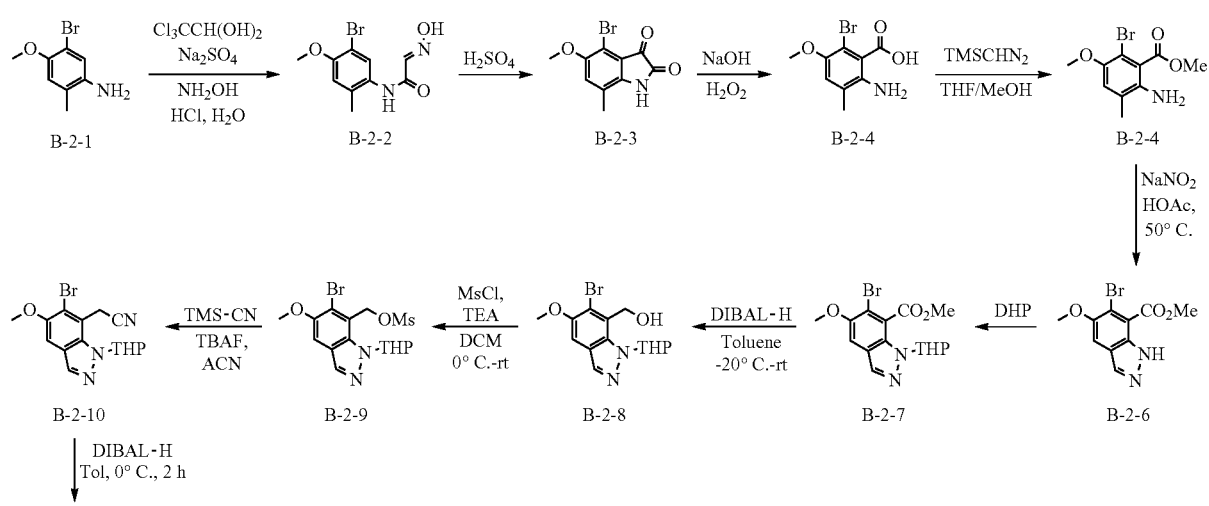

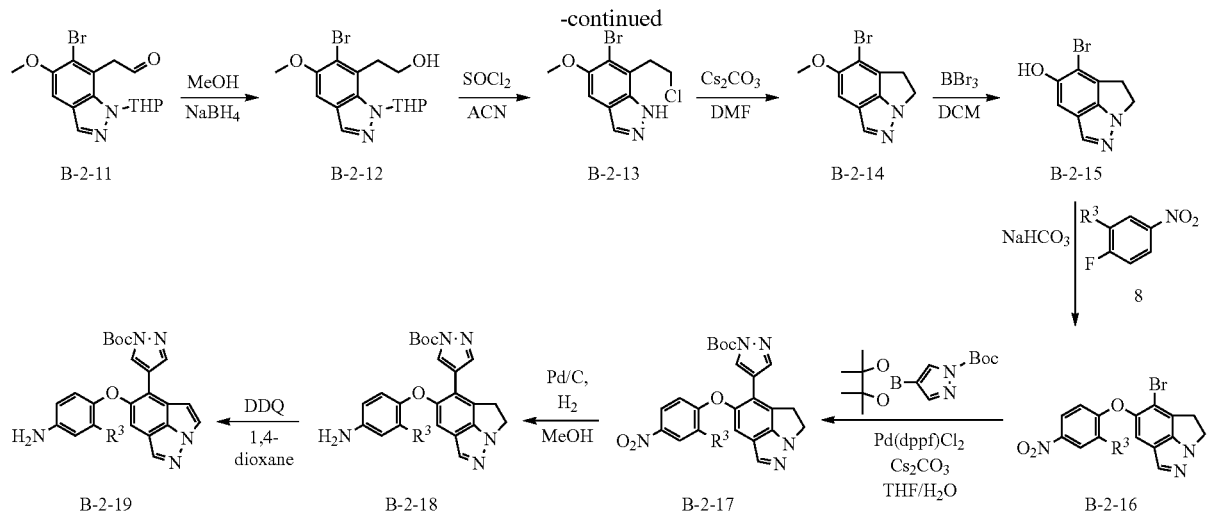

The compound of formula II and the compound of formula III of the present disclosure can be similarly prepared by those skilled in the art with reference to the above-mentioned procedures.

In the preparation methods of the present disclosure and the above-mentioned processes, when necessary, for example, the reaction material contains a functional group that is unstable or reactive under the reaction conditions of the reaction step, then a method known in the art can be applied before the critical step, to introduce a suitable protecting group (T. W. Greene and P. G. M. Wuts, "Protective Groups in Organic Synthesis", 5th edition, Wiley, New York 2014). Such protecting groups can be removed at a later stage of the synthesis using standard methods known in the art. Examples of amino protecting groups include Boc (tert-butoxycarbonyl), Pmb (p-methoxybenzyl), Fmoc (9-fluorenylmethoxycarbonyl), and Cbz (benzyloxycarbonyl).

The experimental materials and reagents used in the above synthesis methods and procedures, unless otherwise specified, can be obtained from commercial channels, prepared according to the methods of the prior art, or prepared according to methods similar to those disclosed in this application. The synthetic conditions used in the above synthetic methods and procedures, unless otherwise specified, can be routinely determined by those skilled in the art.

The technical and scientific terms used herein that are not specifically defined have the meanings commonly understood by those skilled in the art to which the present disclosure belongs.

The general or preferred definitions of designated features in various enumerated embodiments of the present disclosure can be combined with general or preferred definitions of other designated features to obtain additional embodiments of the present disclosure. It is as if the solutions obtained by combining these mutually are listed specifically and one by one in this article, unless the context clearly shows otherwise.

Unless there is an obvious error in the structural formula, when the chemical name of any compound of the present disclosure is inconsistent with the given structural formula, the structural formula shall prevail.

In this specification, several prior publications are cited. These publications are not considered to be relevant to the patentability of the present disclosure, but their entire contents are incorporated herein by reference. The reference to any prior publication (or information derived therefrom) in this specification is not and should not be regarded as confirmation or recognition or any form of inspiration, that is, the corresponding prior publication (or information derived therefrom) constitutes common knowledge in the technical field involved in this specification.

DESCRIPTION OF THE FIGURES

FIG. 1: Anti-tumor activity of the compounds of the present disclosure in a KM12 xenograft mouse model. FIG. 1-A shows the effect of the compounds of the present disclosure on tumor volume; FIG. 1-B shows the concentrations of the compounds of the present disclosure in plasma and tumor tissue 12 days after administration; FIG. 1-C shows the concentrations of the compounds of the disclosure in plasma and tumor tissue.

EXAMPLES

Figure 2:
FIG. 2: Comparison of the activity profile of the compound of Example 12 of the present disclosure and the prior art Merestinib compound.

The present disclosure will be further illustrated in conjunction with the examples as follows. It should be noted that the following examples cannot be recognized as a limitation to the protection scope of the present disclosure.

The experimental methods that do not indicate specific conditions in the following examples usually follow the conventional conditions for this type of reaction or the conditions recommended by the manufacturer. Unless otherwise specified, percentages and parts are percentages by weight and parts by weight. Unless otherwise specified, ratios of the liquid are by volume.

The experimental materials and reagents used in the following examples can be obtained from commercial channels, prepared according to the methods of prior art, or prepared according to a method similar to that disclosed in the present application, unless otherwise specified.

In the following examples, $^1$H-NMR spectra are recorded with Bruker 400 MHz NMR and Agilent 500 MHz NMR nuclear magnetic resonance instruments, and chemical shifts are expressed in δ (ppm); mass spectroscopy is recorded using Agilent 1290 liquid chromatography+6120B mass spectrometry LCMS instrument.

Abbreviations

ACN(MeCN) acetonitrile
Ar argon
BBr$_3$ boron tribromide
tBuONO tert-butyl nitrite
CDCl$_3$ deuterated chloroform
Cs$_2$CO$_3$ cesium carbonate
CuCl cuprous chloride
DCM dichloromethane
DIBAL-H diisobutyl aluminum hydride
DIPEA N,N-diisopropylethylamine
DMF dimethylformamide
DMF-DMA N,N-dimethylformamide dimethyl acetal
DMSO dimethyl sulfoxide
DMSO-d$_6$ deuterated dimethyl sulfoxide
ESI electrospray ionization
EA(EtOAc) ethyl acetate
EDCI 1-ethyl-(3-dimethylaminopropyl)carbodiimide
EtOH ethanol
FaSSGF fasted state simulated gastric fluids
FaSSIF fasted state simulated intestinal fluid
FeSSIF fed state simulated intestinal fluid
h hour
HATU O-(7-azabenzotriazol-1-yl)-N,N,N',N'-tetramethyluronium hexafluorophosphate
HCl hydrochloric acid or hydrogen chloride
HOBt 1-hydroxybenzotriazole
HPLC high performance liquid chromatography
H$_2$O water
K$_3$PO$_4$ potassium phosphate
LCMS liquid chromatography-mass spectrometry
LiOH lithium hydroxide
MeOH methanol
MHz megahertz
MS mass spectrometry
MsCl methanesulfonyl chloride
NaH sodium hydride
NaHCO$_3$ sodium bicarbonate
NaOH sodium hydroxide
NaOMe sodium methoxide
Na$_2$SO$_4$ sodium sulfate
NMR nuclear magnetic resonance
PE petroleum ether
Pd/C palladium/carbon
PdCl$_2$(dbpf) [1,1'-bis(tert-butylphosphino)ferrocene]palladium dichloride
PdCl$_2$(dppf) [1,1'-bis(diphenylphosphino)ferrocene]palladium dichloride
o/n overnight
rt room temperature
SOCl$_2$ thionyl chloride
SiO$_2$ silica, silica gel
TBAF tetra-n-butylammonium fluoride
TEA triethylamine
TEMPO tetramethylpiperidine nitrogen oxide
TFA trifluoroacetic acid
TMS-CN trimethylsilyl cyanide
TFAA trifluoroacetic anhydride
THF tetrahydrofuran
TLC thin layer chromatography
TMSCHN$_2$ trimethylsilyldiazomethane

SYNTHESIS EXAMPLES

Each abbreviation in the following synthesis examples has the meaning commonly understood by one skilled in the art. Unless otherwise stated, all temperatures are given in degrees Celsius; all reagents are commercially available and used without further purification.

Preparation of Intermediate 1:
2,4-dibromo-5-hydroxybenzaldehyde

Bromine (6.72 g, 84 mmol) was slowly added dropwise to a solution of 3-hydroxybenzaldehyde (4.48 g, 40 mmol) in dichloromethane (80 mL) at 20° C. The resulting reaction mixture was stirred at room temperature for 24 hours, and then 15% sodium thiosulfate aqueous solution (40 mL) was added at 40° C. to quench the reaction. The precipitated product was washed with water and dried to obtain 4.6 g of solid. $^1$H NMR (400 MHz, DMSO-d$_6$) δ 11.17 (s, 1H), 10.16-10.06 (m, 1H), 8.01 (d, J=2.2 Hz, 1H), 7.41 (d, J=2.2 Hz, 1H). MS [M+H]$^+$: 279.0.

Preparation of Intermediate 2:
2,4-dibromo-5-(2-fluoro-4-nitrophenoxy) benzaldehyde To a solution of 2,4-dibromo-5-hydroxybenzaldehyde (Intermediate 1, 4.5 g, 16 mmol) in N,N-dimethylformamide (50 mL) was added potassium carbonate powder (3.26 g, 24 mmol) and 1,2-difluoro-4-nitrobenzene (2.68 g, 16.9 mmol), the resulting reaction mixture was stirred at 50° C. for 6 hours, TLC showed that the reaction was complete. The reaction mixture was extracted three times with ethyl acetate (30 mL each time), washed with water five times, dried, and evaporated under reduced pressure to remove the solvent to obtain 5.6 g of a yellow solid. $^1$H NMR (400 MHz, CDCl$_3$) δ 10.18 (s, 1H), 8.08 (dd, J=10.1, 2.5 Hz, 1H), 7.99 (d, J=9.2 Hz, 1H), 7.97 (s, 1H), 7.44 (s, 1H), 6.95 (t, J=8.4 Hz, 1H).

Preparation of Intermediate 3: (E)-1-(2,4-dibromo-5-(2-fluoro-4-nitrophenoxy) benzylidene)-2-isopropylhydrazine To a solution of 2,4-dibromo-5-(2-fluoro-4-nitrophenoxy) benzaldehyde (Intermediate 2, 2.2 g, 5.3 mmol) in N,N-dimethylformamide (50 mL) was added isopropylhydrazine (0.641 g, 5.8 mmol), and the resulting reaction mixture was stirred at 20° C. for 0.5 hours. TLC showed that the reaction was complete. The reaction mixture was extracted three times with ethyl acetate (30 mL each time), washed with water 5 times, dried and evaporated under reduced pressure to remove the solvent to obtain 2.4 g of a yellow solid, which was directly used in the next reaction.

Preparation of Intermediate 4: 6-bromo-5-(2-fluoro-4-nitrophenoxy)-1-isopropyl-1H-indazole To a N$_2$ protected solution of (E)-1-(2,4-dibromo-5-(2-fluoro-4-nitrophenoxy)benzylidene)-2-isopropylhydrazine (Intermediate 3, 2.4 g, 5 mmol) in N,N-dimethylformamide was added potassium carbonate powder (1.1 g, 8 mmol) and cuprous chloride (0.08 g, 0.8 mmol), the resulting reaction mixture was stirred at 100° C. for 3 hours, TLC showed that the reaction was complete. The reaction mixture was cooled to room temperature and extracted three times with ethyl acetate (30 mL each time), washed with water five times, dried, and evaporated under reduced pressure to remove the solvent. The crude product was purified by a silica gel column chromatography, eluted with ethyl acetate/petroleum ether (1:20 to 1:10) to obtain 0.7 g of a yellow solid. $^1$H NMR (400 MHz, CDCl$_3$) δ 8.13 (d, J=10.3 Hz, 1H), 8.01 (s, 1H), 7.83 (s, 1H), 7.45 (s, 1H), 6.74 (t, J=8.5 Hz, 1H), 4.83 (dt, J=13.0, 6.5 Hz, 1H), 1.64 (d, J=6.6 Hz, 6H). MS [M+H]$^+$: 394.0.

Preparation of Intermediate 5: 6-bromo-5-(2-fluoro-4-nitrophenoxy)-1-methyl-1H-indazole The intermediate was prepared according to the synthetic route of Intermediate 4, using Intermediate 2 and methylhydrazine. MS [M+H]$^+$: 366.0.

Preparation of Intermediate 6: 6-bromo-5-(2-fluoro-4-nitrophenoxy)-1-ethyl-1H-indazole The intermediate was prepared according to the synthetic route of Intermediate 4, using Intermediate 2 and ethylhydrazine. $^1$H NMR (400 MHz, CDCl$_3$) δ 7.98 (dd, J=10.3, 2.5 Hz, 1H), 7.84 (s, 1H), 7.79 (d, J=9.1 Hz, 1H), 7.66 (s, 1H), 7.39 (s, 1H), 6.58 (t, J=8.5 Hz, 1H), 4.30 (q, J=7.2 Hz, 2H), 1.42 (t, J=7.2 Hz, 3H).

Preparation of Intermediate 7: N-(4-fluorophenyl)-2-cyanoacetamide

To a solution of 4-fluoroaniline (6.6 g, 56 mmol) in dichloromethane (200 mL) was added HATU (25 g, 75 mmol), N,N-diisopropylethylamine (21.6 g, 166 mmol) and 2-cyanoacetic acid (5.6 g, 75 mmol), the resulting reaction mixture was stirred at room temperature for 2 hours, then washed with saturated aqueous ammonium chloride solution, and dried. The crude product obtained by concentration was purified with a silica gel column and eluted with ethyl acetate-petroleum ether (1:5 to 2:1) to obtain 5 g of a white solid. $^1$H NMR (400 MHz, DMSO-d$_6$) δ 10.38 (s, 1H), 7.56 (dd, J=8.8 Hz, 4.9 Hz, 2H), 7.18 (t, J=8.8 Hz, 2H), 3.90 (s, 2H). MS [M+H]$^+$: 179.1.

Preparation of Intermediate 8: 1-trimethylsilyl-pent-1-yn-3-one

To a solution of bistrimethylsilylacetylene (5.6 g, 35 mmol) in dichloromethane at 0° C. was added propionyl chloride (2.79 g, 30 mmol). The resulting reaction mixture was stirred for 10 minutes and then added with aluminum trichloride (4.8 g, 36 mmol), further stirred at 0° C. for 2 hours, then naturally warmed to room temperature, and stirred for another 2 hours. The reaction mixture was poured into a 10% hydrochloric acid (70 mL) solution in ice-water and stirred for 10 minutes. After the two phases were separated, the aqueous phase was extracted three times with dichloromethane (25 mL each time), dried and evaporated under reduced pressure to remove the solvent to obtain a crude brown oil product, which was directly used in the next reaction.

Preparation of Intermediate 9: (E)-1-methoxy-pent-1-en-3-one

To a solution of 1-trimethylsilyl-pent-1-yn-3-one (Intermediate 8, all crude products) in methanol (20 mL) was slowly added 1,4-diazabicyclo[2,2,2]Octane (6.72 g, 60 mmol), the resulting reaction mixture was stirred at room temperature for 20 minutes and then concentrated, then diluted with ethyl acetate (20 mL), washed twice with saturated brine (10 mL each time), dried, and evaporated under reduced pressure to remove solvent. The crude product was purified by a silica gel column and eluted with ethyl acetate-petroleum ether (1:10) to obtain 2.1 g of the product. $^1$H NMR (400 MHz, CDCl$_3$) δ 7.62 (d, J=12.7 Hz, 1H), 5.60 (d, J=12.7 Hz, 2.4 Hz, 1H), 3.71 (q, J=7.8 Hz, 3H), 1.11 (t, J=7.8 Hz, 3H).

Preparation of Intermediate 10: (E)-1-methoxy-4-methyl-pent-1-en-3-one

The intermediate was prepared from isobutyryl chloride according to the synthetic route of Intermediate 9. $^1$H NMR (400 MHz, CDCl$_3$) δ 7.61 (d, J=12.5, 1H), 5.62 (d, J=12.5, 1H), 2.72-2.56 (m, 1H), 1.12-1.09 (d, 6H).

Preparation of Intermediate 11: (E)-1-cyclopropyl-3-methoxy-prop-2-en-1-one

The intermediate was prepared from cyclopropylformyl chloride according to the synthetic route of Intermediate 9. $^1$H NMR (400 MHz, CDCl$_3$) δ 7.64 (d, J=12.6 Hz, 1H), 5.72 (d, J=12.6 Hz, 1H), 3.72 (d, J=4.7 Hz, 3H), 1.93 (d, J=4.5 Hz, 1H), 1.10-1.02 (m, 2H), 0.91-0.81 (m, 2H).

Preparation of Intermediate 12: 1-(4-fluorophenyl)-6-methyl-3-cyano-2-oxo-1,2-dihydropyridine To a solution of N-(4-fluorophenyl)-2-cyanoacetamide (Intermediate 7, 1 g, 5.6 mmol) in diethylene glycol monoethyl ether (20 mL) was added 1,4-diazabicyclo[2,2,2]octane (0.62 g, 5.6 mmol) and (E)-1-methoxy-but-1-en-3-one (0.84 g, 8.4 mmol), the resulting reaction mixture was stirred at 120° C. for 14 hours. After cooling to room temperature, it was washed with 1N hydrochloric acid and saturated sodium chloride aqueous solution. The crude product was purified with a silica gel column and eluted with ethyl acetate-petroleum ether (1:1) to obtain 0.7 g of yellow solid product. $^1$H NMR (400 MHz, CDCl$_3$) δ 7.81 (d, J=7.4 Hz, 1H), 7.26 (t, J=7.7 Hz, 2H), 7.22-7.16 (m, 2H), 6.27 (d, J=7.4 Hz, 1H), 2.09 (s, 3H). MS [M+H]$^+$: 229.1.

Preparation of Intermediate 13: 1-(4-fluorophenyl)-6-methyl-2-oxo-1,2-dihydropyridine-3-carboxylic acid To 1-(4-fluorophenyl)-6-methyl-3-cyano-2-oxo-1,2-dihydropyridine (Intermediate 12, 0.7 g) was added concentrated sulfuric acid/water (1 mL/1 mL), the resulting reaction mixture was stirred at 100° C. for 15 hours, cooled to room temperature, and extracted with ethyl acetate three times (20 mL each time), and then washed with a saturated aqueous sodium chloride solution. After the solvent was evaporated under reduced pressure, the crude product was dissolved in ethanol (2 mL), added with 2N sodium hydroxide solution, and washed twice with ethyl acetate (10 mL each time). The aqueous solution was acidified with 1N hydrochloric acid, precipitated, filtered, and dried to obtain 0.5 g of the product. $^1$H NMR (400 MHz, DMSO-d$_6$) δ 8.43 (d, J=7.5 Hz, 1H), 7.54 (dd, J=8.8 Hz, 5.1 Hz, 2H), 7.46 (t, J=8.7 Hz, 2H), 6.82 (d, J=7.6 Hz, 1H), 2.11 (s, 3H). MS [M+H]$^+$: 248.1.

Preparation of Intermediate 14: 1-(4-fluorophenyl)-6-ethyl-2-oxo-1,2-dihydropyridine-3-carboxylic acid The intermediate was prepared according to the synthetic route of Intermediate 13 using Intermediate 7 and Intermediate 9. $^1$H NMR (400 MHz, DMSO-d$_6$) δ 14.23 (s, 1H), 8.45 (dd, J=7.7, 2.6 Hz, 1H), 7.58-7.49 (m, 2H), 7.45 (t, J=10.0 Hz, 2H), 6.76 (dd, J=7.8, 2.5 Hz, 1H), 2.31 (q, J=7.4 Hz, 2H), 1.05 (t, J=7.4 Hz, 3H). MS [M+H]$^+$: 262.3.

Preparation of Intermediate 15: 1-(4-fluorophenyl)-6-isopropyl-2-oxo-1,2-dihydropyridine-3-carboxylic acid The intermediate was prepared according to the synthetic route of Intermediate 13 using Intermediate 7 and Intermediate 10. $^1$H NMR (400 MHz, DMSO-d$_6$) δ 8.47 (d, J=7.8 Hz, 1H), 7.58 (dd, J=8.8, 4.9 Hz, 2H), 7.46 (t, J=8.7 Hz, 2H), 6.86 (d, J=7.8 Hz, 1H), 2.46 (m, 1H), 1.13 (t, J=7.2 Hz, 6H). MS [M+H]$^+$: 276.3.

Preparation of Intermediate 16: 1-(4-fluorophenyl)-6-cyclopropyl-2-oxo-1,2-dihydropyridine-3-carboxylic acid The intermediate is prepared according to the synthetic route of Intermediate 13 using Intermediate 7 and Intermediate 11. $^1$H NMR (400 MHz, DMSO-d$_6$) δ 8.37 (d, J=7.8 Hz, 1H), 7.56 (d, J=4.3 Hz, 2H), 7.45 (t, J=8.6 Hz, 2H), 6.54 (d, J=8.0 Hz, 1H), 1.35 (m, 1H), 0.93 (m, 2H), 0.85 (m, 2H). MS [M+H]$^+$: 274.3.

Preparation of Intermediate 17: 1-(4-Fluorophenyl)-6-trifluoromethyl-2-oxo-1,2-dihydropyidine-3-carboxylic acid This intermediate is prepared according to the synthetic route of Intermediate 13, using Intermediate 7 and (E)-1-methoxy-4,4,4-trifluoro-1-buten-3-one (obtained by a method similar to the synthesis of Intermediate 9). $^1$H NMR (400 MHz, DMSO-d$_6$) δ 13.66 (s, 1H), 8.42 (d, J=7.4 Hz, 1H), 7.60-7.51 (m, 2H), 7.42 (t, J=8.7 Hz, 2H), 7.25 (d, J=7.5 Hz, 1H). MS [M+H]$^+$: 302.1.

Preparation of Intermediate 18: 6-bromo-5-(2-fluoro-4-aminophenoxy)-1-isopropyl-1H-indazole In a 100 mL round bottom flask was added 6-bromo-5-(2-fluoro-4-nitrophenoxy)-1-isopropyl-1H-indazole (Intermediate 4, 0.2 g, 0.5 mmol), 10% palladium on carbon (0.1 g) and ethyl acetate. The gas in the flask was replaced with hydrogen 5 times, and then stirred overnight at room temperature. TLC and LCMS showed that the reaction was complete to obtain single product. The palladium/carbon catalyst was removed by filtration, the filter cake was rinsed with ethyl acetate (25 mL), and the product obtained was directly used in the next reaction. MS [M+H]$^+$: 364.0.

Preparation of Intermediate 19: N-(3-fluoro-4-(1-isopropyl-6-bromo-1H-indazol-5-yloxy)phenyl)-6-methyl-2-oxo-1-(4-fluorophenyl)-1,2-dihydmpyridine-3-carboxamide In a 25 mL round bottom flask was added 6-bromo-5-(2-fluoro-4-aminophenoxy)-1-isopropyl-1H-indazole (Intermediate 18, 0.2 g, 0.5 mmol), 1-(4-fluorophenyl)-6-methyl-2-oxo-1,2-dihydropyridine-3-carboxylic acid (Intermediate 13, 0.15 g, 0.6 mmol), 1-ethyl-3-(3-dimethylaminopropyl) carbodiimide hydrochloride (0.215 g, 1.12 mmol), 1-hydroxybenzotriazole (0.105 g, 0.75 mmol), N,N-diisopropylethyl amine (0.325 g, 2.5 mmol) and N,N-dimethylformamide (4.5 mL), the mixture was stirred overnight at room temperature, then distributed in ethyl acetate (25 mL) and saturated aqueous sodium chloride solution (25 mL). The organic phase was separated and washed four times with saturated sodium chloride aqueous solution (25 mL each time), the aqueous phase was extracted three times with ethyl acetate (25 mL each time), the combined organic phase was dried, concentrated, and the crude product was purified with a silica gel column, eluted with ethyl acetate-petroleum ether (1:5 to 1:3) to obtain a yellow solid product. MS [M+H]$^+$: 593.1.

Preparation of Intermediate 20: N-(3-fluoro-4-(1-isopropyl-6-(1-Boc-pyrazol-4-yl)-1H-indazol-5-yloxy)phenyl)-6-methyl-2-oxo-1-(4-fluorophenyl)-1,2-dihydropyridine-3-carboxamide In a 25 mL round bottom flask was added N-(3-fluoro-4-(1-isopropyl-6-bromo-1H-indazol-5-yloxy)phenyl)-6-methyl-2-oxo-1-(4-fluorophenyl)-1,2-dihydropyridine-3-carboxamide (Intermediate 19, 0.5 mmol), tripotassium phosphate (0.223 g, 1.05 mmol), 1-Boc-pyrazole-4-boronic acid pinacol ester (0.182 g, 0.62 mmol), di-tert-butyl dicarbonate (0.022 g, 0.1 mmol), [1,1'-bis(diphenylphosphino)ferrocene]palladium dichloride (0.005 g, 0.0075 mmol), water (1 mL) and tetrahydrofuran (15 mL), the mixture was replaced with nitrogen 8 times, and then stirred at 45° C. overnight. The solvent was evaporated under reduced pressure, and the crude product was purified with a silica gel column, eluted with ethyl acetate-petroleum ether (1:3 to 1:2) to obtain 0.263 g of a yellow solid product. MS [M+H]$^+$: 680.2.

Preparation of Intermediate 21: N-(3-fluoro-4-(1-ethyl-6-(1-Boc-pyrazol-4-yl)-1H-indazol-5-yloxy)phenyl)-6-methyl-2-oxo-1-(4-fluorophenyl)-1,2-dihydmpyridine-3-carboxamide Intermediate 21 was prepared according to the synthetic route of Intermediate 20, using Intermediate 6 (6-bromo-5-(2-fluoro-4-nitrophenoxy)-1-ethyl-1H-indazole) and Intermediate 13 (1-(4-fluorophenyl)-6-methyl-2-oxo-1,2-dihydropyridine-3-carboxylic acid). MS [M+H]$^+$: 667.2.

Preparation of Intermediate 22: N-(3-Fluoro-4-(1-isopropyl-6-(1-Boc-pyrazol-4-yl)-1H-indazol-5-yloxy)phenyl)-6-isopropyl-2-oxo-1-(4-fluorophenyl)-1,2-dihydropyridine-3-carboxamide Intermediate 22 was prepared according the synthetic route of Intermediate 20, using Intermediate 4 (6-bromo-5-(2-fluoro-4-nitrophenoxy)-1-isopropyl-1H-indazole) and Intermediate 15 (1-(4-fluorophenyl)-6-isopropyl-2-oxo-1,2-dihydropyridine-3-carboxylic acid).

Preparation of Intermediate 23: N-(3-fluoro-4-(1-isopropyl-6-(1-Boc-pyrazol-4-yl)-1H-indazol-5-yloxy)phenyl)-6-trifluoromethyl-2-oxo-1-(4-fluorophenyl)-1,2-dihydropyridine-3-carboxamide Intermediate 23 was prepared according the synthetic route of Intermediate 20, using Intermediate 4 (6-bromo-5-(2-fluoro-4-nitrophenoxy)-1-isopropyl-1H-indazole) and Intermediate 17 (1-(4-fluorophenyl)-6-trifluoromethyl-2-oxo-1,2-dihydropyridine-3-carboxylic acid).

Preparation of Intermediate 24: 6-(1-Boc-pyrazol-4-yl(2-fluoro-4-nitrophenoxy)-1-methyl-1H-indazole In a 100 mL round bottom flask was added 6-bromo-5-(2-fluoro-4-nitrophenoxy)-1-methyl-1H-indazole (Intermediate 5, 2.334 g, 6.37 mmol), tripotassium phosphate (2.84 g, 13.4 mmol), 1-Boc-pyrazole-4-boronic acid pinacol ester (2.81 g, 9.6 mmol), di-tert-butyl dicarbonate (0.278 g, 1.27 mmol), [1,1'-bis(diphenylphosphino)ferrocene]palladium dichloride (0.25 g, 0.383 mmol), water (10 mL) and tetrahydrofuran (150 mL), the mixture was replaced with nitrogen 8 times, and then stirred at 45° C. overnight. The solvent was evaporated under reduced pressure, and the crude product was purified with a silica gel column, eluted with ethyl acetate-petroleum ether (1:3 to 1:2) to obtain 3.78 g of a yellow solid product. MS [M+H]$^+$: 454.2.

Preparation of Intermediate 25: 6-(1-Boc-pyrazol-4-yl)-5-(2-fluoro-4-aminophenoxy)-1-methyl-1H-indazole In a 250 mL round bottom flask was added 6-(1-Boc-pyrazol-4-yl)-5-(2-fluoro-4-nitrophenoxy)-1-methyl-1H-indazole (Intermediate 24, 1.89 g, 4.17 mmol), 10% palladium/carbon (1 g) and ethyl acetate (75 mL), replaced the gas in the flask with hydrogen 5 times, and then stirred at 40° C. for 1 hour. TLC and LCMS showed that the reaction was complete with a single product. The palladium/carbon was removed by filtration, and the solvent was evaporated under reduced pressure to obtain 1.2 g of the product which was directly used in the next reaction. MS [M+H]$^+$: 424.2.

Preparation of Intermediate 26: N-(3-fluoro-4-(1-methyl-6-(1-Boc-pyrazol-4-yl)-1H-indazol-5-yloxy)phenyl)-6-ethyl-2-oxo-1-(4-fluorophenyl)-1,2-dihydropyridine-3-carboxamide In a 25 mL round bottom flask was added 6-(1-Boc-pyrazol-4-yl)-5-(2-fluoro-4-aminophenoxy)-1-methyl-1H-indazole (Intermediate 25, 0.212 g, 0.5 mmol), 1-(4-fluorophenyl)-6-ethyl-2-oxo-1,2-dihydropyridine-3-carboxylic acid (Intermediate 14, 0.131 g, 0.5 mmol), 1-ethyl-3-(3-dimethylaminopropyl) carbodiimide hydrochloride (0.215 g, 1.12 mmol), 1-hydroxybenzotriazole (0.105 g, 0.75 mmol), N,N-diisopropylethylamine (0.325 g, 2.5 mmol) and N,N-dimethylformamide (4.5 mL), the mixture was stirred at room temperature overnight, and then distributed in ethyl acetate (25 mL) and saturated sodium chloride aqueous solution (25 mL). The organic phase was separated and washed four times with saturated sodium chloride aqueous solution (25 mL each time), the aqueous phase was extracted three times with ethyl acetate (25 mL each time), the combined organic phase was dried and concentrated, and the crude product was purified with silica gel column, eluted with ethyl acetate-petroleum ether (1:1 to 2:1) to obtain a yellow solid product. MS [M+H]$^+$: 667.2.

Preparation of Intermediate 27: N-(3-fluoro-4-(1-methyl-6-(1-Boc-pyrazol-4-yl)-1H-indazol-5-yloxy)phenyl)-6-isopropyl-2-oxo-1-(4-fluorophenyl)-1,2-dihydropyridine-3-carboxamide Intermediate 27 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 15 (1-(4-fluorophenyl)-6-isopropyl-2-oxo-1,2-dihydropyridine-3-carboxylic acid). MS [M+H]$^+$: 681.2.

Preparation of Intermediate 28: N-(3-Fluor-4-(1-methyl-6-(1-Boc-pyrazol-4-yl)-1H-indazol-5-yloxy)phenyl)-6-cyclopropyl-2-oxo-1-(4-fluorophenyl)-1,2-dihydropyridine-3-carboxamide Intermediate 28 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 16 (1-(4-fluorophenyl)-6-cyclopropyl-2-oxo-1,2-dihydropyridine-3-carboxylic acid). MS [M+H]$^+$: 679.2.

Preparation of Intermediate 29: N-(3-fluoro-4-(1-methyl-6-(1-Boc-pyrazol-4-yl)-1H-indazol-5-yloxy)phenyl)-6-trifluoromethyl-2-oxo-1-(4-fluorophenyl)-1,2-dihydropyridine-3-carboxamide Intermediate 29 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 17 (1-(4-fluorophenyl)-6-trifluoromethyl-2-oxo-1,2-dihydropyridine-3-carboxylic acid). MS [M+H]$^+$: 707.2.

Preparation of Intermediate 30: 3-((4-fluorophenyl)amino)-3-oxo-propionic acid ethyl ester The mixture of monoethyl malonate (10 g, 8.93 mL, 75.69 mmol), 4-fluoroaniline (7.17 mL, 75.69 mmol), EDCI HCl (14.51 g, 75.69 mmol), HOBt (10.23 g, 75.69 mmol), TEA (21.04 mL, 151.38 mmol) and DCM (120 mL) was stirred at room temperature for 16 hours. The reaction was quenched with water (200 mL), acidified to pH=7 with concentrated hydrochloric acid, and extracted with ethyl acetate (3×200 mL). The organic phase was washed with saturated brine (200 mL) and dried over anhydrous Na$_2$SO$_4$. After filtration and concentration, a white solid (17.2 g, 75.7% yield) was obtained. The crude product was used directly in the next reaction without purification. $^1$H NMR (400 MHz, CDCl$_3$) δ 9.26 (s, 1H), 7.54-7.50 (m, 2H), 7.03 (dd, J=11.9, 5.4 Hz, 2H), 4.26 (q, J=7.1 Hz, 2H), 3.47 (s, 2H), 1.33 (t, J=7.2 Hz, 3H). MS-ESI [M+H]$^+$: 226.2.

Preparation of Intermediate 31: ethyl 3-dimethylamino-2-((4-fluorophenyl)carboxamido)acrylate To a solution of 3-((4-fluorophenyl)amino)-3-oxo-propionic acid ethyl ester (3 g, 13.32 mmol) in toluene (50 mL) was added DMF-DMA (2.65 mL, 19.98 mmol). The mixture was stirred at 90° C. for 2 hours. After the reaction mixture was concentrated, the crude product was recrystallized with ethyl acetate/petroleum ether (1:10, 22 mL) to obtain a white solid (1.71 g, 45.8% yield). $^1$H NMR (400 MHz, DMSO-d$_6$) δ 10.03 (s, 1H), 7.65-7.62 (m, 2H), 7.50-7.43 (m, 1H), 7.11 (t, J=8.8 Hz, 2H), 4.07 (q, J=6.9 Hz, 2H), 2.99 (s, 6H), 1.17 (t, J=7.0 Hz, 3H). MS-ESI [M+H]$^+$: 281.2.

Preparation of Intermediate 32: 6-amino-1-(4-fluorophenyl)-5-(methylthio)-2-oxo-1,2-dihydropyrindine-3-carboxylic acid ethyl ester To a solution of cyanomethyl dimethylsulfonium bromide (16.29 g, 89.48 mmol) in DMSO (250 mL) was added Cs$_2$CO$_3$ (72.88 g, 223.69 mmol), and stirred at room temperature for 0.5 hour, and then was added ethyl 3-dimethylamino-2-((4-fluorophenyl)carboxamido)acrylate. The mixture was heated to 100° C. and stirred for 16 hours. The reaction was quenched by adding water (300 mL), filtered, washed with water (2×100 mL), and the crude product was recrystallized with ethyl acetate/petroleum ether (1:2, 90 mL) to obtain a white solid (18 g, 74.9% yield). $^1$H NMR (400 MHz, DMSO-d$_6$) δ 8.15 (s, 1H), 7.39-7.31 (m, 2H), 7.30-7.26 (m, 2H), 7.00 (br, 2H), 4.09 (q, J=7.1 Hz, 2H), 2.20 (s, 3H), 1.19 (t, J=7.2 Hz, 3H). MS-ESI [M+H]$^+$: 323.0.

Preparation of Intermediate 33: ethyl 6-amino-1-(4-fluorophenyl)-2-oxo-1,2-dihydmpyridine-3-carboxylate To a solution of 6-amino-1-(4-fluorophenyl)-5-(methylthio)-2-oxo-1,2-dihydropyridine-3-carboxylic acid ethyl ester (1 g, 3.1 mmol) in THF (30 mL) was added PdCl$_2$ (55 mg, 0.31 mmol) and triethylsilane (0.99 mL, 6.20 mmol), and stirred at room temperature for 16 hours. After filtration and concentration, the reaction was washed with ethyl acetate (2×10 mL) to obtain a white solid 33 (0.5 g, 58.3% yield). $^1$H NMR (400 MHz, DMSO-d$_6$) δ 7.92 (d, J=8.8 Hz, 1H), 7.40-7.35 (m, 2H), 7.28-7.25 (m, 2H), 6.92 (br, 2H), 5.61 (d, J=8.8 Hz, 1H), 4.07 (q, J=7.2 Hz, 2H), 1.18 (t, J=7.2 Hz, 3H). MS-ESI [M+H]$^+$: 277.2.

Preparation of Intermediate 34: ethyl 6-chloro-1-(4-fluorophenyl)-2-oxo-1,2-dihydropyridine-3-carboxylate To a mixture of 6-amino-1-(4-fluorophenyl)-2-oxo-1,2-dihydropyridine-3-carboxylic acid ethyl ester (6 g, 21.7 mmol) and CuCl (2.6 g, 26.1 mmol) in ACN (50 mL) was added t-BuONO (4.8 mg, 35.8 mmol) dropwise, and stirred overnight at room temperature. After the reaction solution was concentrated, the crude product was purified with a silica gel column, eluted with a gradient of 0-20% ethyl acetate/dichloromethane to obtain 34 as a yellow solid (1.6 g, 25% yield). $^1$H NMR (400 MHz, DMSO-d$_6$) δ 8.122 (d, J=8.0 Hz, 1H), 7.46-7.39 (m, 4H), 6.70 (d, J=8.0 Hz, 1H), 4.22 (q, J=7.2 Hz, 2H), 1.25 (t, J=7.2 Hz, 3H). MS-ESI [M+H]$^+$: 295.9.

Preparation of Intermediate 35: 1-(4-fluorophenyl)-6-methoxy-2-oxo-1,2-dihydmpyridine-3-carboxylic acid To a mixture of 6-chloro-1-(4-fluorophenyl)-2-oxo-1,2-dihydropyridine-3-carboxylic acid ethyl ester (0.5 g, 1.69 mmol) in THF (20 mL) was added NaOMe (915 mg, 16.9 mmol), and stirred at room temperature for 2 hours. The reaction solution was quenched with 1N HCl (100 mL) and extracted with ethyl acetate (2×100 mL). The organic phase was washed with saturated brine (100 mL) and dried over anhydrous sodium sulfate. After filtration and concentration, the crude product was prepared by HPLC. A white solid (0.178 g, 40% yield) was obtained. $^1$H NMR (400 MHz, DMSO-d$_6$) δ 13.77 (s, 1H), 8.48 (d, J=8.8 Hz, 1H), 7.47-7.36 (m, 4H), 6.43 (d, J=8.8 Hz, 1H), 3.93 (s, 3H). MS-ESI [M+H]$^+$: 264.1.

Preparation of Intermediate 36: 1-(4-fluorophenyl)-6-ethoxy-2-oxo-1,2-dihydropyridine-3-carboxylic acid Intermediate 36 was prepared according to the synthetic route of Intermediate 35, from Intermediate 34 (6-chloro-1-(4-fluorophenyl)-2-oxo-1,2-dihydropyridine-3-carboxylic acid ethyl ester) and sodium ethoxide. $^1$H-NMR (400 MHz, DMSO-d$_6$) δ 13.80 (s, 1H), 8.46 (d, J=8.4 Hz, 1H), 7.48-7.39 (m, 4H), 6.43 (d, J=8.8 Hz, 1H), 4.29 (q, J=6.8 Hz, 2H), 1.16 (t, J=7.0 Hz, 3H). MS-ESI [M+H]$^+$: 278.1.

Preparation of Intermediate 37: 1-(4-fluorophenyl)-6-cyclopropoxy-2-oxo-1,2-dihydropyridine-3-carboxylic acid Intermediate 37 was prepared according to the synthetic route of Intermediate 35, from Intermediate 34 (6-chloro-1-(4-fluorophenyl)-2-oxo-1,2-dihydropyridine-3-carboxylic acid ethyl ester) and sodium hydride and cyclopropanol. $^1$H NMR (400 MHz, DMSO-d$_6$) δ 13.78 (s, 1H), 8.52 (d, J=8.8 Hz, 1H), 7.44-7.37 (m, 4H), 6.65 (d, J=8.4 Hz, 1H), 4.23-4.18 (m, 1H), 0.831 (t, J=6.4 Hz, 2H), 0.371 (t, J=6.4 Hz, 7.2 Hz, 2H). MS-ESI [M+H]$^+$: 290.0.

Preparation of Intermediate 38: 1-(4-fluorophenyl)-6-isopropoxy-2-oxo-1,2-dihydropyridine-3-carboxylic acid Intermediate 38 was prepared according to the synthetic route of Intermediate 35, from Intermediate 34 (6-chloro-1-(4-fluorophenyl)-2-oxo-1,2-dihydropyridine-3-carboxylic acid ethyl ester) and sodium hydride and isopropanol. $^1$H-NMR (400 MHz, DMSO-d$_6$) δ 13.801 (s, 1H), 8.436 (d, J=8.8 Hz, 1H), 7.442-7.354 (m, 4H), 6.468 (d, J=8.8 Hz, 1H), 4.967-4.876 (m, 1H), 1.180 (d, J=8.8 Hz, 6H). MS-ESI [M+H]$^+$: 292.0.

Preparation of Intermediate 39: 1-(4-fluorophenyl)-6-(2,2,2-trifluoroethoxy)-2-oxo-1,2-dihydropyidine-3-carboxylic acid Intermediate 39 was prepared according to the synthetic route of Intermediate 35, from Intermediate 34 (6-chloro-1-(4-fluorophenyl)-2-oxo-1,2-dihydropyridine-3-carboxylic acid ethyl ester) and sodium hydride and 2,2,2-trifluoroethanol. $^1$H NMR (400 MHz, DMSO-d$_6$) δ 13.68 (s, 1H), 8.52 (d, J=8.5 Hz, 1H), 7.54-7.32 (m, 4H), 6.51 (d, J=8.6 Hz, 1H), 5.05 (q, J=8.4 Hz, 2H). MS-ESI [M+H]$^+$: 332.0.

Preparation of Intermediate 40: 1-(4-fluorophenyl)-6-methylthio-2-oxo-1,2-dihydropyridine-3-carboxylic acid Intermediate 40 was prepared according to the synthetic route of Intermediate 35, from Intermediate 34 (6-chloro-1-(4-fluorophenyl)-2-oxo-1,2-dihydropyridine-3-carboxylic acid ethyl ester) and sodium thiomethoxide. The crude product was directly used in the next reaction. MS-ESI [M+H]$^+$: 280.0.

Preparation of Intermediate 41: 6-amino-1-(4-fluorophenyl)-2-oxo-1,2-dihydropyridine-3-carboxylic acid To 6-amino-1-(4-fluorophenyl)-2-oxo-1,2-dihydropyridine-3-carboxylic acid ethyl ester (1.0 g, 3.62 mmol) and ethanol (15 mL) was added NaOH (2.90 g, 72.39 mmol) and water (8 mL), and stirred at 60° C. for 24 hours. The reaction solution was concentrated and dissolved in water (30 mL), and extracted with DCM (3×50 mL). The aqueous solution was neutralized to pH 6.0 with concentrated HCl, and extracted with ethyl acetate (3×50 mL). The organic phase was dried over anhydrous sodium sulfate, filtered, and concentrated to obtain a yellow solid (0.450 g, 50% yield). The crude product was directly used in the next reaction. $^1$H NMR (400 MHz, DMSO-$d_6$) δ 13.75 (s, 1H), 8.00 (d, J=8.8 Hz, 1H), 7.45 (s, 2H), 7.43 (d, J=3.0 Hz, 2H), 7.22 (dd, J=50.1, 31.4 Hz, 2H), 5.95 (d, J=8.8 Hz, 1H). MS-ESI [M+H]$^+$: 249.0.

Preparation of Intermediate 42: 1-(4-fluorophenyl)-6-chloro-2-oxo-1,2-dihydropyridine-3-carboxylic acid To a mixture of 6-amino-1-(4-fluorophenyl)-2-oxo-1,2-dihydropyridine-3-carboxylic acid (0.45 g, 1.81 mmol) and CuCl (0.179 g, 1.81 mmol) in MeCN (10 mL) was added t-BuONO (0.62 ml, 2.99 mmol) dropwise, and stirred at room temperature for 3 days. The reaction was quenched with aqueous HCl (1N, 20 mL) and extracted with ethyl acetate (5×30 mL). After the organic phase was dried over anhydrous sodium sulfate, filtered, and concentrated, the crude product was subjected to HPLC to obtain a yellow solid (0.080 g, 16.5% yield). $^1$H NMR (400 MHz, CDCl$_3$) δ 13.31 (s, 1H), 8.55 (d, J=7.9 Hz, 1H), 7.32-7.27 (m, 4H), 6.80 (d, J=7.9 Hz, 1H). MS-ESI [M+H]$^+$: 267.9.

Preparation of Intermediate 43: 6-(Boc-amino)-1-(4-fluorophenyl)-2-oxo-1,2-dihydropyridine-3-carboxylic acid ethyl ester To a mixture of ethyl 6-amino-1-(4-fluorophenyl)-2-oxo-1,2-dihydropyridine-3-carboxylate (0.32 g, 1.16 mmol) in DCM (10 mL) was added TEA (0.32 mL, 2.32 mmol) and Boc$_2$O (0.53 mL, 2.32 mmol) dropwise, and stirred at room temperature for 16 hours. The reaction was quenched with water (10 mL) and extracted with ethyl acetate (3×20 mL). After the organic phase was dried over anhydrous sodium sulfate, filtered and concentrated, the crude product was purified with a silica gel column, eluted with a gradient of 1/10 to 1/5 to 1/2 ethyl acetate/dichloromethane to obtain a yellow solid (1.6 g, 25% yield). $^1$H NMR (400 MHz, CDCl$_3$) δ 8.32 (d, J=8.6 Hz, 1H), 7.34-7.26 (m, 4H), 7.12 (d, J=8.4 Hz, 1H), 6.17 (s, 1H), 4.33 (q, J=7.2 Hz, 2H), 1.44 (s, 9H), 1.35 (t, J=7.1 Hz, 3H). MS-ESI [M+H]$^+$: 377.1.

Preparation of Intermediate 44: 6-(Boc-amino)-1-(4-fluorophenyl)-2-oxo-1,2-dihydropyridine-3-carboxylic acid To a mixture of 6-(Boc-amino)-1-(4-fluorophenyl)-2-oxo-1,2-dihydropyridine-3-carboxylic acid ethyl ester (0.18 g, 0.48 mmol) in EtOH (2 mL) was added NaOH (0.382 g, 9.56 mmol) and water (2 mL) dropwise and stirred at room temperature for 64 hours. The reaction solution was diluted with water (10 mL) and extracted with DCM (2×10 mL). The aqueous phase was acidified with concentrated HCl to pH 6, and then extracted with ethyl acetate (4×10 mL). The organic phase was washed with saturated brine (10 mL), dried over anhydrous sodium sulfate, filtered, and concentrated to obtain a yellow solid (0.12 g, 72% yield). The crude product was used directly in the next reaction without purification. $^1$H NMR (400 MHz, CDCl$_3$) δ 13.36 (br s, 1H), 8.56 (d, J=8.8 Hz, 1H), 7.44-7.39 (m, 3H), 7.35-7.28 (m, 2H), 6.29 (s, 1H), 1.46 (s, 9H). MS-ESI [M+H]$^+$: 349.1.

Preparation of Intermediate 45: 6-(methylsulfoxide)-1-(4-fluorophenyl)-2-oxo-1,2-dihydropyrndine-3-carboxylic acid To a mixture of 6-(methylthio)-1-(4-fluorophenyl)-2-oxo-1,2-dihydropyridine-3-carboxylic acid ethyl ester (0.15 g, 0.54 mmol) in MeCN (3 mL) was added 30% H$_2$O$_2$ (0.12 mL, 1.08 mmol) and concentrated HCl (0.06 mL) dropwise, and stirred at room temperature for 16 hours. After the reaction solution was concentrated, it was subjected to HPLC to obtain a white solid (0.08 g, 50.4% yield). MS-ESI [M+H]$^+$: 296.0.

Preparation of Intermediate 46: (E)-N-(5-bromo-4-methoxy-2-methylphenyl)-2-oxime acetamide A mixture of trichloroacetaldehyde hydrate (11.0 g, 66.6 mmol), sodium sulfate (16.0 g, 113 mmol), 5-bromo-4-methoxy-2-methylaniline (13 g, 51.8 mmol), concentrated hydrochloric acid (8 mL), hydroxylamine hydrochloride (13.4 g, 195 mmol) and water (500 mL) was stirred at 100° C. for 6 hours, then cooled to 0° C. The resulting precipitate was collected by filtration, washed with water, and dried to obtain a brown solid (9.0 g, 61% yield). MS-ESI [M+H]$^+$: 286.9.

Preparation of Intermediate 47: 4-bromo-5-methoxy-7-methylindoline-2,3-dione

A mixture of (E)-N-(5-bromo-4-methoxy-2-methylphenyl)-2-oximeacetamide (9.0 g, 31 mmol) and concentrated sulfuric acid (26 mL) was heated to 80° C. and stirred for 2 hours, then cooled to room temperature, slowly poured on ice, and stirred for 1 hour. The resulting precipitate was collected by filtration, dispersed in ethanol (100 mL) at 80° C. and stirred for 1 hour. After cooling to room temperature, a solid precipitated, filtered, and dried to obtain a red solid (6.3 g, 75% yield). MS-ESI [M+H]$^+$: 269.9.

Preparation of Intermediate 48: 2-amino-6-bromo-5-methoxy-3-methylbenzoic acid

At 80° C., to the solution of 4-bromo-5-methoxy-7-methylindoline-2,3-dione (6.0 g, 22 mmol) in 3N NaOH (0.7 mL) was slowly add 30% of aqueous H$_2$O$_2$ (6 mL) dropwise and kept stirring for 2 hours. Then the reaction was cooled to room temperature, adjusted the solution to pH 3-5 with concentrated hydrochloric acid, and stirred for another 1 hour at room temperature. The resulting precipitate was collected by filtration and dried to obtain a light brown solid (4.5 g, 78% yield). MS-ESI [M+H]$^+$: 259.9.

Preparation of Intermediate 49: methyl 2-amino-6-bromo-5-methoxy-3-methylbenzoate To a solution of 2-amino-6-bromo-5-methoxy-3-methylbenzoic acid (4.5 g, 17 mmol) in THF/MeOH (4:1, 50 mL) was added dropwise trimethyl silicon diazomethane solution (2M in hexane, 34 mL) at room temperature, and kept stirring for 2 hours. Then the reaction was treated with 3 mL of glacial acetic acid, the solvent was evaporated, and the residue was purified by silica gel column chromatography, eluted with 3:1 petroleum ether/ethyl acetate, to obtain a light yellow solid (3.0 g, 63% yield). MS-ESI [M+H]$^+$: 273.9.

Preparation of Intermediate 50: methyl 6-bromo-5-methoxy-1H-indazole-7-carboxylate To a mixture of methyl 2-amino-6-bromo-5-methoxy-3-methylbenzoate (3.0 g, 10.98 mmol) and glacial acetic acid (50 mL) was added a solution of NaNO$_2$ (0.91 g, 13 mmol) in water (10 mL), heated to 50° C. and kept stirring for 16 hours. The solvent was evaporated, and the residue was washed with water and dried in vacuo to obtain a pale yellow solid (2.84 g, 91% yield). MS-ESI [M+H]$^+$: 285.0.

Preparation of Intermediate 51: methyl 6-bromo-5-methoxy-1-(tetrahydro-2H-pyran-2-yl)-1H-indazole-7-carboxylate Methyl 6-bromo-5-methoxy-1H-indazole-7-carboxylate (10 g, 35.2 mmol) and DHP (20 mL, 70.4 mmol) were dissolved in THF/CHCl$_3$ (1:2, 240 mL), and TsOH (1.0 g, 5.26 mmol) was added. The mixture was stirred at 50° C. overnight After cooling to room temperature, it was concentrated, and the residue was purified by silica gel column chromatography, eluted with a gradient of 0-20% ethyl acetate/petroleum ether, to obtain a yellow solid (10 g, 77% yield). MS-ESI [M+H]$^+$: 369.1.

Preparation of Intermediate 52: 6-bromo-5-methoxy-1-(tetrahydro-2H-pyran-2-yl)-1H-indazole-7-methanol At −20° C., to a toluene solution of methyl 6-bromo-5-methoxy-1-(tetrahydro-2H-pyran-2-yl)-1H-indazole-7-carboxylate (10 g, 27.1 mmol) was added DIBAL-H (70 mL, 108.4 mmol, 1.5M in toluene). The mixture was slowly warmed to room temperature and kept stirring for 1 hour. The reaction was quenched with water and extracted with ethyl acetate. The organic phase was washed with water, saturated brine, dried over anhydrous Na$_2$SO$_4$ and concentrated. The crude product was purified by silica gel column chromatography, eluted with a gradient of 0-20% ethyl acetate/petroleum ether, to obtain a white solid (9 g, 97% yield). MS-ESI [M+H]$^+$: 341.0.

Preparation of Intermediate 53: (6-bromo-5-methoxy-1-(tetrahydro-2H-pyran-2-yl)-1H-indazol-7-methyl methanesulfonate At 0° C., to a solution of 6-bromo-5-methoxy-1-(tetrahydro-2H-pyran-2-yl)-1H-indazole-7-methanol (10.0 g, 29.4 mmol) in DCM (200 mL) were added TEA (16 mL, 117.6 mmol) and MsCl (0.45 mL, 5.88 mmol). The mixture was slowly warmed to room temperature and stirred for 1 hour. The reaction was quenched with water and extracted with DCM. The organic phase was washed with water, saturated brine, dried over anhydrous Na$_2$SO$_4$ and concentrated. The crude product was used directly in the next reaction. MS-ESI [M+H]$^+$: 356.9.

Preparation of Intermediate 54: 2-(6-bromo-5-methoxy-1-(tetrahydro-2H-pyran-2-yl)-1H-indazol-7-yl)acetonitrile To a solution of (6-bromo-5-methoxy-1-(tetrahydro-2H-pyran-2-yl)-1H-indazol-7-yl)methyl methanesulfonate (10.0 g, 29.4 mmol) in ACN (20 mL) were added TMS-CN (5.9 mL, 44.1 mmol) and TBAF (1M, 44 mL, 117.6 mmol). After the mixture was stirred at room temperature for 3 hours, the reaction was diluted with water and extracted with ethyl acetate. The organic phase was washed with water, saturated brine, dried over anhydrous Na$_2$SO$_4$ and concentrated. The crude product was purified by silica gel column chromatography, eluted with a gradient of 0-20% ethyl acetate/petroleum ether, to obtain a white solid (3.5 g, 35% yield). MS-ESI [M+H]$^+$: 350.1.

Preparation of Intermediate 55: 2-(6-bromo-5-methoxy-1-(tetrahydro-2H-pyran-2-yl)-1H-indazol-7-yl)acetaldehyde At 0° C., to a solution of 2-(6-bromo-5-methoxy-1-(tetrahydro-2H-pyran-2-yl)-1H-indazol-7-yl)acetonitrile (2.50 g, 10 mmol) in toluene (35 mL) was added DIBAL-H (7.16 mL, 15 mmol, 1.5M in toluene). The mixture was slowly warmed to room temperature and stirred for 2 hours. The reaction was quenched with water, extracted with ethyl acetate, the organic phase was washed with water, saturated brine, dried over anhydrous Na$_2$SO$_4$, and concentrated. The crude product was purified by silica gel column chromatography, eluted with a gradient of 0-20% ethyl acetate/petroleum ether, to obtain a white solid (1.5 g, 59% yield). MS-ESI [M+H]$^+$: 269.0.

Preparation of Intermediate 56: 2-(6-bromo-5-methoxy-1-(tetrahydro-2H-pyran-2-yl)-1H-indazol-7-yl)ethanol To a solution of 2-(6-bromo-5-methoxy-1-(tetrahydro-2H-pyran-2-yl)-1H-indazol-7-yl)acetaldehyde (1.5 g, 2.6 mmol) in methanol (30 mL) was added NaBH$_4$ (0.66 g, 5.2 mmol). The mixture was stirred at room temperature for 2 hours. The reaction was quenched with water, extracted with DCM, the organic phase was washed with water, saturated brine, dried over anhydrous Na$_2$SO$_4$ and concentrated. The crude product was purified by silica gel column chromatography, eluted with a gradient of 0-20% ethyl acetate/petroleum ether, to obtain a white solid (1.3 g, 86% yield). MS-ESI [M+H]$^+$: 255.0.

Preparation of Intermediate 57: 6-bromo-7-(2-chloroethyl)-5-methoxy-1H-indazole

At 0° C., to a solution of 2-(6-bromo-5-methoxy-1-(tetrahydro-2H-pyran-2-yl)-1H-indazol-7-yl)ethanol (0.35 g, 0.99 mmol) in ACN (35 mL) were added DMF (2 drops) and SOCl$_2$ (3.5 mL). The mixture was warmed to room temperature and stirred for 48 hours. The reaction solution was concentrated to obtain the crude product as a brown solid, which was used directly in the next reaction. MS-ESI [M+H]$^+$: 291.0.

Preparation of Intermediate 58: 5-bromo-4-methoxy-6,7-dihydropyrrolo[3,2,1-hi]-indazole At room temperature, to a solution of 6-bromo-7-(2-chloroethyl)-5-methoxy-1H-indazole (0.6 g, 2.07 mmol) in DMF (60 mL) was added Cs$_2$CO$_3$ (3.38 g, 10.36 mmol). The mixture was heated to 100° C. and stirred for 4 hours. The reaction mixture was filtered and concentrated, and the crude product was purified by silica gel column chromatography, eluted with a gradient of 0-40% ethyl acetate/petroleum ether to obtain a yellow solid 58 (0.11 g, 44% yield in two steps). MS-ESI [M+H]$^+$: 255.0.

Preparation of Intermediate 59: 5-bromo-6,7-dihydropyrrolo[3,2,1-hi]-indazol-4-ol At 0° C., to a solution of 5-bromo-4-methoxy-6,7-dihydropyrrolo[3,2,1-hi]-indazole (0.15 g, 0.592 mmol) in DCM (5 mL) was added BBr$_3$ Solution (17% wt in DCM, 5.93 mL, 10 mmol). The mixture was warmed to room temperature and stirred for 12 hours. The reaction was quenched with ice water and extracted with DCM. The organic phase was concentrated to obtain crude product as a brown solid. MS-ESI [M+H]$^+$: 241.1.

Preparation of Intermediate 60: 5-bromo-4-(2-fluoro-4-nitrophenoxy)-6,7-dihydropyrrolo[3,2,1-hi]-indazole To a solution of 5-bromo-6,7-dihydropyrrole [3,2,1-hi]-indazol-4-ol (0.25 g) in DMF (10 ml) were added NaHCO$_3$ (0.263 g, 3.14 mmol) and 1,2-difluoro-4-nitrobenzene (0.166 g, 1.05 mmol). The mixture was heated to 60° C. and stirred for 12 hours. The reaction mixture was filtered and concentrated, and the crude product was purified by silica gel column chromatography, eluted with a gradient of 0-30% ethyl acetate/petroleum ether to obtain a solid (0.08 g, 36% yield in two steps). MS-ESI [M+H]$^+$: 380.0.

Preparation of Intermediate 61: tert-butyl 4-(4-(2-fluoro-4-nitrophenoxy)-6,7-dihydropyrrolo[3,2,1-hi]-indazol-5-yl)-1H-pyrazole-1-carboxylate To a solution of 5-bromo-4-(2-fluoro-4-nitrophenoxy)-6,7-dihydropyrrolo[3,2,1-hi]-indazole (60 mg, 0.158 mmol) in THF (6 mL) and water (0.6 mL) were added K$_3$PO$_4$ (67 mg, 0.316 mmol) and Pd(dbpf)Cl$_2$ (4.9 mg, 0.08 mmol). The mixture was heated to 60° C. and stirred for 12 hours. The reaction solution was washed with water, extracted with ethyl acetate, the organic phase was concentrated, and the crude product was purified by silica gel column chromatography, eluted with a gradient of 0-50% ethyl acetate/petroleum ether, to obtain a solid (40 mg, 54% yield). MS-ESI [M+H]$^+$: 466.2.

Preparation of Intermediate 62: tert-butyl 4-(4-(4-amino-2-fluorophenoxy)-6,7-dihydropyrrolo[3,2,1-hi]-indazol-5-yl)-1H-pyrazole-1-carboxylate To a solution of 4-(4-(2-fluoro-4-nitrophenoxy)-6,7-dihydropyrrolo[3,2,1-hi]-indazol-5-yl)-1H-pyrazole-1-carboxylic acid tert-butyl ester (50 mg, 0.1 mmol) in THF (5 ml) was added Pd/C (10%, 30 mg). The mixture was stirred at room temperature for 12 hours under hydrogen atmosphere. The hydroxylamine intermediate was detected by LCMS, the reaction mixture was filtered, added additional Pd/C (10%, 30 mg), and stirred for another 8 hours at room temperature under hydrogen atmosphere, filtered and concentrated to give the crude product as a solid (68 mg). $^1$H NMR (400 MHz, CDCl$_3$) δ 13.31 (s, 1H), 8.55 (d, J=7.9 Hz, 1H), 7.32-7.27 (m, 4H), 6.80 (d, J=7.9 Hz, 1H). MS-ESI [M+H]$^+$: 267.9.

Preparation of Intermediate 63: 6-(1-Boc-pyrazol-4-yl)-5-(2-fluoro-4-aminophenoxy)-1-ethyl-1H-indazole Intermediate 63 was prepared according to the synthetic route of Intermediate 25 from Intermediate 14 6-bromo-5-(2-fluoro-4-nitrophenoxy)-1-ethyl-1H-indazole. MS-ESI [M+H]$^+$: 438.3.

Preparation of Intermediate 64: N-(3-fluoro-4-(1-methyl-6-(1-Boc-pyrazol-4-yl)-1H-indazol-5-yloxy) phenyl)-6-Chloro-2-oxo-1-(4-fluorophenyl)-1,2-dihydropyridine-3-carboxamide Intermediate 64 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 42 (1-(4-fluorophenyl)-6-chloro-2-oxo-1,2-dihydropyridine-3-carboxylic acid). MS-ESI [M+H]$^+$: 673.3.

Preparation of Intermediate 65: N-(3-fluoro-4-(1-methyl-6-(1-Boc-pyrazol-4-yl)-1H-indazol-5-yloxy) phenyl)-6-(Boc amino)-2-oxo-1-(4-fluorophenyl)-1,2-dihydmpyridine-3-carboxamide Intermediate 65 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 44 (1-(4-fluorophenyl)-6-(Boc amino)-2-oxo-1,2-dihydropyridine-3-carboxylic acid). MS-ESI [M+H]$^+$: 754.3, Preparation of Intermediate 66: N-(3-fluoro-4-(1-methyl-6-(1-Boc-pyrazol-4-yl)-1H-indazol-5-yloxy) phenyl)-6-methylthio-2-oxo-1-(4-fluorophenyl)-12-dihydropyridine-3-carboxamide Intermediate 66 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 40 (1-(4-fluorophenyl)-6-methylthio-2-oxo-1,2-dihydropyridine-3-carboxylic acid). MS-ESI [M+H]$^+$: 685.2.

Preparation of Intermediate 67: N-(3-fluoro-4-(1-methyl-6-(1-Boc-pyrazol-4-yl)-1H-indazol-5-yloxy) phenyl)-6-methylsulfoxide-2-oxo-1-(4-fluorophenyl)-12-dihydro pyridine-3-carboxamide Intermediate 67 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 45 (1-(4-fluorophenyl)-6-methylsulfoxide-2-oxo-1,2-dihydropyridine-3-carboxylic acid). MS-ESI [M+H]$^+$: 701.2.

Preparation of Intermediate 68: N-(3-fluoro-4-(1-methyl-6-(1-Boc-pyrazol-4-yl)-1H-indazol-5-yloxy) phenyl)-6-methoxy-2-oxo-1-(4-fluorophenyl)-12-dihydropyridine-3-carboxamide Intermediate 68 was prepared according to the synthetic route of Intermediate 26, starting from Intermediate 25 (6-(1-Boc-pyrazol-4-yl)-5-(2-fluoro-4-aminophenoxy)-1-methyl-1H-indazole) and Intermediate 35 (1-(4-fluorophenyl)-6-methoxy-2-oxo-1,2-dihydropyridine-3-carboxylic acid). MS-ESI [M+H]$^+$: 669.1.

Preparation of Intermediate 69: N-(3-fluoro-4-(1-methyl-6-(1-Boc-pyrazol-4-yl)-1H-indazol-5-yloxy) phenyl)-6-ethoxy-2-oxo-1-(4-fluorophenyl)-1,2-dihydropyridine-3-carboxamide Intermediate 69 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 36 (1-(4-fluorophenyl)-6-ethoxy-2-oxo-1,2-dihydropyridine-3-carboxylic acid). MS-ESI [M+H]$^+$: 683.2.

Preparation of Intermediate 70: N-(3-fluoro-4-(1-methyl-6-(1-Boc-pyrazol-4-yl)-1H-indazol-5-yloxy)phenyl)-6-cyclopropoxy-2-oxo-1-(4-fluorophenyl)-1,2-dihydropyridine-3-carboxamide Intermediate 70 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 37 (1-(4-fluorophenyl)-6-cyclopropoxy-2-oxo-1,2-dihydropyridine-3-carboxylic acid). MS-ESI [M+H]$^+$: 695.2.

Preparation of Intermediate 71: N-(3-fluoro-4-(1-methyl-6-(1-Boc-pyrazol-4-yl)-1H-indazol-5-yloxy)phenyl)-isopropoxy-2-oxo-1-(4-fluorophenyl)-1,2-dihydropyridine-3-carboxamide Intermediate 71 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 38 (1-(4-fluorophenyl)-6-isopropoxy-2-oxo-1,2-dihydropyridine-3-carboxylic acid). MS-ESI [M+H]$^+$: 697.2.

Preparation of Intermediate 72: N-(3-fluoro-4-(1-methyl-6-(1-Boc-pyrazol-4-yl)-1H-indazol-5-yloxy)phenyl)-6-(2,2,2-trifluoroethoxy)-2-oxo-1-(4-fluorophenyl)-12-dihydropyridine-3-carboxamide Intermediate 72 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 39 (1-(4-fluorophenyl)-6-(2,2,2-trifluoroethoxy)-2-oxo-1,2-dihydropyridine-3-carboxylic acid). MS-ESI [M+H]$^+$: 737.1.

Preparation of Intermediate 73: N-(3-fluoro-4-(1-ethyl-6-(1-Boc-pyrazol-4-yl)-1H-indazol-5-yloxy)phenyl)-6-ethyl-2-oxo-1-(4-fluorophenyl)-1,2-dihydropyridine-3-carboxamide Intermediate 73 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 14 (1-(4-fluorophenyl)-6-ethyl-2-oxo-1,2-dihydropyridine-3-carboxylic acid). MS-ESI [M+H]$^+$: 681.0.

Preparation of Intermediate 74: N-(3-fluoro-4-(1-ethyl-6-(1-Boc-pyrazol-4-yl)-1H-indazol-5-yloxy)phenyl)-6-cyclopropyl-2-oxo-1-(4-fluorophenyl)-1,2-dihydropyridine-3-carboxamide Intermediate 74 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 16 (1-(4-fluorophenyl)-6-cyclopropyl-2-oxo-1,2-dihydropyridine-3-carboxylic acid). MS-ESI [M+H]$^+$: 693.0.

Preparation of Intermediate 75: N-(3-fluoro-4-(1-ethyl-6-(1-Boc-pyrazol-4-yl)-1H-indazol-5-yloxy)phenyl)-6-chloro-2-oxo-1-(4-fluorophenyl)-1,2-dihydropyridine-3-carboxamide Intermediate 75 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 42 (1-(4-fluorophenyl)-6-chloro-2-oxo-1,2-dihydropyridine-3-carboxylic acid). MS-ESI [M+H]$^+$: 687.1.

Preparation of Intermediate 76: N-(3-fluoro-4-(1-ethyl-6-(1-Boc-pyrazol-4-yl)-1H-indazol-5-yloxy)phenyl)-6-Boc amino-2-oxo-1-(4-fluorophenyl)-1,2-dihydropyridine-3-carboxamide Intermediate 76 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 44 (1-(4-fluorophenyl)-6-Bocamino-2-oxo-1,2-dihydropyridine-3-carboxylic acid). MS-ESI [M+H]$^+$: 766.4.

Preparation of Intermediate 77: N-(3-fluoro-4-(1-ethyl-6-(1-Boc-pyrazol-4-yl)-1H-indazol-5-yloxy)phenyl)-6-methylthio-2-oxo-1-(4-fluorophenyl)-12-dihydropyridine-3-carboxamide Intermediate 77 6 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 40 (1-(4-fluorophenyl)-6-methylthio-2-oxo-1,2-dihydropyridine-3-carboxylic acid). MS-ESI [M+H]$^+$: 699.1.

Preparation of Intermediate 78: N-(3-fluoro-4-(1-ethyl-6-(1-Boc-pyrazol-4-yl)-1H-indazol-5-yloxy)phenyl)-6-methoxy-2-oxo-1-(4-fluorophenyl)-12-dihydropyridine-3-carboxamide Intermediate 78 was prepared according to the synthetic route of Intermediate 26, starting from Intermediate 63 (6-(1-Boc-pyrazol-4-yl)-5-(2-fluoro-4-aminophenoxy)-1-ethyl-1H-indazole) and Intermediate 35 (1-(4-fluorophenyl)-6-methoxy-2-oxo-1,2-dihydropyridine-3-carboxylic acid). MS-ESI [M+H]$^+$: 683.3.

Preparation of Intermediate 79: N-(3-fluoro-4-(1-ethyl-6-(1-Boc-pyrazol-4-yl)-1H-indazol-5-yloxy)phenyl)-6-ethoxy-2-oxo-1-(4-fluorophenyl)-1,2-dihydropyridine-3-carboxamide Intermediate 79 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 36 (1-(4-fluorophenyl)-6-ethoxy-2-oxo-1,2-dihydropyridine-3-carboxylic acid). MS-ESI [M+H]$^+$: 697.3.

Preparation of Intermediate 80: N-(3-fluoro-4-(1-ethyl-6-(1-Boc-pyrazol-4-yl)-1H-indazol-5-yloxy)phenyl)-6-cyclopropoxy-2-oxo-1-(4-fluorophenyl)-1,2-dihydropyridine-3-carboxamide Intermediate 80 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 37 (1-(4-fluorophenyl)-6-cyclopropoxy-2-oxo-1,2-dihydropyridine-3-carboxylic acid). MS-ESI [M+H]$^+$: 709.1.

Preparation of Intermediate 81: N-(3-fluoro-4-(1-ethyl-6-(1-Boc-pyrazol-4-yl)-1H-indazol-5-yloxy)phenyl)-6-isopropoxy-2-oxo-1-(4-fluorophenyl)-1,2-dihydropyridine-3-carboxamide Intermediate 81 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 38 (1-(4-fluorophenyl)-6-isopropoxy-2-oxo-1,2-dihydropyridine-3-carboxylic acid). MS-ESI [M+H]$^+$: 711.3.

Preparation of Intermediate 82: N-(3-fluoro-4-(1-ethyl-6-(1-Boc-pyrazol-4-yl)-1H-indazol-5-yloxy)phenyl)-6-(2,2,2-trifluoroethoxy)-2-oxo-1-(4-fluorophenyl)-12-dihydropyridine-3-carboxamide Intermediate 82 was prepared according to the synthetic route of Intermediate 26, from Intermediate 63 (6-(1-Boc-pyrazol-4-yl)-5-(2-fluoro-4-aminophenoxy)-1-ethyl-1H-indazole) and Intermediate 39 (1-(4-fluorophenyl)-6-(2,2,2-trifluoroethoxy)-2-oxo-1,2-dihydropyridine-3-carboxylic acid). MS-ESI [M+H]$^+$: 751.2.

Preparation of Intermediate 83: tert-butyl4-(4-(2-fluoro-4-(1-(4-fluorophenyl)-6-methyl-2-oxo-1,2-dihydmpyridine-3-carboxamido)phenoxy)-6,7-dihydropyrrolo[3,2,1-hi]4-indazol-5-yl)-1H-pyrazole-1-carboxylate Intermediate 83 was prepared according to the synthetic route of Intermediate 26, from Intermediate 62 (tert-butyl 4-(4-(4-amino-2-fluorophenoxy)-6,7-dihydropyrrolo[3,2,1-hi]-indazol-5-yl)-1H-pyrazole-1-carboxylate) and Intermediate 13 (1-(4-fluorophenyl)-6-methyl-2-oxo-1,2-dihydropyridine-3-carboxylic acid). MS-ESI [M+H]$^+$: 665.5.

Preparation of Intermediate 84: tert-butyl4-(4-(2-fluoro-4-(1-(4-fluorophenyl)-6-methoxy-2-oxo-1,2-dihydropyridine-3-carboxamido)phenoxy)-6,7-dihydropyrrolo[3,2,1-hi]I-indazol-5-yl)-1H-pyrazole-1-carboxylate Intermediate 84 was prepared according to the synthetic route of Intermediate 26, from Intermediate 62 (tert-butyl 4-(4-(4-amino-2-fluorophenoxy)-6,7-dihydropyrrolo[3,2,1-hi]-indazol-5-yl)-1H-pyrazole-1-carboxylate) and Intermediate 35 (1-(4-fluorophenyl)-6-methoxy-2-oxo-1,2-dihydropyridine-3-carboxylic acid). MS-ESI [M+H]$^+$: 681.2.

Preparation of Intermediate 85: tert-butyl4-(4-(2-fluoro-4-(1-(4-fluorophenyl)-6-ethoxy-2-oxo-1,2-dihydmpyridine-3-carboxamido)phenoxy)-6,7-dihydropyrrolo[3,2,1-hi]4-indazol-5-yl)-1H-pyrazole-1-carboxylate Intermediate 85 was prepared according to the synthetic route of Intermediate 26, from Intermediate 62 (tert-butyl 4-(4-(4-amino-2-fluorophenoxy)-6,7-dihydropyrrolo[3,2,1-hi]-indazol-5-yl)-1H-pyrazole-1-carboxylate) and Intermediate 36 (1-(4-fluorophenyl)-6-ethoxy-2-oxo-1,2-dihydropyridine-3-carboxylic acid). MS-ESI [M+H]$^+$: 695.2.

Preparation of Intermediate 86: tert-butyl 4-(4-(2-fluoro-4-(1-(4-fluorophenyl)-6-cyclopropoxy-2-oxo-1,2-dihydropyridine-3-carboxamido)phenoxy)-6,7-dihydropyrrolo[3,2,1-hi]I-indazol-5-yl)-1H-pyrazole-1-carboxylate Intermediate 86 was prepared according to the synthetic route of Intermediate 26, from Intermediate 62 (tert-butyl 4-(4-(4-amino-2-fluorophenoxy)-6,7-dihydropyrrolo[3,2,1-hi]-indazol-5-yl)-1H-pyrazole-1-carboxylate) and Intermediate 37 (1-(4-fluorophenyl)-6-cyclopropoxy-2-oxo-1,2-dihydropyridine-3-carboxylic acid). MS-ESI [M+H]$^+$: 707.2.

Preparation of Intermediate 87: tert-butyl 4-(4-(2-fluoro-4-(1-(4-fluorophenyl)-6-isopropoxy-2-oxo-1,2-dihydropyridine-3-carboxamido)phenoxy)-6,7-dihydropyrrolo[3,2,1-hi]I-indazol-5-yl)-1H-pyrazole-1-carboxylate Intermediate 87 was prepared according to the synthetic route of Intermediate 26, from Intermediate 62 (tert-butyl 4-(4-(4-amino-2-fluorophenoxy)-6,7-dihydropyrrolo[3,2,1-hi]-indazol-5-yl)-1H-pyrazole-1-carboxylate) and Intermediate 38 (1-(4-fluorophenyl)-6-isopropoxy-2-oxo-1,2-dihydropyridine-3-carboxylic acid). MS-ESI [M+H]$^+$: 709.3.

Preparation of Intermediate 88: methyl 6-difluoromethoxynicotinate

To a solution of methyl 6-hydroxynicotinate (1.5 g, 9.8 mmol) in ACN (50 ml) was added NaH (0.979 g, 24.49 mmol). After stirring at room temperature for 0.5 hours, 2,2-difluoro-2-fluorosulfonylacetic acid (2.62 g, 14.69 mmol) was added. The reaction mixture was stirred at 25° C. for 2 hours, quenched with water (50 mL), and extracted with ethyl acetate (5×50 mL). The organic phase was washed with saturated brine (50 mL) and dried over anhydrous $Na_2SO_4$. After filtration and concentration, the crude product was purified by silica gel column, eluted with a gradient of 0-10% ethyl acetate/petroleum ether, to obtain a white solid (1.70 g, 85.4% yield). $^1$H NMR (400 MHz, $CDCl_3$) δ 8.84 (d, J=2.3 Hz, 1H), 8.32 (dd, J=8.6, 2.3 Hz, 1H), 7.53 (t, J=72.3 Hz, 1H), 6.95 (d, J=8.6 Hz, 1H), 3.94 (s, 3H). MS (m/z): 204.0[M+H].

Preparation of Intermediate 89: 6-difluoromethoxy-5-methoxycarbonylpyridine-1-N-oxide To a solution of methyl 6-difluoromethoxynicotinate (0.8 g, 3.94 mmol) in DCM (40 mL) was added urea-hydrogen peroxide (3.70 g, 39.38 mmol) and TFAA (5.5 mL, 39.38 mmol). The reaction mixture was stirred at 25° C. for 16 hours, quenched with water (50 mL), and extracted with ethyl acetate (5×50 mL). The organic phase was washed sequentially with saturated sodium thiosulfate (50 mL), saturated $NaHCO_3$ (3×50 mL) and saturated brine (50 mL), and dried over anhydrous $Na_2SO_4$. After filtration and concentration, the crude product was obtained as a white solid (0.735 g, 85% yield), which was used directly in the next reaction. MS (m/z): 220.0[M+H].

Preparation of Intermediate 90: 6-difluoromethoxy-2-oxo-1,2-dihydropyridine-3-carboxylic acid methyl ester To a solution of 6-difluoromethoxy-5-methoxycarbonylpyridine-1-N-oxide (0.5 g, 2.28 mmol) in THF (20 mL) were added TFAA (1.29 mL, 9.13 mmol) and TEA (1.27 mL, 9.13 mmol). The reaction mixture was stirred at 25° C. for 2 hours. After concentration, the crude product was purified by a silica gel column, eluted with a gradient of 0-5% ethyl acetate/petroleum ether, to obtain a white solid (0.360 g, 72% yield). MS (m/z): 220.0 [M+H].

Preparation of Intermediate 91: 6-difluoromethoxy-1-(4-fluorophenyl)-2-oxo-1,2-dihydropyridine-3-carboxylic acid methyl ester Under the protection of Ar, to a solution of methyl 6-difluoromethoxy-2-oxo-1,2-dihydropyridine-3-carboxylate (150 mg, 0.684 mmol) in 1,4-dioxane (3 mL) was added 4-fluorophenylboronic acid (95.8 mg, 0.684 mmol), copper acetate (248.7 mg, 1.36 mmol), TEMPO (128.4 mg, 0.821 mmol) and pyridine (541.7 mg, 6.84 mmol). The reaction mixture was stirred at 80° C. for 0.5 hours, LCMS showed 10% product 4-fluorophenylboronic acid (0.5 equivalent) was added into the reaction mixture every half hour, totally 8 times, and the LCMS yield reached to 69%. After filtration and concentration, the crude product was purified by a silica gel column, eluted with THF/petroleum ether (1:10), to obtain 1.0 g of a yellow solid, which was further purified by reverse phase preparative HPLC to obtain a white solid (50 mg, 23% yield). MS (m/z): 314.0 [M+H].

Preparation of Intermediate 92: 6-difluoromethoxy-1-(4-fluorophenyl)-2-oxo-1,2-dihydropyridine-3-carboxylic acid To a solution of 6-difluoromethoxy-1-(4-fluorophenyl)-2-oxo-1,2-dihydropyridine-3-carboxylic acid methyl ester (150 mg, 0.477 mmol) in THF/water (4 mL/0.8 mL) was added LiOH H$_2$O (22 mg, 0.525 mmol) at 0° C., the reaction mixture was stirred overnight at room temperature under the protection of Ar. Then the reaction was adjusted to pH 3-4 with 1N HCl, extracted with ethyl acetate (3×20 mL). The organic phase was washed with saturated brine (3×50 mL), dried over anhydrous sodium sulfate, filtered and concentrated. The crude product was recrystallized from petroleum ether to obtain a white solid (100 mg, 70% yield). $^1$H NMR (400 MHz, DMSO-d$_6$) δ 13.16 (s, 1H), 8.37 (d, J=8.0 Hz, 1H), 7.35 (s, 0.28H), 7.26-7.22 (m, 4H), 7.17 (s, 0.49H), 6.99 (s, 0.23H), 6.85 (d, J=8.4 Hz, 1H). MS-ESI [M+H]$^+$: 300.0.

Preparation of Intermediate 93: tert-butyl 4-(4-(2-fluoro-4-(1-(4-fluorophenyl)-6-(2,2,2-trifluoroethoxy)-2-oxo-1,2-dihydropyridine-3-carboxamido)phenoxy)-6,7-dihydropyrrolo[3,2,1-hi]-indazol-5-yl)-1H-pyrazole-1-carboxylate Intermediate 93 was prepared according to the synthetic route of Intermediate 26, from Intermediate 62 (tert-butyl 4-(4-(4-amino-2-fluorophenoxy)-6,7-dihydropyrrolo[3,2,1-hi]-indazol-5-yl)-1H-pyrazole-1-carboxylate) and Intermediate 39 (1-(4-fluorophenyl)-6-(2,2,2-trifluoroethoxy)-2-oxo-1,2-dihydropyridine-3-carboxylic acid). MS-ESI [M+H]$^+$: 749.2.

Preparation of Intermediate 94: N-(3-fluoro-4-(1-methyl-6-(1-Boc-pyrazol-4-yl)-1H-indazol-5-yloxy)phenyl)-6-difluoromethoxy-2-oxo-1-(4-fluorophenyl)-1,2-dihydropyridine-3-carboxamide Intermediate 94 was prepared according to the synthetic route of Intermediate 26, from Intermediate 25 (6-(1-Boc-pyrazol-4-yl)-5-(2-fluoro-4-aminophenoxy)-1-methyl-1H-indazole) and Intermediate 92 (1-(4-fluorophenyl)-6-difluoromethoxy-2-oxo-1,2-dihydropyridine-3-carboxylic acid). MS-ESI [M+H]$^+$: 705.2.

Preparation of Intermediate 95: tert-butyl 4-(4-(2-fluoro-4-(1-(4-fluorophenyl)-6-difluoromethoxy-2-oxo-1,2-dihydropyridine-3-carboxamido)phenoxy)-6,7-dihydropyrrolo[3,2,1-hi]-indazol-5-yl)-1H-pyrazole-1-carboxylate Intermediate 95 was prepared according to the synthetic route of Intermediate 26, from Intermediate 62 (tert-butyl 4-(4-(4-amino-2-fluorophenoxy)-6,7-dihydropyrrolo[3,2,1-hi]-indazol-5-yl)-1H-pyrazole-1-carboxylate) and Intermediate 92 (1-(4-fluorophenyl)-6-difluoromethoxy-2-oxo-1,2-dihydropyridine-3-carboxylic acid). MS-ESI [M+H]$^+$: 717.2.

Example 1: Preparation of N-(3-fluoro-4-(1-methyl-6-(1H-pyrazol-4-yl)-1H-indazol-5-yloxy)phenyl)-1-(4-fluorophenyl)-6-trifluoromethyl-2-oxo-1,2-dihydrmpyridine-3-carboxamide monomethanesulfonate

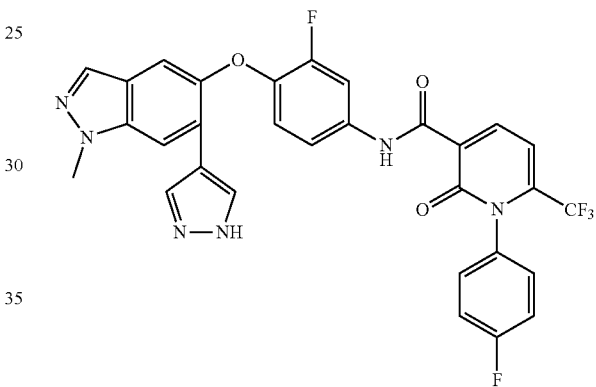

To a solution of N-(3-fluoro-4-(1-methyl-6-(1-Boc-pyrazol-4-yl)-1H-indazol-5-yloxy)phenyl)-6-trifluoromethyl-2-oxo-1-(4-fluorophenyl)-1,2-dihydropyridine-3-carboxamide (Intermediate 29, 255 mg, 0.33 mmol) in dichloromethane (15 mL) was added trifluoroacetic acid (3 mL), the resulting reaction mixture was stirred at room temperature for 1 hour, and the solvent was evaporated under reduced pressure. The crude product was dissolved in ethyl acetate (50 mL), neutralized by adding saturated sodium bicarbonate aqueous solution (25 mL), then washed twice with saturated sodium chloride aqueous solution (25 mL each time), dried and concentrated to obtain free base solid 200 mg as shown by the chemical structure above.

The above free base was dissolved in anhydrous methanol (5 mL) and dichloromethane (5 mL), and a methanol (5 mL) solution of methanesulfonic acid (32 mg, 0.33 mmol) was added. After mixing thoroughly, the solvent was evaporated under reduced pressure and dried to obtain about 230 mg of a yellow solid. $^1$H NMR (400 MHz, DMSO-d$_6$) δ 11.56 (s, 1H), 8.55 (d, J=7.6 Hz, 1H), 8.04 (s, 2H), 7.94 (s, 1H), 7.90 (dd, J=13.2, 2.5 Hz, 1H), 7.85 (s, 1H), 7.51 (dd, J=8.6, 4.9 Hz, 2H), 7.35 (t, J=8.6 Hz, 2H), 7.30-7.20 (m, 3H), 6.79 (t, J=9.1 Hz, 1H), 4.73 (s, b, 2H), 4.01 (s, 3H), 2.29 (s, 3H). MS [M+H]$^+$: 607.1.

Example 2: Preparation of N-(3-fluoro-4-(1-methyl-6-(1H-pyrazol-4-yl)-1H-indazol-5-yloxy)phenyl)-1-(4-fluorophenyl)-6-cyclopropyl-2-oxo-1,2-dihydmpyridine-3-carboxamide

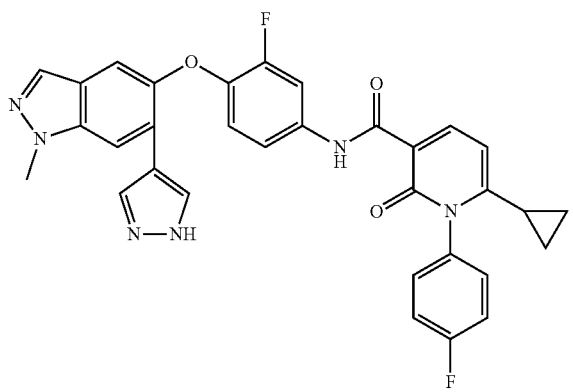 [SMILES: Cn1ncc2cc(Oc3ccc(NC(=O)c4ccc(C5CC5)n(-c5ccc(F)cc5)c4=O)cc3F)c(-c3cn[nH]c3)cc21]

This compound was prepared according to the synthetic route of Example 1, from Intermediate 28 (N-(3-fluoro-4-(1-methyl-6-(1-Boc-pyrazol-4-yl)-1H-indazole)-5-yloxy)phenyl)-6-cyclopropyl-2-oxo-1-(4-fluorophenyl)-1,2-dihydropyridine-3-carboxamide). MS [M+H]$^+$: 579.2 $^1$H NMR (500 MHz, chloroform-d) δ 11.82 (s, 1H), 8.62 (d, J=7.8 Hz, 1H), 8.23 (s, 2H), 7.89 (dd, J=12.7, 2.5 Hz, 1H), 7.84 (s, 1H), 7.57 (s, 1H), 7.34-7.28 (m, 4H), 7.20 (d, J=9.1 Hz, 1H), 7.17 (s, 1H), 6.88 (t, J=8.8 Hz, 1H), 6.22 (d, J=7.8 Hz, 1H), 4.11 (s, 3H), 3.54 (s, b, 3H), 2.95 (s, 3H), 1.41-1.13 (m, 2H), 1.00-0.64 (m, 2H).

Example 3: Preparation of N-(3-fluoro-4-(1-ethyl-6-(1H-pyrazol-4-yl)-1H-indazol-5-yloxy)phenyl)-1-(4-fluorophenyl)-6-methyl-2-oxo-1,2-dihydmpyridine-3-carboxamide

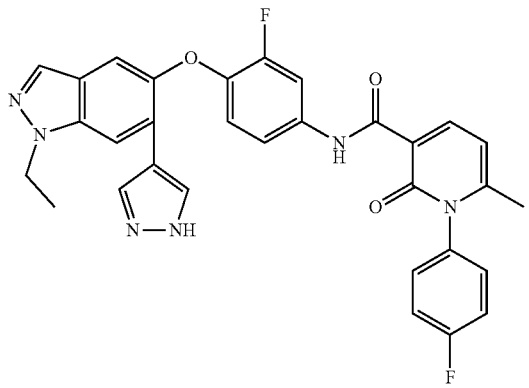 [SMILES: CCn1ncc2cc(Oc3ccc(NC(=O)c4ccc(C)n(-c5ccc(F)cc5)c4=O)cc3F)c(-c3cn[nH]c3)cc21]

This compound was prepared according to the synthetic route of Example 1, from Intermediate 21 (N-(3-fluoro-4-(1-ethyl-6-(1-Boc-pyrazol-4-yl)-1H-indazole-5-yloxy)phenyl)-6-methyl-2-oxo-1-(4-fluorophenyl)-1,2-dihydropyridine-3-carboxamide). $^1$H NMR (400 MHz, DMSO-d$_6$) δ 11.87 (s, 1H), 8.40 (d, J=7.5 Hz, 1H), 8.06 (s, 2H), 7.97 (s, 1H), 7.90 (dd, J=13.4, 2.4 Hz, 1H), 7.86 (s, 1H), 7.52-7.27 (m, 4H), 7.25-7.10 (m, 2H), 6.80 (t, J=9.1 Hz, 1H), 6.63 (d, J=7.6 Hz, 1H), 5.29 (s, b, 2H), 4.40 (q, J=7.2 Hz, 2H), 2.30 (s, 4H), 2.00 (s, 3H), 1.35 (t, J=7.2 Hz, 3H). MS [M+H]$^+$: 567.2.

Example 4: Preparation of N-(3-fluoro-4-(1-isopropyl-6-(1H-pyrazol-4-yl)-1H-indazol-5-yloxy)phenyl)-1-(4-fluorophenyl)-6-methyl-2-oxo-1,2-dihydmpyridine-3-carboxamide

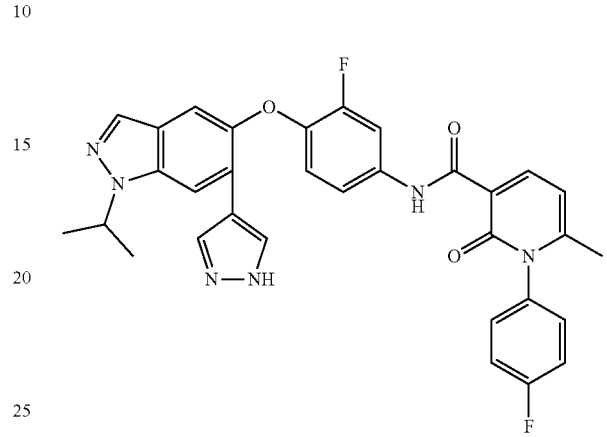

This compound was prepared according to the synthetic route of Example 1, from Intermediate (N-(3-fluoro-4-(1-isopropyl-6-(1-Boc-pyrazol-4-yl)-1H-indazol-5-yloxy)phenyl)-6-methyl-2-oxo-1-(4-fluorophenyl)-1,2-dihydropyridine-3-carboxamide). $^1$H NMR (400 MHz, DMSO-d$_6$) δ 11.87 (s, 1H), 8.40 (d, J=7.6 Hz, 1H), 8.06 (s, 2H), 7.98 (s, 1H), 7.90 (dd, J=13.3, 2.5 Hz, 1H), 7.87 (s, 1H), 7.47-7.29 (m, 4H), 7.23-7.10 (m, 2H), 6.79 (t, J=9.1 Hz, 1H), 6.63 (d, J=7.6 Hz, 1H), 5.07 (s, b, 2H), 5.01 (h, J=6.7 Hz, 1H), 2.30 (s, 3H), 2.00 (s, 3H), 1.43 (d, J=6.5 Hz, 6H). MS [M+H]$^+$: 581.2.

Example 5: Preparation of N-(3-fluoro-4-(1-methyl-6-(1H-pyrazol-4-yl)-1H-indazol-5-yloxy)phenyl)-1-(4-fluorophenyl)-6-ethyl-2-oxo-1,2-dihydropyridine-3-carboxamide

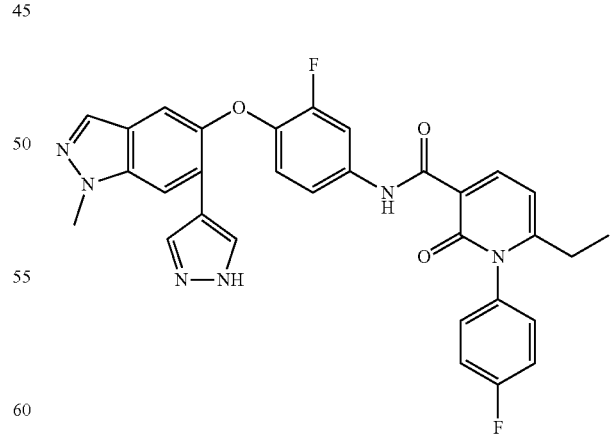

This compound was prepared according to the synthetic route of Example 1, from Intermediate 26 (N-(3-fluoro-4-(1-methyl-6-(1-Boc-pyrazol-4-yl)-1H-indazol-5-yloxy)phenyl)-6-ethyl-2-oxo-1-(4-fluorophenyl)-1,2-dihydropyridine-3-carboxamide). $^1$H NMR (400 MHz, DMSO-d$_6$) δ 11.94 (s, 1H), 8.52 (d, J=7.7 Hz, 1H), 8.12 (s, 2H), 8.01 (s, 1H), 7.97 (dd, J=13.2, 2.4 Hz, 1H), 7.92 (s, 1H), 7.58-7.34 (m, 4H), 7.30-7.16 (m, 2H), 6.86 (t, J=9.1 Hz, 1H), 6.67 (d, J=7.7 Hz, 1H), 5.27 (s, b, 2H), 4.08 (s, 3H), 2.37 (s, 3H), 2.30 (q, J=7.4 Hz, 2H), 1.05 (t, J=7.4 Hz, 3H). MS [M+H]⁺: 567.2, Example 6: Preparation of N-(3-fluoro-4-(1-methyl-6-(1H-pyrazol-4-yl)-1H-indazol-5-yloxy)phenyl)-1-(4-fluorophenyl)-6-isopropyl-2-oxo-1,2-dihydropyridine-3-carboxamide

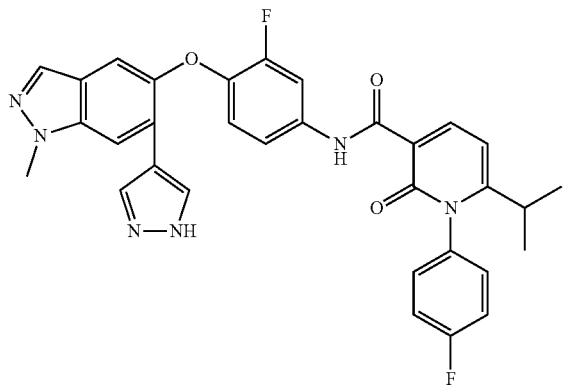 [SMILES: CC(C)c1ccc(C(=O)Nc2ccc(Oc3cc4cnn(C)c4cc3-c3cn[nH]c3)c(F)c2)c(=O)n1-c1ccc(F)cc1]

This compound was prepared according to the synthetic route of Example 1, from Intermediate 27 (N-(3-fluoro-4-(1-methyl-6-(1-Boc-pyrazol-4-yl)-1H-indazol-5-yloxy)phenyl)-6-isopropyl-2-oxo-1-(4-fluorophenyl)-1,2-dihydropyridine-3-carboxamide). ¹H NMR (400 MHz, DMSO-d₆) δ 11.86 (s, 1H), 8.46 (d, J=7.8 Hz, 1H), 8.05 (s, 2H), 7.94 (s, 1H), 7.90 (dd, J=13.5, 2.4 Hz, 1H), 7.84 (s, 1H), 7.46 (dd, J=8.7, 4.9 Hz, 2H), 7.36 (t, J=8.6 Hz, 2H), 7.19 (d, J=7.7 Hz, 2H), 6.79 (t, J=9.1 Hz, 1H), 6.69 (d, J=7.9 Hz, 1H), 5.05 (s, b, 2H), 4.01 (s, 3H), 2.39 (h, 1H), 2.29 (s, 3H), 1.05 (d, J=6.8 Hz, 6H). MS [M+H]⁺: 581.2.

Example 7: Preparation of N-(3-fluoro-4-(1-isopropyl-6-(1H-pyrazol-4-yl)-1H-indazol-5-yloxy)phenyl)-1-(4-fluorophenyl)-6-isopropyl-2-oxo-1,2-dihydropyridine-3-carboxamide

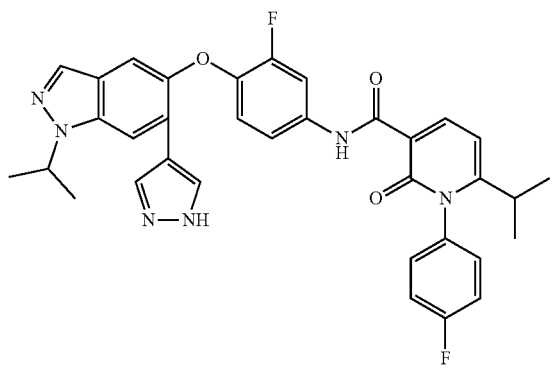 [SMILES: CC(C)c1ccc(C(=O)Nc2ccc(Oc3cc4cnn(C(C)C)c4cc3-c3cn[nH]c3)c(F)c2)c(=O)n1-c1ccc(F)cc1]

This compound was prepared according to the synthetic route of Example 1, from Intermediate 22 (N-(3-fluoro-4-(1-methyl-6-(1-Boc-pyrazol-4-yl)-1H-indazol-5-yloxy)phenyl)-6-isopropyl-2-oxo-1-(4-fluorophenyl)-1,2-dihydropyridine-3-carboxamide). ¹H NMR (500 MHz, chloroform-d) δ 11.85 (s, 1H), 8.69 (d, J=7.8 Hz, 1H), 8.49 (s, 2H), 7.93-7.85 (m, 2H), 7.63 (s, 1H), 7.31 (t, J=8.4 Hz, 2H), 7.30-7.21 (m, 3H), 7.12 (s, 1H), 6.97 (t, J=8.7 Hz, 1H), 6.56 (d, J=7.8 Hz, 1H), 6.12 (s, b, 2H), 4.88 (s, 1H), 2.96 (s, 3H), 2.60 (hept, J=6.8 Hz, 1H), 1.61 (d, J=4.7 Hz, 6H), 1.18 (d, J=6.8 Hz, 6H).

Example 8: Preparation of N-(3-fluoro-4-(1-isopropyl-6-(1H-pyrazol-4-yl)-1H-indazol-5-yloxy)phenyl)-1-(4-fluorophenyl)-6-trifluoromethyl-2-oxo-1,2-dihydropyridine-3-carboxamide

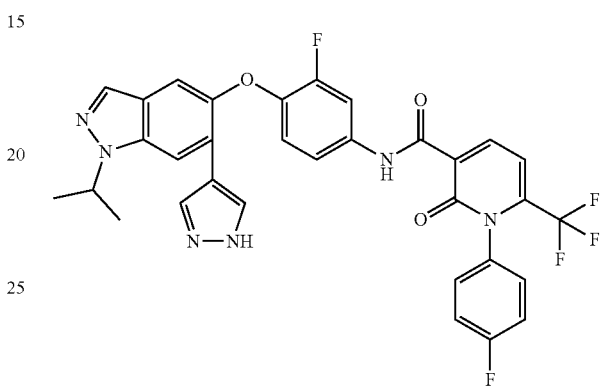

This compound was prepared according to the synthetic route of Example 1, from Intermediate 23 (N-(3-fluoro-4-(1-methyl-6-(1-Boc-pyrazol-4-yl)-1H-indazol-5-yloxy)phenyl)-6-isopropyl-2-oxo-1-(4-fluorophenyl)-1,2-dihydropyridine-3-carboxamide). ¹H NMR (500 MHz, chloroform-d) δ 11.62 (s, 1H), 8.78 (d, J=7.6 Hz, 1H), 8.53 (s, 2H), 7.89 (s, 1H), 7.88 (dd, J=10.1 Hz, 2.5 Hz, 1H), 7.64 (s, 1H), 7.33-7.22 (m, 5H), 7.14 (s, 1H), 7.09 (d, J=7.6 Hz, 1H), 6.98 (t, J=8.8 Hz, 1H), 5.60 (s, b, 2H), 4.88 (hept, J=6.7 Hz, 1H), 2.95 (s, 3H), 1.61 (d, J=6.6 Hz, 6H).

Example 9: Preparation of N-(3-fluoro-4-(1-methyl-6-(1H-pyrazol-4-yl)-1H-indazol-5-yloxy)phenyl)-1-(4-fluorophenyl)-6-chloro-2-oxo-1,2-dihydropyridine-3-carboxamide

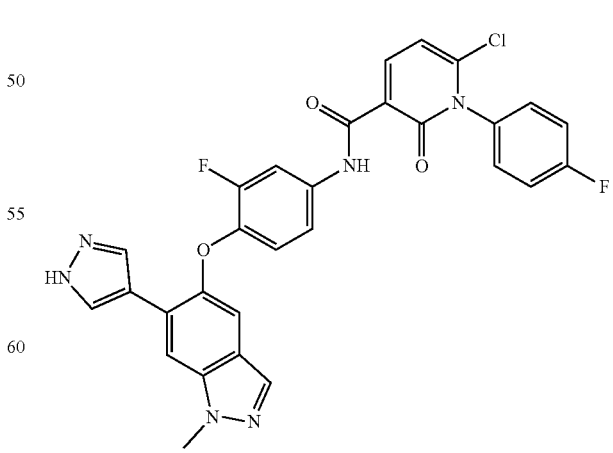

This compound was prepared according to the synthetic route of Example 1, from Intermediate 64 (N-(3-fluoro-4-

(1-methyl-6-(1-Boc-pyrazol-4-yl)-1H-indazol-5-yloxy)phenyl)-6-chloro-2-oxo-1-(4-fluorophenyl)-1,2-dihydropyridine-3-carboxamide). $^1$H NMR (400 MHz, DMSO-d$_6$) δ 12.97 (s, 1H), 11.57 (s, 1H), 8.51 (d, J=7.9 Hz, 1H), 8.15 (s, 1H), 8.02 (s, 1H), 8.00 (s, 1H), 7.95 (d, J=14.5 Hz, 1H), 7.91 (s, 1H), 7.56 (s, 2H), 7.44 (t, J=8.5 Hz, 2H), 7.28 (s, 2H), 7.01 (d, J=8.0 Hz, 1H), 6.85 (t, J=9.1 Hz, 1H), 4.07 (s, 3H). MS-ESI [M+H]$^+$: 573.1.

Example 10: Preparation of N-(3-fluoro-4-(1-methyl-6-(1H-pyrazol-4-yl)-1H-indazol-5-yloxy)phenyl)-1-(4-fluorophenyl)-6-amino-2-oxo-1,2-dihydropyidine-3-carboxamide

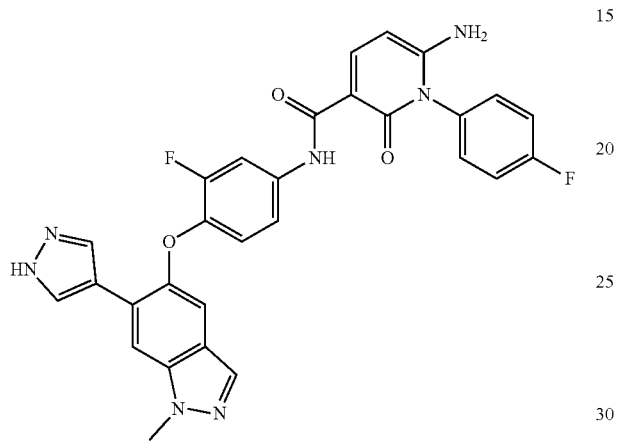

This compound was prepared according to the synthetic route of Example 1, from Intermediate 65 (N-(3-fluoro-4-(1-methyl-6-(1-Boc-pyrazol-4-yl)-1H-indazol-5-yloxy)phenyl)-6-(Bocamino)-2-oxo-1-(4-fluorophenyl)-1,2-dihydropyridine-3-carboxamide). $^1$H NMR (400 MHz, DMSO-d$_6$) δ 12.67 (s, 1H), 11.73 (s, 1H), 8.15 (d, J=8.8 Hz, 1H), 8.10 (s, 2H), 7.98 (s, 1H), 7.94 (dd, J=13.6, 2.4 Hz, 1H), 7.89 (d, J=0.6 Hz, 1H), 7.41 (d, J=1.8 Hz, 2H), 7.40 (s, 2H), 7.21 (s, 1H), 7.14 (d, J=10.0 Hz, 1H), 6.84 (t, J=9.2 Hz, 1H), 5.88 (d, J=8.8 Hz, 1H), 4.07 (s, 3H). MS-ESI [M+H]$^+$: 554.2.

Example 11: Preparation of N-(3-fluoro-4-(1-methyl-6-(1H-pyrazol-4-yl)-1H-indazol-5-yloxy)phenyl)-1-(4-fluorophenyl)-6-methylthio-2-oxo-1,2-dihydropyidine-3-carboxamide

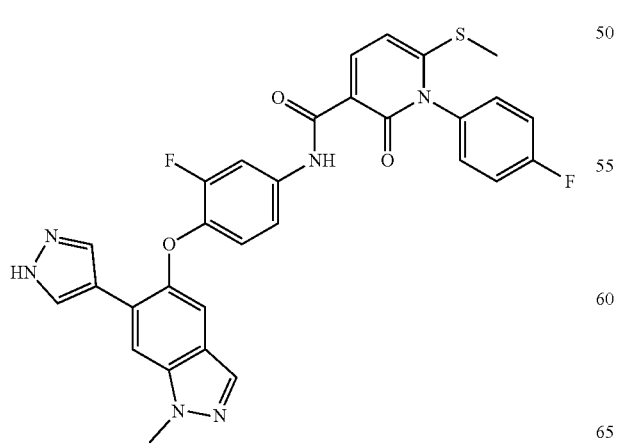

This compound was prepared according to the synthetic route of Example 1, from Intermediate 66 (N-(3-fluoro-4-(1-methyl-6-(1-Boc-pyrazol-4-yl)-1H-indazol-5-yloxy)phenyl)-6-methylthio-2-oxo-1-(4-fluorophenyl)-1,2-dihydropyridine-3-carboxamide). $^1$H NMR (400 MHz, CDCl$_3$) δ 11.66 (s, 1H), 8.62 (d, J=8.4 Hz, 1H), 8.32 (s, 2H), 7.90 (dd, J=12.4, 2.4 Hz, 1H), 7.84 (s, 1H), 7.54 (s, 1H), 7.30-7.27 (m, 4H), 7.25-7.20 (m, 1H), 7.14 (s, 1H), 6.94 (t, J=8.8 Hz, 1H), 6.33 (d, J=8.4 Hz, 1H), 4.11 (s, 3H), 2.47 (s, 3H). MS-ESI [M+H]$^+$: 585.1.

Example 12: Preparation of N-(3-fluoro-4-(1-methyl-6-(1H-pyrazol-4-yl)-1H-indazol-5-yloxy)phenyl)-1-(4-fluorophenyl)-6-methoxy-2-oxo-1,2-dihydropyridine-3-carboxamide

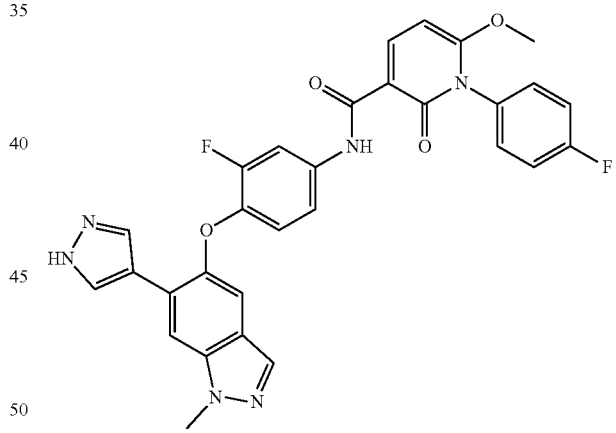

This compound was prepared according to the synthetic route of Example 1, from Intermediate 68 (N-(3-fluoro-4-(1-methyl-6-(1-Boc-pyrazol-4-yl)-1H-indazol-5-yloxy)phenyl)-6-methoxy-2-oxo-1-(4-fluorophenyl)-1,2-dihydropyridine-3-carboxamide). $^1$H NMR (400 MHz, DMSO-d$_6$) δ 12.95 (br s, 1H), 11.69 (s, 1H), 8.56 (d, J=8.6 Hz, 1H), 8.09 (br s, 2H), 7.99 (s, 1H), 7.95 (dd, J=13.4, 2.4 Hz, 1H), 7.91 (s, 1H), 7.46-7.33 (m, 4H), 7.25 (s, 1H), 7.23 (d, J=9.0 Hz, 1H), 6.86 (t, J=9.1 Hz, 1H), 6.34 (d, J=8.7 Hz, 1H), 4.07 (s, 3H), 3.90 (s, 3H). MS-ESI [M+H]$^+$: 569.1.

Example 13: Preparation of N-(3-fluoro-4-(1-methyl-6-(1H-pyrazol-4-yl)-1H-indazol-5-yloxy)phenyl)-1-(4-fluorophenyl)-6-methylsulfoxide-2-oxo-12-dihydropyridine-3-carboxamide

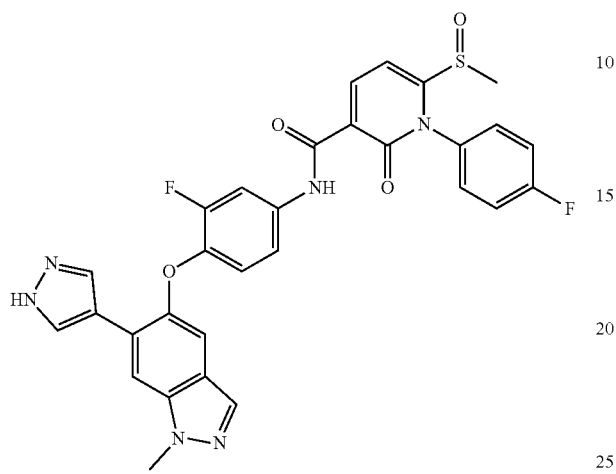

This compound was prepared according to the synthetic route of Example 1, from Intermediate 67 (N-(3-fluoro-4-(1-methyl-6-(1-Boc-pyrazol-4-yl)-1H-indazol-5-yloxy)phenyl)-6-methylsulfoxide-2-oxo-1-(4-fluorophenyl)-1,2-dihydropyridine-3-carboxamide). $^1$H NMR (400 MHz, DMSO-d$_6$) δ 12.96 (br, 1H), 11.71 (s, 1H), 8.75 (d, J=7.6 Hz, 1H), 8.06 (br, 2H), 8.00 (s, 1H), 7.99-7.94 (m, 1H), 7.92 (s, 1H), 7.77-7.71 (m, 1H), 7.67 (d, J=5.0 Hz, 1H), 7.46 (t, J=8.8 Hz, 2H), 7.30 (d, J=9.8 Hz, 2H), 7.22 (d, J=7.7 Hz, 1H), 6.86 (t, J=9.1 Hz, 1H), 4.07 (s, 3H), 2.60 (s, 3H). MS-ESI [M+H]$^+$: 601.0.

Example 14: Preparation of N-(3-fluoro-4-(1-methyl-6-(1H-pyrazol-4-yl)-1H-indazol-5-yloxy)phenyl)-1-(4-fluorophenyl)-6-ethoxy-2-oxo-12-dihydropyridine-3-carboxamide

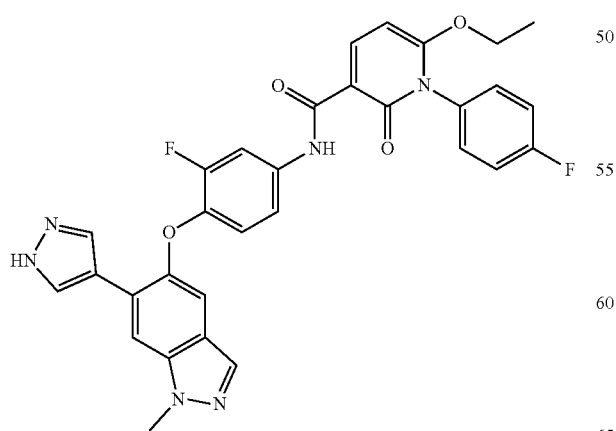

This compound was prepared according to the synthetic route of Example 1, starting from Intermediate 69 (N-(3-fluoro-4-(1-methyl-6-(1-Boc-pyrazol-4-yl)-1H-indazol-5-yloxy)phenyl)-6-ethoxy-2-oxo-1-(4-fluorophenyl)-1,2-dihydropyridine-3-carboxamide). $^1$H NMR (400 MHz, DMSO-d) S 12.94 (br s, 1H), 11.70 (s, 1H), 8.53 (d, J=8.6 Hz, 1H), 8.09 (br s, 2H), 7.99 (s, 1H), 7.95 (d, J=13.5 Hz, 1H), 7.90 (s, 1H), 7.46-7.33 (m, 4H), 7.27-7.17 (m, 2H), 6.85 (t, J=9.2 Hz, 1H), 6.33 (d, J=8.6 Hz, 1H), 4.30-4.20 (q, J=6.4 Hz, 2H), 4.07 (s, 3H), 1.14 (t, J=6.3 Hz, 3H). MS-ESI [M+H]$^+$: 583.1.

Example 15: Preparation of N-(3-fluoro-4-(1-methyl-6-(1H-pyrazol-4-yl)-1H-indazol-5-yloxy)phenyl)-1-(4-fluorophenyl)-6-cyclopropoxy-2-oxo-1,2-dihydropyridine-3-carboxamide

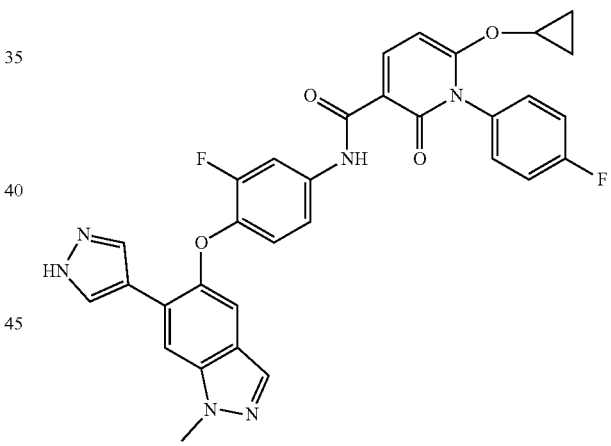

This compound was prepared according to the synthetic route of Example 1, from Intermediate 70 (N-(3-fluoro-4-(1-methyl-6-(1-Boc-pyrazol-4-yl)-1H-indazol-5-yloxy)phenyl)-6-cyclopropoxy-2-oxo-1-(4-fluorophenyl)-1,2-dihydropyridine-3-carboxamide). $^1$H NMR (400 MHz, CDCl$_3$) δ 11.62 (s, 1H), 8.72 (d, J=8.4 Hz, 1H), 8.27 (br s, 2H), 7.89 (dd, J=12.8, 2.0 Hz, 1H), 7.84 (s, 1H), 7.55 (s, 1H), 7.24-7.09 (m, 6H), 6.91 (t, J=8.8 Hz, 1H), 6.35 (d, J=8.8 Hz, 1H), 4.11 (s, 3H), 3.93-3.90 (m, 1H), 0.90-0.85 (m, 2H), 0.76-0.72 (m, 2H). MS-ESI [M+H]$^+$: 595.2.

Example 16: Preparation of N-(3-fluoro-4-(1-methyl-6-(1H-pyrazol-4-yl)-1H-indazol-5-yloxy)phenyl)-1-(4-fluorophenyl)-6-isopropoxy-2-oxo-1,2-dihydropyridine-3-carboxamide

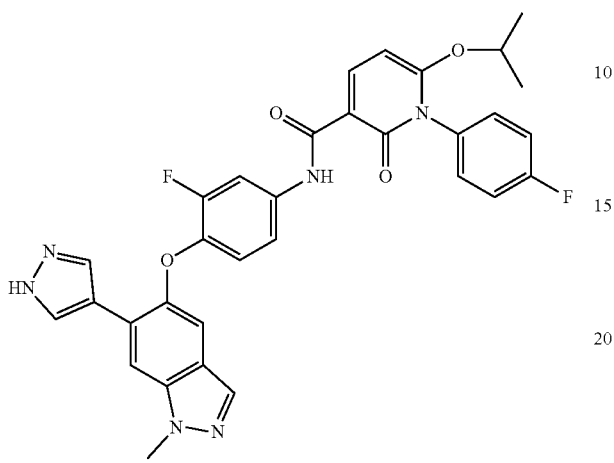

This compound was prepared according to the synthetic route of Example 1, from Intermediate 71 (N-(3-fluoro-4-(1-methyl-6-(1-Boc-pyrazol-4-yl)-1H-indazol-5-yloxy)phenyl)-6-isopropoxy-2-oxo-1-(4-fluorophenyl)-1,2-dihydropyridine-3-carboxamide). $^1$H NMR (400 MHz, CDCl$_3$) δ 11.60 (s, 1H), 8.68 (d, J=8.8 Hz, 1H), 8.15 (br s, 2H), 7.88 (dd, J=12.8, 2.2 Hz, 1H), 7.83 (s, 1H), 7.56 (s, 1H), 7.22 (d, J=8.2 Hz, 2H), 7.20-7.12 (m, 4H), 6.84 (t, J=8.9 Hz, 1H), 5.96 (d, J=8.8 Hz, 1H), 4.73-4.67 (m, 1H), 4.10 (s, 3H), 1.27 (d, J=6.0 Hz, 6H). MS-ESI [M+H]$^+$: 597.2.

Example 17: Preparation of N-(3-fluoro-4-(1-methyl-6-(1H-pyrazol-4-yl)-1H-indazol-5-yloxy)phenyl)-1-(4-fluorophenyl)-6-(2,2,2-trifluoroethoxy)-2-oxo-1,2-dihydropyidine-3-carboxamide

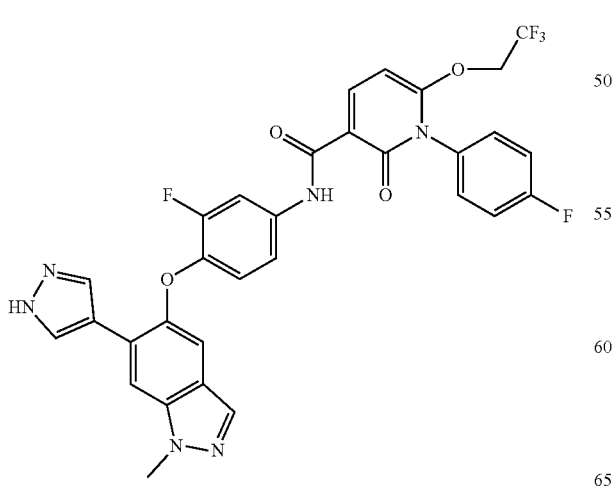

This compound was prepared according to the synthetic route of Example 1, from Intermediate 72 (N-(3-fluoro-4-(1-methyl-6-(1-Boc-pyrazol-4-yl)-1H-indazol-5-yloxy)phenyl)-6-(2,2,2-trifluoroethoxy)-2-oxo-1-(4-fluorophenyl)-1,2-dihydropyridine-3-carboxamide). $^1$H NMR (400 MHz, DMSO-d$_6$) δ 11.63 (s, 1H), 8.59 (d, J=8.8 Hz, 1H), 8.09 (s, 2H), 7.99 (s, 1H), 7.95 (dd, J=13.2, 2.4 Hz, 1H), 7.91 (s, 1H), 7.46-7.35 (m, 4H), 7.28-7.21 (m, 2H), 6.86 (t, J=9.1 Hz, 1H), 6.45 (d, J=8.8 Hz, 1H), 5.02 (q, J=8.4 Hz, 2H), 4.07 (s, 3H). MS-ESI [M+H]$^+$: 637.0.

Example 18: Preparation of N-(3-fluoro-4-(1-ethyl-6-(1H-pyrazol-4-yl)-1H-indazol-5-yloxy)phenyl)-1-(4-fluorophenyl)-6-ethyl-2-oxo-1,2-dihydropyridine-3-carboxamide This compound was prepared according to the synthetic route of Example 1, from Intermediate 73 (N-(3-fluoro-4-(1-ethyl-6-(1-Boc-pyrazol-4-yl)-1H-indazol-5-yloxy)phenyl)-6-ethyl-2-oxo-1-(4-fluorophenyl)-1,2-dihydropyridine-3-carboxamide). $^1$H NMR (400 MHz, Methanol-d$_4$) δ 8.58 (d, J=7.6 Hz, 1H), 8.10 (s, 2H), 7.93-7.81 (m, 3H), 7.41-7.28 (m, 4H), 7.23 (s, 1H), 7.17-7.11 (m, 1H), 6.86 (t, J=9.0 Hz, 1H), 6.67 (d, J=7.8 Hz, 1H), 4.49 (q, J=7.2 Hz, 2H), 2.39 (q, J=7.4 Hz, 2H), 1.49 (t, J=7.2 Hz, 3H), 1.14 (t, J=7.4 Hz, 3H). MS-ESI [M+H]$^+$: 581.3.

Example 19: Preparation of N-(3-fluoro-4-(1-ethyl-6-(1H-pyrazol-4-yl)-1H-indazol-5-yloxy)phenyl)-1-(4-fluorophenyl)-6-cyclopropyl-2-oxo-1,2-dihydropyridine-3-carboxamide

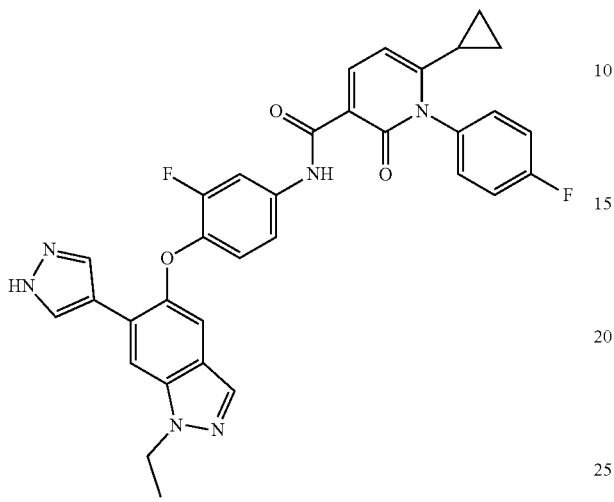

This compound was prepared according to the synthetic route of Example 1, from Intermediate 74 (N-(3-fluoro-4-(1-ethyl-6-(1-Boc-pyrazol-4-yl)-1H-indazol-5-yloxy)phenyl)-6-cyclopropyl-2-oxo-1-(4-fluorophenyl)-1,2-dihydropyridine-3-carboxamide). $^1$H NMR (400 MHz, Methanol-$d_4$) δ 8.54 (d, J=7.6 Hz, 1H), 8.20 (s, 2H), 7.89 (s, 2H), 7.86 (dd, J=12.8, 2.4 Hz, 1H), 7.43-7.30 (m, 4H), 7.24 (s, 1H), 7.18-7.14 (m, 1H), 6.88 (d, J=9.2 Hz, 1H), 6.43 (d, J=8.0 Hz, 1H), 4.50 (q, J=7.2 Hz, 2H), 1.47 (t, J=7.2 Hz, 3H), 1.45-1.41 (m, 1H), 0.92-0.89 (m, 4H). MS-ESI [M+H]$^+$: 593.2.

Example 20: Preparation of N-(3-fluoro-4-(1-ethyl-6-(1H-pyrazol-4-yl)-1H-indazol-5-yloxy)phenyl)-1-(4-fluorophenyl)-6-chloro-2-oxo-1,2-dihydropyridine-3-carboxamide

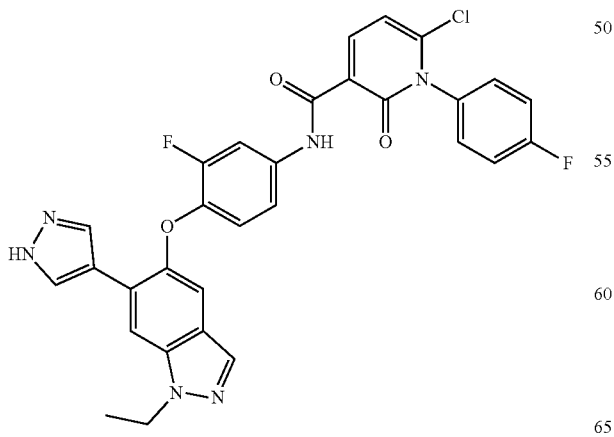

This compound was prepared according to the synthetic route of Example 1, from Intermediate 75 (N-(3-fluoro-4-(1-ethyl-6-(1-Boc-pyrazol-4-yl)-1H-indazol-5-yloxy)phenyl)-6-chloro-2-oxo-1-(4-fluorophenyl)-1,2-dihydropyridine-3-carboxamide). $^1$H NMR (400 MHz, DMSO-$d_6$) δ 12.96 (br s, 1H), 11.57 (s, 1H), 8.51 (d, J=8.0 Hz, 1H), 8.02 (br s, 3H), 7.96 (dd, J=13.2, 2.5 Hz, 1H), 7.93 (d, J=0.8 Hz, 1H), 7.61-7.52 (m, 2H), 7.49-7.40 (m, 2H), 7.31-7.24 (m, 2H), 7.01 (d, J=8.0 Hz, 1H), 7.01-6.86 (m, 1H), 4.47 (q, J=7.2 Hz, 2H), 1.42 (t, J=7.2 Hz, 3H). MS-ESI [M+H]$^+$: 587.2.

Example 21: Preparation of N-(3-Fluoro-4-(1-ethyl-6-(1H-pyrazol-4-yl)-1H-indazol-5-yloxy)phenyl)-1-(4-fluorophenyl)-6-amino-2-oxo-1,2-dihydropyridine-3-carboxamide

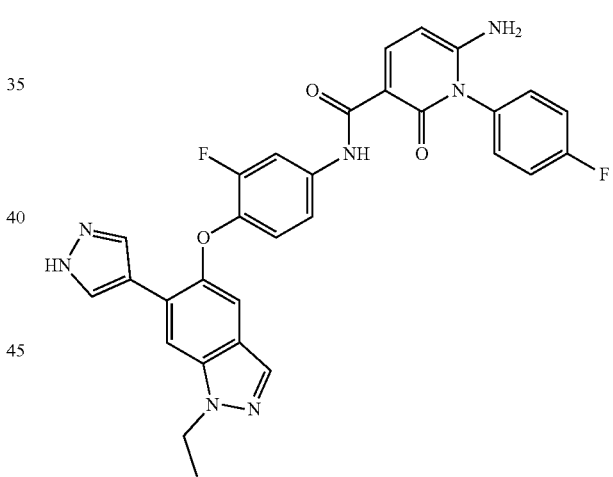

This compound was prepared according to the synthetic route of Example 1, from Intermediate 76 (N-(3-fluoro-4-(1-ethyl-6-(1-Boc-pyrazol-4-yl)-1H-indazol-5-yloxy)phenyl)-6-Boc-amino-2-oxo-1-(4-fluorophenyl)-1,2-dihydropyridine-3-carboxamide). $^1$H NMR (400 MHz, DMSO-$d_6$) δ 12.89 (br s, 1H), 11.72 (s, 1H), 8.16 (d, J=8.8 Hz, 1H), 8.10 (br s, 2H), 8.01 (s, 1H), 7.94 (dd, J=13.6, 2.4 Hz, 1H), 7.91 (s, 1H), 7.42-7.40 (m, 4H), 7.21 (s, 1H), 7.13 (d, J=10.0 Hz, 1H), 6.85 (t, J=9.2 Hz, 1H), 5.88 (d, J=8.8 Hz, 1H), 4.46 (q, J=7.1 Hz, 2H), 1.42 (t, J=7.2 Hz, 3H). MS-ESI [M+H]$^+$: 568.2.

Example 22: Preparation of N-(3-fluoro-4-(1-ethyl-6-(1H-pyrazol-4-yl)-1H-indazol-5-yloxy)phenyl)-1-(4-fluorophenyl)-6-methylthio-2-oxo-1,2-dihydropyidine-3-carboxamide

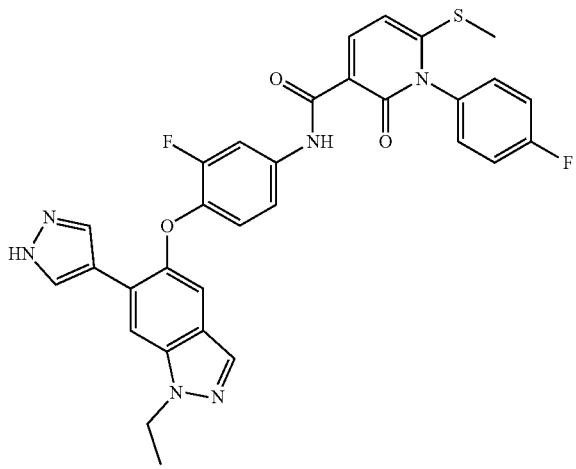 [SMILES: CCn1ncc2cc(Oc3ccc(NC(=O)c4ccc(SC)n(-c5ccc(F)cc5)c4=O)cc3F)c(-c3cn[nH]c3)cc21]

This compound was prepared according to the synthetic route of Example 1, from Intermediate 77 (N-(3-fluoro-4-(1-ethyl-6-(1-Boc-pyrazol-4-yl)-1H-indazol-5-yloxy)phenyl)-6-methylthio-2-oxo-1-(4-fluorophenyl)-1,2-dihydropyridine-3-carboxamide). $^1$H NMR (400 MHz, DMSO-$d_6$) δ 12.95 (br s, 1H), 11.70 (s, 1H), 8.43 (d, J=8.0 Hz, 1H), 8.09 (br, 2H), 8.02 (s, 1H)), 7.95 (d, J=15.2 Hz, 1H), 7.92 (s, 1H), 7.55-7.46 (m, 2H), 7.42 (t, J=8.8 Hz, 2H), 7.24 (d, J=12.8 Hz, 2H), 6.85 (t, J=9.2 Hz, 1H), 6.61 (d, J=8.4 Hz, 1H), 4.46 (q, J=7.2 Hz, 2H), 2.50 (s, 3H), 1.42 (t, J=7.2 Hz, 3H). MS-ESI [M+H]$^+$: 599.1.

Example 23: Preparation of N-(3-fluoro-4-(1-ethyl-6-(1H-pyrazol-4-yl)-1H-indazol-5-yloxy)phenyl)-1-(4-fluorophenyl)-6-methoxy-2-oxo-1,2-dihydropyridine-3-carboxamide

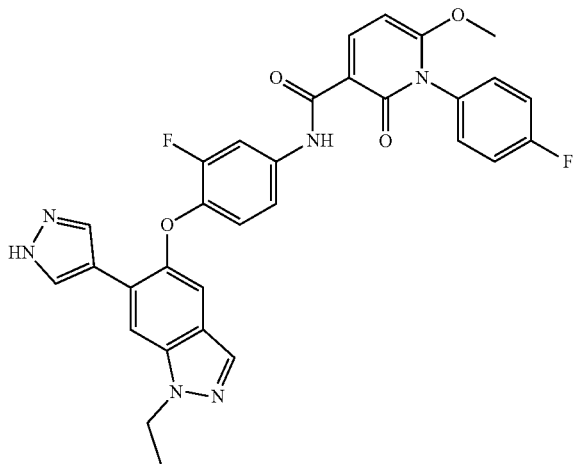 [SMILES: CCn1ncc2cc(Oc3ccc(NC(=O)c4ccc(OC)n(-c5ccc(F)cc5)c4=O)cc3F)c(-c3cn[nH]c3)cc21]

This compound was prepared according to the synthetic route of Example 1, from Intermediate 78 (N-(3-fluoro-4-(1-ethyl-6-(1-Boc-pyrazol-4-yl)-1H-indazol-5-yloxy)phenyl)-6-methoxy-2-oxo-1-(4-fluorophenyl)-1,2-dihydropyridine-3-carboxamide). $^1$H NMR (400 MHz, DMSO-$d_6$) δ 12.94 (br s, 1H), 11.69 (s, 1H), 8.56 (d, J=8.6 Hz, 1H), 8.09 (br s, 2H), 8.02 (s, 1H), 7.96 (dd, J=13.4, 2.4 Hz, 1H), 7.92 (s, 1H), 7.47-7.33 (m, 4H), 7.25 (s, 1H), 7.22 (d, J=10.1 Hz, 1H), 6.86 (t, J=9.2 Hz, 1H), 6.34 (d, J=8.7 Hz, 1H), 4.47 (q, J=7.1 Hz, 2H), 3.90 (s, 3H), 1.42 (t, J=7.2 Hz, 3H). MS-ESI [M+H]$^+$: 583.1.

Example 24: Preparation of N-(3-fluoro-4-(1-ethyl-6-(1H-pyrazol-4-yl)-1H-indazol-5-yloxy)phenyl)-1-(4-fluorophenyl)-6-ethoxy-2-oxo-12-dihydropyridine-3-carboxamide

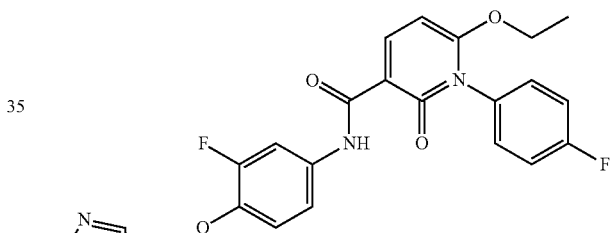

This compound was prepared according to the synthetic route of Example 1, from Intermediate 79 (N-(3-fluoro-4-(1-ethyl-6-(1-Boc-pyrazol-4-yl)-1H-indazol-5-yloxy)phenyl)-6-ethoxy-2-oxo-1-(4-fluorophenyl)-1,2-dihydropyridine-3-carboxamide). $^1$H NMR (400 MHz, DMSO-$d_6$) δ 12.97 (br s, 1H), 11.70 (s, 1H), 8.53 (d, J=8.4 Hz, 1H), 8.09-8.04 (m, 2H), 8.01 (s, 1H), 7.95 (dd, J=13.4, 2.3 Hz, 1H), 7.92 (s, 1H), 7.48-7.32 (m, 4H), 7.25 (s, 1H), 7.21 (d, J=9.2 Hz, 1H), 6.86 (t, J=9.2 Hz, 1H), 6.32 (d, J=8.8 Hz, 1H), 4.46 (q, J=7.2 Hz, 2H), 4.25 (q, J=7.2 Hz, 2H), 1.42 (t, J=7.0 Hz, 3H), 1.14 (t, J=7.0 Hz, 3H). MS-ESI [M+H]$^+$: 597.1.

Example 25: Preparation of N-(3-fluoro-4-(1-ethyl-6-(1H-pyrazol-4-yl)-1H-indazol-5-yloxy)phenyl)-1-(4-fluorophenyl)-6-cyclopropoxy-2-oxo-1,2-dihydropyridine-3-carboxamide

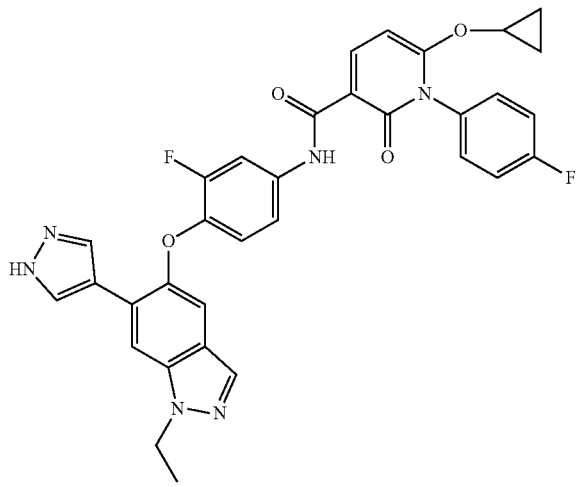 [SMILES: CCn1ncc2cc(Oc3ccc(NC(=O)c4ccc(OC5CC5)n(-c5ccc(F)cc5)c4=O)cc3F)c(-c3cn[nH]c3)cc21]

This compound was prepared according to the synthetic route of Example 1, from Intermediate 80 (N-(3-fluoro-4-(1-ethyl-6-(1-Boc-pyrazol-4-yl)-1H-indazol-5-yloxy)phenyl)-6-cyclopropoxy-2-oxo-1-(4-fluorophenyl)-1,2-dihydropyridine-3-carboxamide). $^1$H NMR (400 MHz, DMSO-d$_6$) δ 12.95 (br s, 1H), 11.69 (s, 1H), 8.59 (d, J=8.4 Hz, 1H), 8.09 (br s, 2H), 8.02 (s, 1H), 7.96 (dd, J=13.3, 2.4 Hz, 1H), 7.92 (s, 1H), 7.43-7.31 (m, 4H), 7.27-7.18 (m, 2H), 6.86 (t, J=9.1 Hz, 1H), 6.56 (d, J=8.4 Hz, 1H), 4.47 (q, J=7.2 Hz, 2H), 4.17-4.13 (m, 1H), 1.42 (t, J=7.2 Hz, 3H), 0.84-0.76 (m, 2H), 0.69-0.60 (m, 2H). MS-ESI [M+H]$^+$: 609.1.

Example 26: Preparation of N-(3-fluoro-4-(1-ethyl-6-(1H-pyrazol-4-yl)-1H-indazol-5-yloxy)phenyl)-1-(4-fluorophenyl)-6-isopropoxy-2-oxo-1,2-dihydropyridine-3-carboxamide

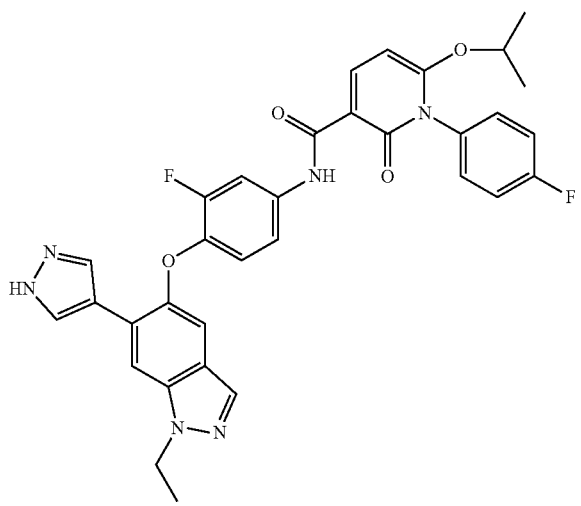 [SMILES: CCn1ncc2cc(Oc3ccc(NC(=O)c4ccc(OC(C)C)n(-c5ccc(F)cc5)c4=O)cc3F)c(-c3cn[nH]c3)cc21]

This compound was prepared according to the synthetic route of Example 1, from Intermediate 81 (N-(3-fluoro-4-(1-ethyl-6-(1-Boc-pyrazol-4-yl)-1H-indazol-5-yloxy)phenyl)-6-isopropoxy-2-oxo-1-(4-fluorophenyl)-1,2-dihydropyridine-3-carboxamide). $^1$H NMR (400 MHz, DMSO-d$_6$) δ 12.96 (br, 1H), 11.71 (s, 1H), 8.52 (d, J=8.8 Hz, 1H), 8.09 (br s, 2H), 8.02 (s, 1H), 7.96 (dd, J=13.4, 2.4 Hz, 1H), 7.92 (s, 1H), 7.43-7.30 (m, 4H), 7.25 (s, 1H), 7.21 (d, J=8.9 Hz, 1H), 6.86 (t, J=9.1 Hz, 1H), 6.37 (d, J=8.8 Hz, 1H), 4.89-4.84 (m, 1H), 4.47 (q, J=7.2 Hz, 2H), 1.42 (t, J=7.2 Hz, 3H), 1.17 (d, J=6.0 Hz, 6H). MS-ESI [M+H]$^+$: 611.2.

Example 27: Preparation of N-(3-fluoro-4-(1-ethyl-6-(1H-pyrazol-4-yl)-1H-indazol-5-yloxy)phenyl)-1-(4-fluorophenyl)-6-(2,2,2-trifluoroethoxy)-2-oxo-1,2-dihydropyidine-3-carboxamide

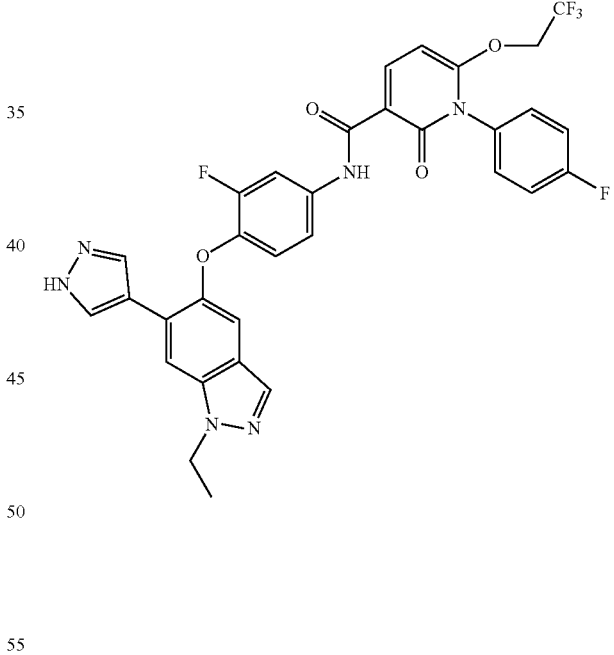

This compound was prepared according to the synthetic route of Example 1, from Intermediate 82 (N-(3-fluoro-4-(1-ethyl-6-(1-Boc-pyrazol-4-yl)-1H-indazol-5-yloxy)phenyl)-6-(2,2,2-trifluoroethoxy)-2-oxo-1-(4-fluorophenyl)-1,2-dihydropyridine-3-carboxamide). $^1$H NMR (400 MHz, DMSO-d$_6$) δ 11.63 (s, 1H), 8.59 (d, J=8.4 Hz, 1H), 8.09 (s, 2H), 8.02 (s, 1H), 7.96 (dd, J=13.3, 2.4 Hz, 1H), 7.92 (s, 1H), 7.48-7.35 (m, 4H), 7.24 (d, J=11.9 Hz, 2H), 6.86 (t, J=9.1 Hz, 1H), 6.45 (d, J=8.4 Hz, 1H), 5.02 (q, J=8.4 Hz, 2H), 4.47 (q, J=7.2 Hz, 2H), 1.42 (t, J=7.2 Hz, 3H). MS-ESI [M+H]$^+$: 651.1.

Example 28: Preparation of N-(4-((5-(1H-pyrazol-4-yl)-6,7-dihydropyrrolo[3,2,1-hi]-indazol-4-yl)oxy)-3-fluorophenyl)-1-(4-fluorophenyl)-6-methoxy-2-oxo-1,2-dihydropyidine-3-carboxamide

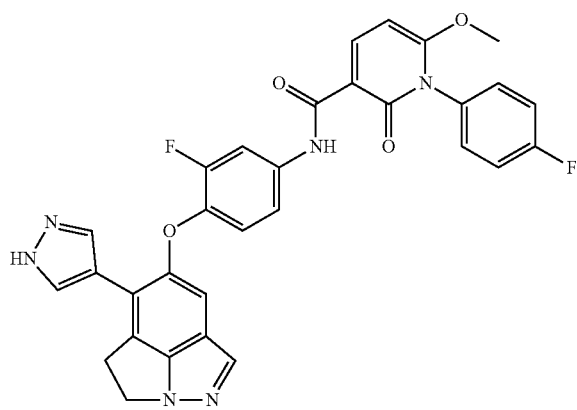 [SMILES: COc1ccc(C(=O)Nc2ccc(Oc3cc4cnn5c4c(c3-c3cn[nH]c3)CC5)c(F)c2)c(=O)n1-c1ccc(F)cc1]

This compound was prepared according to the synthetic route of Example 1, from Intermediate 84 (tert-butyl4-(4-(2-fluoro-4-(1-(4-fluorophenyl)-6-methoxy-2-oxo-1,2-dihydropyridine-3-carboxamido)phenoxy)-6,7-dihydropyrrolo[3,2,1-hi]-indazol-5-yl)-1H-pyrazole-1-carboxylate). ¹H NMR (400 MHz, CDCl₃) δ 8.65 (d, J=8.8 Hz, 1H), 8.07 (s, 2H), 7.86-7.69 (m, 2H), 7.19 (m, 4H), 7.06 (d, J=8.8 Hz, 1H), 6.96 (s, 1H), 6.76 (t, J=8.8 Hz, 1H), 5.99 (d, J=8.4 Hz, 1H), 4.71 (t, J=6.4 Hz, 2H), 4.04 (t, J=6.4 Hz, 2H), 3.88 (s, 3H). MS-ESI [M+H]⁺: 581.1.

Example 29: Preparation of N-(3-fluoro-4-(1-methyl-6-(1H-pyrazol-4-yl)-1H-indazol-5-yloxy)phenyl)-1-(4-fluorophenyl)-6-hydroxy-2-oxo-1,2-dihydropyridine-3-carboxamide

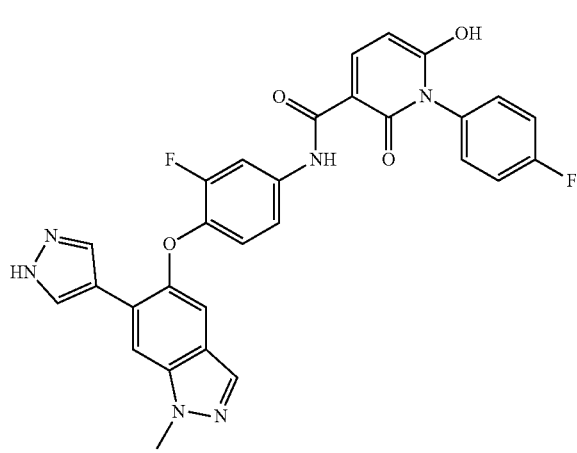 [SMILES: Cn1ncc2cc(Oc3ccc(NC(=O)c4ccc(O)n(-c5ccc(F)cc5)c4=O)cc3F)c(-c3cn[nH]c3)cc21]

To a solution of Example 9 (N-(3-fluoro-4-(1-(1H-pyrazol-4-yl)-1H-indazol-5-yloxy)phenyl)-1-(4-fluorophenyl)-6-chloro-2-oxo-1,2-dihydropyridine-3-carboxamide) (0.130 g, 0.19 mmol) in THF (2 mL) were added NaOH (0.076 g, 1.90 mmol) and water (0.8 mL). The mixture was stirred at room temperature for 16 hours, then diluted with water (5 mL), neutralized to pH 7 with concentrated HCl, and extracted with ethyl acetate (5×10 mL). The organic phase was dried and concentrated and purified by HPLC to obtain a yellow solid (3 mg, 2.8% yield). ¹H NMR (400 MHz, DMSO-d₆) δ 12.95 (br s, 1H), 12.19 (s, 1H), 8.14-8.06 (m, 2H), 8.00-7.92 (m, 2H), 7.91-7.87 (m, 2H), 7.27-7.16 (m, 3H), 7.15-7.03 (m, 3H), 6.95 (s, 1H), 6.85 (t, J=9.2 Hz, 1H), 5.34 (d, J=9.2 Hz, 1H), 4.06 (s, 3H). MS-ESI [M+H]⁺: 553.1.

Example 30: Preparation of N-(3-fluoro-4-(1-ethyl-6-(1H-pyrazol-4-yl)-1H-indazol-5-yloxy)phenyl)-1-(4-fluorophenyl)-6-hydroxy-2-oxo-1,2-dihydropyridine-3-carboxamide

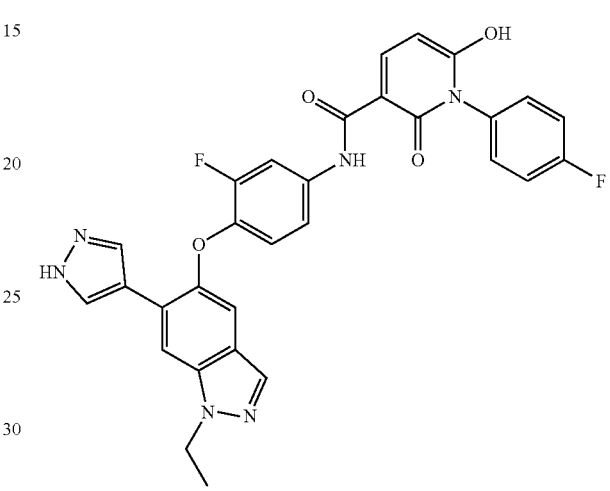

This compound was prepared according to the synthetic route of Example 29, from Example 20 (N-(3-fluoro-4-(1-ethyl-6-(1H-pyrazol-4-yl)-1H-indazol-5-yloxy)phenyl)-1-(4-fluorophenyl)-6-chloro-2-oxo-1,2-dihydropyridine-3-carboxamide). ¹H NMR (400 MHz, DMSO-d₆) δ 12.94 (br s, 1H), 12.19 (s, 1H), 8.11 (br s, 2H), 7.99-7.92 (m, 2H), 7.90 (s, 1H), 7.83 (d, J=8.1 Hz, 1H), 7.26-7.08 (m, 6H), 6.95 (s, 1H), 6.85 (t, J=9.2 Hz, 1H), 5.49 (d, J=9.1 Hz, 1H), 4.46 (q, J=7.2 Hz, 2H), 1.41 (t, J=7.2 Hz, 3H). MS-ESI [M+H]⁺: 567.1.

Example 31: Preparation of N-(4-((5-(1H-pyrazol-4-yl)-6,7-dihydropyrrolo[3,2,1-hi]-indazol-4-yl)oxy)-3-fluorophenyl)-1-(4-fluorophenyl)-6-methyl-2-oxo-1,2-dihydropyridine-3-carboxamide

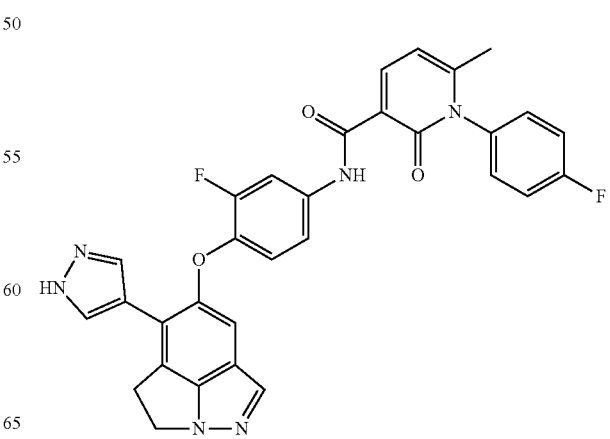

This compound was prepared according to the synthetic route of Example 1, from Intermediate 83 (tert-butyl4-(4-(2-fluoro-4-(1-(4-fluorophenyl)-6-methyl-2-oxo-1,2-dihydropyridine-3-carboxamido)phenoxy)-6,7-dihydropyrrolo[3,2,1-hi]-indazol-5-yl)-1H-pyrazole-1-carboxylate). ¹H NMR (400 MHz, CDCl₃) δ 11.63 (s, 1H), 8.62-8.46 (m, 1H), 8.05-7.28 (m, 6H), 7.21 (s, 2H), 7.04-6.73 (m, 2H), 6.45 (d, J=4.3 Hz, 2H), 4.71 (s, 2H), 4.06 (s, 2H), 2.08 (s, 3H). MS-ESI [M+H]⁺: 565.3.

Example 32: Preparation of-N-(4-((5-(1H-pyrazol-4-yl)-6,7-dihydropyrrolo[3,2,1-hi]-indazol-4-yl)oxy)-3-fluorophenyl)-6-ethoxy-1-(4-fluorophenyl)-2-oxo-12-dihydropyridine-3-carboxamide

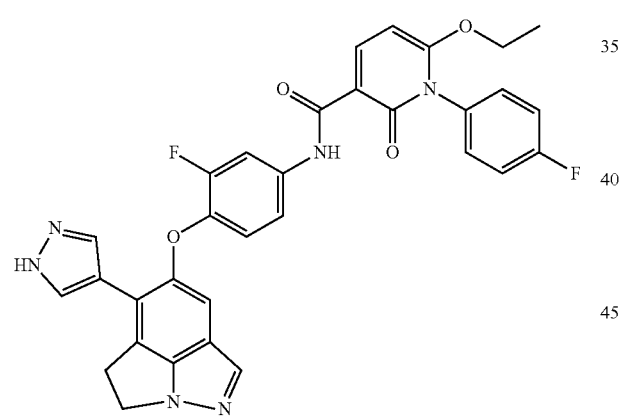

This compound was prepared according to the synthetic route of Example 1, from Intermediate 85 (tert-butyl 4-(4-(2-fluoro-4-(1-(4-fluorophenyl)-6-ethoxy-2-oxo-1,2-dihydropyridine-3-carboxamido)phenoxy)-6,7-dihydropyrrolo[3,2,1-hi]-indazol-5-yl)-1H-pyrazole-1-carboxylate). ¹H NMR (400 MHz, DMSO-d₆) δ 11.66 (s, 1H), 8.52 (d, J=8.7 Hz, 1H), 8.02-7.90 (m, 3H), 7.82 (s, 1H), 7.45-7.32 (m, 4H), 7.14 (d, J=9.3 Hz, 1H), 7.04 (s, 1H), 6.73 (t, J=9.2 Hz, 1H), 6.32 (d, J=8.8 Hz, 1H), 4.71 (t, J=6.5 Hz, 2H), 4.24 (q, J=7.0 Hz, 2H), 4.07 (t, J=6.6 Hz, 2H), 1.13 (t, J=7.0 Hz, 3H). MS-ESI [M+H]⁺: 595.2.

Example 33: Preparation of N-(4-((5-(1H-pyrazol-4-yl)-6,7-dihydropyrrolo[3,2,1-hi]-indazol-4-yl)oxy)-3-fluorophenyl)-6-cyclopropoxy-1-(4-fluorophenyl)-2-oxo-1,2-dihydropyridine-3-carboxamide

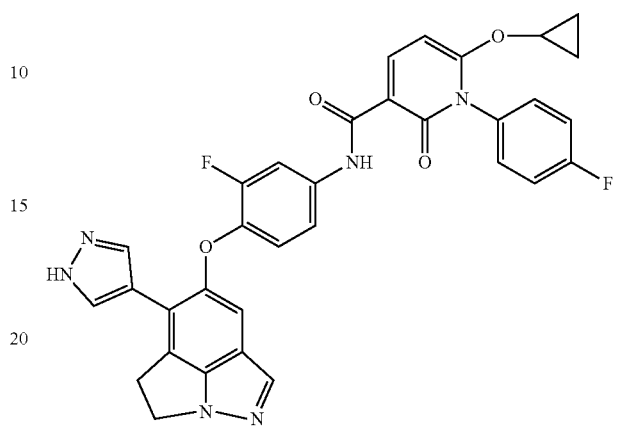

This compound was prepared according to the synthetic route of Example 1, from Intermediate 86 (tert-butyl 4-(4-(2-fluoro-4-(1-(4-fluorophenyl)-6-cyclopropoxy-2-oxo-1,2-dihydropyridine-3-carboxamido)phenoxy)-6,7-dihydropyrrolo[3,2,1-hi]-indazol-5-yl)-1H-pyrazole-1-carboxylate). ¹H NMR (400 MHz, DMSO-d₆) δ11.65 (s, 1H), 8.57 (d, J=8.6 Hz, 1H), 8.00-7.89 (m, 3H), 7.82 (s, 1H), 7.44-7.28 (m, 4H), 7.21-7.12 (m, 1H), 7.05 (s, 1H), 6.73 (t, J=9.2 Hz, 1H), 6.55 (d, J=8.6 Hz, 1H), 4.71 (t, J=6.6 Hz, 2H), 4.14 (dd, J=6.0, 3.2 Hz, 1H), 4.07 (t, J=6.5 Hz, 2H), 0.88-0.81 (m, 2H), 0.64 (s, 2H). MS-ESI [M+H]⁺: 607.2.

Example 34: Preparation of N-(4-((5-(1H-pyrazol-4-yl)-6,7-dihydropyrrolo[3,2,1-hi]-indazol-4-yl)oxy)-3-fluorophenyl)-1-(4-fluorophenyl)-6-isopropoxy-2-oxo-12-dihydropyrndine-3-carboxamide

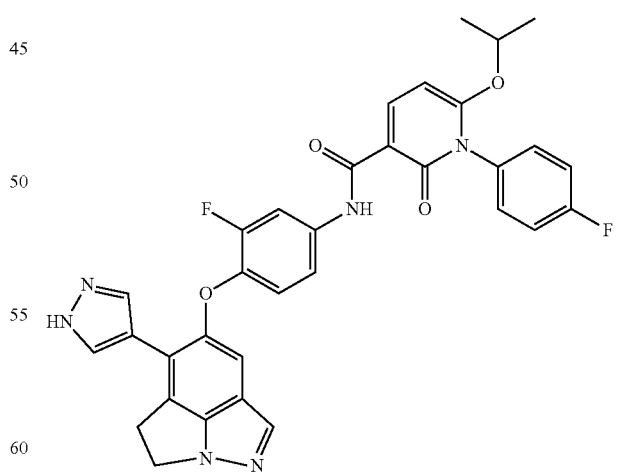

This compound was prepared according to the synthetic route of Example 1, from Intermediate 87 (tert-butyl 4-(4-(2-fluoro-4-(1-(4-fluorophenyl)-6-isopropoxy-2-oxo-1,2-dihydropyridine-3-carboxamido)phenoxy)-6,7-dihydropyrrolo[3,2,1-hi]-indazol-5-yl)-1H-pyrazole-1-carboxylate). ¹H NMR (400 MHz, DMSO-d$_6$) δ 11.67 (s, 1H), 8.50 (d, J=8.6 Hz, 1H), 8.03-7.88 (m, 3H), 7.82 (s, 1H), 7.45-7.30 (m, 4H), 7.20-7.10 (m, 1H), 7.04 (s, 1H), 6.73 (t, J=9.2 Hz, 1H), 6.36 (d, J=8.9 Hz, 1H), 4.93-4.79 (m, 1H), 4.71 (t, J=6.5 Hz, 2H), 4.07 (t, J=6.6 Hz, 2H), 1.16 (d, J=6.1 Hz, 6H). MS-ESI [M+H]$^+$: 609.2.

Example 35: Preparation of N-(4-((5-(1H-pyrazol-4-yl)-6,7-dihydropyrrolo[3,2,1-hi]-indazol-4-yl)oxy)-3-fluorophenyl)-1-(4-fluorophenyl)-2-oxo-6-(2,2,2-trifluoroethoxy)-1,2-dihydropyridine-3-carboxamide

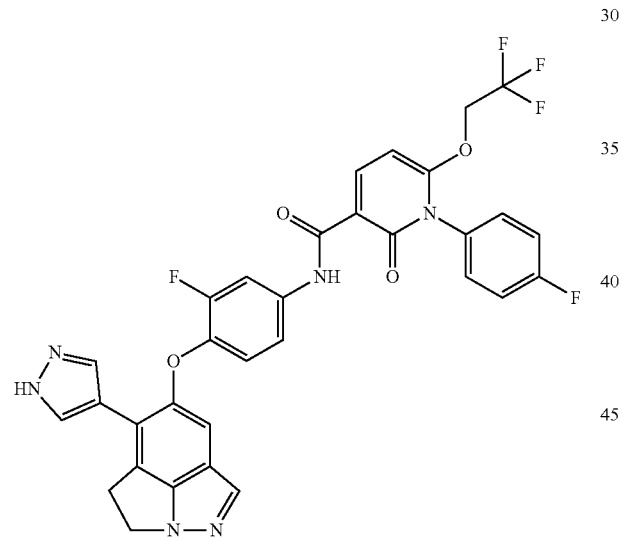

This compound was prepared according to the synthetic route of Example 1, from Intermediate 93 (tert-butyl4-(4-(2-fluoro-4-(1-(4-fluorophenyl)-2-oxo-6-(2,2,2-trifluoroethoxy)-1,2-dihydropyridine-3-carboxamido)phenoxy)-6,7-dihydropyrrolo[3,2,1-hi]-indazol-5-yl)-1H-pyrazole-1-carboxylate). $^1$H NMR (400 MHz, DMSO-d$_6$) δ 13.03 (s, 1H), 11.60 (s, 1H), 8.57 (d, J=8.6 Hz, 1H), 7.94 (dd, J=13.4, 2.6 Hz, 3H), 7.83 (s, 1H), 7.50-7.32 (m, 4H), 7.21-7.13 (m, 1H), 7.05 (s, 1H), 6.74 (t, J=9.2 Hz, 1H), 6.44 (d, J=8.7 Hz, 1H), 5.00 (t, J=8.5 Hz, 2H), 4.71 (t, J=6.6 Hz, 2H), 4.07 (t, J=6.6 Hz, 2H). MS-ESI [M+H]$^+$: 649.1.

Example 36: Preparation of N-(3-fluoro-4-(1-methyl-6-(1H-pyrazol-4-yl)-1H-indazol-5-yloxy)phenyl)-1-(4-fluorophenyl)-6-difluoromethoxy-2-oxo-12-dihydropyridine-3-carboxamide

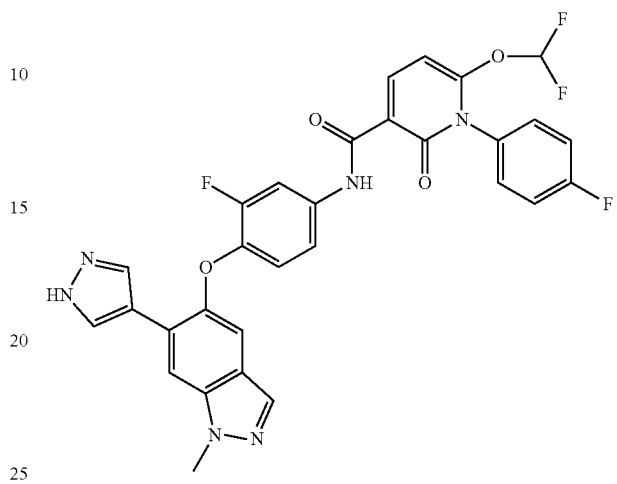

This compound was prepared according to the synthetic route of Example 1, from Intermediate 94 (N-(3-fluoro-4-(1-methyl-6-(1-Boc-pyrazol-4-yl)-1H-indazol-5-yloxy)phenyl)-6-difluoromethoxy-2-oxo-1-(4-fluorophenyl)-1,2-dihydropyridine-3-carboxamide). $^1$H NMR (400 MHz, DMSO-d$_6$) δ10.53 (s, 1H), 8.24 (d, J=8.1 Hz, 1H), 8.09 (s, 2H), 7.99 (s, 1H), 7.92-7.84 (m, 2H), 7.44-7.18 (m, 7H), 7.07-6.88 (m, 2H), 4.07 (s, 3H). MS-ESI [M+H]$^+$: 605.1.

Example 37: Preparation of N-(4-((5-(1H-pyrazol-4-yl)-6,7-dihydropyrrolo[3,2,1-hi]-indazol-4-yl)oxy)-3-fluorophenyl)-6-(difluoromethoxy)-1-(4-fluorophenyl)-2-oxo-1,2-dihydropyridine-3-carboxamide

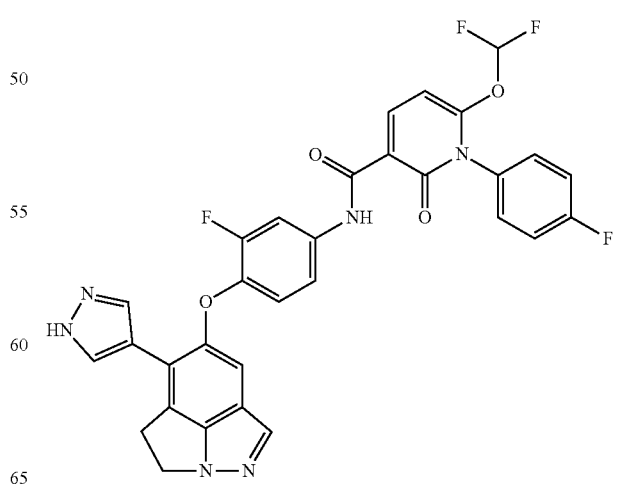

This compound was prepared according to the synthetic route of Example 1, from Intermediate 95 (tert-butyl 4-(4-(2-fluoro-4-(1-(4-fluorophenyl)-6-(difluoromethoxy)-2-oxo-1,2-dihydropyridine-3-carboxamido) phenoxy)-6,7-dihydropyrrolo[3,2,1-hi]-indazol-5-yl)-1H-pyrazole-1-carboxylate). 1H NMR (400 MHz, DMSO-d$_6$) δ 13.03 (s, 1H), 10.47 (s, 1H), 8.23 (d, J=8.1 Hz, 1H), 7.84 (d, J=12.2 Hz, 4H), 7.44-7.16 (m, 6H), 7.04 (d, J=8.2 Hz, 1H), 6.91 (d, J=8.1 Hz, 1H), 6.84 (t, J=9.2 Hz, 1H), 4.72 (t, J=6.6 Hz, 2H), 4.07 (t, J=6.5 Hz, 2H). MS-ESI [M+H]$^+$: 617.1.

The following compounds were essentially made by a similar method of Example 37 above.

| Example number | Structure | MS data |
|---|---|---|
| Example 38 | 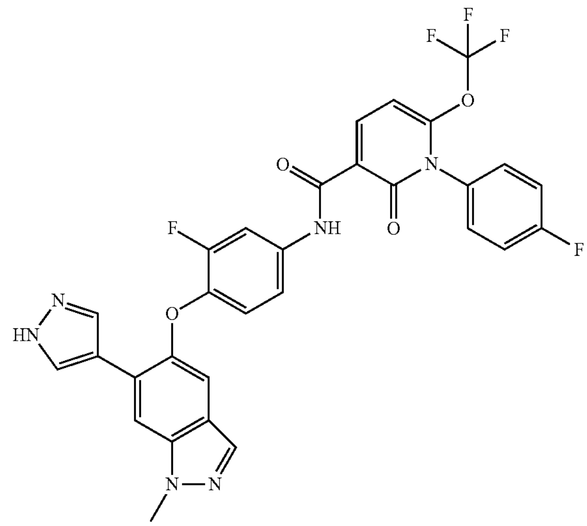 [SMILES: Cn1ncc2cc(Oc3ccc(NC(=O)c4ccc(OC(F)(F)F)n(-c5ccc(F)cc5)c4=O)cc3F)c(-c3cn[nH]c3)cc21] | 623.2 |
| Example 39 | 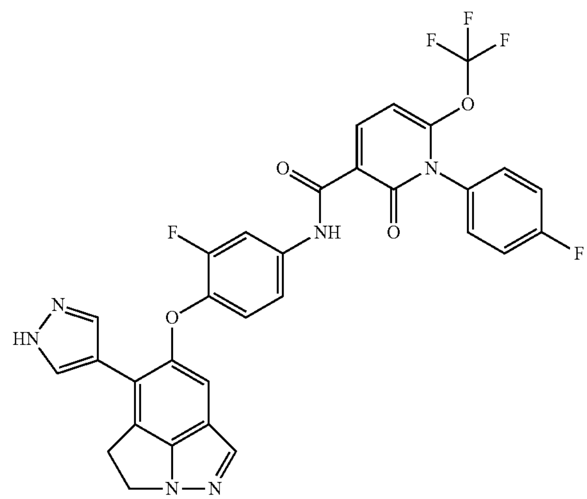 [SMILES: O=C(Nc1ccc(Oc2cc3cnn4c3c(c2-c2cn[nH]c2)CC4)c(F)c1)c1ccc(OC(F)(F)F)n(-c2ccc(F)cc2)c1=O] | 635.2 |
| Example 40 | 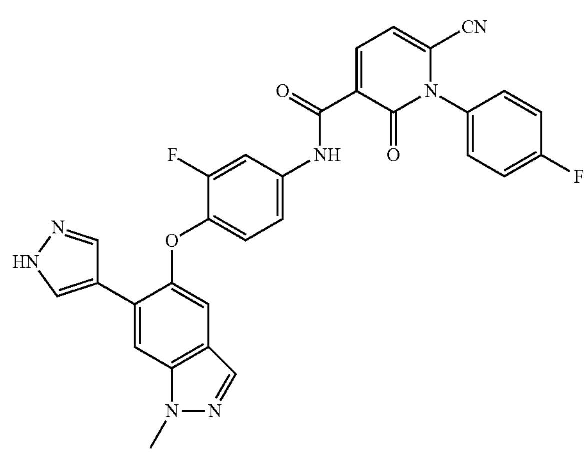 [SMILES: Cn1ncc2cc(Oc3ccc(NC(=O)c4ccc(C#N)n(-c5ccc(F)cc5)c4=O)cc3F)c(-c3cn[nH]c3)cc21] | 564.2 |

-continued
| Example number | Structure | MS data |
|---|---|---|
| Example 41 | 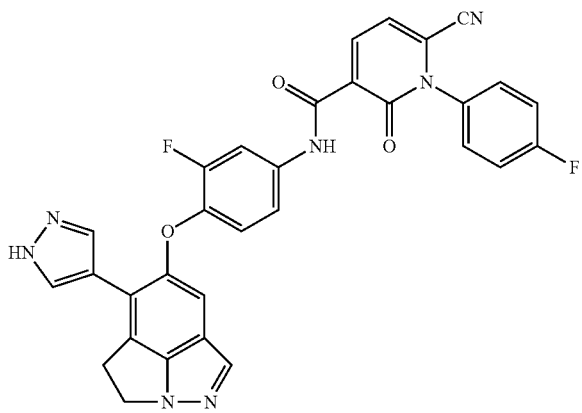 [SMILES: N#Cc1ccc(C(=O)Nc2ccc(Oc3cc4cnn5c4c(c3-c3cn[nH]c3)CC5)c(F)c2)c(=O)n1-c1ccc(F)cc1] | 576.2 |
| Example 42 | 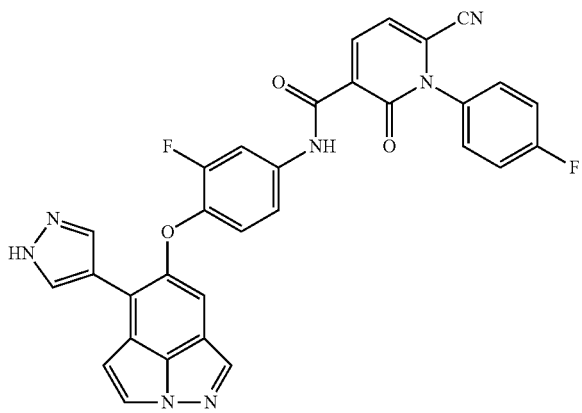 [SMILES: N#Cc1ccc(C(=O)Nc2ccc(Oc3cc4cnn5ccc(c3-c3cn[nH]c3)c45)c(F)c2)c(=O)n1-c1ccc(F)cc1] | 563.2 |
| Example 43 | 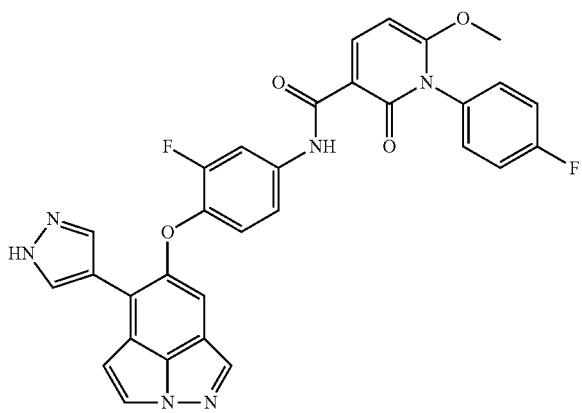 [SMILES: COc1ccc(C(=O)Nc2ccc(Oc3cc4cnn5ccc(c3-c3cn[nH]c3)c45)c(F)c2)c(=O)n1-c1ccc(F)cc1] | 579.2 |

| Example number | Structure | MS data |
|---|---|---|
| Example 44 | 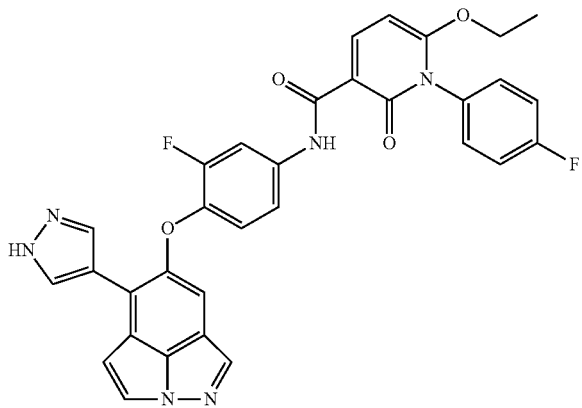 [SMILES: CCOc1ccc(C(=O)Nc2ccc(Oc3cc4cnn5ccc(c3-c3cn[nH]c3)c45)c(F)c2)c(=O)n1-c1ccc(F)cc1] | 593.2 |
| Example 45 | 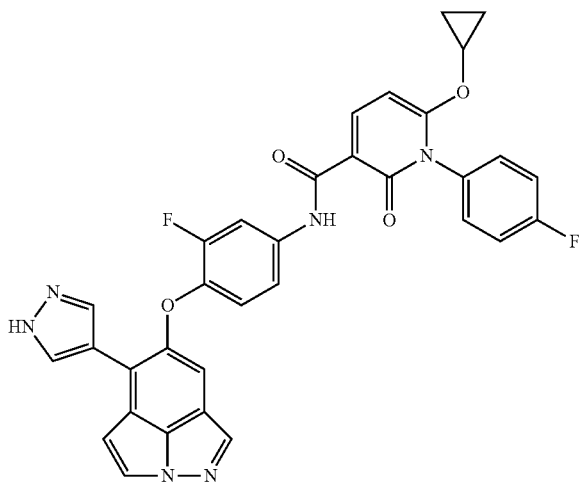 [SMILES: O=C(Nc1ccc(Oc2cc3cnn4ccc(c2-c2cn[nH]c2)c34)c(F)c1)c1ccc(OC2CC2)n(-c2ccc(F)cc2)c1=O] | 605.2 |
| Example 46 | 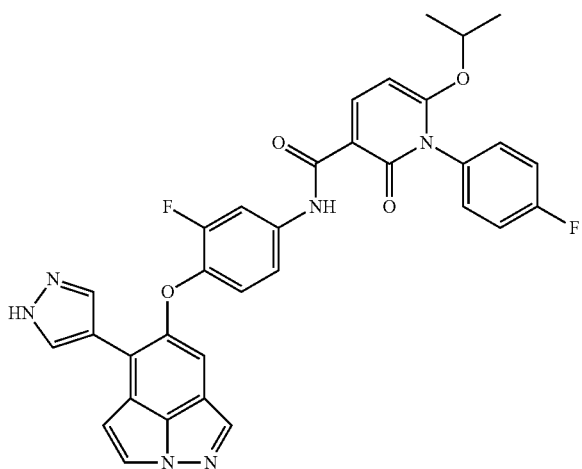 [SMILES: CC(C)Oc1ccc(C(=O)Nc2ccc(Oc3cc4cnn5ccc(c3-c3cn[nH]c3)c45)c(F)c2)c(=O)n1-c1ccc(F)cc1] | 607.2 |

-continued

| Example number | Structure | MS data |
| --- | --- | --- |
| Example 47 | 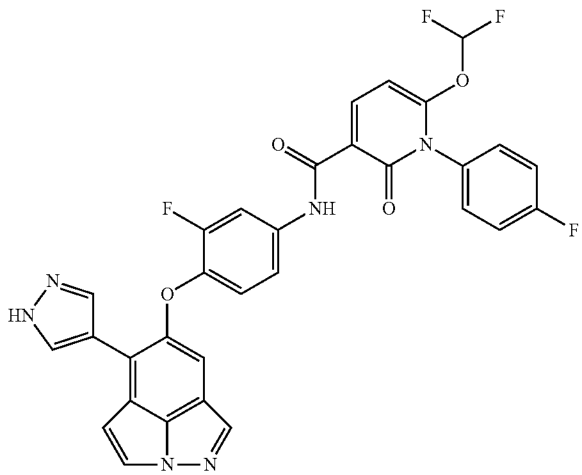 [SMILES: O=C(Nc1ccc(Oc2cc3cnn4ccc(c2-c2cn[nH]c2)c34)c(F)c1)c1ccc(OC(F)F)n(-c2ccc(F)cc2)c1=O] | 615.2 |
| Example 48 | 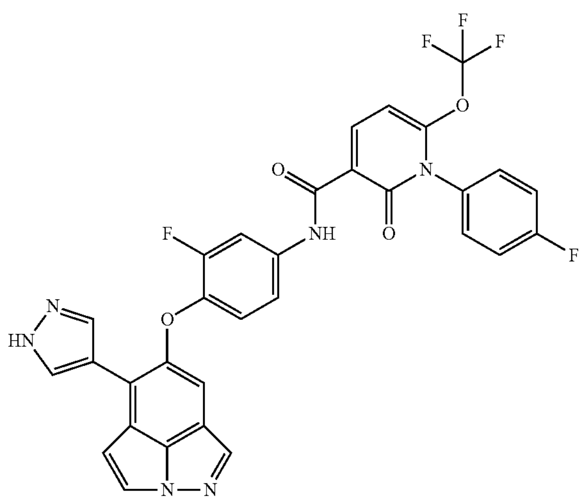 [SMILES: O=C(Nc1ccc(Oc2cc3cnn4ccc(c2-c2cn[nH]c2)c34)c(F)c1)c1ccc(OC(F)(F)F)n(-c2ccc(F)cc2)c1=O] | 633.2 |
| Example 49 | 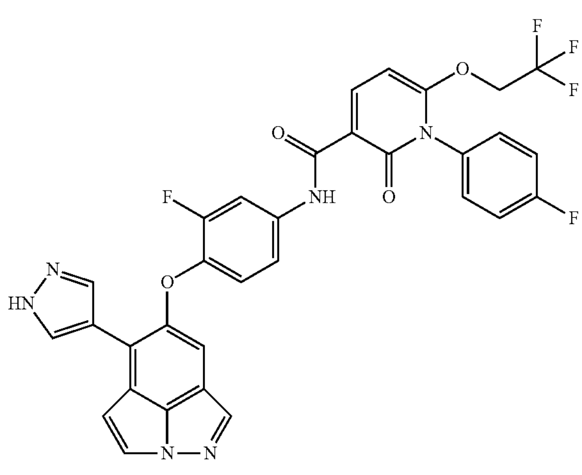 [SMILES: O=C(Nc1ccc(Oc2cc3cnn4ccc(c2-c2cn[nH]c2)c34)c(F)c1)c1ccc(OCC(F)(F)F)n(-c2ccc(F)cc2)c1=O] | 647.2 |

| Example number | Structure | MS data |
|---|---|---|
| Example 50 | 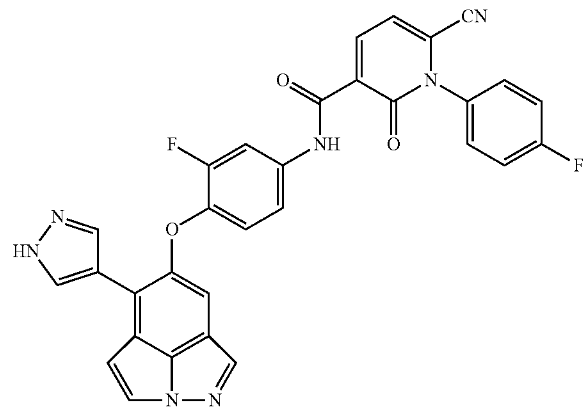 [SMILES: N#Cc1ccc(C(=O)Nc2ccc(Oc3cc4cnn5ccc(c3-c3cn[nH]c3)c45)c(F)c2)c(=O)n1-c1ccc(F)cc1] | 574.2 |

ACTIVITY EXAMPLES

Example 1: Inhibitory Activity of the Compounds of the Present Disclosure on the Proliferation of KM12 Cells KM12 is a human colon cancer cell line in which NTRK1 is highly expressed, and gene fusion occurs with TPM3 to form TPM3-NTRK1.

[Test method]: Promega's CellTiter-Glo® Luminescent Cell Viability Assay kit was used to evaluate the inhibitory activity of the compounds on the proliferation of KM12 cells.

[Instrument]: Spectramax M3 multifunctional microplate reader from Molecular Devices.

[Test materials]: KM12 cell line (ATCC, item number CRL-12496), 96-well transparent flat-bottomed black-walled cell culture plate (Corning, item number #3603), RPMI-1640 media (GE, cat #SH30027.01), Fetal Bovine Serum FBS (Thermo Fisher, cat #10099-141), CellTiter-Glo® Luminescent Cell Viability Assay Kit (Promega, cat #G7572), PBS (Solarbio, cat #P1020), Trypsin (Thermo Fisher, cat #25200072), DMSO (Sigma, cat #D2650).

[Experimental procedure]: When resuscitating KM12 cells, the freezing tube was quickly shaken in a 37° C. water bath to melt within 1 minute. The thawed cell suspension was mixed uniformly with RPMI1640 medium containing 10% FBS, centrifuged at 1000 rpm for 5 minutes, and the supernatant discarded. 5 mL of complete medium (RPMI1640 medium with 10% FBS) was taken to resuspend the cell pellets, charged into a cell culture flask with a bottom area of 25 cm², and incubated in a cell incubator at 37° C., 95% humidity and 5% $CO_2$. Cells were allowed to passage when the cell confluence rate reached about 80%. For cell passage, the old medium was discarded, and the cells were washed twice with PBS, and 0.5 mL trypsin was added to digest the cells. Upon dispersing into single cells and exfoliating from the bottom of the cell culture flask, 4.5 mL of new complete medium was added to terminate the digestion. After pipetting the cell suspension evenly, 1/5 of the cell suspension was kept and added with 4 mL of new complete medium, and after pipetting evenly, the cell flask was placed in the cell incubator for further culturing. Cell plating was performed when the cell confluence rate reached about 80% again. For cell plating, 1/5 of the cell suspension was kept for further culturing as in the cell passage method, and the remaining 4/5 of the cell suspension was placed in a 15 mL centrifuge tube, detected for cell viability by Trypan blue exclusion method to ensure that cell viability was above 90%. A cell suspension with a density of 3.33× $10^4$ viable cells/mL was prepared with complete medium, and 90 μL of such cell suspension was added to a 96-well cell culture plate to obtain a cell density of 3000 viable cells/mL in the cell culture plate. A control group containing no cells, no compound and only complete medium (i.e. culture medium control) and a control group containing no compound but containing cells (i.e. cell control) were set. The cell plate was placed in a cell incubator overnight.

The 10 mM compound stock solution in DMSO was first serially diluted with DMSO at a dilution factor of 3.16 times, to obtain 9 concentrations, and the 10th concentration was set as DMSO control without compound. Then, PBS was used to dilute the DMSO solutions of compounds of different concentrations, at a dilution factor of 100 times, so that the DMSO concentration in the compound solution of each concentration was 1%. Finally, 10 μL of each of the above solutions was added to the corresponding cell culture plate, so that the initial compound concentration was 10 μM, with the remaining concentrations being successively diluted at a dilution factor of 3.16 times, and the DMSO content in the cell culture plate was 0.1%.

The cell plate was placed in a cell incubator and cultured for 72 hours. For endpoint detection, the CellTiter-Glo reagent was melted, and the cell plate was moved to room temperature to equilibrate for 30 minutes, added with 100 μL of CellTiter-Glo for each well, and shaken on an orbital shaker for 5 minutes to fully lyse the cells. The plate was kept at room temperature for 20 minutes to stabilize the luminescence signal, and the luminescence value of each well was scanned with a multi-functional microplate reader at full wavelength.

[Test samples] The compounds of Example 1-6 and Cisplatin (positive control compound)

LOXO-101:

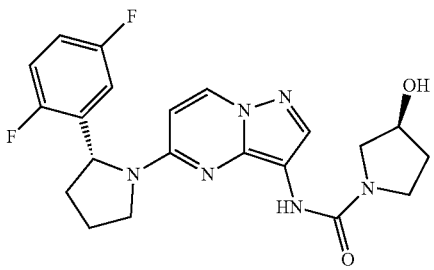 [SMILES: O=C(Nc1cnn2ccc(N3CCC[C@@H]3c3cc(F)ccc3F)nc12)N1CC[C@H](O)C1]

(Doebele, R. C. et al., *Cancer Discov.* 2015, 5, 1049-1057)

RXDX-101:

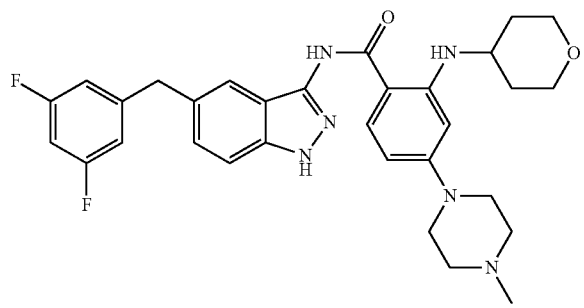 [SMILES: CN1CCN(c2ccc(C(=O)Nc3n[nH]c4ccc(Cc5cc(F)cc(F)c5)cc34)c(NC3CCOCC3)c2)CC1]

(C. Rolfo et al., *Expert Opin. Investig. Drugs* 2015, 24(11), 1493-1500)

Merestinib:

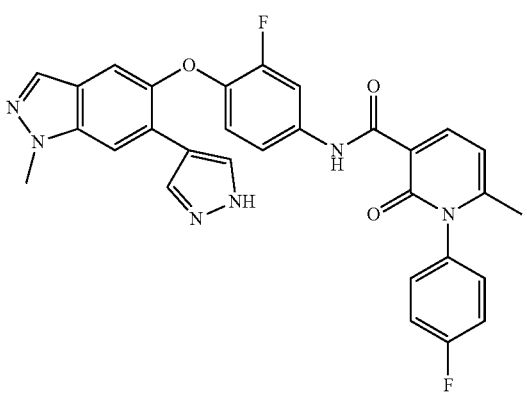 [SMILES: Cc1ccc(C(=O)Nc2ccc(Oc3cc4cnn(C)c4cc3-c3cn[nH]c3)c(F)c2)c(=O)n1-c1ccc(F)cc1]

[Data analysis] The following formula was used to calculate the cell survival rate under the action of each concentration of the compounds:

Cell survival rate (%)=($Lum_{drug\ to\ be\ tested}$ −$Lum_{medium\ control}$)/($Lum_{cell\ control}$ −$Lum_{medium\ control}$)×100%

GraphPad Prism 5.0 software was used to analyze the data, and nonlinear S-curve regression was used to fit the data to obtain a dose-response curve, and the IC50 values were calculated therefrom.

TABLE 1

The inhibitory activity of the compounds of Examples 1-6 on the proliferation of KM12 cells (IC50, μM)

| Compound | KM-12, IC50 (μM) |
|---|---|
| Example 1 | 0.0156 |
| Example 2 | 0.0091 |
| Example 3 | 0.0167 |
| Example 4 | 0.0310 |
| Example 5 | 0.0051 |
| Example 6 | 0.0063 |
| Merestinib | 0.0087 |
| LOXO-101 | 0.0083 |
| RXDX-101 | 0.0051 |
| Cisplatin | 27.3059 |

The inhibitory activity of the compounds of the following examples on the proliferation of KM12 cells was investigated in separate tests as compared with merestinib using experimental methods, conditions, and procedures basically analogous to the above. The results are shown in the following tables.

TABLE 1-1

| Compound | KM-12, IC50 (μM) |
|---|---|
| Merestinib | 0.033 |
| Example 18 | 0.032 |
| Example 19 | 0.032 |
| Example 12 | 0.016 |
| Example 23 | 0.032 |

TABLE 1-2

| Compound | KM-12, IC50 (μM) |
|---|---|
| Merestinib | 0.059 |
| Example 14 | 0.024 |
| Example 15 | 0.017 |
| Example 16 | 0.007 |
| Example 17 | 0.019 |
| Example 11 | 0.035 |
| Example 25 | 0.029 |

TABLE 1-3

| Compound | KM-12, IC50 (μM) |
|---|---|
| Merestinib | 0.027 |
| Example 24 | 0.023 |
| Example 26 | 0.018 |

Example 2: Inhibitory Activity of the Compounds of the Present Disclosure on the Proliferation of Ba/F3 ETV6-NTRK2 Cells Ba/F3 ETV6-NTRK2 cell is a stable transgenic cell line constructed by KYinno Biotechnology Co., Ltd. on mouse primary B cell Ba/F3 wherein NTRK2 is highly expressed and fused with ETV6 to form ETV6-NTRK2.

[Test method]: Promega's CellTiter-Glo® Luminescent Cell Viability Assay kit was used to evaluate the inhibitory activity of the compounds on the proliferation of Ba/F3 ETV6-NTRK2C cells.

[Instrument]: Spectramax M3 multifunctional microplate reader from Molecular Devices.

[Test materials]: Ba/F3 ETV6-NTRK2 cell line (constructed by KYinno Biotechnology Co., Ltd. (Beijing)), 96-well transparent flat-bottomed black-walled cell culture plate (Corning, cat #3603), RPMI-1640 media (GE, cat #SH30027.01), fetal bovine serum FBS (Thermo Fisher, cat #10099-141), CellTiter-Glo® Luminescent Cell Viability Assay kit (Promega, cat #G7572), PBS (Solarbio, cat #P1020), DMSO (Sigma, cat #D2650).

[Experimental procedure]: When resuscitating Ba/F3 ETV6-NTRK2 cells, the freezing tube was quickly shaken in a 37° C. water bath to melt within 1 minute. The thawed cell suspension was mixed uniformly with RPMI1640 medium containing 10% FBS, centrifuged at 1000 rpm for 5 minutes, and the supernatant discarded. 5 mL of complete medium (RPMI1640 medium with 10% FBS) was taken to resuspend the cell pellets, charged into a cell culture flask with a bottom area of 25 cm$^2$, and incubated in a cell incubator at 37° C., 95% humidity and 5% $CO_2$. Cells were allowed to passage when the number of cells reached about $10^6$ cells/mL. For cell passage, the old cell suspension was directly pipetted evenly, 1/5 of the cell suspension was kept, 4 mL of new complete medium was added, and after pipetting evenly, the cell flask was placed in the cell incubator for further culturing. Cell plating was performed when the number of cells reached about $10^6$ cells/mL again. For cell plating, 1/5 of the cell suspension was kept for further culturing as in the cell passage method, and the remaining 4/5 of the cell suspension was placed in a 15 mL centrifuge tube, detected for cell viability by Trypan blue exclusion method to ensure that cell viability was above 90%. A cell suspension with a density of 5.56×10$^4$ viable cells/mL was prepared with complete medium, and 90 μL of such cell suspension was added to a 96-well cell culture plate to obtain a cell density of 5000 viable cells/mL in the cell culture plate. A control group containing no cells, no compound and only complete medium (i.e, culture medium control) and a control group containing no compound but containing cells (i.e, cell control) were set. The cell plate was placed in a cell incubator overnight. The 10 mM compound stock solution in DMSO was first serially diluted with DMSO at a dilution factor of 3.16 times, to obtain 9 concentrations, and the 10th concentration was set as DMSO control without compound. Then, PBS was used to dilute the DMSO solutions of compounds of different concentrations, at a dilution factor of 100 times, so that the DMSO concentration in the compound solution of each concentration was 1%. Finally, 10 μL of each of the above solutions was added to the corresponding cell culture plate, so that the initial compound concentration was 10 μM, with the remaining concentrations being successively diluted at a dilution factor of 3.16 times, and the DMSO content in the cell culture plate was 0.1%. The cell plate was placed in a cell incubator and cultured for 72 hours. For endpoint detection, the CellTiter-Glo reagent was melted, and the cell plate was moved to room temperature to equilibrate for 30 minutes, added with 100 μL of CellTiter-Glo for each well, and shaken on an orbital shaker for 5 minutes to fully lyse the cells. The plate was kept at room temperature for 20 minutes to stabilize the luminescence signal, and the luminescence value of each well was scanned with a multi-functional microplate reader at full wavelength.

[Test sample] Compounds of Example 1-6 and LOXO-101 (positive control compound), Merestinib (comparative compound)

[Data analysis] The following formula was used to calculate the cell survival rate under the action of each concentration of the compounds:

Cell survival rate (%)=($Lum_{drug\ to\ be\ tested} - Lum_{medium\ control}$)/($Lum_{cell\ control} - Lum_{medium\ control}$)×100%

GraphPad Prism 5.0 software was used to analyze the data, and nonlinear S-curve regression was used to fit the data to obtain a dose-response curve, and the IC50 values were calculated therefrom.

TABLE 2

The inhibitory activity of the example compounds on the proliferation of Ba/F3 ETV6-NTRK2 cells (IC50, μM)

| Compound | Ba/F3 ETV6-NTRK2, IC50 (μM) |
| --- | --- |
| Example 1 | 0.428 |
| Example 2 | 0.269 |
| Example 3 | 0.341 |
| Example 4 | 0.876 |
| Example 5 | 0.128 |
| Example 6 | 0.209 |
| Merestinib | 0.211 |
| LOXO-101 | 0.069 |

Example 3: Inhibitory Activity of the Compounds of Present Disclosure on the Proliferation of Ba/F3 ETV6-NTRK3 Cells Ba/F3 ETV6-NTRK3 is a stable transgenic cell line constructed by KYinno Biotechnology Co., Ltd. on mouse primary B cell Ba/F3 wherein NTRK3 is highly expressed and fused with ETV6 to form ETV6-NTRK3.

[Test method]: Promega's CellTiter-Glo® Luminescent Cell Viability Assay kit was used to evaluate the inhibitory activity of the compounds on the proliferation of Ba/F3 ETV6-NTRK3 cells.

[Instrument]: Spectramax M3 multifunctional microplate reader from Molecular Devices.

[Test materials]: Ba/F3 ETV6-NTRK3 cell line (constructed by KYinno Biotechnology Co., Ltd. (Beijing)), 96-well transparent flat-bottomed black-walled cell culture plate (Corning, cat #3603), RPMI-1640 media (GE, cat #SH30027.01), fetal bovine serum FBS (Thermo Fisher, cat #10099-141), CellTiter-Glo® Luminescent Cell Viability Assay kit (Promega, cat #G7572), PBS (Solarbio, cat #P1020), DMSO (Sigma, cat #D2650).

[Experimental procedure]: When resuscitating Ba/F3 ETV6-NTRK3 cells, the freezing tube was quickly shaken in a 37° C. water bath to melt within 1 minute. The thawed cell suspension was mixed uniformly with RPMI1640 medium containing 10% FBS, centrifuged at 1000 rpm for 5 minutes, and the supernatant discarded. 5 mL of complete medium (RPMI1640 medium with 10% FBS) was taken to resuspend the cell pellets, charged into a cell culture flask with a bottom area of 25 cm$^2$, and incubated in a cell incubator at 37° C., 95% humidity and 5% $CO_2$. Cells were allowed to passage when the number of cells reached about $10^6$ cells/mL. For cell passage, the old cell suspension was directly pipetted evenly, 1/5 of the cell suspension was kept, 4 mL of new complete medium was added, after pipetting evenly, the cell flask was placed in the cell incubator for further culturing. Cell plating was performed when the number of cells reached about $10^6$ cells/mL again. For cell plating, 1/5 of the cell suspension was kept for further culturing as in the cell passage method, and the remaining 4/5 of the cell suspension was placed in a 15 mL centrifuge tube, detected for cell viability by Trypan blue exclusion method to ensure that cell viability was above 90%. A cell suspension with a density of $5.56 \times 10^4$ viable cells/mL was prepared with complete medium, and 90 µL of such cell suspension was added to a 96-well cell culture plate to obtain the cell density of 5000 viable cells/mL in the cell culture plate. A control group containing no cells, no compound and only complete medium (i.e. culture medium control) and a control group containing no compound but containing cells (i.e. cell control) were set. The cell plate was placed in a cell incubator overnight. The 10 mM compound stock solution in DMSO was first serially diluted with DMSO at a dilution factor of 3.16 times, to obtain 9 concentrations, and the 10th concentration was set as DMSO control without compound. Then, PBS was used to dilute the DMSO solutions of compounds of different concentrations, at a dilution factor of 100 times, so that the DMSO concentration in the compound solution of each concentration was 1%. Finally, 10 µL of each of the above solutions was added to the corresponding cell culture plate, so that the initial compound concentration was 10 µM, with the remaining concentrations being successively diluted at a dilution factor of 3.16 times, and the DMSO content in the cell culture plate was 0.1%. The cell plate was placed in a cell incubator and cultured for 72 hours. For endpoint detection, the CellTiter-Glo reagent was melted, and the cell plate was moved to room temperature to equilibrate for 30 minutes, added with 100 µL of CellTiter-Glo for each well, and shaken on an orbital shaker for 5 minutes to fully lyse the cells. The plate was kept at room temperature for 20 minutes to stabilize the luminescence signal, and the luminescence value of each well was scanned with a multi-functional microplate reader at full wavelength.

[Test samples] Example compounds, LOXO-101 (positive control compound), Merestinib (comparative compound)

[Data analysis] The following formula was used to calculate the cell survival rate under the action of each concentration of the compounds:

Cell survival rate (%)=$(\text{Lum}_{drug\ to\ be\ tested} - \text{Lum}_{medium\ control})/(\text{Lum}_{cell\ control} - \text{Lum}_{medium\ control}) \times 100\%$ GraphPad Prism 5.0 software was used to analyze the data, and nonlinear S-curve regression was used to fit the data to obtain a dose-response curve, and the IC50 values were calculated therefrom.

TABLE 3

| Compound | Ba/F3 ETV6-NTRK3, IC50 (µM) |
|---|---|
| Example 1 | 0.435 |
| Example 2 | 0.094 |
| Example 3 | 0.663 |
| Example 4 | 0.762 |

The inhibitory activity (IC50, µM) of the examples on the proliferation of Ba/F3 ETV6-NTRK3 cells TABLE 3-continued

| Compound | Ba/F3 ETV6-NTRK3, IC50 (µM) |
|---|---|
| Example 5 | 0.060 |
| Example 6 | 0.284 |
| Merestinib | 0.684 |
| LOXO-101 | 0.005 |

The inhibitory activity (IC50, µM) of the examples on the proliferation of Ba/F3 ETV6-NTRK3 cells Example 4: Inhibitory Activity of the Compounds of the Present Disclosure on the Proliferation of Ba/F3 LMNA-NTRK1-G667C Cells Ba/F3 LMNA-NTRK1-G667C is a stable transgenic cell line constructed by KYinno Biotechnology Co., Ltd. on mouse primary B cell Ba/F3 wherein NTRK1 has a mutation of G to C at position 667 and is highly expressed and fused with LMNA to form LMNA-NTRK1-G667C.

[Test method]: Promega's CellTiter-Glo® Luminescent Cell Viability Assay kit was used to evaluate the inhibitory activity of the compounds on the proliferation of Ba/F3 LMNA-NTRK1-G667C cells.

[Instrument]: Spectramax M3 multifunctional microplate reader from Molecular Devices.

[Test materials]: Ba/F3 LMNA-NTRK1-G667C cell line (constructed by KYinno Co., Ltd. (Beijing)), 96-well transparent flat-bottomed black-walled cell culture plate (Corning, cat #3603), RPMI-1640 media (GE, cat #SH30027.01), fetal bovine serum FBS (Thermo Fisher, cat #10099-141), CellTiter-Glo® Luminescent Cell Viability Assay kit (Promega, cat #G7572), PBS (Solarbio, cat #P1020), DMSO (Sigma, cat #D2650).

[Experimental procedure]: When resuscitating Ba/F3 LMNA-NTRK1-G667C cells, the freezing tube was quickly shaken in a 37° C. water bath to melt within 1 minute. The thawed cell suspension was mixed uniformly with RPMI1640 medium containing 10% FBS, centrifuged at 1000 rpm for 5 minutes, and the supernatant discarded. 5 mL of complete medium (RPMI1640 medium with 10% FBS) was taken to resuspend the cell pellets, charged into a cell culture flask with a bottom area of 25 cm², and incubated in a cell incubator at 37° C., 95% humidity and 5% $CO_2$. Cells were allowed to passage when the number of cells reached about $10^6$ cells/mL. For cell passage, the old cell suspension was directly pipetted evenly, 1/5 of the cell suspension was kept, 4 mL of new complete medium was added, after pipetting evenly, the cell flask was placed in the cell incubator for further culturing. Cell plating was performed when the number of cells reached about $10^6$ cells/mL again. For cell plating, 1/5 of the cell suspension was kept for further culturing as in the cell passage method, and the remaining 4/5 of the cell suspension was placed in a 15 mL centrifuge tube, detected for cell viability by Trypan blue exclusion method to ensure that cell viability was above 90%. A cell suspension with a density of $5.56 \times 10^4$ viable cells/mL was prepared with complete medium, and 90 µL of such cell suspension was added to a 96-well cell culture plate to obtain the cell density of 5000 viable cells/mL in the cell culture plate. A control group containing no cells, no compound and only complete medium (i.e. culture medium control) and a control group containing no compound but containing cells (i.e. cell control)

were set. The cell plate was placed in a cell incubator overnight. The 10 mM compound stock solution in DMSO was first serially diluted with DMSO at a dilution factor of 3.16 times, to obtain 9 concentrations, and the 10th concentration was set as DMSO control without compound. Then, PBS was used to dilute the DMSO solutions of compounds of different concentrations, at a dilution factor of 100 times, so that the DMSO concentration in the compound solution of each concentration was 1%. Finally, 10 μL of each of the above solutions was added to the corresponding cell culture plate, so that the initial compound concentration was 10 μM, with the remaining concentrations being successively diluted at a dilution factor of 3.16 times, and the DMSO content in the cell culture plate was 0.1%. The cell plate was placed in a cell incubator and cultured for 72 hours. For endpoint detection, the CellTiter-Glo reagent was melted, and the cell plate was moved to room temperature to equilibrate for 30 minutes, added with 100 μL of CellTiter-Glo for each well, and shaken on an orbital shaker for 5 minutes to fully lyse the cells. The plate was kept at room temperature for 20 minutes to stabilize the luminescence signal, and the luminescence value of each well was scanned with a multi-functional microplate reader at full wavelength.

[Test samples] Example compounds and LOXO-101 (positive control compound)

[Data analysis] The following formula was used to calculate the cell survival rate under the action of each concentration of the compounds:

Cell survival rate (%)=$(Lum_{drug\ to\ be\ tested} - Lum_{medium\ control})/(Lum_{cell\ control} - Lum_{medium\ control}) \times 100\%$ GraphPad Prism 5.0 software was used to analyze the data, and nonlinear S-curve regression was used to fit the data to obtain a dose-response curve, and the IC50 values were calculated therefrom.

TABLE 4

The inhibitory activity (IC50, μM) of the exampleompounds on Ba/F3 LMNA-NTRK1-G667C cell proliferation

| Compound | Ba/F3 LMNA-NTRK1-G667C, IC50 (μM) |
| --- | --- |
| Example 1 | 0.0020 |
| Example 2 | 0.0011 |
| Example 3 | 0.0016 |
| Example 4 | 0.0028 |
| Example 5 | <0.001 |
| Example 6 | 0.00066 |
| Merestinib | 0.0011 |
| LOXO-101 | 2.409 |

The inhibitory activity of some compounds of the present disclosure on the proliferation of Ba/F3 LMNA-NTRK1-G667C cells was investigated in separate tests as compared with merestinib using experimental methods, conditions, and procedures basically analogous to the above. The results are shown in the following tables.

TABLE 4-1

| Compound | Ba/F3 LMNA-NTRK1-G667C, IC50 (μM) |
| --- | --- |
| Merestinib | 0.001 |
| Example 18 | 0.001 |
| Example 19 | 0.002 |

TABLE 4-1-continued

| Compound | Ba/F3 LMNA-NTRK1-G667C, IC50 (μM) |
| --- | --- |
| Example 12 | <0.001 |
| Example 23 | 0.001 |

TABLE 4-2

| Compound | Ba/F3 LMNA-NTRK1-G667C, IC50 (μM) |
| --- | --- |
| Merestinib | 0.0141 |
| Example 14 | 0.0086 |
| Example 15 | 0.0108 |
| Example 16 | 0.0107 |
| Example 11 | 0.0105 |
| Example 24 | 0.0173 |
| Example 26 | 0.0175 |

Example 5: Inhibitory Activity of the Compounds of the Present Disclosure on the Proliferation of Ba/F3 LMNA-NTRK1-G595R Cells Ba/F3 LMNA-NTRK1-G595R is a stable transgenic cell line constructed by KYinno Biotechnology Co., Ltd. on mouse primary B cell Ba/F3 wherein NTRK1 is highly expressed with a mutation of G at position 595 to R, and fused with LMNA to form LMNA-NTRK1.

[Test method]: Promega's CellTiter-Glo® Luminescent Cell Viability Assay kit was used to evaluate the inhibitory activity of the compounds on the proliferation of Ba/F3 LMNA-NTRK1-G595R cells.

[Instrument]: Spectramax M3 multifunctional microplate reader from Molecular Devices.

[Test materials]: Ba/F3 LMNA-NTRK1-G595R cell line (constructed by KYinno Biotechnology Co., Ltd. (Beijing)), 96-well transparent flat-bottomed black-walled cell culture plate (Corning, cat #3603), RPMI-1640 media (GE, cat #SH30027.01), fetal bovine serum FBS (Thermo Fisher, cat #10099-141), CellTiter-Glo® Luminescent Cell Viability Assay kit (Promega, cat #G7572), PBS (Solarbio, cat #P1020), DMSO (Sigma, cat #D2650).

[Experimental procedure]: When resuscitating Ba/F3 LMNA-NTRK1-G595R cells, the freezing tube was quickly shaken in a 37° C. water bath to melt within 1 minute. The thawed cell suspension was mixed uniformly with RPMI1640 medium containing 10% FBS, centrifuged at 1000 rpm for 5 minutes, and the supernatant discarded. 5 mL of complete medium (RPMI1640 medium with 10% FBS) was taken to resuspend the cell pellets, charged into a cell culture flask with a bottom area of 25 cm², and incubated in a cell incubator at 37° C., 95% humidity and 5% $CO_2$. Cells were allowed to passage when the number of cells reached about $10^6$ cells/mL. For cell passage, the old cell suspension was directly pipetted evenly, 1/5 of the cell suspension was kept, 4 mL of new complete medium was added, after pipetting evenly, the cell flask was placed in the cell incubator for further culturing. Cell plating was performed when the number of cells reached about $10^6$ cells/mL again. For cell plating, 1/5 of the cell suspension was kept for further culturing as in the cell passage method, and the remaining 4/5 of the cell suspension was placed in a 15 mL centrifuge tube, detected for cell viability by Trypan blue exclusion method to ensure that cell viability was above 90%. A cell suspension with a density of 5.56×10⁴ viable cells/mL was prepared with complete medium, and 90 μL of such cell suspension was added to a 96-well cell culture plate to obtain the cell density of 5000 viable cells/mL in the cell culture plate. A control group containing no cells, no compound and only complete medium (i.e. culture medium control) and a control group containing no compound but containing cells (i.e. cell control) were set. The cell plate was placed in a cell incubator overnight. The 10 mM compound stock solution in DMSO was first serially diluted with DMSO at a dilution factor of 3.16 times, to obtain 9 concentrations, and the 10th concentration was set as DMSO control without compound. Then, PBS was used to dilute the DMSO solutions of compounds of different concentrations, at a dilution factor of 100 times, so that the DMSO concentration in the compound solution of each concentration was 1%. Finally, 10 μL of each of the above solutions was added to the corresponding cell culture plate, so that the initial compound concentration was 10 μM, with the remaining concentrations being successively diluted at a dilution factor of 3.16 times, and the DMSO content in the cell culture plate was 0.1%. The cell plate was placed in a cell incubator and cultured for 72 hours. For endpoint detection, the CellTiter-Glo reagent was melted, and the cell plate was moved to room temperature to equilibrate for 30 minutes, added with 100 μL of CellTiter-Glo for each well, and shaken on an orbital shaker for 5 minutes to fully lyse the cells. The plate was kept at room temperature for 20 minutes to stabilize the luminescence signal, and the luminescence value of each well was scanned with a multi-functional microplate reader at full wavelength.

[Test samples] Example compounds and LOXO-101 (positive control compound)

[Data analysis] The following formula was used to calculate the cell survival rate under the action of each concentration of the compounds:

Cell survival rate (%)=(Lum$_{drug\ to\ be\ tested}$ −Lum$_{medium\ control}$)/(Lum$_{cell\ control}$ −Lum$_{medium\ control}$)×100%

GraphPad Prism 5.0 software was used to analyze the data, and nonlinear S-curve regression was used to fit the data to obtain a dose-response curve, and the IC50 values were calculated therefrom.

TABLE 5

The inhibitory activity of the example compounds on the Ba/F3 LMNA-NTRK1-G595R cell proliferation (IC50, μM)

| Compound | Ba/F3 LMNA-NTRK1-G595R, IC50 (μM) |
| --- | --- |
| Example 1 | 1.435 |
| Example 2 | 0.752 |
| Example 3 | 3.152 |
| Example 4 | 4.654 |
| Example 5 | 0.799 |
| Example 6 | 0.747 |
| Merestinib | 1.015 |
| LOXO-101 | 3.657 |

Example 6: Inhibitory Activity of the Compounds of the Present Disclosure on the Proliferation of Ba/F3 ETV6-NTRK2-G639R Cells Ba/F3 ETV6-NTRK2-G639R is a stable transgenic cell line constructed by KYinno Biotechnology Co., Ltd. on mouse primary B cell Ba/F3 wherein NTRK2 is highly expressed with a mutation of G at position 639 to R, and fused with ETV6 to form ETV6-NTRK2.

[Test method]: Promega's CellTiter-Glo® Luminescent Cell Viability Assay kit was used to evaluate the inhibitory activity of the compounds on the proliferation of Ba/F3 ETV6-NTRK2-G639R cells.

[Instrument]: Spectramax M3 multifunctional microplate reader from Molecular Devices.

[Test materials]: Ba/F3 ETV6-NTRK2-G639R cell line (constructed by KYinno Biotechnology Co., Ltd. (Beijing)), 96-well transparent flat-bottomed black-walled cell culture plate (Corning, catalog #3603), RPMI-1640 media (GE, cat #SH30027.01), fetal bovine serum FBS (Thermo Fisher, cat #10099-141), CellTiter-Glo® Luminescent Cell Viability Assay kit (Promega, cat #G7572), PBS (Solarbio, cat #P1020), DMSO (Sigma, cat #D2650).

[Experimental procedure]: When resuscitating Ba/F3 ETV6-NTRK2-G639R cells, the freezing tube was quickly shaken in a 37° C. water bath to melt within 1 minute. The thawed cell suspension was mixed uniformly with RPMI1640 medium containing 10% FBS, centrifuged at 1000 rpm for 5 minutes, and the supernatant discarded. 5 mL of complete medium (RPMI1640 medium with 10% FBS) was taken to resuspend the cell pellets, charged into a cell culture flask with a bottom area of 25 cm², and incubated in a cell incubator at 37° C., 95% humidity and 5% $CO_2$. Cells were allowed to passage when the number of cells reached about 10⁶ cells/mL. For cell passage, the old cell suspension was directly pipetted evenly, 1/5 of the cell suspension was kept, 4 mL of new complete medium was added, after pipetting evenly, the cell flask was placed in the cell incubator for further culturing. Cell plating was performed when the number of cells reached about 10⁶ cells/mL again. For cell plating, 1/5 of the cell suspension was kept for further culturing as in the cell passage method, and the remaining 4/5 of the cell suspension was placed in a 15 mL centrifuge tube, detected for cell viability by Trypan blue exclusion method to ensure that cell viability was above 90%. A cell suspension with a density of 5.56×10⁴ viable cells/mL was prepared with complete medium, and 90 μL of such cell suspension was added to a 96-well cell culture plate to obtain the cell density of 5000 viable cells/mL in the cell culture plate. A control group containing no cells, no compound and only complete medium (i.e. culture medium control) and a control group containing no compound but containing cells (i.e. cell control) were set. The cell plate was placed in a cell incubator overnight. The 10 mM compound stock solution in DMSO was first serially diluted with DMSO at a dilution factor of 3.16 times, to obtain 9 concentrations, and the 10th concentration was set as DMSO control without compound. Then, PBS was used to dilute the DMSO solutions of compounds of different concentrations, at a dilution factor of 100 times, so that the DMSO concentration in the compound solution of each concentration was 1%. Finally, 10 μL of each of the above solutions was added to the corresponding cell culture plate, so that the initial compound concentration was 10 μM, with the remaining concentrations being successively diluted at a dilution factor of 3.16 times, and the DMSO content in the cell culture plate was 0.1%. The cell plate was placed in a cell incubator and cultured for 72 hours. For endpoint detection, the CellTiter-Glo reagent was melted, and the cell plate was moved to room temperature to equilibrate for 30 minutes, added with 100 µL of CellTiter-Glo for each well, and shaken on an orbital shaker for 5 minutes to fully lyse the cells. The plate was kept at room temperature for 20 minutes to stabilize the luminescence signal, and the luminescence value of each well was scanned with a multi-functional microplate reader at full wavelength.

[Test samples] Example compounds and LOXO-101 (positive control compound)

[Data analysis] The following formula was used to calculate the cell survival rate under the action of each concentration of the compounds:

Cell survival rate (%)=(Lum$_{drug\ to\ be\ tested}$−Lum$_{medium\ control}$)/(Lum$_{cell\ control}$−Lum$_{medium\ control}$)×100%

GraphPad Prism 5.0 software was used to analyze the data, and nonlinear S-curve regression was used to fit the data to obtain a dose-response curve, and the IC50 values were calculated therefrom.

TABLE 6

The inhibitory activity of example compounds on Ba/F3 ETV6-NTRK2-G639R cell proliferation (IC50, µM)

| Compound | Ba/F3 ETV6-NTRK2-G639R, IC50 (µM) |
| --- | --- |
| Example 1 | 3.116 |
| Example 2 | 1.878 |
| Example 3 | 9.866 |
| Example 4 | >10 |
| Example 5 | 2.691 |
| Example 6 | 2.792 |
| Merestinib | 3.038 |
| LOXO-101 | >10 |

Example 7: Inhibitory Activity of the Compounds of the Present Disclosure on the Proliferation of Ba/F3 ETV6-NTRK3-G696C Cells Ba/F3 ETV6-NTRK3-G696C is a stable transgenic cell line constructed by KYinno Biotechnology Co., Ltd. on mouse primary B cell Ba/F3 wherein NTRK3 is highly expressed with a mutation of G at position 639 to C and fused with ETV6 to form ETV6-NTRK3.

[Test method]: Promega's CellTiter-Glo® Luminescent Cell Viability Assay kit was used to evaluate the inhibitory activity of the compounds on the proliferation of Ba/F3 ETV6-NTRK3-G696C cells.

[Instrument]: Spectramax M3 multifunctional microplate reader from Molecular Devices.

[Test materials]: Ba/F3 ETV6-NTRK3-G696C cell line (constructed by KYinno Biotechnology Co., Ltd. (Beijing)), 96-well transparent flat-bottomed black-walled cell culture plate (Corning, cat #3603), RPMI-1640 media (GE, product number #SH30027.01), fetal bovine serum FBS (Thermo Fisher, cat #10099-141), CellTiter-Glo® Luminescent Cell Viability Assay kit (Promega, cat #G7572), PBS (Solarbio, cat #P1020), DMSO (Sigma, cat #D2650).

[Experimental procedure]: When resuscitating Ba/F3 ETV6-NTRK3-G696C cells, the freezing tube was quickly shaken in a 37° C. water bath to melt within 1 minute. The thawed cell suspension was mixed uniformly with RPMI1640 medium containing 10% FBS, centrifuged at 1000 rpm for 5 minutes, and the supernatant discarded. 5 mL of complete medium (RPMI1640 medium with 10% FBS) was taken to resuspend the cell pellets, charged into a cell culture flask with a bottom area of 25 cm$^2$, and incubated in a cell incubator at 37° C., 95% humidity and 5% $CO_2$. Cells were allowed to passage when the number of cells reached about 10$^6$ cells/mL. For cell passage, the old cell suspension was directly pipetted evenly, 1/5 of the cell suspension was kept, 4 mL of new complete medium was added, after pipetting evenly, the cell flask was placed in the cell incubator for further culturing. Cell plating was performed when the number of cells reached about 10$^6$ cells/mL again. For cell plating, 1/5 of the cell suspension was kept for further culturing as in the cell passage method, and the remaining 4/5 of the cell suspension was placed in a 15 mL centrifuge tube, detected for cell viability by Trypan blue exclusion method to ensure that cell viability was above 90%. A cell suspension with a density of 5.56×10$^4$ viable cells/mL was prepared with complete medium, and 90 µL of such cell suspension was added to a 96-well cell culture plate to obtain the cell density of 5000 viable cells/mL in the cell culture plate. A control group containing no cells, no compound and only complete medium (i.e. culture medium control) and a control group containing no compound but containing cells (i.e. cell control) were set. The cell plate was placed in a cell incubator overnight. The 10 mM compound stock solution in DMSO was first serially diluted with DMSO at a dilution factor of 3.16 times, to obtain 9 concentrations, and the 10th concentration was set as DMSO control without compound. Then, PBS was used to dilute the DMSO solutions of compounds of different concentrations, at a dilution factor of 100 times, so that the DMSO concentration in the compound solution of each concentration was 1%. Finally, 10 µL of each of the above solutions was added to the corresponding cell culture plate, so that the initial compound concentration was 10 µM, with the remaining concentrations being successively diluted at a dilution factor of 3.16 times, and the DMSO content in the cell culture plate was 0.1%. The cell plate was placed in a cell incubator and cultured for 72 hours. For endpoint detection, the CellTiter-Glo reagent was melted, and the cell plate was moved to room temperature to equilibrate for 30 minutes, added with 100 µL of CellTiter-Glo for each well, and shaken on an orbital shaker for 5 minutes to fully lyse the cells. The plate was kept at room temperature for 20 minutes to stabilize the luminescence signal, and the luminescence value of each well was scanned with a multi-functional microplate reader at full wavelength.

[Test samples] Example compounds and LOXO-101 (positive control compound)

[Data analysis] The following formula was used to calculate the cell survival rate under the action of each concentration of the compounds:

Cell survival rate (%)=(Lum$_{drug\ to\ be\ tested}$−Lum$_{medium\ control}$)/(Lum$_{cell\ control}$−Lum$_{medium\ control}$)×100%

GraphPad Prism 5.0 software was used to analyze the data, and nonlinear S-curve regression was used to fit the data to obtain a dose-response curve, and the IC50 values were calculated therefrom.

TABLE 7

The inhibitory activity of example compounds on Ba/F3 ETV6-NTRK3-G696C cell proliferation (IC50, μM)

| Compound | Ba/F3 ETV6-NTRK3-G696C, IC50 (μM) |
| --- | --- |
| Example 1 | 0.033 |
| Example 2 | 0.020 |
| Example 3 | 0.018 |
| Example 4 | 0.034 |
| Example 5 | 0.0068 |
| Example 6 | 0.016 |
| Merestinib | 0.010 |
| LOXO-101 | 1.891 |

The inhibitory activity of some compounds of the present disclosure on the proliferation of Ba/F3 ETV6-NTRK3-G696C cells was investigated in separate tests as compared with merestinib using experimental methods, conditions, and procedures basically analogous to the above. The results are shown in the following tables.

TABLE 7-1

| Compound | Ba/F3 ETV6-NTRK3-G696C, IC50 (μM) |
| --- | --- |
| Merestinib | 0.013 |
| Example 18 | 0.012 |
| Example 19 | 0.014 |
| Example 12 | 0.003 |
| Example 23 | 0.011 |

TABLE 7-2

| Compound | Ba/F3 ETV6-NTRK3-G696C, IC50 (μM) |
| --- | --- |
| Merestinib | 0.0017 |
| Example 14 | 0.0016 |
| Example 15 | 0.0019 |
| Example 16 | 0.0012 |
| Example 17 | 0.0037 |
| Example 11 | 0.0018 |
| Example 25 | 0.0063 |
| Example 24 | 0.0035 |
| Example 27 | 0.0030 |
| Example 26 | 0.0031 |

Example 8: Inhibitory Activity of the Compounds of the Present Disclosure on the Proliferation of MKN45 Cells MKN45 is a human poorly differentiated gastric cancer cell line with high MET expression. Cell proliferation experiments were performed according to literature methods (Zhang, D. et al. *Bioorg. Med. Chem.* 2013, 21, 6804; Riss, T. L.; Moravec, R. A.; Niles, A. L.; et al. *Cell Viability Assays* 2013 May 1 [Updated 2016 Jul. 1]. In: Sittampalam, G. S.; Grossman, A.; Brimacombe, K.; et al., editors. *Assay Guidance Manual* [Internet]. Bethesda (MD): Eli Lilly & Company and the National Center for Advancing Translational Sciences; 2004-. Available from: https://www.ncbi.nlm.nih.gov/books/NBK144065/).

TABLE 8

Inhibitory activity of some example compounds on the proliferation of MKN45 cells (IC50, μM)

| Compound | MKN45, IC50 (μM) |
| --- | --- |
| Example 12 | 0.004 |
| Example 14 | 0.011 |
| Example 16 | 0.009 |
| Example 17 | 0.015 |
| Example 11 | 0.012 |
| Merestinib | 0.019 |
| LOXO-101 | >10 |

The experimental results show that the compounds of the present disclosure have a more effective inhibitory effect on MKN45 cells which highly express the main target of Merestinib, namely Met.

Example 9: Inhibitory Activity of Selected Compounds of the Present Disclosure on the Proliferation of KM12, Ba/F3 LMNA-NTRK1-G667C, Ba/F3 ETV6-NTRK3-G696C Cells Using experimental methods and conditions analogous to the above activity examples 1, 4 and 7, the inhibitory activity of the following selected compounds of the disclosure on each of the cell lines was investigated, and the results are shown in the following table:

TABLE 9

Cell proliferation inhibitory activity (IC50, μM) of some example compounds

| Compound | KM12 | Ba/F3 LMNA-NTRK1-G667C | Ba/F3 ETV6-NTRK3-G696C |
| --- | --- | --- | --- |
| Example 28 | 0.056 | 0.0198 | 0.0036 |
| Example 31 | 0.071 | 0.0330 | 0.0053 |
| Example 32 | 0.067 | 0.0190 | 0.0047 |
| Example 34 | 0.037 | 0.0237 | 0.0048 |

Example 10: Inhibitory Activity of the Compounds of the Present Disclosure on Other Oncogenic Kinases The experiment was performed according to the standard kinase activity determination protocol by Eurofins DiscoverX Corporation (11180 Roselle St. Suite D, San Diego, CA, USA, www.discoverX.com). Specifically, the experiment was conducted using the KINOMEscan™ screening platform, which adopts an active site-directed competition binding assay to quantitatively measure the interaction between test compounds and more than hundreds of human kinases and disease-related mutants. The working principle of the screening platform and kinase assay methods are well known in the art, for example, see www.discoverX.com.

The compound Example 12 of the present disclosure showed >90% inhibitory activity on the kinases listed in Table 10 at a concentration of 2 μM.

TABLE 10

| Kinases | % inhibition |
| --- | --- |
| CDK11 | 100 |
| CDKL2 | 100 |

TABLE 10-continued

| Kinases | % inhibition |
|---|---|
| DDR2 | 100 |
| FLT3(N841I) | 100 |
| KIT(L576P) | 100 |
| MYO3B | 100 |
| AXL | 100 |
| DDR1 | 100 |
| KIT(V559D) | 100 |
| TRKA | 100 |
| KIT | 100 |
| LOK | 100 |
| CSF1R | 100 |
| MKNK2 | 100 |
| MET(M1250T) | 99 |
| FLT3 | 99 |
| MET(Y1235D) | 99 |
| TIE1 | 99 |
| TIE2 | 99 |
| KIT(V559D, T670I) | 99 |
| MST1R | 98 |
| PDGFRB | 98 |
| FLT3(ITD) | 98 |
| MUSK | 98 |
| IKK-alpha | 97 |
| TRKC | 97 |
| IKK-beta | 97 |
| HIPK4 | 97 |
| LCK | 97 |
| MERTK | 97 |
| ROS1 | 97 |
| RET | 97 |
| EPHA8 | 96 |
| CDK7 | 96 |
| RET(M918T) | 95 |
| MKNK1 | 95 |
| EPHB6 | 95 |
| NEK9 | 95 |
| BLK | 95 |
| TRKB | 94 |
| FLT3(K663Q) | 93 |
| MET | 93 |
| FLT3(D835V) | 93 |
| RAF1 | 92 |
| FLT4 | 92 |
| PLK4 | 90 |

Experimental results show that, in addition to inhibiting the activities of TRKA, TRKB and TRKC kinases, the compounds of the present disclosure also inhibit other confirmed, under-research, and emerging anticancer drug kinase targets (ROS1, RAF1, PDGFRB, CSF1R, LCK, IKKa, IKKb, PLK, AXL, TIE, LOK, TIE1, DDR), as well as those anticancer drug targets in applications and their drug-resistant mutant targets (FLT3, FLT3 (N841I), FLT3 (K663Q), FLT3 (D835V), FLT3 (ITD), KIT, KIT (L576P), KIT (V559D), KIT (V559D, T670I), MET, MET (Y1235D), MET (Y1250T), RET, RET (M918T)), etc., therefore are believed to show a broad-spectrum anti-cancer effect in clinical practice.

Example 11: Anti-Tumor Activity of the Compounds of the Present Disclosure in a KM12 Xenograft Mouse Model

[Instrument]: API-400-Qtrap Shimadzu 20AC

[Test materials and conditions]: KM12 cell line was provided by Via Biotechnology, BALB/c nude mice, female, purchased from Shanghai Lingchang Biotechnology Co., Ltd.

[Experimental procedure]: 7-week-old athymic female nude mice were injected subcutaneously with $5 \times 10^6$ KM12 cells on the right side of the ribs. The tumors were measured every 3 days at 3 dimensions to calculate the volume $V=D \times d \times d/2$, and the mouse body weights were measured at the same time. When the average tumor size reached 180 mm$^3$ about 6 days after tumor inoculation, the mice were dosed for 12 days (or 18 days) prior sacrifice. For pharmacokinetic and pharmacodynamic analysis, plasma samples and tumor samples were taken from animals at 4 hours and 8 hours after the last dose.

The tumor samples from the animals treated as above were weighed, 9 volumes of ice water were added, and the resulting tumor tissue was homogenized by a tissue homogenizer. 50 μL of plasma or tumor homogenate sample was transferred to a 96-well plate, and added with 250 μL of ACN (containing 260 ng/ml dexamethasone as an internal standard) to precipitate protein. The plate was centrifuged at 4000 rpm at 4° C. for 20 minutes, 150 μL of supernatant was transferred to another new 96-well plate, mixed with 150 μL of 0.1% FA water, and 10 μL was injected into LC-MS/MS to collect data.

[Experiment Results] The data on the 12th day after administration show that, the tested example compounds of the present disclosure significantly inhibited the growth of tumors, for example, some of the compounds showed superior tumor growth inhibition activity than Merestinib (FIG. 1-A). The drug concentrations in plasma and tumor tested on the 12th and 18th days after administration show that, the tested compounds of the present disclosure can be enriched in plasma and tumor tissue at a higher concentration than Merestinib (FIG. 1-B, FIG. 1-C), which is expected to exert stronger anti-tumor activity.

Example 12: Comparison of Kinase Profile of the Compounds of the Present Disclosure and Merestinib The inhibitory activity of Example 12 of the present disclosure on various kinases at a concentration of 2 μM was compared with that of Merestinib. The experiment was performed according to the standard kinase activity determination protocol by Eurofins DiscoverX Corporation (11180 Roselle St. Suite D, San Diego, CA USA, www.discoverX.com). At a concentration of 2 μM, Example 12 of the present disclosure shows a significantly different trend in the kinase activity profile, as compared with Merestinib, as shown in FIG. 2 (kinases with a difference of inhibition rate >20%).

The physicochemical properties of a compound determine its druggability. The property parameters that affect the druggability of a compound and the established experimental methods can refer to Kems, Edward H. and Di Li (2008). Drug-like Properties: Concepts. Structure Design and Methods: from ADME to Toxicity Optimization. San Diego: Academic Press. The experimental results of the present disclosure show that the compound of the present disclosure is significantly superior to the prior art inhibitors such as Merestinib in many properties related to druggability. The following examples illustrate the significant advantages of the overall druggability of the compound of the present disclosure over the prior art by the metabolic stability in liver microsomes, P450 enzyme inhibition, and solubility.

Example 13: Metabolic Stability Test in Liver Microsomes of the Compound of the Present Disclosure According to standard methods conventional in the art for in vitro metabolic stability studies, for example those protocols described in Kems, Edward H. and Di Li (2008). *Drug-like Properties: Concepts. Structure Design and Methods: from ADME to Toxicity Optimization.* San Diego: Academic Press; Di, Li et al., *Optimization of a Higher Throughput Microsomal Stability Screening Assay for Profiling Drug Discovery Candidates, J. Biomol. Screen.* 2003, 8(4), 453., the metabolic stability test in liver microsomes of the present compound was performed analogously as follows.

The in vitro metabolic stability of the compound in 5 species (mouse, rat, dog, monkey, and human) was evaluated by liver microsomal stability test. 0.1M potassium phosphate buffer solution (pH 7.4, containing 1.0 mM EDTA) was prepared. The test compound and the control compound were prepared into a 10 mM DMSO solution, and then 10 µL of the 10 mM DMSO compound solution was added to 190 µL of acetonitrile to prepare a 500 µM compound solution. Liver microsomes (Sekisui XenoTech, LLC., human liver microsomes, cat. #H0610; Beagle dog liver microsomes, cat. #D1000; cynomolgus monkey liver microsomes, cat. #P2073; rat liver microsomes, cat. #R1073; mouse Liver microsomes, cat. #M1000) were taken and slowly melted on ice, then 18.75 µL of the liver microsome solution (20 mg/mL) and 1.5 µL of 500 µM compound solution were added to 479.75 µL of 0.1M potassium phosphate buffer solution to prepare a 0.75 mg/mL liver microsome working solution with a concentration of 1.5 µM compound. 6 mM NADPH (SIGMA, cat. #V900362) aqueous solution was prepared. 0.2 mL 2 mg/mL internal standard stock solution (imipramine solution in acetonitrile) was added to 1000 mL acetonitrile (SIGMA, cat. #271004) to prepare the reaction stop solution and stored at 4° C.

Six deep-well plates were labeled as T0, T5, T15, T30, T45 and NCF60 (negative control, without NADPH). 30 µL of 1.5 mM control compound or test compound solution in 0.75 mg/mL liver microsome working solution was added to each well of the corresponding plates. After being sealed with film, all the microplates were placed in a 37° C. water bath to preheat for 5 minutes, and 6 mM NADPH solution was placed in a 37° C. water bath to preheat for 5 minutes. Then 15 µL of NADPH solution was added to each cell successively in reverse time order, that is, first adding the T45 plate, 15 minutes later the T30 plate, 15 minutes later again the T15 plate, and 10 minutes later gain the T5 plate. NCF60 plate was not added with NADPH but 15 µL of deionized water. At this time, to the T0 plate were added 135 µL of ice-cooled reaction stop solution and 15 µL of NADPH solution. By the end of the reaction, 135 µL of ice-precooled reaction stop solution was added successively to each well of the T5, T15, T30, and T45 plates. All samples were centrifuged at 4° C. at 600 rpm for 10 minutes, and then at 5594 g for 15 minutes (Thermo Multifugex 3R). Six 96-well plates were respectively labeled and added 50 µL of ultrapure water (Millipore, ZMQS50F01) to each well, then 50 µL of the centrifuged supernatant was added to the corresponding well of the corresponding plate, for LC-MS/MS-014 (API4000), UPLC-MS/MS-11 (API4000), LC-MS/MS-034 (API-6500+) analysis. The concentration (C0) of the test compound at T0 time point was taken as 100%, and the concentrations at other incubation time points were converted into residue percentages.

The natural logarithm of the residue percentage at each time point was subjected to linearly regression as a factor of incubation time to obtain Slope k, and then the liver microsome clearance rate ($CL_{int}^{mic}$) and in vitro half-life (T½) were calculated according to the following formula:

$$C_t = \frac{1}{2}C_0$$

$$T_{1/2} = \frac{\ln 2}{K} = \frac{0.693}{K}$$

$$CL_{int}^{mic} = \frac{K}{\text{mg/ml Incubated microsomal protein}}$$

TABLE 11

Comparison of liver microsomal metabolism parameters between Example 12 of the present disclosure and Merestinib

| | human | mouse | Rat | dog | monkey |
|---|---|---|---|---|---|
| | T½ (minute) | | | | |
| Merestinib | 78.95 | 27.52 | 52.01 | 89.91 | 25.04 |
| Example 12 | 288.48 | 39.21 | 73.39 | 74.28 | 55.99 |
| | $Cl_{int}$ (mL/min/kg) | | | | |
| Merestinib | 22.02 | 90.26 | 104.93 | 38.43 | 80.96 |
| Example 12 | 6.03 | 63.34 | 74.36 | 46.51 | 36.20 |

The study of the present disclosure shows that, the compounds of the present disclosure such as Example 12 showed significantly improved metabolic stability in liver microsomes, a longer metabolic half-life, and a lower intrinsic clearance rate as compared with the prior art inhibitor Merestinib. Therefore, it is expected to provide a longer-lasting effect in clinical use, and correspondingly can reduce the drug dose required to achieve the same therapeutic strength.

Example 14: Inhibition of the Compounds of the Present Disclosure on Cytochrome P450 Enzyme System According to the standard methods conventional in the art for cytochrome P450 enzyme system study, for example those described in Kerns, Edward H. and Di Li (2008). *Drug-like Properties: Concepts. Structure Design and Methods: from ADME to Toxicity Optimization*. San Diego: Academic Press; Lin, Tong et al., *In Vitro Assessment of Cytochrome P450 Inhibition: Strategies for Increasing LC/MS-Based Assay Throughput Using a One-Point IC50 Method and Multiplexing High-Performance Liquid Chromatography*; J. Pharm. Sci. 2007, 96(9), 2485.), the inhibitory effect of the compounds of the present disclosure on the cytochrome P450 enzyme system was investigated analogously as follows.

The test compounds were evaluated by detecting the metabolism of human liver microsomes for the substrates of different subtypes of Cyp450. The metabolites, substrates and specific inhibitors of each Cyp450 enzyme are shown in Tables 12-14. The liver microsomes (Sekisui XenoTech, LLC., human liver microsomes, cat. #H0610) were slowly melted on ice, and 0.482 mL of the liver microsome solution (20 mg/mL) was added to 30 mL of 100 mM potassium phosphate solution to prepare a liver microsome working solution with a concentration of 0.316 mg/mL. The test compound and specific inhibitors of different Cyp450 subtypes (as a control) were prepared into 10 mM DMSO solutions, and then 20 µL of the 10 mM DMSO compound solution was added to 180 µL of acetonitrile to obtain a 1 mM compound solution. 2 µL of such 1 mM test compound or inhibitor solution was added to 150 µL of 0.316 mg/mL liver microsome working solution to obtain a 13.16 µM compound working solution. 45.3 mg of NADPH (SIGMA, cat. #V900362) was weighted and added into 13.59 mL of deionized water to prepare a 4 mM NADPH aqueous solution. 0.2 mL of 2 mg/mL internal standard stock solution (dexamethasone in acetonitrile) was added to 1000 mL of acetonitrile (SIGMA, cat. #271004) to prepare a reaction stop solution and stored at 4° C.

TABLE 12

Sources of P450 metabolites

| P450 subtype | Metabolites | Vendor | cat# |
|---|---|---|---|
| 1A2 | Acetaminophen | Sigma | PHR1531 |
| 2C9 | 4'-Hydroxydiclofenac | Sigma | 32412 |
| 2C19 | 4'-Hydroxymephenytoin | Sigma | H146 |
| 2D6 | Dextrorphan | Sigma | PHR1974 |
| 3A4 | 1'-Hydroxymidazolam | Caymen | 10385 |
| 3A4 | 6'-Hydroxytestosterone | Sigma | H2898 |

TABLE 13

Sources of P450 specific inhibitors

| P450 subtype | specific inhibitors | Vendor | cat# |
|---|---|---|---|
| 1A2 | 7-ethoxycoumarin | Sigma | E1379 |
| 2C9 | Sulfaphenazole | Sigma | S0758 |
| 2C19 | Omeprazole | Sigma | PHR1059 |
| 2D6 | Promethazine | Sigma | PHR1467 |
| 3A4 | Fluconazole | Sigma | PHRU60 |
| 3A4 | Ketoconazole | Sigma | PHR1385 |

TABLE 14

P450 substrate sources and substrate solutions (diluted in potassium phosphate solution)

| P450 Subtype | Substrate | Vendor | cat # | Methanol Storage sol. | Working sol. concentration (at 4mM NADPH) | Final concentration (mg/ml) |
|---|---|---|---|---|---|---|
| 1A2 | Phenacetin | Sigma | V900730 | 10 mM | 40 uM | 10 uM |
| 2C9 | Diclofenac | Sigma | PHR1144 | 10 mM | 40 uM | 10 uM |
| 2C19 | S-Mephenytoin | Sigma | UC175 | 40 mM | 160 uM | 40 uM |
| 2D6 | Dextromethorphan | Sigma | D0740000 | 10 mM | 40 uM | 10 uM |
| 3A4 | Midazolam | Tocris | 2832 | 3 mM | 20 uM | 5 uM |
| 3A4 | Testosterone | Tocris | 2822 | 50 mM | 500 uM | 125 uM |

TABLE 15

Human liver microsome solution prepared according to the following table (diluted with potassium phosphate solution)

| P450 subtype | Protein con. of working solution (mg/ml) | Final protein con. (mg/ml) |
|---|---|---|
| 1A2  | 0.133  | 0.10 |
| 2C9  | 0.0668 | 0.05 |
| 2C19 | 0.266  | 0.20 |
| 2D6  | 0.133  | 010  |
| 3A4  | 0.0668 | 0.05 |
| 3A4  | 0.133  | 0.10 |

150 μL 0.316 mg/mL human liver microsome working solution was added to each well of a 96-well deep plate, and 2 μL of 1 mM specific inhibitor or test compound solution was added to the corresponding wells, and then added to each well 50 μL preheated working solution of each substrate (in 4 mM NADPH solution). After incubating for 5-40 minutes respectively (different enzymes have different incubation times), 200 μL of pre-cooled reaction stop solution was added. All samples were centrifuged at 4000 rpm for 20 minutes. 150 μL of the centrifugal supernatant was then added to a new 96-well deep plate, and added to each well 150 μL of 0.1% formic acid aqueous solution, for analysis by LC/MS/MS (SCI AP4000). The single point IC50 values were calculated according to the following formula.

$$IC_{50} = C_0 * \frac{100\% - \% \text{ inhibition at } C_0}{\% \text{ inhibition at } C_0}$$

(Assuming Hill slope=1)

$C_0$=concentration of test compound and inhibitor solution

TABLE 16

Comparison of the inhibitory activity of Example 12 of the present disclosure and Merestinib on several CYP450 isoenzymes

| P450 Enzyme | IC50 (μM) | | | | |
|---|---|---|---|---|---|
| | 1A2 | 2C9 | 2C19 | 2D6 | 3A4 |
| Control    | 6.3 | 0.7 | 8.9 | 3.2 | 7.3 |
| Merestinib | >10 | 4.2 | >10 | >10 | >10 |
| Example 12 | >10 | 9.8 | >10 | >10 | >10 |

(Control 10 μM, test compound 10 μM)

Among the tested CYP450 isoenzymes, the protein encoded by the P450 2C9 gene is abundant in human liver microsomes, accounting for about 20% of the total P450. P450 2C9 can metabolize many drugs of different properties, and plays a role in the activation of pre-carcinogen/protoxins and mutagenic agents. The results of this experiment show that, the inhibitory activity of the compounds of the present disclosure, such as Example 12, on $2C_9$ is significantly lower than that of the prior inhibitor Merestinib. This indicates that the compound of the present disclosure has a smaller effect on P450 $2C_9$ than Merestinib, and thus is expected to have a smaller impact on the metabolism of other co-administered drugs, that is, the potential of drug interaction is expected to be significantly reduced.

Example 15: Investigation of Solubility of the Compounds of the Present Disclosure According to the well-known standard methods conventional in the art for solubility determination, for example those described in Kems, Edward H. and Di Li (2008). Drug-like Properties: *Concepts, Structure Design and Methods: from ADME to Toxicity Optimization*. San Diego: Academic Press), the solubility properties of the compounds of the present disclosure were investigated as follows, in testing systems of FaSSGF (pH 1.6) (Biorelevant, Fasted State Simulated gastric fluids), FeSSIF (pH 5.8) (Biorelevant, Fed State Simulated Intestinal Fluid), FaSSIF (pH 6.5) (Biorelevant, Fasted State Simulated Intestinal Fluid) and PBS buffer (Hyclone, Cat No. SH30256.01B).

Accurately weighed ~1 mg of test compound dry powder was charged into a glass bottle, and added an appropriate volume of each of the above test system solutions, to prepare a 4 mg/mL working solution. The sample bottle was placed on a shaker at room temperature (25° C.) and shook at 1000 rpm for 1 hour, then stood overnight for equilibrium. All samples were centrifuged at 12000 rpm at 25° C. for 10 minutes. Solutions of different concentrations for each compound were prepared in DMSO as the standard solutions. 580 μL of 20% (v/v) acetonitrile aqueous solution (containing 40 ng/mL tolbutamide as internal standard) was added into each well of three microplates, and mixed uniformly. 20 μL of 4 mg/mL working solution or standard solution was added to the wells of the first microplate and mixed uniformly, from which 20 μL was taken and added to the corresponding well of the second microplate, and mixed uniformly, from which again 20 μL was taken from each well and added to the corresponding wells of the third microplate, and mixed uniformly. Mass spectrometry was adopted to analyze the samples (LC-MS/MS-014, API4000), a standard curve was developed based on the concentrations of the standard solutions, and the solubility of the test compound was calculated.

TABLE 17

Comparison of the solubility of Example 12 of the present disclosure and Merestinib

| | Solubility (μg/mL) | | | |
|---|---|---|---|---|
| | FaSSGF (pH 1.6) | FeSSEF (pH 5.8) | FaSSIF (pH 6.5) | PBS (pH 7.4) |
| Merestinib | 19.28 | 33.70 | 3.07 | 0.02 |
| Example 12 | 27.66 | 53.30 | 5.47 | 0.01 |

The above data show that, the compounds of the present disclosure such as Example 12 show a significantly improved solubility as compared with Merestinib, which could provide better pharmaceutical properties and is expected to have improved bioavailability.

We claim:
1. A compound of formula I:

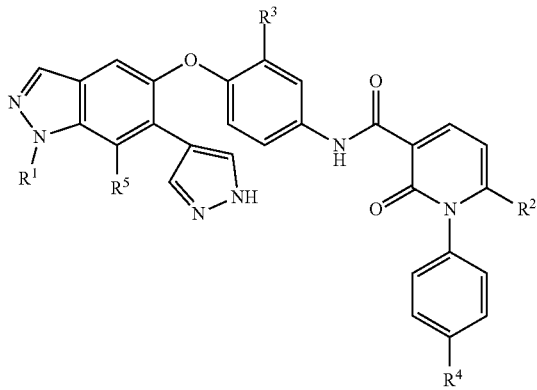

wherein:
R¹ is $C_{1-6}$ alkyl or $C_{3-6}$ cycloalkyl, optionally substituted by one or more halogens, —OR$^a$, $C_{1-6}$ alkyl or amino;
R⁵ is H, halogen, —OR$^a$ or optionally substituted $C_{1-6}$ alkyl, and the substituent is selected from one or more halogen, —OR$^a$, $C_{1-6}$ alkyl or amino;
or R¹ and R⁵ together with the atoms to which they are attached form a cyclic structure of the following formula:

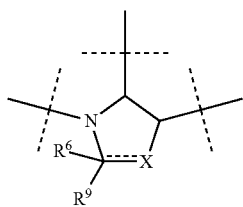

(a)

where X is —CR⁷R⁸—, =CR⁷—, —CR⁷R⁸—CR⁷R⁸— or —CR⁷=CR⁸—;
R⁶, R⁷, R⁸ and R⁹ are independently selected from H, halogen, —OR$^a$, optionally substituted $C_{1-6}$ alkyl or $C_{3-6}$ cycloalkyl, wherein the substituent is selected from one or more halogens, —OR$^a$, $C_{1-6}$ alkyl or amino; or
R⁶ and R⁹ or R⁷ and R⁸ attached to the same carbon atom can form =O or =S together, or form a $C_{3-6}$ cycloalkyl group together with the carbon atom to which they are attached;
R² is $C_{1-6}$ alkyl optionally substituted by one or more halogens, $C_{1-6}$ alkyl, $C_{1-6}$ alkoxy or amino; $C_{3-6}$ cycloalkyl or $C_{3-6}$ heterocyclic group, optionally substituted by one or more halogens, —OR$^a$, $C_{1-6}$ alkyl or amino; nitro, cyano, acyl, halogen, mercapto, $C_{1-6}$ alkylthio, $C_{1-6}$ alkylsulfonyl, $C_{1-6}$ alkyl sulfinyl or carboxy;
R³ and R⁴ are each independently selected from H, halogen, nitro, cyano, acyl or carboxy;

R$^a$ is selected from H or $C_{1-6}$ alkyl;
provided that R¹ and R² are not methyl at the same time, or isomers thereof, or their pharmaceutically acceptable salts or solvates.

2. The compound of claim 1, isomers thereof or their pharmaceutically acceptable salts or solvates, wherein R¹ is methyl, ethyl or isopropyl, or R¹ is cyclopropyl, cyclobutyl, cyclopentyl, or cyclohexyl.

3. The compound of claim 1, isomers thereof, or their pharmaceutically acceptable salts or solvates, wherein R⁵ is H.

4. The compound of claim 1, isomers thereof or their pharmaceutically acceptable salts or solvates, wherein R¹ and R⁵ together with the atoms to which they are attached form a cyclic structure of formula (a), wherein —X— is —CR⁷R⁸— or —CR⁷R⁸—CR⁷R⁸—, and R⁶, R⁷, R⁸ and R⁹ are each independently H, halogen, hydroxy, $C_{1-6}$ alkyl or $C_{3-6}$ cycloalkyl.

5. The compound of claim 1, isomers thereof or their pharmaceutically acceptable salts or solvates, wherein R¹ and R⁵ together with the atoms to which they are attached form a cyclic structure of formula (a), wherein —X— is =CR⁷— or —CR⁷=CR⁸—, and R⁶, R⁷, R⁸ and R⁹ are each independently H, halogen, $C_{1-6}$ alkyl or $C_{3-6}$ cycloalkyl.

6. The compound of claim 1, isomers thereof or their pharmaceutically acceptable salts or solvates, wherein R² is $C_{1-6}$ alkyl or $C_{3-6}$ cycloalkyl optionally substituted by one or more halogens.

7. The compound of claim 1, isomers thereof or their pharmaceutically acceptable salts or solvates, wherein R² is selected from the group consisting of methyl, ethyl, isopropyl, trifluoromethyl and cyclopropyl.

8. The compound of claim 1, isomers thereof or their pharmaceutically acceptable salts or solvates, wherein each of R³ and R⁴ is F.

9. A compound of formula III-a, isomers thereof or their pharmaceutically acceptable salts or solvates III-a

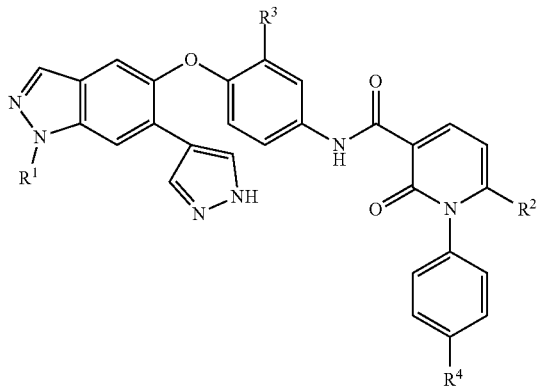

wherein
R¹ is $C_{1-6}$ alkyl;
R² is —NR$^a$R$^b$ or —OR$^b$;
R³ and R⁴ are each independently selected from H or halogen;
R$^a$ and R$^b$ are each independently selected from H, $C_{1-6}$ alkyl optionally substituted by one or more halogens, or $C_{3-6}$ cycloalkyl optionally substituted by one or more halogens, or $R^a$ and $R^b$ together with the N to which they are attached form a 3-6 membered ring optionally substituted by one or more halogens.

10. The compound of claim 9, isomers or their pharmaceutically acceptable salts or solvates, wherein $R^1$ is $C_{1-6}$ alkyl; $R^2$ is —$OR^b$, wherein $R^b$ is selected from $C_{1-6}$ alkyl or $C_{3-6}$ cycloalkyl, optionally substituted by one or more halogens; wherein each of $R^3$ and $R^4$ is an independently selected halogen.

11. A compound of formula III-b, isomers thereof or their pharmaceutically acceptable salts or solvates,

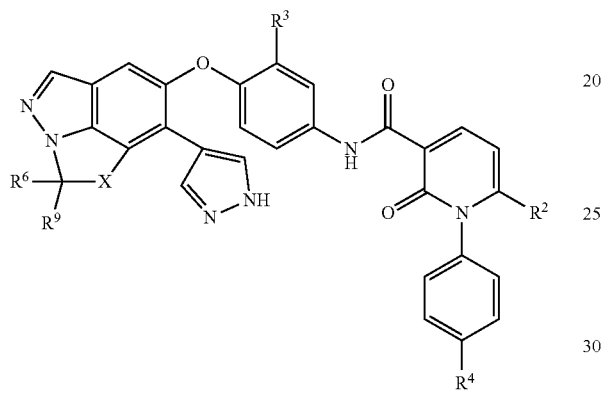

III-b wherein:
$R^2$ is —$NR^aR^b$ or —$OR^b$;
X is —$CR^7R^8$—, =$CR^7$—, —$CR^7R^8$—$CR^7R^8$— or —$CR^7$=$CR^8$—;
$R^6$ and $R^9$ are each independently H, halogen, —OH, $C_{1-6}$ alkyl or $C_{3-6}$ cycloalkyl;
$R^7$ and $R^8$ are each independently H, halogen, —OH, $C_{1-6}$ alkyl optionally substituted with one or more halogens or $C_{3-6}$ cycloalkyl optionally substituted with one or more halogens, or $R^7$ and $R^8$ attached to the same carbon atom together form a $C_{3-6}$ cycloalkyl;
$R^3$ and $R^4$ are each independently selected from H or halogen;
$R^a$ and $R^b$ are each independently selected from H, $C_{1-6}$ alkyl optionally substituted by one or more halogens, or $C_{3-6}$ cycloalkyl optionally substituted by one or more halogens, or $R^a$ and $R^b$ together with N to which they are attached form a 3-6 membered ring optionally substituted with one or more halogens.

12. The compound of claim 11, its isomers or their pharmaceutically acceptable salts or solvates, wherein X is —$CR^7R^8$— or —$CR^7R^8$—$CR^7R^8$—; $R^2$ is —$OR^b$, wherein $R^b$ is selected from $C_{1-6}$ alkyl optionally substituted by one or more halogens, or $C_{3-6}$ cycloalkyl optionally substituted by one or more halogens; wherein each of $R^3$ and $R^4$ is an independently selected halogen.

13. The compound of claim 11, its isomers or their pharmaceutically acceptable salts or solvates, wherein X is =$CR^7$— or —$CR^7$=$CR^8$—; $R^2$ is —$OR^b$, wherein $R^b$ is $C_{1-6}$ alkyl optionally substituted by one or more halogens, or $C_{3-6}$ cycloalkyl optionally substituted with one or more halogens; and each of $R^3$ and $R^4$ is an independently selected halogen.

14. A compound, isomers thereof or their pharmaceutically acceptable salts or solvates, selected from:

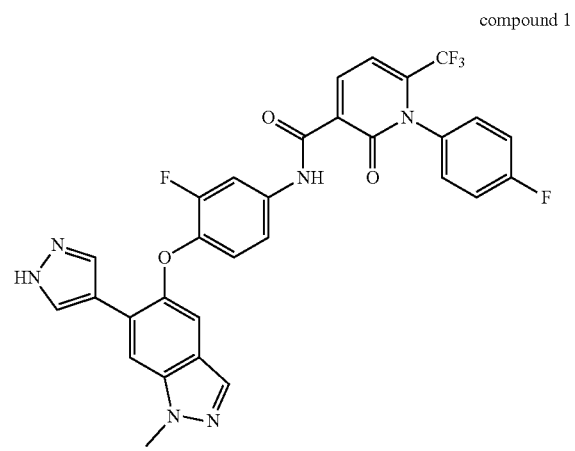

compound 1

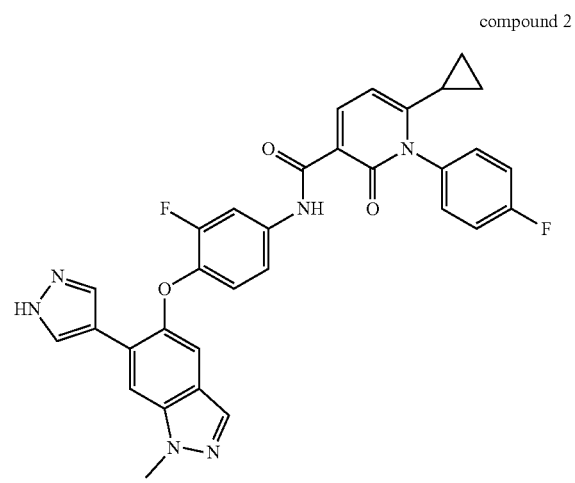

compound 2

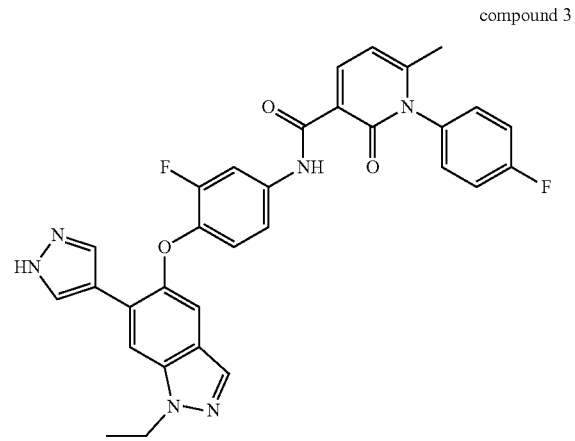

compound 3

-continued
compound 4
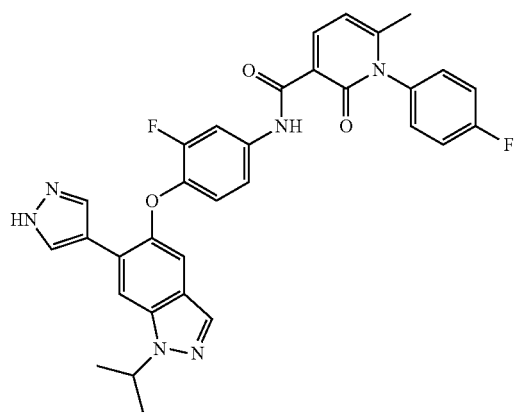
compound 5
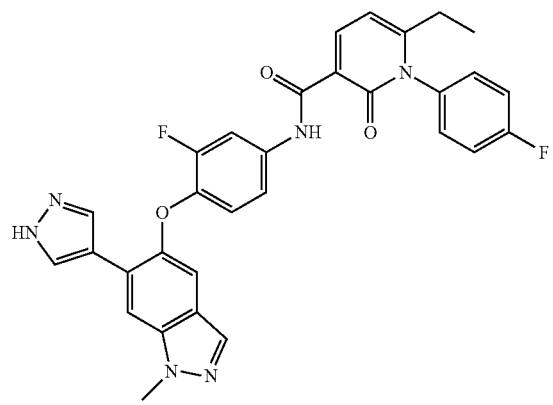
compound 6
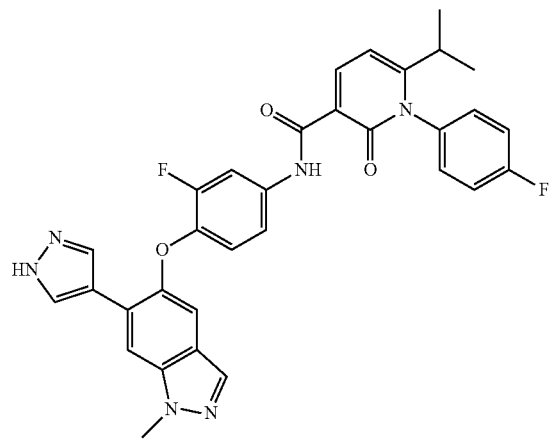
-continued
compound 7
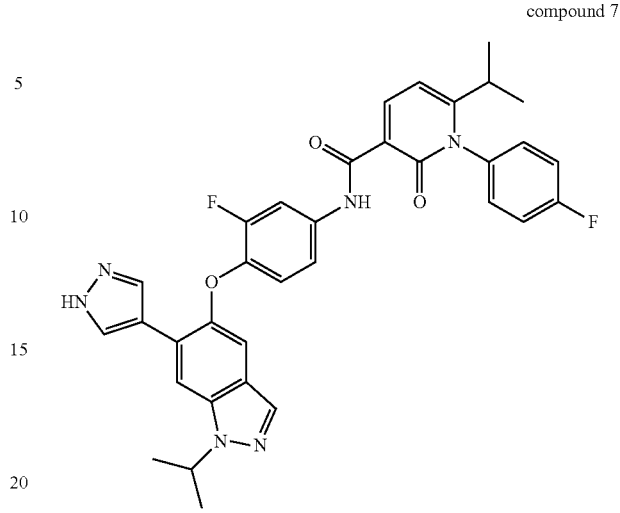
compound 8
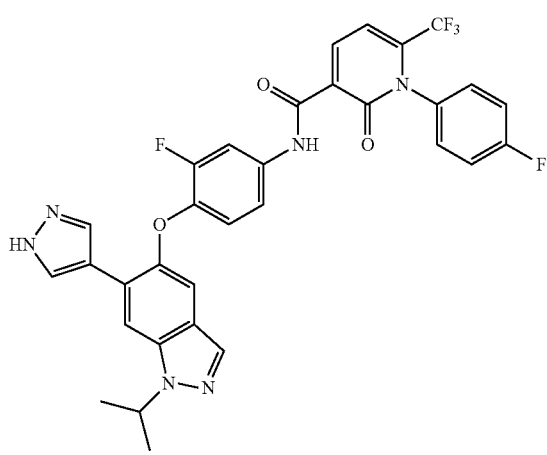
compound 9
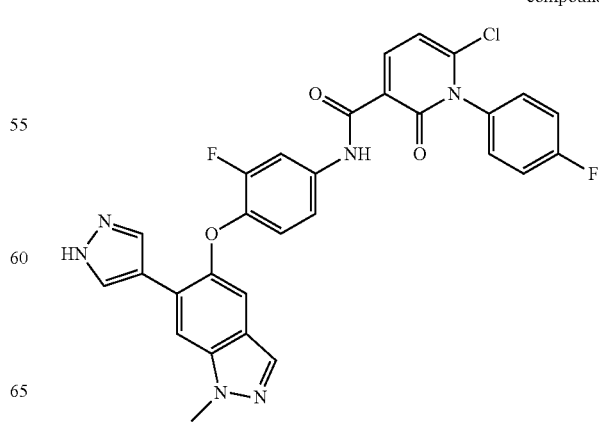

compound 10
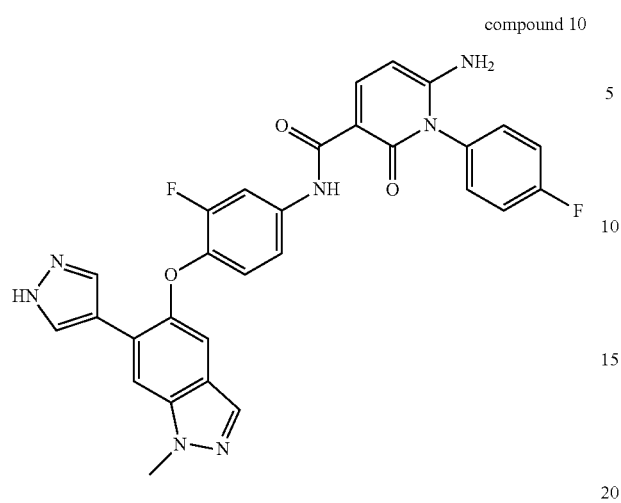
compound 13
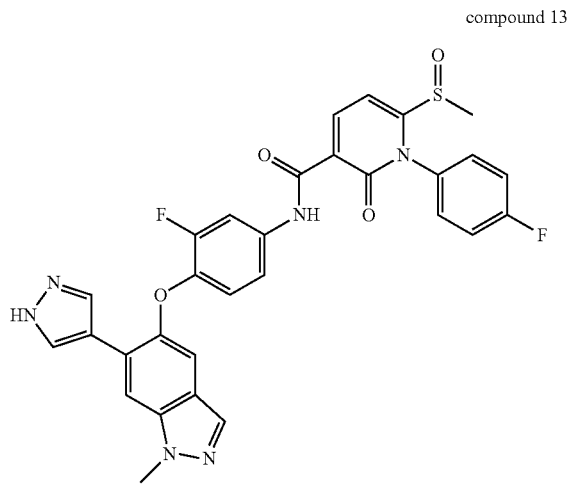
compound 11
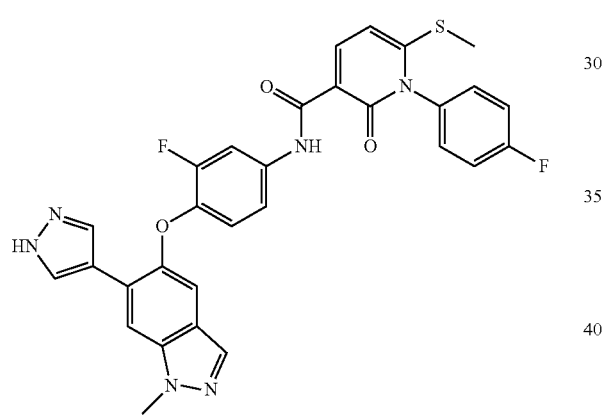
compound 14
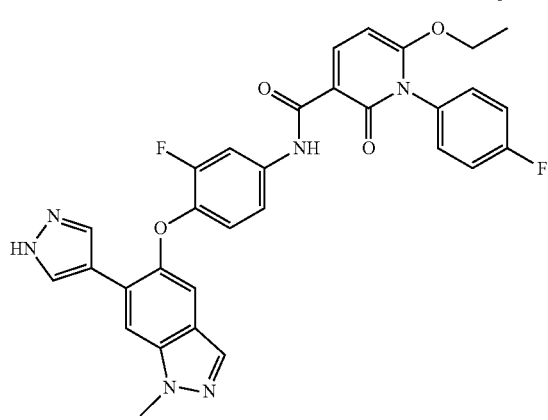
compound 12
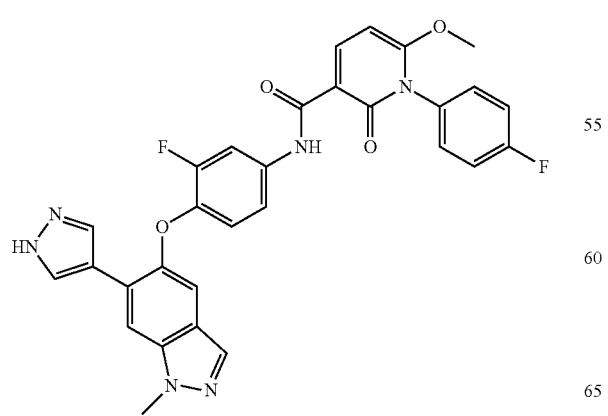
compound 15
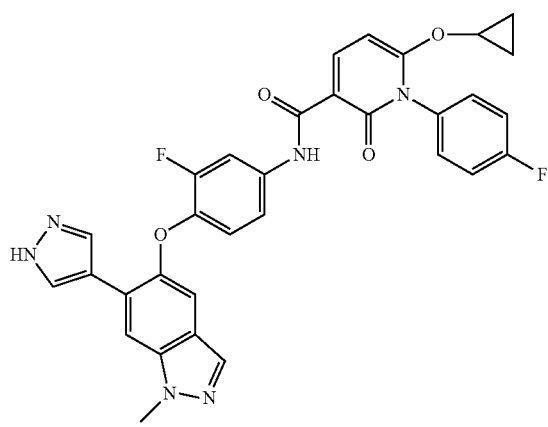

compound 16
compound 17
compound 18
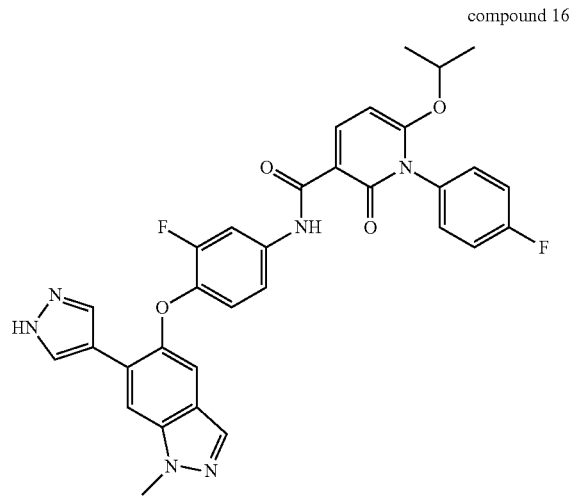
compound 19
compound 20
compound 21
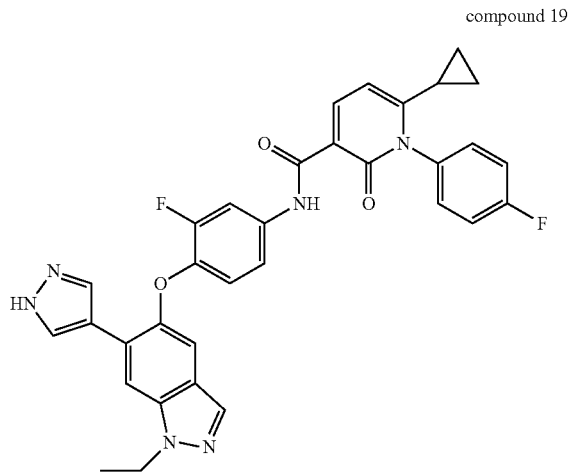

compound 22
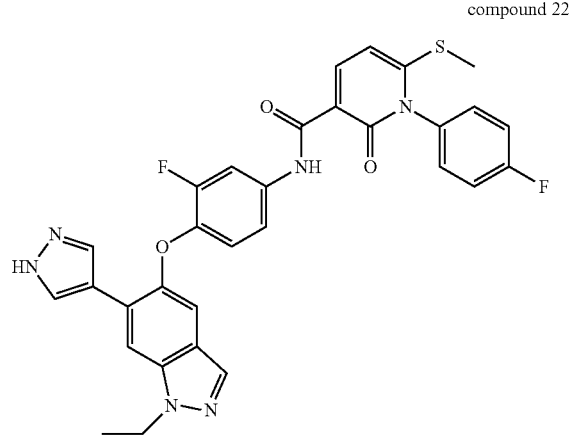
compound 23
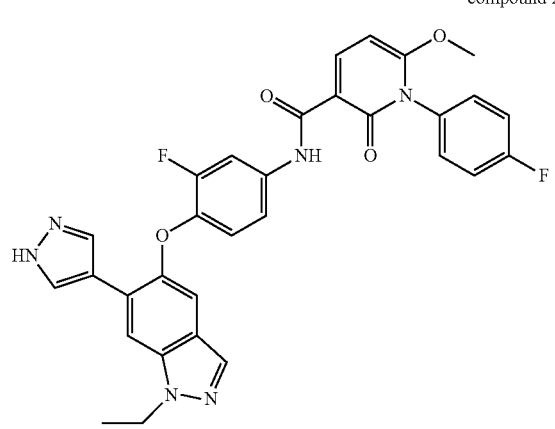
compound 24
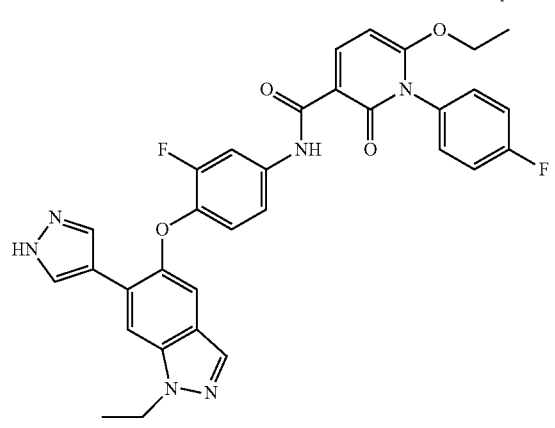
compound 25
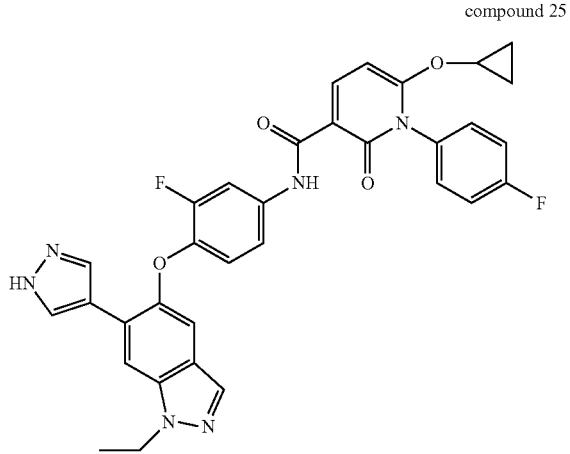
compound 26
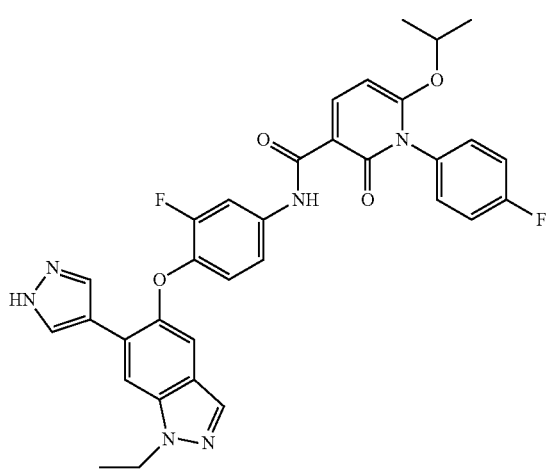
compound 27
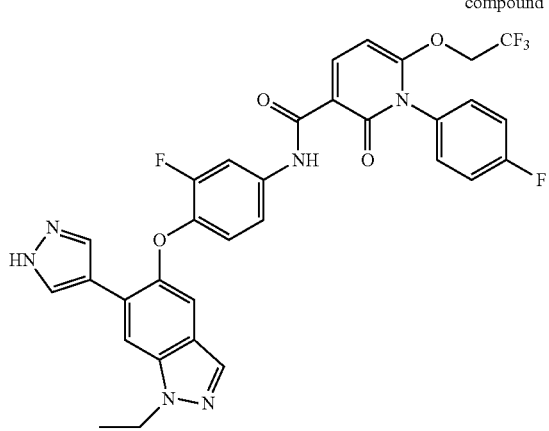

compound 28
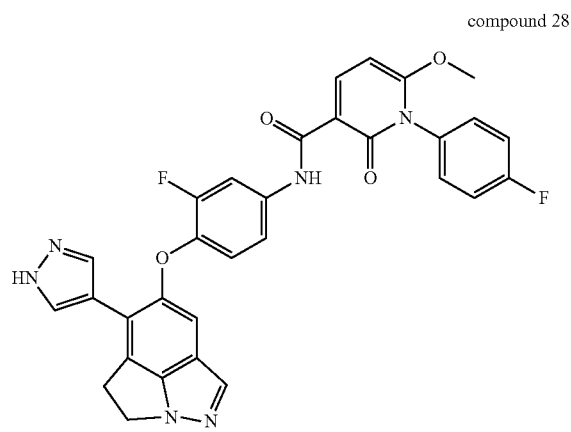
compound 31
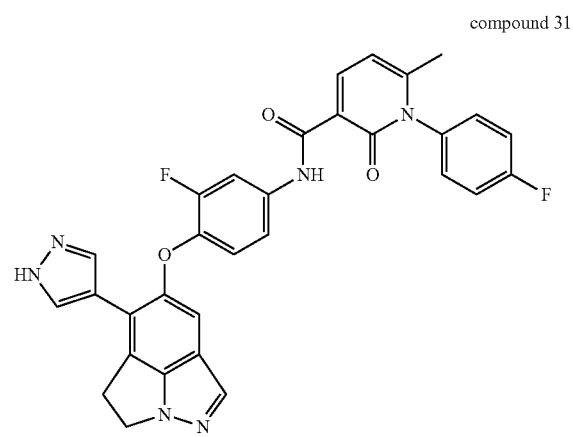
compound 29
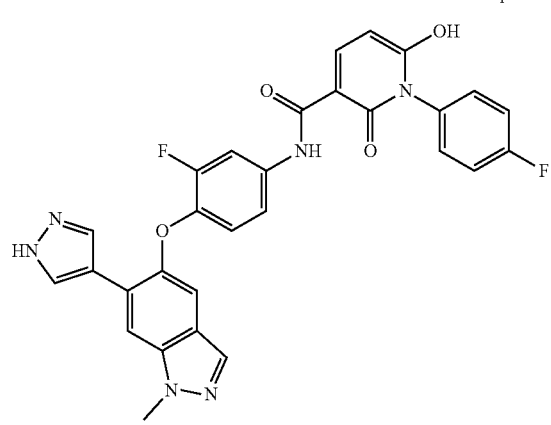
compound 32
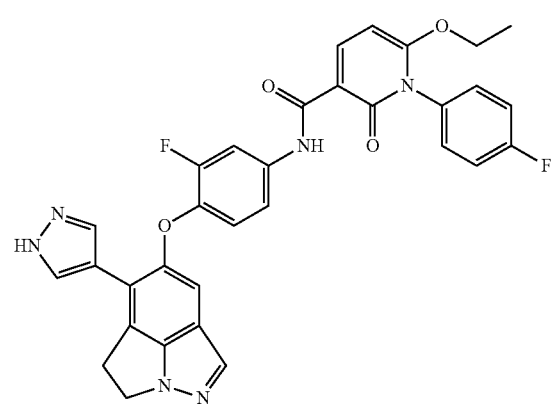
compound 30
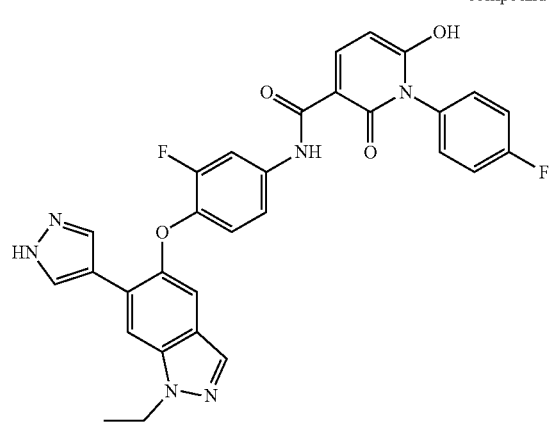
compound 33
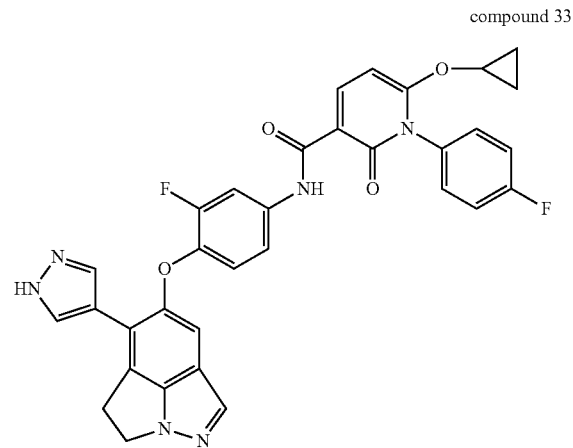

compound 34
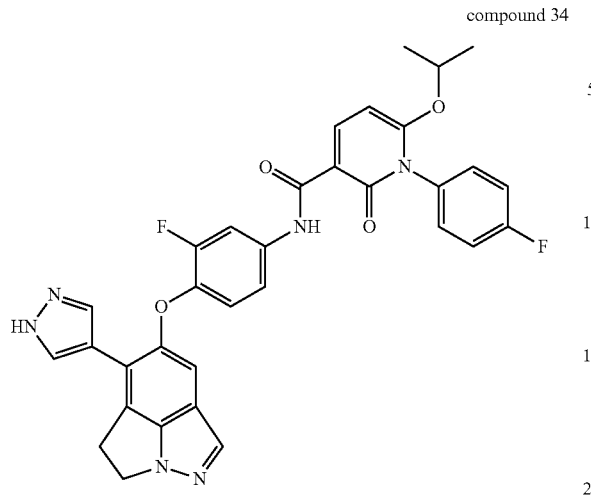
compound 35
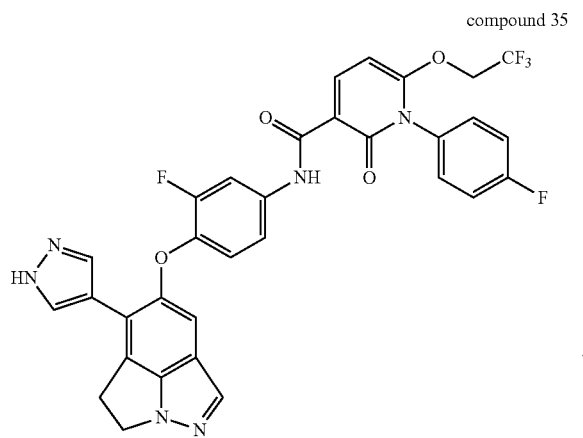
compound 36
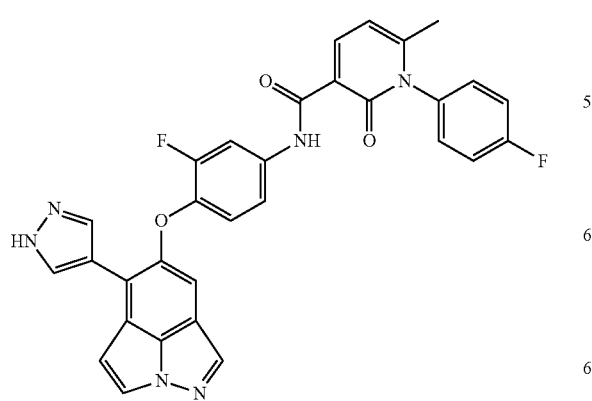
compound 37
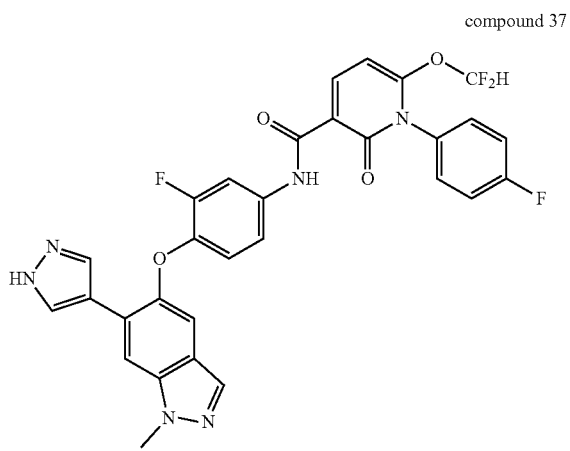
compound 38
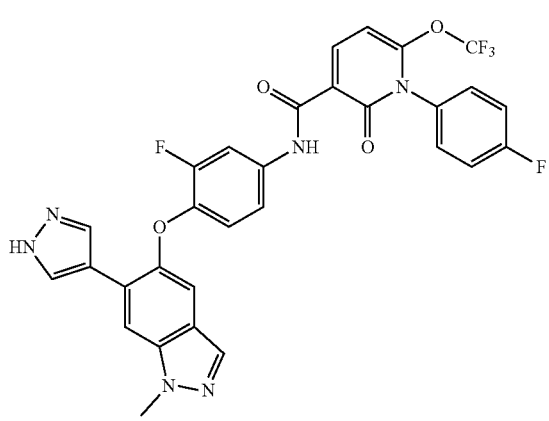
compound 39
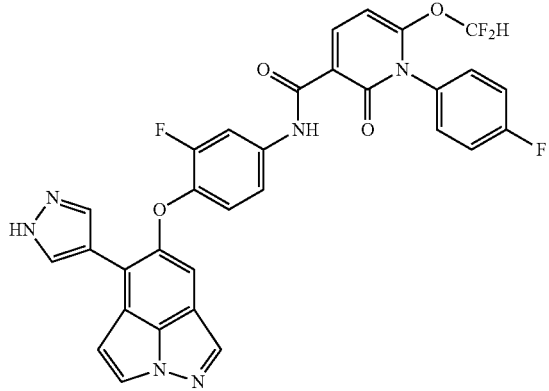

-continued
compound 40
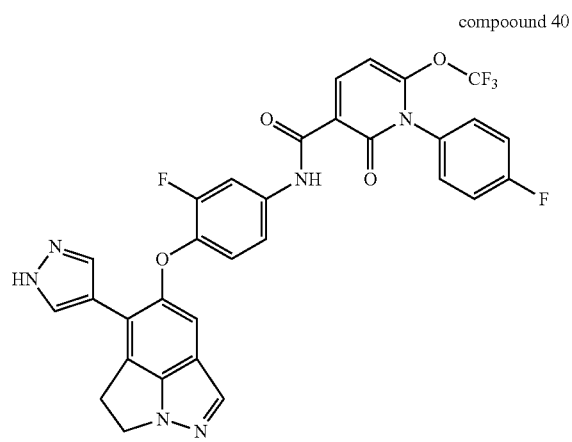
compound 41
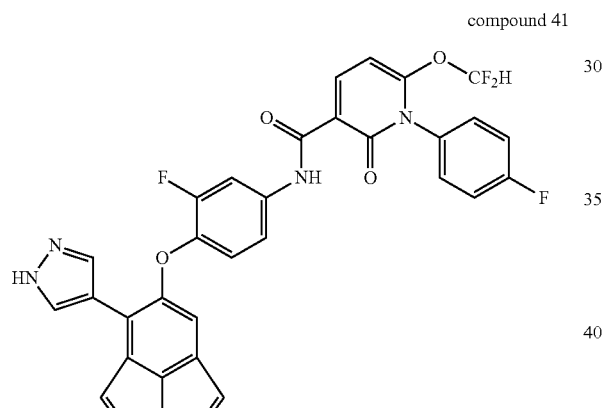
compound 42
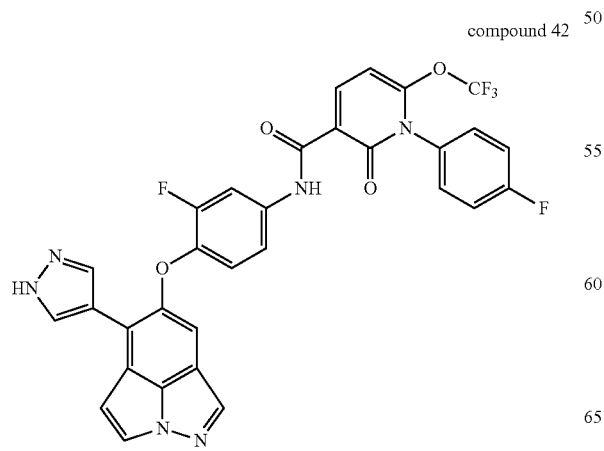
-continued
compound 43
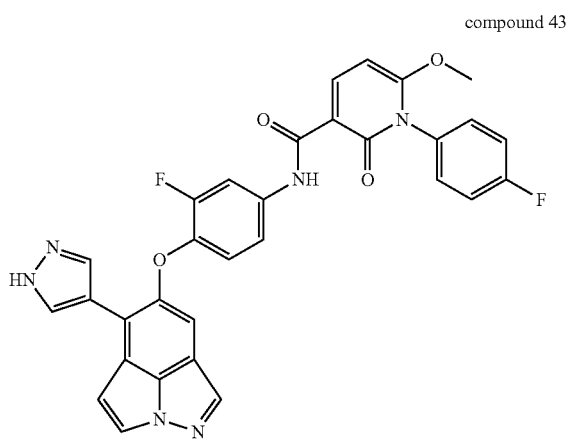
compound 44
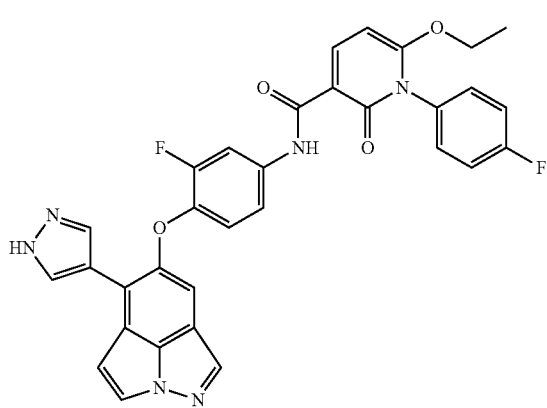
compound 45
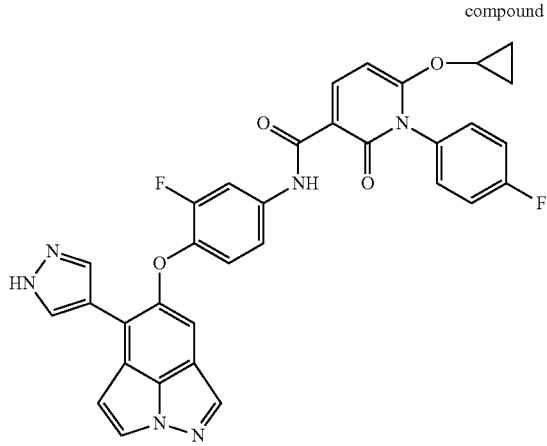

-continued compound 46 compound 47 compound 48

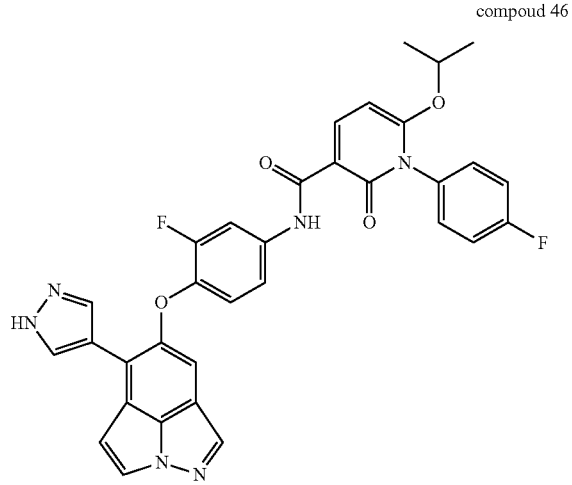

-continued compound 49 compound 50

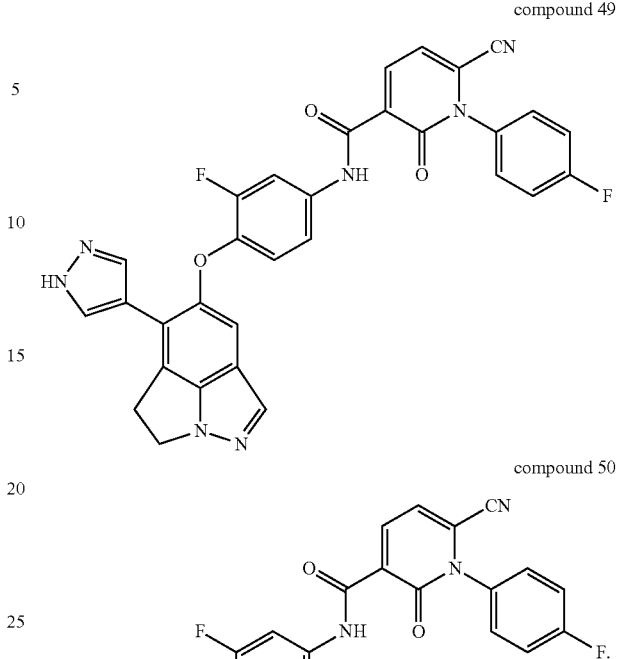

15. The compound of claim 1, isomers thereof or their pharmaceutically acceptable salts or solvates, wherein the pharmaceutically acceptable salt is p-toluenesulfonate, benzenesulfonate, or methanesulfonate.

16. A pharmaceutical composition comprising the compound of claim 1, isomers thereof or their pharmaceutically acceptable salts or solvates, and a pharmaceutically acceptable carrier, diluent or excipient, and optionally other therapeutically active agents selected from: other Trk inhibitors, kinase inhibitors, antibody drugs, immunotherapeutics, anti-cancer agents, anti-inflammatory drugs, analgesics, cardiovascular drugs, lipid-lowering drugs, antibacterial agents, antiviral agents, antidiabetic agents, antiproliferative agents, antiangiogenic agents or antiallergic agents.

17. A method for the treatment or the inhibition of development of diseases or disorders wherein the activity of Trk plays a role or is involved or diseases or disorders wherein the kinases shown in the following table play a role or are involved

| Kinases |
| --- |
| CDK11 |
| CDKL2 |
| DDR2 |
| FLT3(N841I) |
| KIT(L576P) |
| MYO3B |
| AXL |
| DDR1 |

| Kinases |
| --- |
| KIT(V559D) |
| TRKA |
| KIT |
| LOK |
| CSF1R |
| MKNK2 |
| MET(M1250T) |
| FLT3 |
| MET(Y1235D) |
| TIE1 |
| TIE2 |
| KIT(V559D,T670I) |
| MST1R |
| PDGFRB |
| FLT3(ITD) |
| MUSK |
| IKK-alpha |
| TRKC |
| IKK-beta |
| HIPK4 |
| LCK |
| MERTK |
| ROS1 |
| RET |
| EPHA8 |
| CDK7 |
| RET(M918T) |
| MKNK1 |
| EPHB6 |
| NEK9 |
| BLK |
| TRKB |
| FLT3(K663Q) |
| MET |
| FLT3(D835V) |
| RAF1 |
| FLT4 |
| PLK4, | the method comprising administering the compound of claim 1, isomers thereof or their pharmaceutically acceptable salts or solvates, or a pharmaceutical composition comprising the compound to a mammal in need thereof.

18. The method of claim 17, wherein the diseases or disorders are tumors or cancers selected from the group consisting of sarcoma skin cancer, neuroblastoma, ovarian cancer, breast cancer, prostate cancer, pancreatic cancer, salivary gland cancer, multiple myeloma, astrocytoma and medulloblastoma, neuroglioma, melanoma, thyroid cancer, lung adenocarcinoma, large cell neuroendocrine tumors, head and neck cancer and colorectal cancer, cholangiocarcinoma, glioblastoma, glioma, secretory breast cancer, mammary secretory carcinoma, acute myeloid leukemia, congenital mesoderm nephroma, congenital fibrosarcoma, acute lymphoblastic leukemia, colon adenocarcinoma, gastrointestinal stromal tumor.

19. A method for preparing the compound of claim 1, isomers thereof or their pharmaceutically acceptable salts or solvates thereof, which comprises:

(a) reacting a compound of formula A

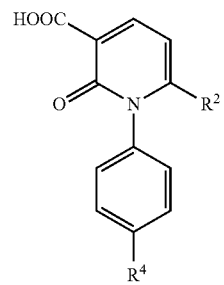

with a compound of formula B in the presence of a condensing reagent to form an amide, to obtain a compound of formula C or (a') reacting a compound of formula A

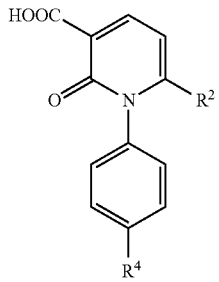

A with a compound of formula D in the presence of a condensing reagent to form an amide,

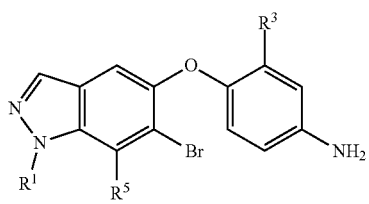

D to obtain a compound of formula E,

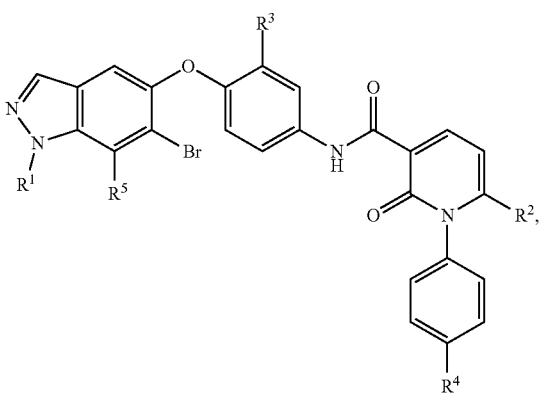

E the compound of formula E is subjected to a Suzuki coupling reaction to obtain the compound of formula C; and (b) deprotecting the compound of formula C to obtain the compound of formula I

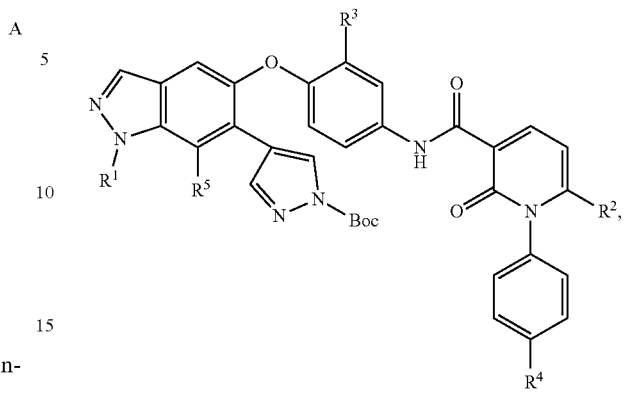

I wherein $R^1$ to $R^5$ are as defined in claim 1.

20. The compound of claim 1, isomers thereof or their pharmaceutically acceptable salts or solvates, wherein $R^1$ is methyl, or $R^1$ and $R^5$ together with the atoms to which they are attached form a cyclic structure of formula (a), wherein —X— is —$CR^7R^8$— or =$CR^7$—, and each of $R^6$, $R^7$, $R^8$ and $R^9$ is H.

21. The compound of claim 9, isomers thereof or their pharmaceutically acceptable salts or solvates, wherein $R^1$ is methyl; $R^2$ is selected from the group consisting of —OMe, —OEt, —O-nPr, —O-iPr, —O-cPr, —$OCF_3$, —$OCF_2H$ and —$OCH_2CF_3$; and each of $R^3$ and $R^4$ is F.

22. The compound of claim 11, isomers thereof or their pharmaceutically acceptable salts or solvates, wherein $R^2$ is —$OR^b$, wherein $R^b$ is $C_{1-6}$ alkyl optionally substituted by one or more halogens; X is —$CR^7R^8$— or =$CR^7$—, and each of $R^6$, $R^7$, $R^8$ and $R^9$ is H; and each of $R^3$ and $R^4$ is an independently selected halogen.

23. The compound of claim 11, isomers thereof or their pharmaceutically acceptable salts or solvates, wherein $R^2$ is selected from the group consisting of —OMe, —OEt, —O-nPr, —O-iPr, —O-cPr, —$OCF_3$, —$OCF_2H$ and —$OCH_2CF_3$; and each of $R^3$ and $R^4$ is F.

24. The method of claim 17, wherein the diseases or disorders are selected from the group consisting of infantile fibrosarcoma carcinoma, lung adenocarcinoma, intrahepatic cholangiocarcinoma, colorectal cancer, papillary thyroid carcinoma, spitzoid neoplasm, glioblastoma, astrocytoma, head and neck cancer, low-grade glioma, secretory breast cancer, acute myeloid leukemia, congenital mesodermal nephroma, congenital fibrosarcoma, acute lymphoblastic leukemia, colorectal adenocarcinoma, thyroid carcinoma, cutaneous melanoma and pediatric glioma sarcoma.

* * * * *